(12) United States Patent
Fushimi et al.

(10) Patent No.: US 8,324,176 B2
(45) Date of Patent: *Dec. 4, 2012

(54) PYRAZOLE DERIVATIVES, MEDICINAL COMPOSITION CONTAINING THE SAME, MEDICINAL USE THEREOF, AND INTERMEDIATE FOR PRODUCTION THEREOF

(75) Inventors: Nobuhiko Fushimi, Nagano (JP); Kazuo Shimizu, Nagano (JP); Shigeru Yonekubo, Nagano (JP); Hirotaka Teranishi, Nagano (JP); Masaki Tomae, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 527 days.

This patent is subject to a terminal disclaimer.

(21) Appl. No.: 12/421,236

(22) Filed: Apr. 9, 2009

(65) Prior Publication Data

US 2009/0203633 A1    Aug. 13, 2009

Related U.S. Application Data

(63) Continuation of application No. 10/525,197, filed as application No. PCT/JP03/10551 on Aug. 21, 2003, now Pat. No. 7,635,684.

(30) Foreign Application Priority Data

Aug. 23, 2002  (JP) .................................. 2002-244381
Nov. 7, 2002   (JP) .................................. 2002-324076

(51) Int. Cl.
*A61K 31/7028* (2006.01)
*C07H 17/02* (2006.01)

(52) U.S. Cl. ........................................ 514/27; 536/17.4

(58) Field of Classification Search .................. None
See application file for complete search history.

(56) References Cited

U.S. PATENT DOCUMENTS

| 6,815,428 | B2 * | 11/2004 | Ohsumi et al. ................ 514/25 |
| 7,084,123 | B2 | 8/2006 | Fujikura et al. |
| 7,375,087 | B2 * | 5/2008 | Teranishi et al. .............. 514/25 |
| 7,576,063 | B2 * | 8/2009 | Fujikura et al. ............... 514/27 |
| 7,576,064 | B2 * | 8/2009 | Kikuchi et al. ................ 514/27 |
| 7,655,632 | B2 * | 2/2010 | Teranishi et al. .............. 514/27 |

FOREIGN PATENT DOCUMENTS

| EP | 1 213 296 A1 | 6/2002 |
| EP | 1 338 603 A1 | 8/2003 |
| EP | 1 354 888 A1 | 10/2003 |

OTHER PUBLICATIONS

Silverman, "The Organic Chemistry of Drug Design and Drug Action", published 1992 by Academic Press, pp. 352-397.*

Merriam-Webster's Collegiate Dictionary, Tenth Edition, published 1998 by Merriam-Webster, incorporated, p. 924.*
The Merck Manual of Diagnosis and Therapy, published 1999 by Merck Research Laboratories, pp. 165-177.*
Silverman, R., "The Organic Chemistry of Drug Design and Drug Action" Published 1992 by Academic Press, pp. 352-397.
2006 Chemical Abstracts catalog, published 2006 by Chemical Abstracts Service, p. 52.
Biochemical Society Transactions, Feb. 1998, vol. 26, No. 2, p. S180 (1998).

* cited by examiner

*Primary Examiner* — Eric S Olson
(74) *Attorney, Agent, or Firm* — Sughrue Mion, PLLC

(57) ABSTRACT

The present invention provides pyrazole derivatives represented by the general formula:

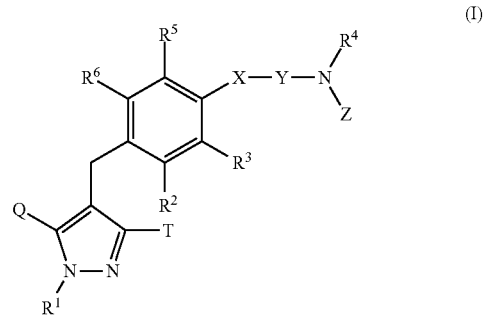

wherein $R^1$ represents H, an optionally substituted $C_{1-6}$ alkyl group etc.; one of Q and T represents a group represented by the general formula:

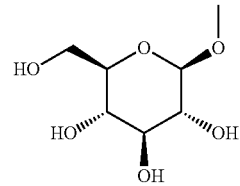

or a group represented by the general formula:

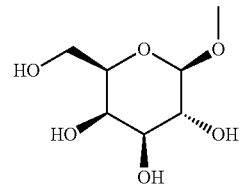

while the other represents an optionally substituted $C_{1-6}$ alkyl group etc.; $R^2$ represents H, a halogen atom, OH, an optionally substituted $C_{1-6}$ alkyl group etc.; X represents a single bond, O or S; Y represents an optionally substituted $C_{1-6}$ alkylene group etc.; Z represents —$R^B$, —$COR^C$ etc. in which $R^B$ represents an optionally substituted $C_{1-6}$ alkyl group etc.; and $R^C$ represents an optionally substituted $C_{1-6}$ alkyl group etc.; $R^4$ represents H, an optionally substituted $C_{1-6}$ alkyl group etc.; and $R^3$, $R^5$ and $R^6$ represent H, a halogen atom etc., pharmaceutically acceptable salts thereof or prodrugs thereof, which exhibit an excellent inhibitory activity in human SGLT1 and are useful as agents for the prevention or treatment of a disease associated with hyperglycemia such as diabetes, impaired glucose tolerance, impaired fasting glycemia, diabetic complications or obesity, and a disease associated with the increase of blood galactose level such as galactosemia, and pharmaceutical compositions comprising the same, pharmaceutical uses thereof, and intermediates for production thereof.

3 Claims, No Drawings

PYRAZOLE DERIVATIVES, MEDICINAL COMPOSITION CONTAINING THE SAME, MEDICINAL USE THEREOF, AND INTERMEDIATE FOR PRODUCTION THEREOF

CROSS REFERENCE TO RELATED APPLICATIONS

This application is a continuation application of application Ser. No. 10/525,197, filed Feb. 22, 2005, now U.S. Pat. No. 7,635,684 which is a 371 of PCT/JP2003/010551 filed Aug. 21, 2003, claiming the benefit of Japanese Application No. 244381/2002 filed Aug. 23, 2002 and Japanese Application No. 234076/2002 dated Nov. 7, 2002, all of which are hereby incorporated by reference.

TECHNICAL FIELD

The present invention relates to pyrazole derivatives, pharmaceutically acceptable salts thereof or prodrugs thereof which are useful as medicaments, pharmaceutical compositions comprising the same, pharmaceutical uses thereof and intermediates for production thereof.

More particularly, the present invention relates to pyrazole derivatives having an inhibitory activity in human SGLT1, pharmaceutically acceptable salts thereof or prodrugs thereof which are useful as agents for the prevention or treatment of a disease associated with hyperglycemia such as diabetes, impaired glucose tolerance, impaired fasting glycemia, diabetic complications or obesity, and a disease associated with the increase of blood galactose level such as galactosemia, pharmaceutical compositions comprising the same, pharmaceutical uses thereof and intermediates for production thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. In addition, it has been confirmed by large-scale clinical trial that it is necessary to practice a long-term control of blood sugar level strictly so as to prevent patients with diabetes from occurring and advancing diabetic complications by receiving treatment (see the following References 1 and 2). Furthermore, many epidemiologic studies on impaired glucose tolerance and macroangiopathy show that impaired glucose tolerance as the boundary type is also a risk factor in macroangiopathy as well as diabetes. Thus, needs to improve postprandial hyperglycemia have been focused (see the following Reference 3).

In recent years, development of various antidiabetic agents has been progressing with the background of a rapid increase of patients with diabetes. For example, α-glucosidase inhibitors, which delay carbohydrate digestion and absorption at the small intestine, are used to improve postprandial hyperglycemia. It has been also reported that acarbose, one of α-glucosidase inhibitors, has an effect of preventing or delaying the incidence of diabetes by applying to patients with impaired glucose tolerance (see the following Reference 4). However, since α-glucosidase inhibitors do not affect elevated glucose levels by ingesting a monosaccharide of glucose (see the following Reference 5), with recently changing compositions of sugars in meals, it has been desired to develop agents which exert a wider range of activities inhibiting carbohydrate absorption.

In the meantime, it has been known that SGLT1, sodium-dependent glucose transporter 1, exists in the small intestine which controls carbohydrate absorption. It has been also reported that insufficiency of glucose and galactose absorption arises in patients with dysfunction due to congenital abnormalities of human SGLT1 (see the following References 6-8). In addition, it has been confirmed that SGLT1 is involved in glucose and galactose absorption (see the following References 9 and 10).

Furthermore, it is confirmed that mRNA and protein of SGLT1 increase and absorption of glucoses are accelerated in OLETF rats and rats with streptozotocin-induced diabetic symptoms (see the following References 11 and 12). Generally inpatients with diabetes, carbohydrate digestion and absorption are increased. For example, it is confirmed that mRNA and protein of SGLT1 are highly increased in the human small intestine (see the following Reference 13).

Therefore, blocking a human SGLT1 activity inhibits absorption of carbohydrates such as glucose at the small intestine, subsequently can prevent increase of blood sugar level. Especially, it is considered that delaying glucose absorption based on the above mentioned mechanism is effective to normalize postprandial hyperglycemia. In addition, since increase of SGLT1 in the small intestine is thought to contribute to increased carbohydrate absorption, fast development of agents, which have a potent inhibitory activity in human SGLT1, has been desired for the prevention or treatment of diabetes.

Reference 1: The Diabetes Control and Complications Trial Research Group, N. Engl. J. Med., 1993.9, Vol. 329, No. 14, pp. 977-986;
Reference 2: UK Prospective Diabetes Study Group, Lancet, 1998.9, Vol. 352, No. 9131, pp. 837-853;
Reference 3: Makoto, TOMINAGA, Endocrinology & Diabetology, 2001.11, Vol. 13, No. 5, pp. 534-542;
Reference 4: Jean-Louis Chiasson and 5 persons, Lancet, 2002.6, Vol. 359, No. 9323, pp. 2072-2077;
Reference 5: Hiroyuki, ODAKA and 3 persons, Journal of Japanese Society of Nutrition and Food Science, 1992, Vol. 45, No. 1, pp. 27-31;
Reference 6: Tadao, BABA and 1 person, Supplementary volume of Nippon Rinsho, Ryoikibetsu Shokogun, 1998, No. 19, pp. 552-554;
Reference 7: Michihiro, KASAHARA and 2 persons, Saishin Igaku, 1996.1, Vol. 51, No. 1, pp. 84-90;
Reference 8: Tomofusa, TSUCHIYA and 1 person, Nippon Rinsho, 1997.8, Vol. 55, No. 8, pp. 2131-2139;
Reference 9: Yoshikatsu, KANAI, Kidney and Dialysis, 1998.12, Vol. 45, extra edition, pp. 232-237;
Reference 10: E. Turk and 4 persons, Nature, 1991.3, Vol. 350, pp. 354-356;
Reference 11: Y. Fujita and 5 persons, Diabetologia, 1998, Vol. 41, pp. 1459-1466;
Reference 12: J. Dyer and 5 persons, Biochemical Society Transactions, 1997, Vol. 25, p. 479S;
Reference 13: J. Dyer and 4 persons, American Journal of Physiology, 2002.2, Vol. 282, No. 2, pp. G241-G248

DISCLOSURE OF THE INVENTION

The present inventors have studied earnestly to find compounds having an inhibitory activity in human SGLT1. As a result, it was found that certain pyrazole derivatives represented by the following general formula (I) show an inhibitory activity in human SGLT1 at the small intestine and exert an excellent inhibitory activity in increase of blood glucose level as shown below, thereby forming the basis of the present invention.

The present invention is to provide novel pyrazole derivatives which exert an excellent inhibitory activity of blood glucose level increase by showing an inhibitory activity in human SGLT1 and inhibiting absorption of carbohydrate such as glucose at the small intestine, pharmaceutically acceptable salts thereof or prodrugs thereof, and to provide pharmaceutical compositions comprising the same, pharmaceutical uses thereof and intermediates for production thereof.

This is, the present invention relates to

[1] a pyrazole derivative represented by the general formula:

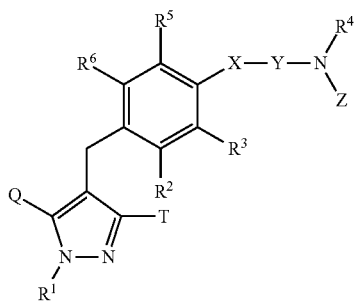

(I)

wherein $R^1$ represents a hydrogen atom, a $C_{1-6}$ alkyl group, a $C_{2-6}$ alkenyl group, a hydroxy($C_{2-6}$ alkyl) group, a $C_{3-7}$ cycloalkyl group, a $C_{3-7}$ cycloalkyl-substituted ($C_{1-6}$ alkyl) group, an aryl group which may have the same or different 1 to 3 substituents selected from the group consisting of a halogen atom, a hydroxy group, an amino group, a $C_{1-6}$ alkyl group and a $C_{1-6}$ alkoxy group, or an aryl($C_{1-6}$ alkyl) group which may have the same or different 1 to 3 substituents selected from the group consisting of a halogen atom, a hydroxy group, an amino group, a $C_{1-6}$ alkyl group and a $C_{1-6}$ alkoxy group on the ring;

one of Q and T represents a group represented by the formula:

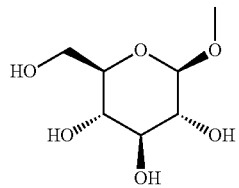

or a group represented by the formula:

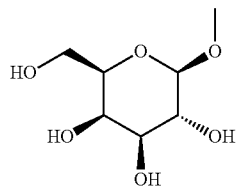

while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;

$R^2$ represents a hydrogen atom, a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or $-A-R^A$ in which A represents a single bond, an oxygen atom, a methylene group, an ethylene group, $-OCH_2-$ or $-CH_2O-$; and $R^A$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, or a heteroaryl group which may have a substituent selected from the group consisting of a halogen atom and a $C_{1-6}$ alkyl group;

X represents a single bond, an oxygen atom or a sulfur atom;

Y represents a $C_{1-6}$ alkylene group which may be substituted by a hydroxy group or a $C_{2-6}$ alkenylene group;

Z represents $-R^B$, $-COR^C$, $-SO_2R^C$, $-CON(R^D)R^E$, $-SO_2NHR^F$ or $-C(=NR^G)N(R^H)R^I$;

$R^C$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i);

$R^4$, $R^B$, $R^D$, $R^E$ and $R^F$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), or both of $R^4$ and $R^B$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, or both of $R^D$ and $R^E$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group;

$R^G$, $R^H$ and $R^I$ are the same or different, and each represents a hydrogen atom, a cyano group, a carbamoyl group, a $C_{2-7}$ acyl group, a $C_{2-7}$ alkoxycarbonyl group, an aryl($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (i), or both of $R^G$ and $R^H$ bind to form an ethylene group, or both of $R^H$ and $R^I$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group;

$R^3$, $R^5$ and $R^6$ are the same or different, and each represents a hydrogen atom, a halogen atom, a $C_{1-6}$ alkyl group or a $C_{1-6}$ alkoxy group; and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON($R^J$)$R^K$ in which $R^J$ and $R^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of $R^J$ and $R^K$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent, or a pharmaceutically acceptable salt thereof;

[2] a pyrazole derivative described in the above [1] wherein $R^4$ represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituents elected from the group consisting of a halogen atom, an amino group and a $C_{1-6}$ alkyl group, or a $C_{1-6}$ alkyl group which may have the same or different 1 to 5 groups selected from the following substituent group (i); $R^B$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i); $R^C$ represents an aryl group which has the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which has the same or different 1 to 5 groups selected from the following substituent group (i); and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON($R^J$)$R^K$ in which $R^J$ and $R^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of $R^J$ and $R^K$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent, or a pharmaceutically acceptable salt thereof;

[3] a pyrazole derivative described in the above [2] wherein Z represents —$R^B$; $R^B$ represents an aryl group which has the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which has the same or different 1 to 5 groups selected from the following substituent group (i); and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl) sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON($R^J$)$R^K$ in which $R^J$ and $R^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of $R^J$ and $R^K$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent,
or a pharmaceutically acceptable salt thereof;

[4] a pyrazole derivative described in the above [3] wherein $R^4$ represents a hydrogen atom; $R^B$ represents a $C_{1-6}$ alkyl group which has the same or different 1 to 5 groups selected from the following substituent group (iA); and substituent group (iA) consists of a hydroxy group, an amino group, a mono or di($C_{1-6}$ alkyl)amino group, a carboxy group, a $C_{2-7}$ alkoxycarbonyl group and —CON($R^{JA}$)$R^{KA}$ in which $R^{JA}$ and $R^{KA}$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group and a carbamoyl group, or both of $R^{JA}$ and $R^{KA}$ bind together with the neighboring nitrogen atom to form a $C_{2-6}$ cyclic amino group which may have a substituent selected from the group consisting of a $C_{1-6}$ alkyl group and a hydroxy($C_{1-6}$ alkyl) group,
or a pharmaceutically acceptable salt thereof;

[5] a pyrazole derivative described in the above [4] wherein $R^B$ represents a $C_{1-6}$ alkyl group which has a carbamoyl group, or a pharmaceutically acceptable salt thereof;

[6] a pyrazole derivative described in the above [2] wherein Z represents —CON($R^D$)$R^E$, or a pharmaceutically acceptable salt thereof;

[7] a pyrazole derivative described in the above [6] wherein $R^D$ represents a hydrogen atom; $R^E$ represents a $C_{1-6}$ alkyl group which has the same or different 1 to 5 groups selected from the following substituent group (iB); and substituent group (iB) consists of a hydroxy group, an amino group, a mono or di($C_{1-6}$ alkyl)amino group and —CON($R^{JB}$)$R^{KB}$ in which $R^{JB}$ and $R^{KB}$ are the same or different, and each represents a hydrogen atom, a $C_{1-6}$ alkyl group which may have the same or different 1 to 3 substituents selected from the group consisting of a hydroxy group, an amino group and a mono or di($C_{1-6}$ alkyl)amino group, or pharmaceutically acceptable salt thereof;

[8] a pyrazole derivative described in the above [2] wherein Z represents —C(=$NR^G$)N($R^H$)$R^I$, or pharmaceutically acceptable salt thereof;

(9) a pyrazole derivative described in the above [8] wherein $R^G$ represents a hydrogen atom or a $C_{1-6}$ alkylsulfonyl group; $R^H$ represents a hydrogen atom; $R^I$ represents a hydrogen atom or a $C_{1-6}$ alkyl group which may have the same or different 1 to 5 groups selected from the following substituent group (iC); and substituent group (iC) consists of a hydroxy group, an amino group, a mono or di($C_{1-6}$ alkyl)amino group, or pharmaceutically acceptable salt thereof;

[10] a pyrazole derivative described in the above [2] wherein Z represents —COR$^C$; $R^C$ represents a $C_{1-6}$ alkyl group which has a group selected from the following substituent group (iD); and substituent group (iD) consists of an amino group and —CON($R^{JC}$)$R^{KC}$ in which both of $R^{JC}$ and $R^{KC}$ bind together with the neighboring nitrogen atom to form a $C_{2-6}$ cyclic amino group which may have a substituent selected from the group consisting of a $C_{1-6}$ alkyl group and a hydroxy($C_{1-6}$ alkyl) group, or
pharmaceutically acceptable salt thereof;

[11] a pyrazole derivative described in any one of the above [1]-[10] wherein X represents a single bond or an oxygen atom; and Y represents an ethylene group or a trimethylene group, or pharmaceutically acceptable salt thereof;

[12] a pyrazole derivative described in any one of the above [1]-[11] wherein $R^1$ represents a hydrogen atom or a hydroxy($C_{2-6}$ alkyl) group; T represents a group represented by the formula:

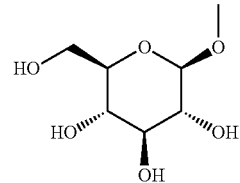

or a group represented by the formula:

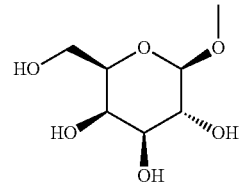

Q represents a $C_{1-6}$ alkyl group or a halo($C_{1-6}$ alkyl) group; and $R^3$, $R^5$ and $R^6$ represent a hydrogen atom, or a pharmaceutically acceptable salt thereof;

[13] a pyrazole derivative described in any one of the above [1]-[11] wherein one of Q and T represents a group represented by the formula:

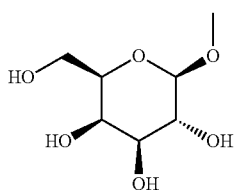

the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group, or a pharmaceutically acceptable salt thereof;

[14] a pyrazole derivative described in the above [12] or [13] wherein T represents a group represented by the formula:

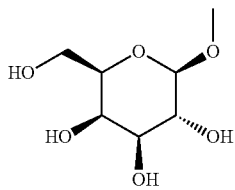

or a pharmaceutically acceptable salt thereof;

[15] a pyrazole derivative described in the above [12] or [14] wherein Q represents an isopropyl group, or a pharmaceutically acceptable salt thereof;

[16] a prodrug of a pyrazole derivative described in any one of the above [1]-[15] or a pharmaceutically acceptable salt thereof;

[17] a prodrug described in the above [16] wherein T represents a group represented by the formula:

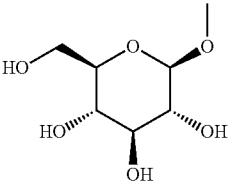

or a group represented by the formula:

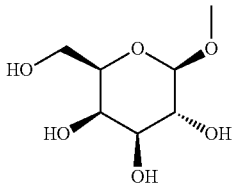

in which the hydroxy group at the 4-position is substituted by a glucopyranosyl group or a galactopyranosyl group, or the hydroxy group at the 6-position is substituted by a glucopyranosyl group, a galactopyranosyl group, a $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, an aryl($C_{2-7}$ alkoxycarbonyl) group or a $C_{1-6}$ alkoxy-substituted ($C_{2-7}$ alkoxycarbonyl) group;

[18] a pyrazole derivative described in the above [1] which is a compound selected from the group consisting of compounds described in the following Example numbers and pharmaceutically acceptable salts thereof, Example 28, Example 29, Example 32, Example 33, Example 45, Example 48, Example 51, Example 52 (Example 111), Example 55, Example 56, Example 57, Example 59, Example 66, Example 67, Example 71, Example 77, Example 79, Example 81, Example 82, Example 83, Example 84, Example 87, Example 90, Example 94, Example 107, Example 108, Example 109, Example 114, Example 117, Example 118, Example 119, Example 121, Example 123, Example 124, Example 126, Example 127, Example 128, Example 129, Example 130, Example 134, Example 141, Example 147, Example 150, Example 151, Example 170, Example 175, Example 177, Example 178, Example 179, Example 180 and Example 181;

[19] a pharmaceutical composition comprising as an active ingredient a pyrazole derivative described in any one of the above [1]-[18], a pharmaceutically acceptable salt thereof or a prodrug thereof;

[20] a human SGLT1 inhibitor comprising as an active ingredient a pyrazole derivative described in any one of the above [1]-[18], a pharmaceutically acceptable salt thereof or a prodrug thereof;

[21] an agent for inhibiting postprandial hyperglycemia comprising as an active ingredient a pyrazole derivative described in any one of the above [1]-[18], a pharmaceutically acceptable salt thereof or a prodrug thereof;

[22] an agent for the prevention or treatment of a disease associated with hyperglycemia, which comprises as an active ingredient a pyrazole derivative described in any one of the above [1]-[18], a pharmaceutically acceptable salt thereof or a prodrug thereof;

[23] an agent for the prevention or treatment described in the above [22] wherein the disease associated with hyperglycemia is a disease selected from the group consisting of diabetes, impaired glucose tolerance, impaired fasting glycemia, diabetic complications, obesity, hyperinsulinemia, hyperlipidemia, hypercholesterolemia, hypertriglyceridemia, lipid metabolism disorder, atherosclerosis, hypertension, congestive heart failure, edema, hyperuricemia and gout;

[24] an agent for the inhibition of advancing impaired glucose tolerance or impaired fasting glycemia into diabetes in a subject, which comprises as an active ingredient a pyrazole derivative described in any one of the above [1]-[18], a pharmaceutically acceptable salt thereof or a prodrug thereof;

[25] an agent for the prevention or treatment of a disease associated with the increase of blood galactose level, which comprises as an active ingredient a pyrazole derivative described in any one of the above [1]-[18], a pharmaceutically acceptable salt thereof or a prodrug thereof;

[26] an agent for the prevention or treatment described in the above [25] wherein the disease associated with the increase of blood galactose level is galactosemia;

[27] a pharmaceutical composition described in the above [19] wherein the dosage form is sustained release formulation;

[28] an agent described in any one of the above [20]-[26] wherein the dosage form is sustained release formulation;

[29] a method for the prevention or treatment of a disease associated with hyperglycemia, which comprises administering an effective amount of a pyrazole derivative described in any one of the above [1]-[18], a pharmaceutically acceptable salt thereof or a prodrug thereof;

[30] a method for the inhibition of advancing impaired glucose tolerance or impaired fasting glycemia into diabetes in a subject, which comprises administering an effective amount of a pyrazole derivative described in any one of the above [1]-[18], a pharmaceutically acceptable salt thereof or a prodrug thereof;

[31] a method for the prevention or treatment of a disease associated with the increase of blood galactose level, which comprises administering an effective amount of a pyrazole derivative described in any one of the above [1]-[18], a pharmaceutically acceptable salt thereof or a prodrug thereof;

[32] a use of a pyrazole derivative described in any one of the above [1]-[18], a pharmaceutically acceptable salt thereof or a prodrug thereof for the manufacture of a pharmaceutical composition for the prevention or treatment of a disease associated with hyperglycemia;

[33] a use of a pyrazole derivative described in any one of the above [1]-[18], a pharmaceutically acceptable salt thereof or a prodrug thereof for the manufacture of a pharmaceutical composition for the inhibition of advancing impaired glucose tolerance or impaired fasting glycemia into diabetes in a subject;

[34] a use of a pyrazole derivative described in any one of the above [1]-[18], a pharmaceutically acceptable salt thereof or a prodrug thereof for the manufacture of a pharmaceutical composition for the prevention or treatment of a disease associated with the increase of blood galactose level;

[35] a pharmaceutical combination which comprises (A) a pyrazole derivative described in any one of the above [1]-[18], a pharmaceutically acceptable salt thereof or a prodrug thereof, and (B) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-1, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, antidiarrhoics, cathartics, a hydroxymethylglutaryl coenzyme A reductase inhibitor, a fibric acid derivative, a β$_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an antiplatelets agent, a uric acid synthesis inhibitor, a uricosuric agent and a urinary alkalinizer;

[36] a method for the prevention or treatment of a disease associated with hyperglycemia or a disease associated with the increase of blood galactose level, which comprises administering an effective amount of a drug selected from the above group (A) and at least one member selected from the above group (B);

[37] a method for the inhibition of advancing impaired glucose tolerance or impaired fasting glycemia into diabetes in a subject, which comprises administering an effective amount of a drug selected from the above group (A) and at least one member selected from the above group (B);

[38] a use of a drug selected from the above group (A) and at least one member selected from the above group (B) for the manufacture of a pharmaceutical composition for the prevention or treatment of a disease associated with hyperglycemia or a disease associated with the increase of blood galactose level;

[39] a use of a drug selected from the above group (A) and at least one member selected from the above group (B) for the manufacture of a pharmaceutical composition for the inhibition of advancing impaired glucose tolerance or impaired fasting glycemia into diabetes in a subject;

[40] a pyrazole derivative represented by the general formula:

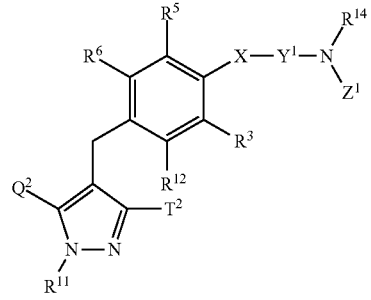

wherein $R^{11}$ represents a hydrogen atom, a $C_{1-6}$ alkyl group, a $C_{2-6}$ alkenyl group, a hydroxy($C_{2-6}$ alkyl) group which may have a protective group, a $C_{3-7}$ cycloalkyl group, a $C_{3-7}$ cycloalkyl-substituted ($C_{1-6}$ alkyl) group, an aryl group which may have the same or different 1 to 3 substituents selected from the group consisting of a halogen atom, a hydroxy group which may have a protective group, an amino group which may have a protective group, a $C_{1-6}$ alkyl group and a $C_{1-6}$ alkoxy group, or an aryl($C_{1-6}$ alkyl) group which may have the same or different 1 to 3 substituents selected from the group consisting of a halogen atom, a hydroxy group which may have a protective group, an amino group which may have a protective group, a $C_{1-6}$ alkyl group and a $C_{1-6}$ alkoxy group on the ring;

one of $Q^2$ and $T^2$ represents a 2,3,4,6-tetra-O-acetyl-β-D-glucopyranosyloxy group, a 2,3,4,6-tetra-O-pivaloyl-β-D-glucopyranosyloxy group, a 2,3,4,6-tetra-O-acetyl-β-D-galactopyranosyloxy group or a 2,3,4,6-tetra-O-pivaloyl-β-D-galactopyranosyloxy group, while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;

$R^{12}$ represents a hydrogen atom, a halogen atom, a hydroxy group which may have a protective group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or —A—$R^{14}$ in which A represents a single bond, an oxygen atom, a methylene group, an ethylene group, —OCH$_2$— or —CH$_2$O—; and $R^{14}$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group which may have a protective group, an amino group which may have a protective group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group which may have a protective group, a carboxy group which may have a protective group, a $C_{2-7}$ alkoxycarbonyl group, a cyano group and a nitro group, or a heteroaryl group which may have a substituent selected from the group consisting of a halogen atom and a $C_{1-6}$ alkyl group;

X represents a single bond, an oxygen atom or a sulfur atom;

$Y^1$ represents a $C_{1-6}$ alkylene group which may be substituted by a hydroxy group which may have a protective group, or a $C_{2-6}$ alkenylene group;

$Z^1$ represents —$R^{1B}$, —$COR^{1C}$, —$SO_2R^{1C}$, —$CON(R^{1D})R^{1E}$, —$SO_2NHR^{1F}$ or —$C(=NR^{1G})N(R^{1H})R^{1I}$, $R^{1C}$ represents an aryl group which may have the same or different 1 to 3 substituents selected from the group consisting of a halogen atom, a hydroxy group which may have a protective group, an amino group which may have a protective group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group which may have a protective group and a $C_{1-6}$ alkyl group, or a $C_{1-6}$ alkyl group which may have the same or different 1 to 5 groups selected from the following substituent group (ii);

$R^{14}$, $R^{1B}$, $R^{1D}$, $R^{1E}$ and $R^{1F}$ are the same or different, and each represents a hydrogen atom, an aryl group which may have the same or different 1 to 3 substituents selected from the group consisting of a halogen atom, a hydroxy group which may have a protective group, an amino group which may have a protective group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group which may have a protective group and a $C_{1-6}$ alkyl group, or a $C_{1-6}$ alkyl group which may have the same or different 1 to 5 groups selected from the following substituent group (ii), or both of $R^{14}$ and $R^{1B}$ bind together with the neighboring nitrogen atom to form a $C_{2-6}$ cyclic amino group which may have a substituent selected from the group consisting of a hydroxy group which may have a protective group, a carbamoyl group, a $C_{1-6}$ alkyl group, an oxo group, a carbamoyl($C_{1-6}$ alkyl) group, a hydroxy($C_{1-6}$ alkyl) group which may have a protective group and a $C_{1-6}$ alkylsulfonylamino-substituted ($C_{1-6}$ alkyl) group, or both of $R^{1D}$ and $R^{1E}$ bind together with the neighboring nitrogen atom to form a $C_{2-6}$ cyclic amino group which may have a substituent selected from the group consisting of a hydroxy group which may have a protective group, a carbamoyl group, a $C_{1-6}$ alkyl group, an oxo group, a carbamoyl($C_{1-6}$ alkyl) group, a hydroxy($C_{1-6}$ alkyl) group which may have a protective group and a $C_{1-6}$ alkylsulfonylamino-substituted ($C_{1-6}$ alkyl) group;

$R^{1G}$, $R^{1H}$ and $R^{1I}$ are the same or different, and each represents a hydrogen atom, a cyano group, a carbamoyl group, a $C_{2-7}$ acyl group, a $C_{2-7}$ alkoxycarbonyl group, an aryl($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (ii), or both of $R^{1G}$ and $R^{1H}$ bind to form an ethylene group, or both of $R^{1H}$ and $R^{1I}$ bind together with the neighboring nitrogen atom to form a $C_{2-6}$ cyclic amino group which may have a substituent selected from the group consisting of a hydroxy group which may have a protective group, a carbamoyl group, a $C_{1-6}$ alkyl group, an oxo group, a carbamoyl($C_{1-6}$ alkyl) group, a hydroxy($C_{1-6}$ alkyl) group which may have a protective group and a $C_{1-6}$ alkylsulfonylamino-substituted ($C_{1-6}$ alkyl) group;

$R^3$, $R^5$ and $R^6$ are the same or different, and each represents a hydrogen atom, a halogen atom, a $C_{1-6}$ alkyl group or a $C_{1-6}$ alkoxy group; and substituent group (ii) consists of a hydroxy group which may have a protective group, a $C_{1-6}$ alkoxy group, a $C_{1-6}$ alkylthio group, an amino group which may have a protective group, a mono or di($C_{1-6}$ alkyl)amino group which may have a protective group, a mono or di[hydroxy($C_{1-6}$ alkyl)]amino group which may have a protective group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group which may have a protective group, a $C_{2-7}$ alkoxycarbonyl group, —$CON(R^{1J})R^{1K}$ in which $R^{1J}$ and $R^{1K}$ are the same or different, and each represents a hydrogen atom or a $C_{1-6}$ alkyl group which may have the same or different 1 to 3 substituents selected from the group consisting of a hydroxy group which may have a protective group, an amino group which may have a protective group, a mono or di($C_{1-6}$ alkyl)amino group which may have a protective group, a mono or di[hydroxy($C_{1-6}$ alkyl)]amino group which may have a protective group, an ureido group, a mono or di($C_{1-6}$ alkyl)ureido group, a $C_{2-7}$ acylamino group, a $C_{1-6}$ alkylsulfonylamino group and a carbamoyl group, or both of $R^{1J}$ and $R^{1K}$ bind together with the neighboring nitrogen atom to form a $C_{2-6}$ cyclic amino group which may have a substituent selected from the group consisting of a hydroxy group which may have a protective group, a carbamoyl group, a $C_{1-6}$ alkyl group, an oxo group, a carbamoyl($C_{1-6}$ alkyl) group, a hydroxy($C_{1-6}$ alkyl) group which may have a protective group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group which may have a protective group, an amino group which may have a protective group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group which may have a protective group, an amino group which may have a protective group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group which may have a protective group, an amino group which may have a protective group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group which may have a protective group and a $C_{1-6}$ alkyl group, a $C_{2-6}$ cyclic amino group which may have a substituent selected from the group consisting of a hydroxy group which may have a protective group, a carbamoyl group, a $C_{1-6}$ alkyl group, an oxo group, a carbamoyl($C_{1-6}$ alkyl) group, a hydroxy($C_{1-6}$ alkyl) group which may have a protective group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent, or a salt thereof; and the like.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{1-6}$ alkylene group" means a straight-chained or branched alkylene group having 1 to 6 carbon atoms such as a methylene group, an ethylene group, a trimethylene group, a tetramethylene group, a propylene group, a 1,1-dimethylethylene group or the like; the term "hydroxy($C_{1-6}$ alkyl) group" means the above $C_{1-6}$ alkyl group substituted by a hydroxy group; the term "$C_{2-6}$ alkyl group" means a straight-chained or branched alkyl group having 2 to 6 carbon atoms such as an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "hydroxy($C_{2-6}$ alkyl) group" means the above $C_{2-6}$ alkyl group substituted by a hydroxy group, such as a 2-hydroxyethyl group, a 3-hydroxypropyl group or the like; the term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; the term "$C_{1-6}$ alkoxy-substituted ($C_{1-6}$ alkyl) group" means the above $C_{1-6}$ alkyl group substituted by the above $C_{1-6}$ alkoxy group; the term "$C_{1-6}$ alkoxy-substituted ($C_{1-6}$ alkoxy) group" means the above $C_{1-6}$ alkoxy group substituted by the above $C_{1-6}$ alkoxy group, such as a methoxymethoxy group or the like; the term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; the term "$C_{2-6}$ alkenylene group" means a straight-chained or branched alkenylene group having 2 to 6 carbon atoms such as a vinylene group, a 1-propenylene group, a 2-propenylene group or the like; the term "$C_{2-6}$ alkenyloxy group" means the above $C_{1-6}$ alkoxy group except for a methoxy group which has an unsaturated bond, such as an allyloxy group or the like; the term "$C_{1-6}$ alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like; the term "carbamoyl($C_{1-6}$ alkyl) group" means the above $C_{1-6}$ alkyl group substituted by a carbamoyl group; the term "mono or di($C_{1-6}$ alkyl)amino group" means an amino group mono-substituted by the above $C_{1-6}$ alkyl group or di-substituted by the same or different $C_{1-6}$ alkyl groups as defined above; the term "mono or di[hydroxy($C_{1-6}$ alkyl)]amino group" means an amino group mono-substituted by the above hydroxy($C_{1-6}$ alkyl) group or di-substituted by the same or different hydroxy($C_{1-6}$ alkyl) groups as defined above; the term "mono or di($C_{1-6}$ alkyl)ureido group" means an ureido group mono-substituted by the above $C_{1-6}$ alkyl group or di-substituted by the same or different $C_{1-6}$ alkyl groups as defined above; the term "mono or di($C_{1-6}$ alkyl)sulfamide group" means a sulfamide group mono-substituted by the above $C_{1-6}$ alkyl group or di-substituted by the same or different $C_{1-6}$ alkyl groups as defined above; the term "$C_{2-7}$ acyl group" means a straight-chained or branched acyl group having 2 to 7 carbon atoms, such as an acetyl group, a propionyl group, a butyryl group, an isobutyryl group, a valeryl group, a pivaloyl group, a hexanoyl group or the like; the term "$C_{2-7}$ acylamino group" means an amino group substituted by the above $C_{2-7}$ acyl group; the term "$C_{1-6}$ alkylsulfonyl group" means a straight-chained or branched alkylsulfonyl group having 1 to 6 carbon atoms, such as a methanesulfonyl group, an ethanesulfonyl group or the like; the term "$C_{1-6}$ alkylsulfonylamino group" means an amino group substituted by the above $C_{1-6}$ alkylsulfonyl group; the term "$C_{1-6}$ alkylsulfonylamino-substituted ($C_{1-6}$ alkyl) group" means the above $C_{1-6}$ alkyl group substituted by the above $C_{1-6}$ alkylsulfonylamino group; the term "$C_{3-7}$ cycloalkyl group" means a cyclopropyl group, a cyclobutyl group, a cyclopentyl group, a cyclohexyl group or a cycloheptyl group; the term "$C_{3-7}$ cycloalkyl-substituted ($C_{1-6}$ alkyl) group" means the above $C_{1-6}$ alkyl group substituted by the above $C_{3-7}$ cycloalkyl group; the term "$C_{3-7}$ cycloalkyl-substituted ($C_{2-6}$ alkoxy) group" means the above $C_{1-6}$ alkoxy group except for a methoxy group substituted by the above $C_{3-7}$ cycloalkyl group; the term "$C_{2-6}$ heterocycloalkyl group" means the above $C_{3-7}$ cycloalkyl group containing the same or different 1 or 2 hetero atoms other than the binding position selected from a nitrogen atom, an oxygen atom and a sulfur atom in the ring, which is derived from morpholine, thiomorpholine, tetrahydrofuran, tetrahydropyran, aziridine, azetidine, pyrrolidine, imidazolidine, oxazoline, piperidine, piperazine, pyrazolidine or the like; the term "halogen atom" means a fluorine atom, a chlorine atom, a bromine atom or an iodine atom; the term "halo($C_{1-6}$ alkyl) group" means the above $C_{1-6}$ alkyl group substituted by the same or different 1 to 5 halogen atoms as defined above, such as a trifluoromethyl group, a pentafluoroethyl group or the like; the term "halo ($C_{1-6}$ alkoxy) group" means the above $C_{1-6}$ alkoxy group substituted by the same or different 1 to 5 halogen atoms as defined above; the term "$C_{2-7}$ alkoxycarbonyl group" means a straight-chained or branched alkoxycarbonyl group having 2 to 7 carbon atoms, such as a methoxycarbonyl group, an ethoxycarbonyl group, a propoxycarbonyl group, an isopropoxycarbonyl group, a butoxycarbonyl group, an isobutyloxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like; the term "aryl group" means mono to tricyclic aromatic hydrocarbon group such as a phenyl group, a naphthyl group, or the like; the term "aryl($C_{1-6}$ alkyl) group" means the above $C_{1-6}$ alkyl group substitute by the above aryl group; the term "aryl($C_{1-6}$ alkoxy) group" means the above $C_{1-6}$ alkoxy group substitute by the above aryl group; the term "aryl($C_{1-6}$ alkylthio) group" means the above $C_{1-6}$ alkylthio group substitute by the above aryl group; the term "aryl($C_{2-7}$ alkoxycarbonyl) group" means the above $C_{2-7}$ alkoxycarbonyl group substitute by the above aryl group, such as a benzyloxycarbonyl group or the like; the term "heteroaryl group" means a 5 or 6-membered heteroaryl group containing the same or different 1 to 4 hetero atoms other than the binding position selected from a nitrogen atom, an oxygen atom and a sulfur atom in the ring, which is derived from thiazole, oxazole, isothiazole, isooxazole, pyridine, pyrimidine, pyrazine, pyridazine, pyrrole, thiophene, imidazole, pyrazole, oxadiazole, thiodiazole, tetrazole, furazan or the like; the term "$C_{2-6}$ cyclic amino group" means a 5 or 6-membered monocyclic amino group having 2 to 6 carbon atoms which may contain one hetero atom other than the nitrogen atom at the binding position selected from a nitrogen atom, an oxygen atom and a sulfur atom in the ring, such as a morpholino group, a thiomorpholino group, a 1-aziridinyl group, a 1-azetidinyl group, a 1-pyrrolidinyl group, a piperidino group, a 1-imidazolidinyl group, a 1-piperazinyl group, a pyrazolidinyl group or the like; the term "$C_{1-4}$ aromatic cyclic amino group" means a 5-membered aromatic monocyclic amino group having 1 to 4 carbon atoms which may contain 1 to 3 nitrogen atoms other than the nitrogen atom at the binding position, such as a 1-imidazolyl group, a 1-pyrrolyl group, a pyrazolyl group, a 1-tetrazolyl group or the like; the term "hydroxy-protective group" means a hydroxy-protective group used in general organic synthesis such as a benzyl group, a methoxymethyl group, an acetyl group, a pivaloyl group, a benzoyl group, a tert-butyldimethylsilyl group, a triisopropylsilyl group, an allyl group or the like; the term "amino-protective group" means an amino-protective group used in general organic synthesis such as a benzyloxycarbonyl group, a tert-butoxycarbonyl group, a benzyl group, a trifluoroacetyl group or the like; and the term "carboxy-protective group" means a carboxy-protective group used in general organic synthesis such as a benzyl group, a tert-butyldimethylsilyl group, an allyl group or the like.

In the present invention, for example, $R^1$ is preferably a hydrogen atom or a hydroxy($C_{2-6}$ alkyl) group, and is more preferably a hydrogen atom; T is preferably a group of the formula:

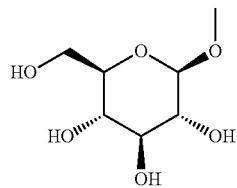

or a group of the formula:

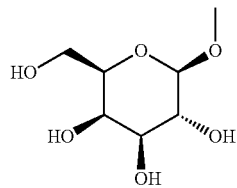

Q is preferably a $C_{1-6}$ alkyl group or a halo($C_{1-6}$ alkyl) group, and is more preferably a $C_{1-6}$ alkyl group; the $C_{1-6}$ alkyl group in Q is preferably an ethyl group or an isopropyl group, and is more preferably an isopropyl group; X is preferably a single bond or an oxygen atom; Y is preferably a $C_{1-6}$ alkylene group or a $C_{2-6}$ alkenylene group, and is more preferably a $C_{1-6}$ alkylene group; the $C_{1-6}$ alkylene group in Y is preferably an ethylene group, a trimethylene group or a tetramethylene group, and is more preferably an ethylene group or a trimethylene group. Z is preferably —$R^B$, —$COR^C$, —$CON(R^D)R^E$ or —$C(=NR^G)N(R^H)R^I$, and is more preferably —$R^B$ or —$CON(R^D)R^E$, and is most preferably —$R^B$; $R^B$ in Z is preferably a $C_{1-6}$ alkyl group which has the same or different 1 to 5 groups selected from the above substituent group (iA), and is more preferably a $C_{1-6}$ alkyl group having a carbamoyl group; $R^D$ in Z is preferably a hydrogen atom; $R^E$ is preferably a $C_{1-6}$ alkyl group which has the same or different 1 to 5 groups selected from the above substituent group (iB); $R^G$ in Z is preferably a hydrogen atom or a $C_{1-6}$ alkylsulfonyl group; $R^H$ is preferably a hydrogen atom; $R^I$ is preferably a hydrogen atom or a $C_{1-6}$ alkyl group which may have the same or different 1 to 5 groups selected from the above substituent group (iC); and $R^C$ in Z is preferably a $C_{1-6}$ alkyl group which has the same or different 1 to 5 groups selected from the above substituent group (iD). $R^4$ is preferably a hydrogen atom; $R^2$ is preferably a hydrogen atom, a halogen atom, a $C_{1-6}$ alkyl group, a $C_{1-6}$ alkoxy group, a $C_{1-6}$ alkoxy-substituted ($C_{1-6}$ alkoxy) group, a $C_{3-7}$ cycloalkyl-substituted ($C_{2-6}$ alkoxy) group or a group of the general formula: —A—$R^A$ in which A and $R^A$ have the same meanings as defined above, and is more preferably a hydrogen atom, a chlorine atom, a fluorine atom or a methyl group; and $R^3$, $R^5$ and $R^6$ are preferably a hydrogen atom or a halogen atom, and all of them are more preferably a hydrogen atom.

As concrete compounds in the present invention, compounds described in Examples 1-187 are exemplified. Specifically, the following compounds or pharmaceutically acceptable salts thereof are preferable.

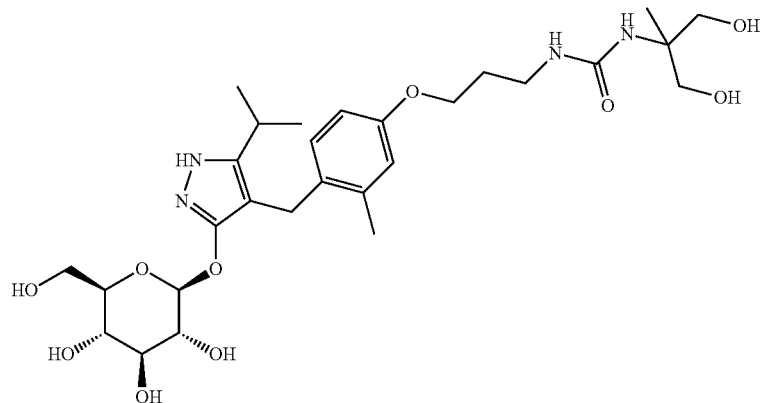
[Example 28]
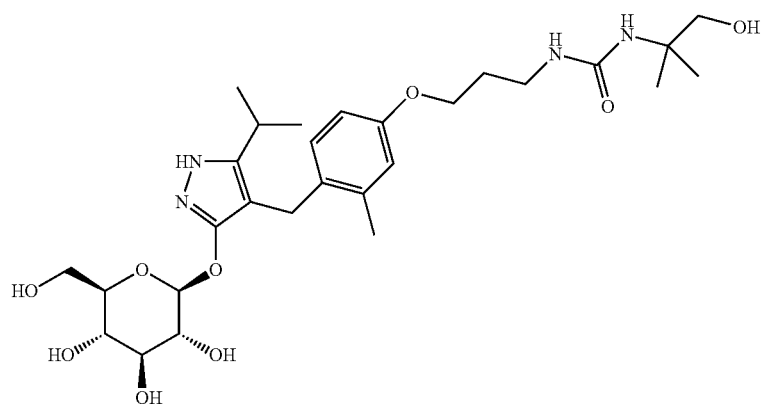
[Example 29]
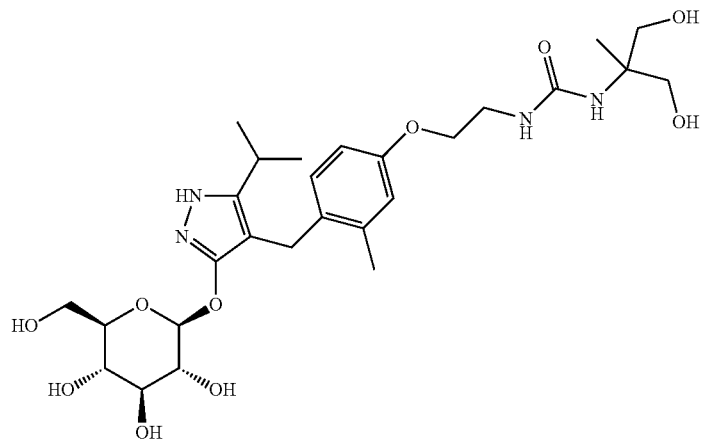
[Example 32]
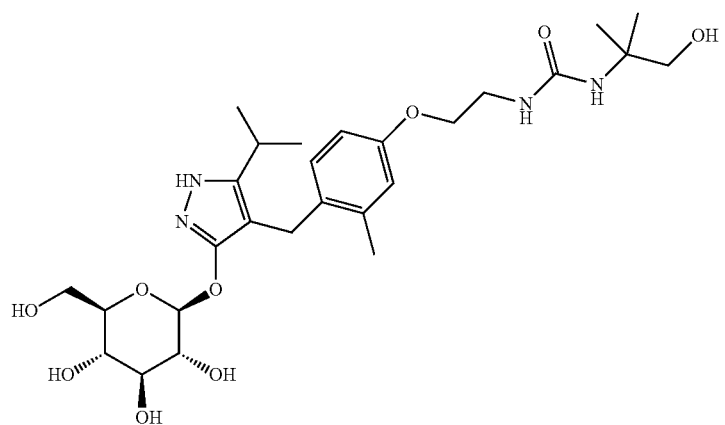
[Example 33]

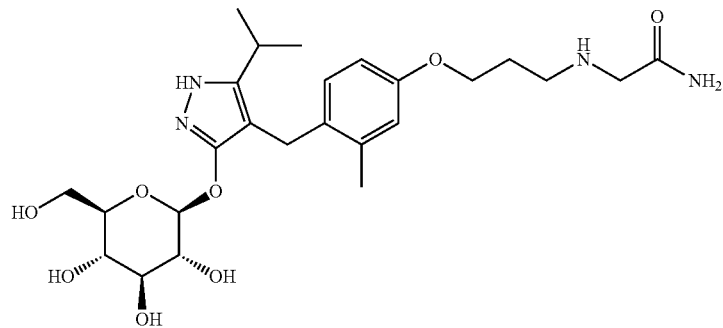
[Example 45]
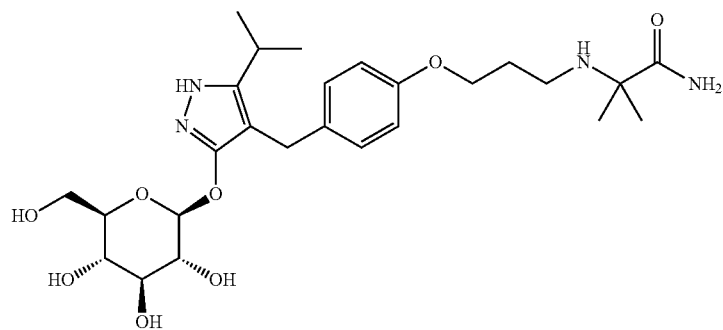
[Example 48]
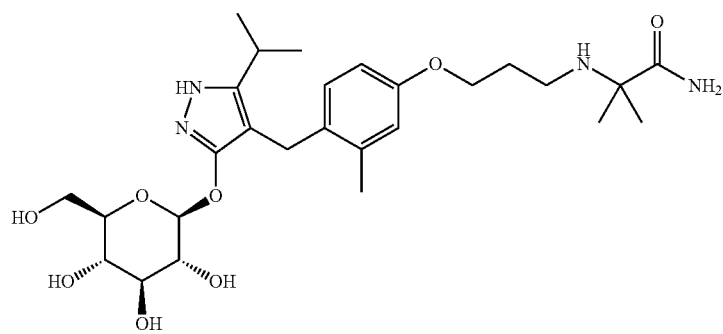
[Example 51]
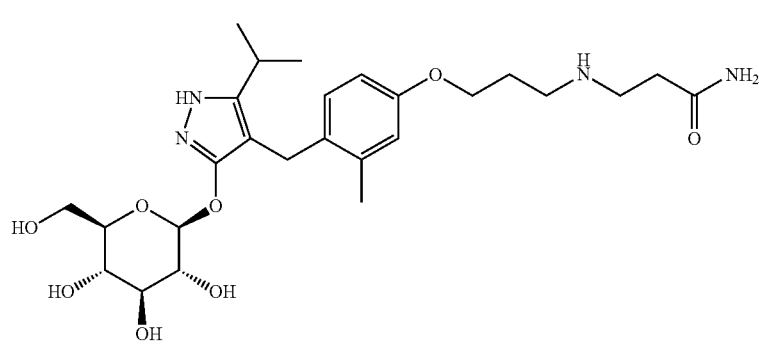
[Example 52/111]

[Example 55]
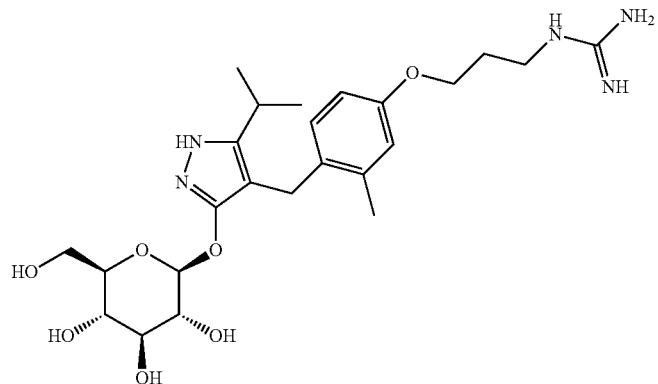
[Example 56]
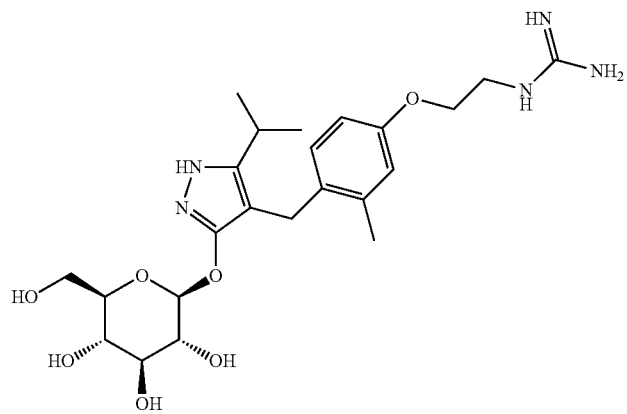
[Example 57]
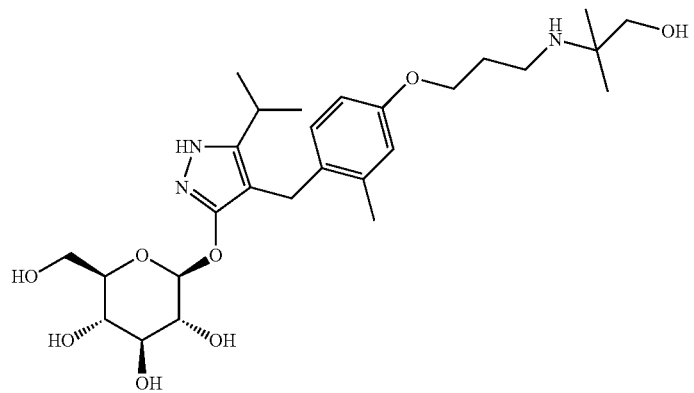
[Example 59]
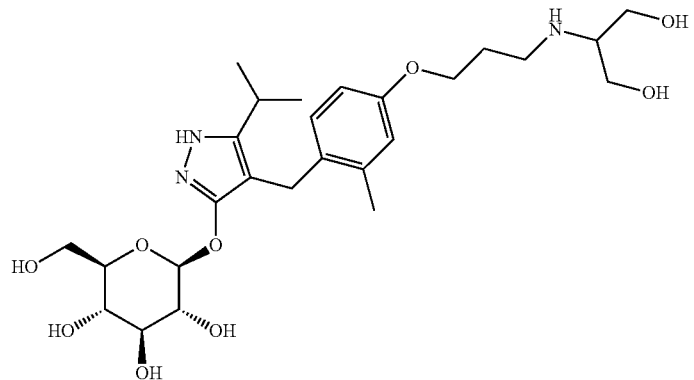

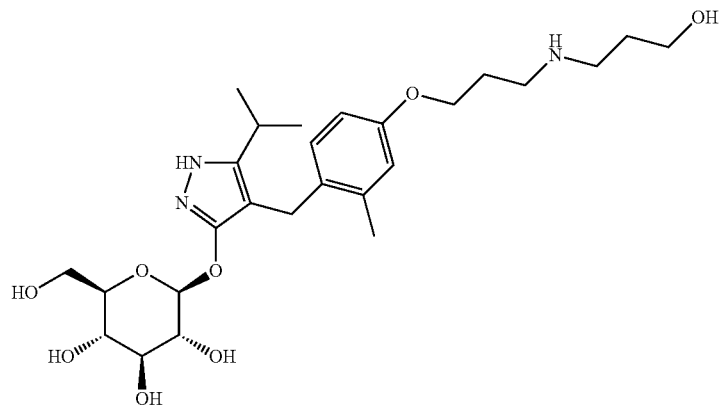
[Example 66]
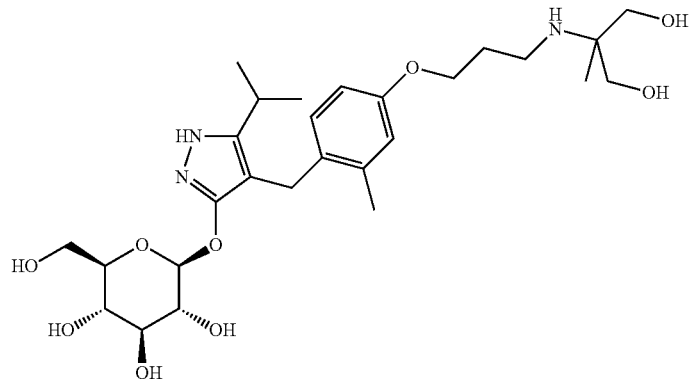
[Example 67]
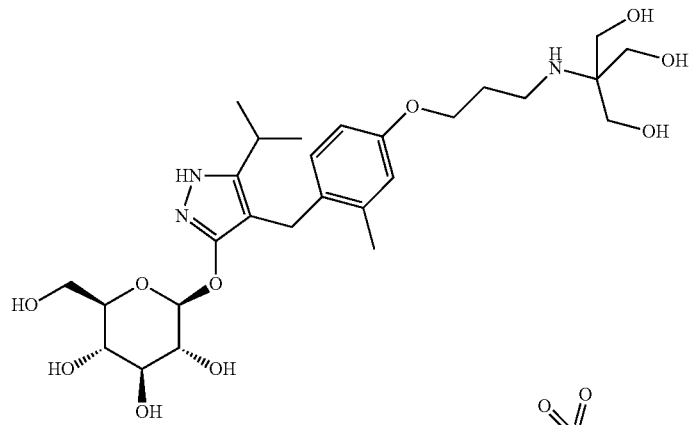
[Example 71]
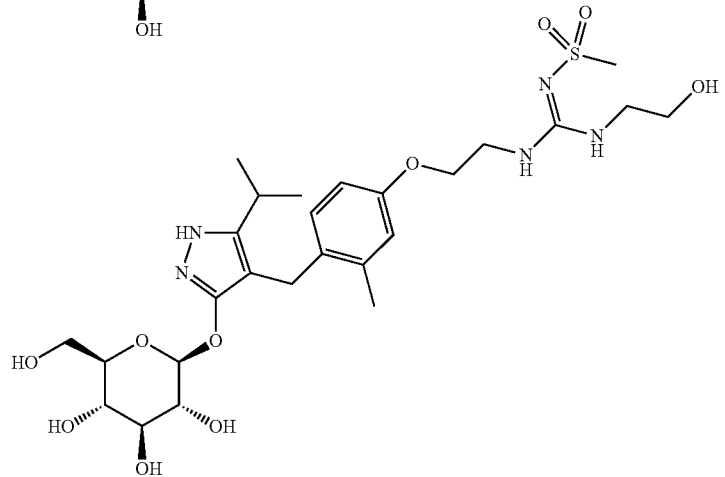
[Example 77]

-continued
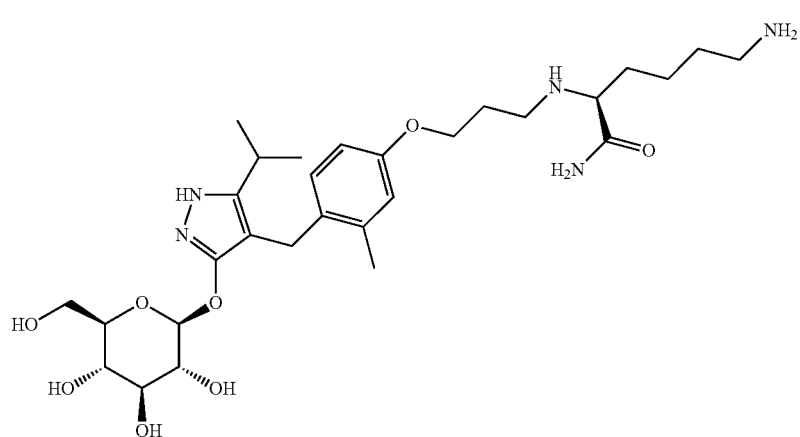
[Example 79]
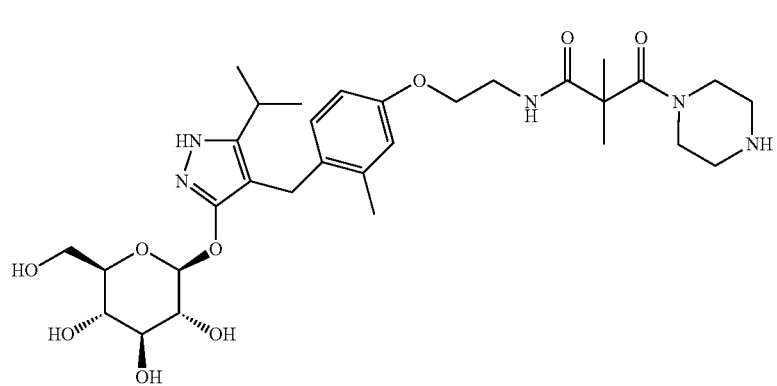
[Example 81]
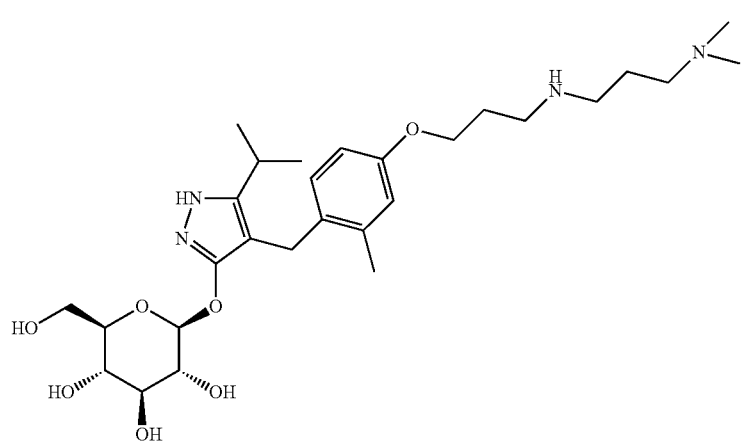
[Example 82]
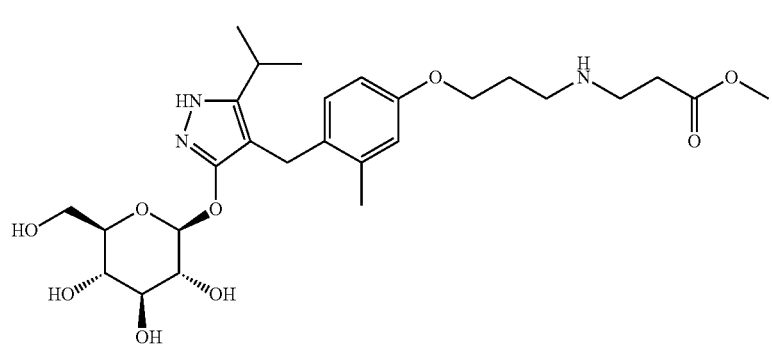
[Example 83]

-continued
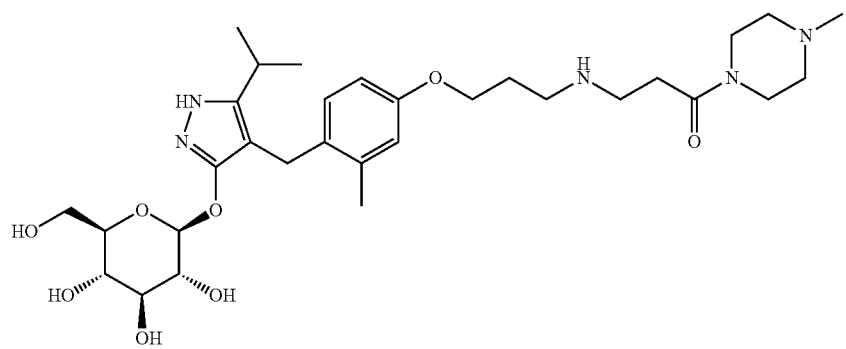
[Example 84]
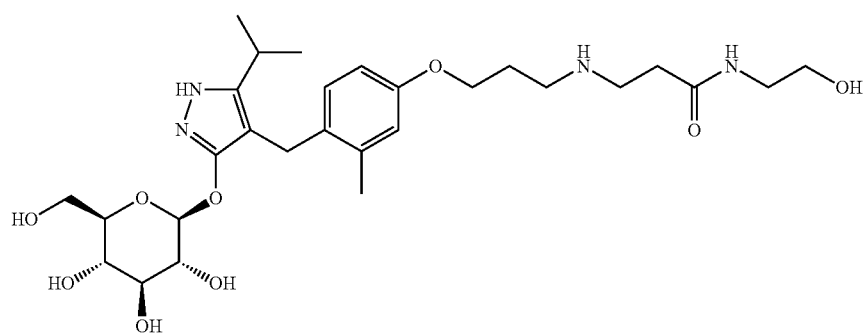
[Example 87]
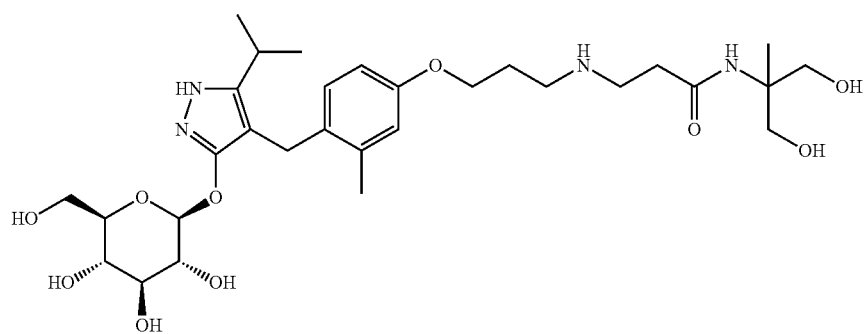
[Example 90]
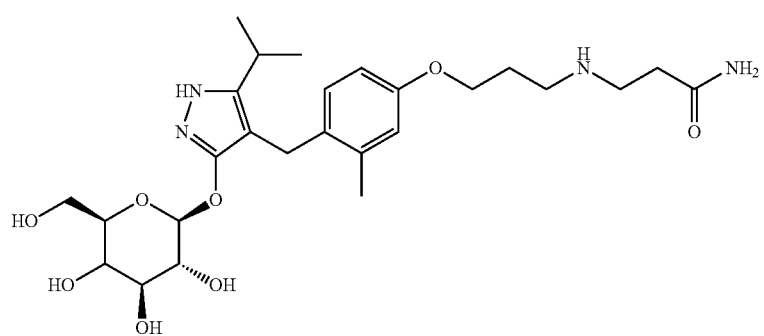
[Example 94]

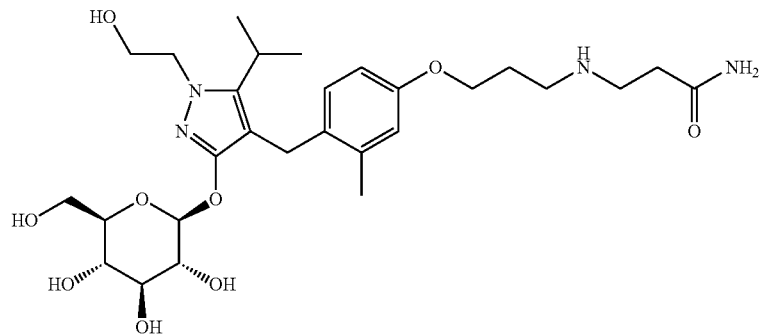
[Example 107]
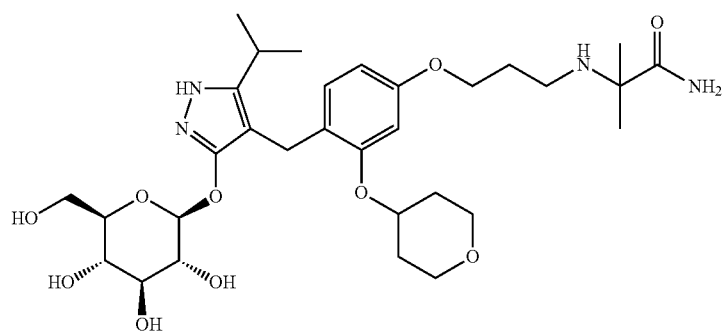
[Example 108]
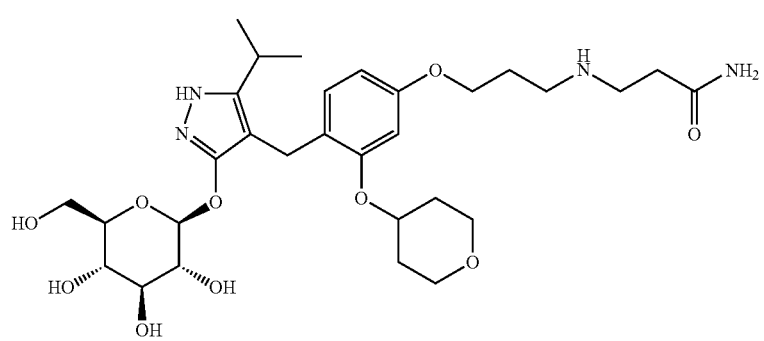
[Example 109]
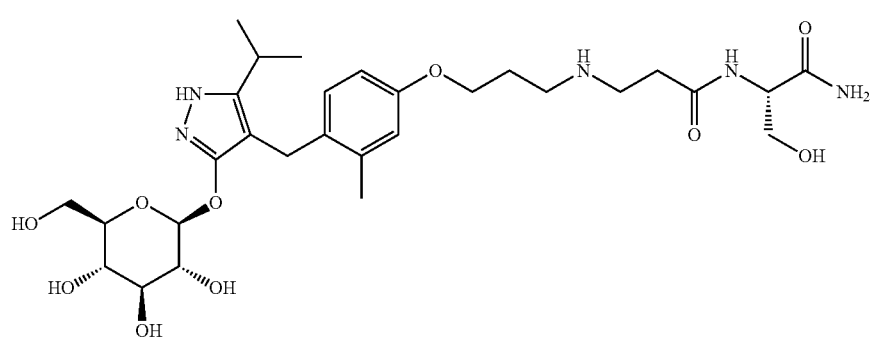
[Example 114]

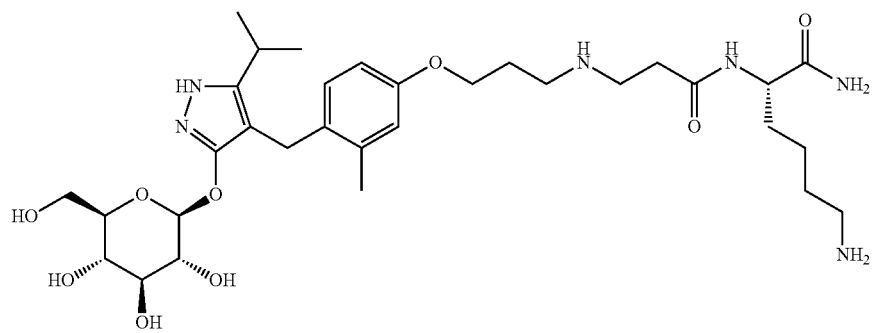
[Example 117]
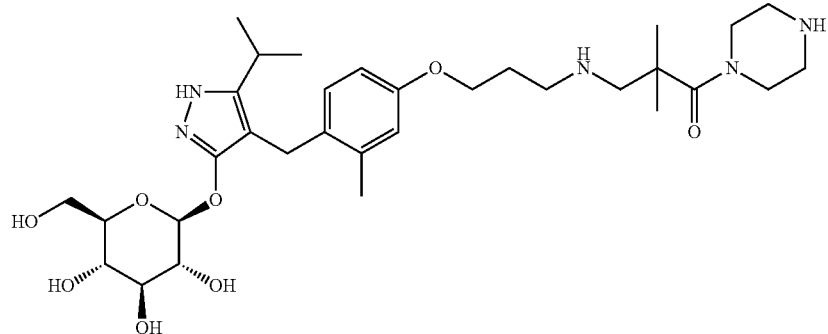
[Example 118]
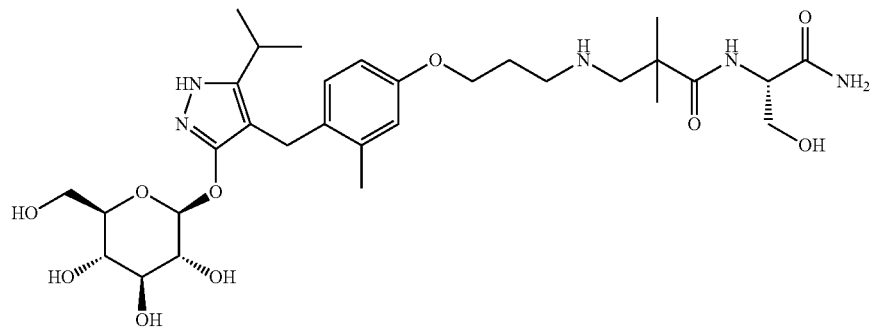
[Example 119]
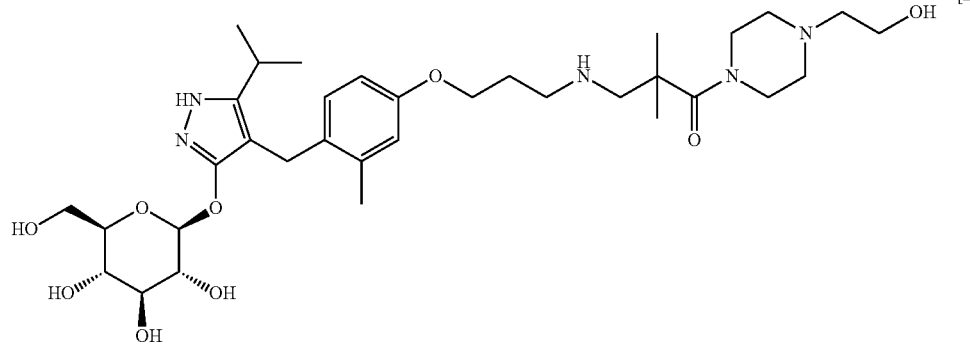
[Example 121]

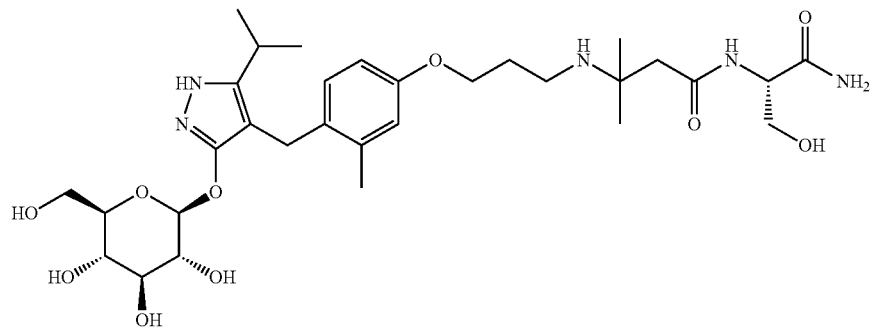
[Example 123]
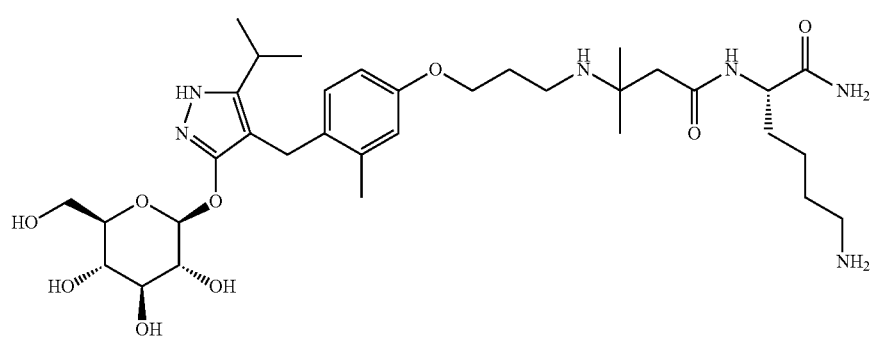
[Example 124]
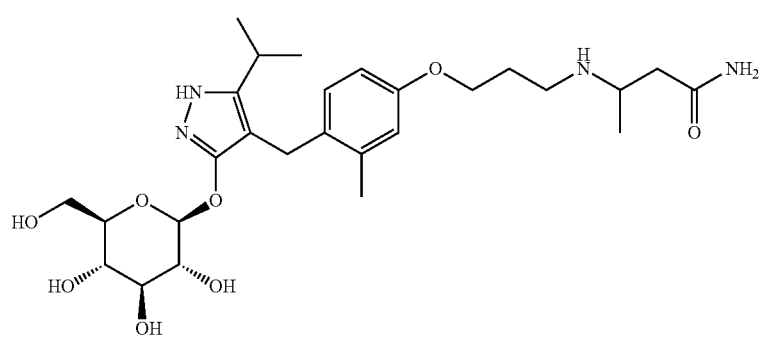
[Example 126]
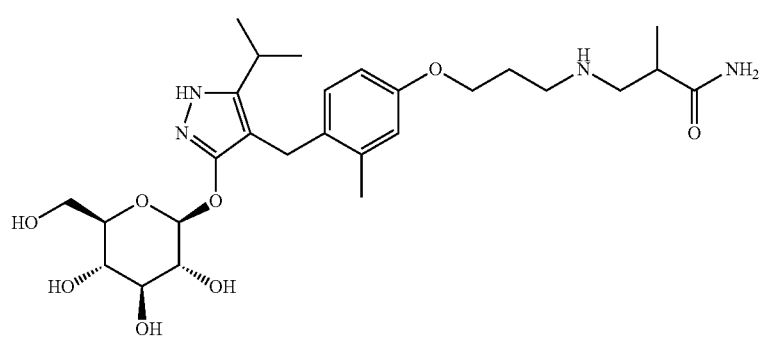
[Example 127]

-continued
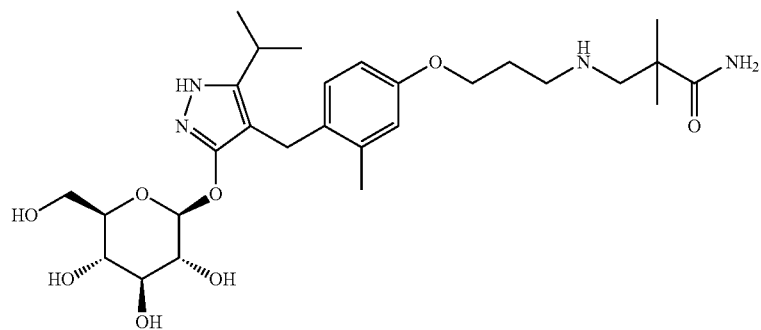
[Example 128]
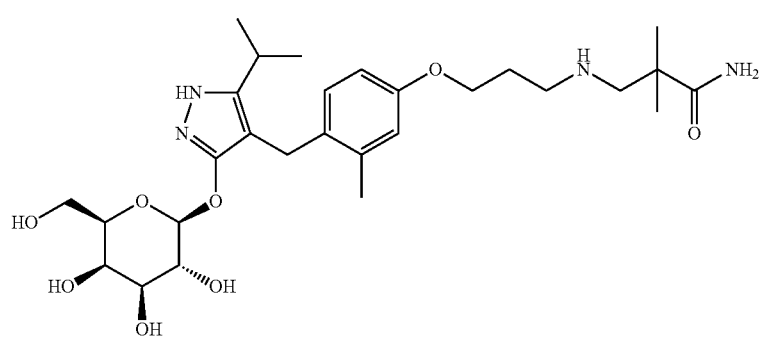
[Example 129]
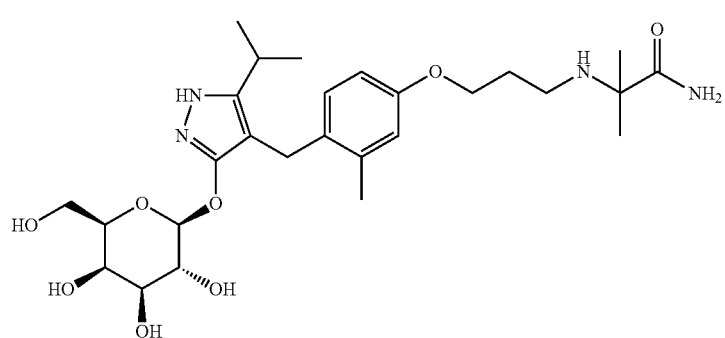
[Example 130]
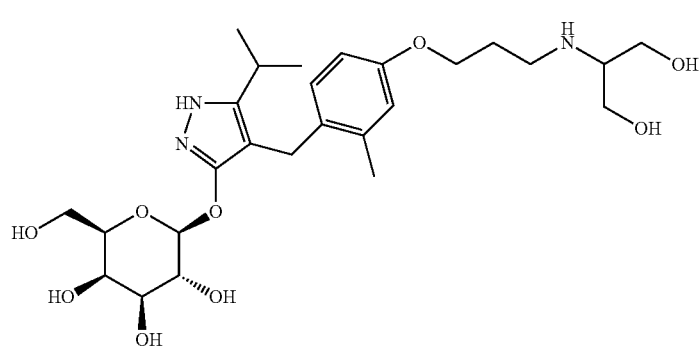
[Example 134]

-continued
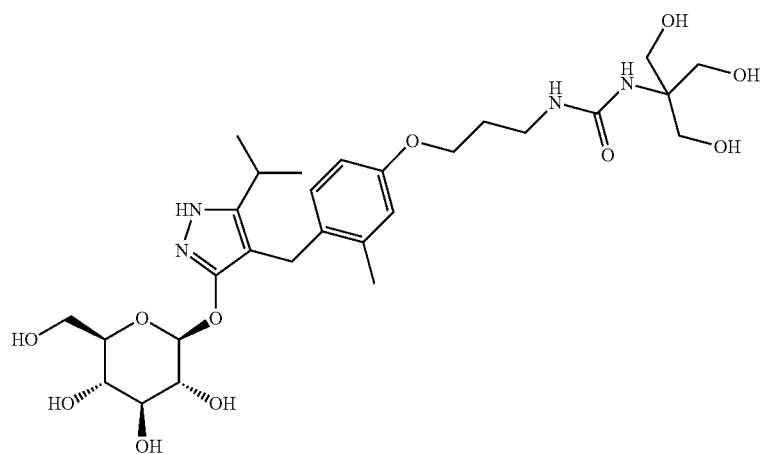
[Example 141]
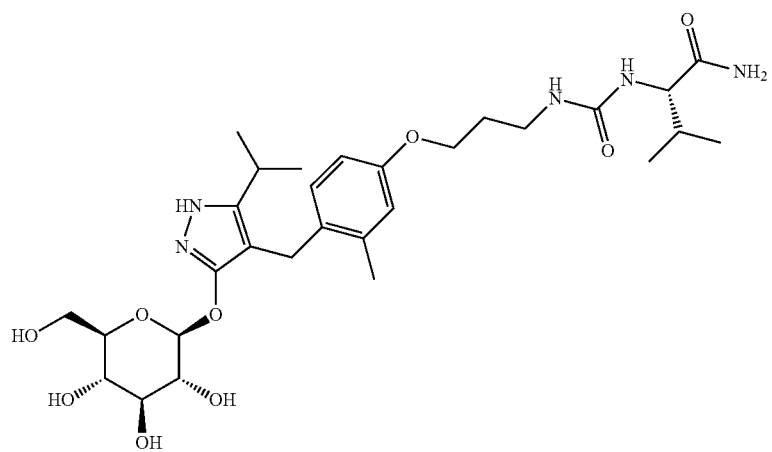
[Example 147]
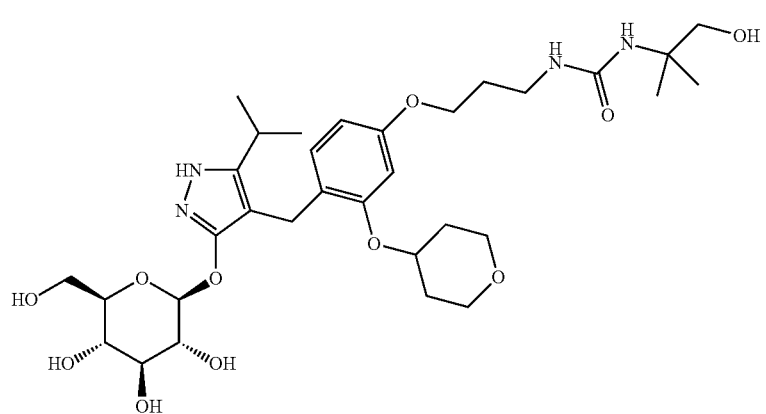
[Example 150]

-continued
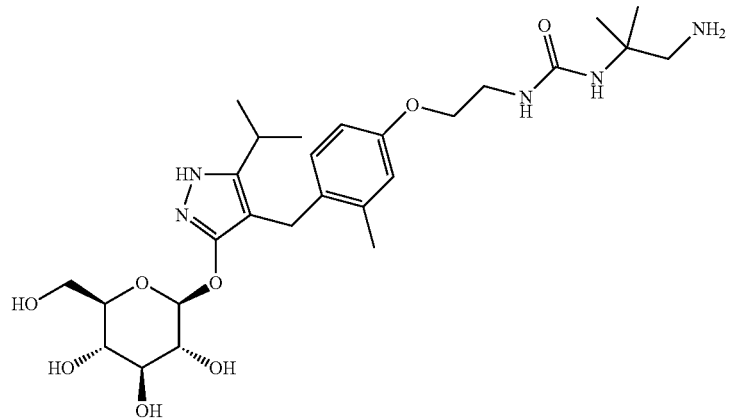
[Example 151]
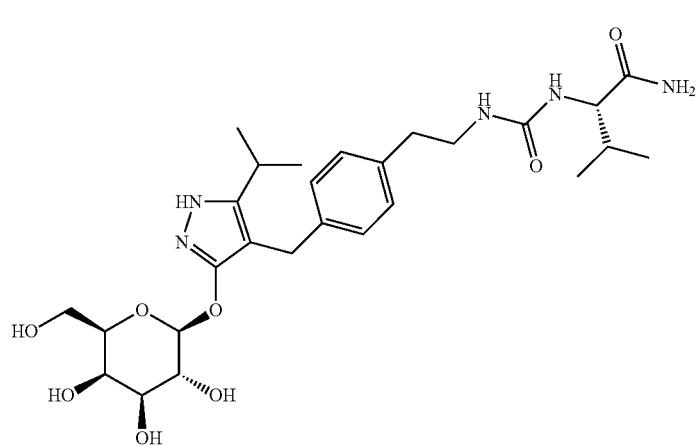
[Example 170]
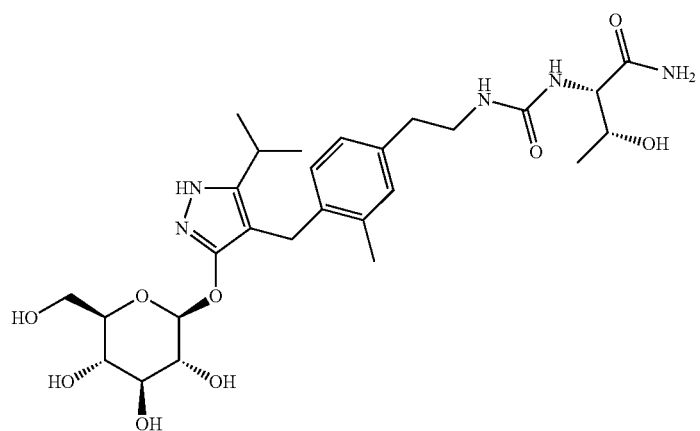
[Example 175]

-continued
[Example 177]
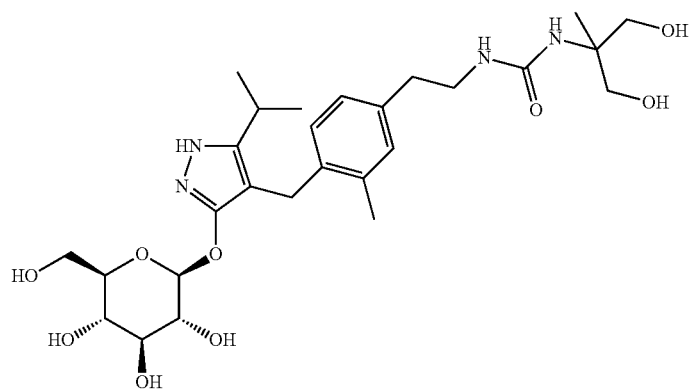
[Example 178]
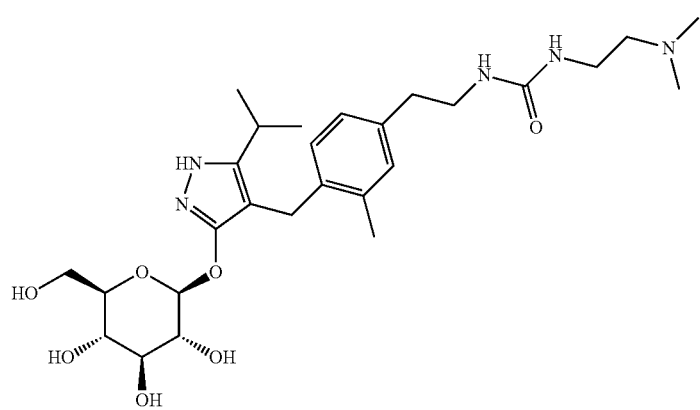
[Example 179]
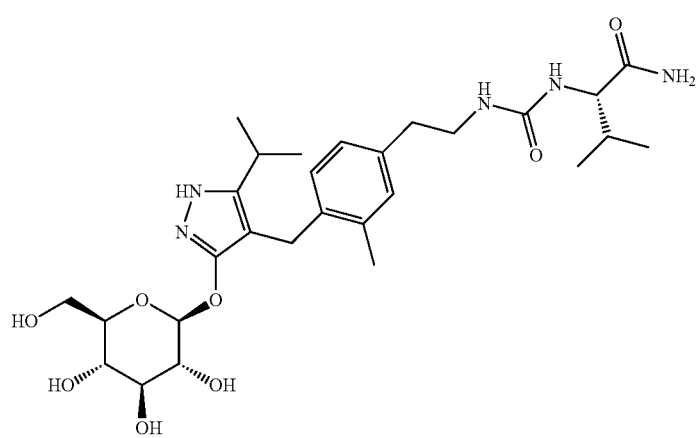
[Example 180]
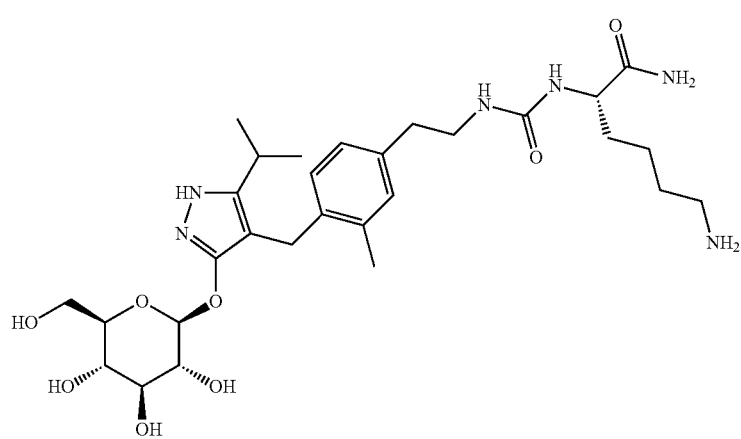

[Example 181]
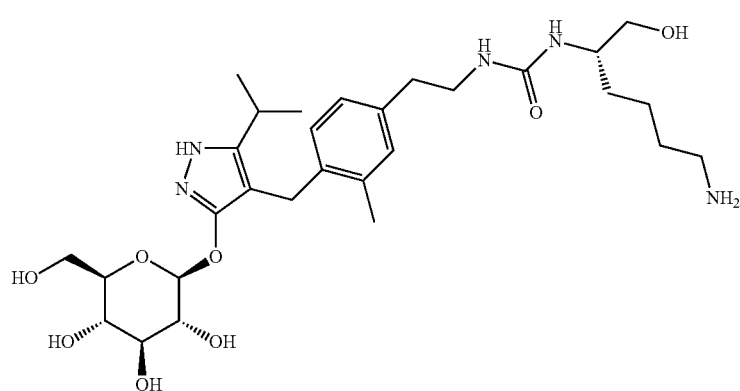
For example, the compounds represented by the above general formula (I) of the present invention can be prepared according to the following procedure:
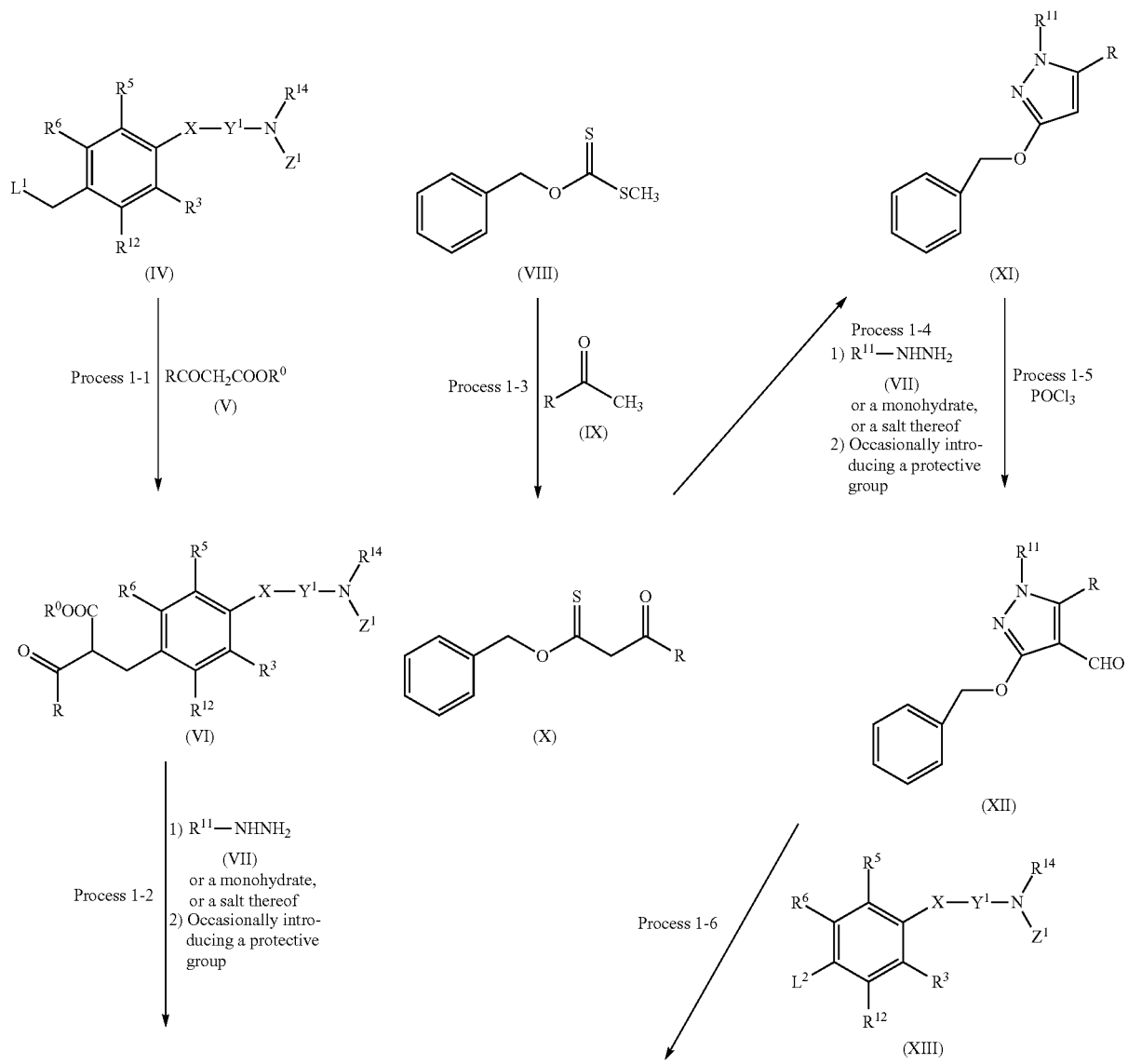

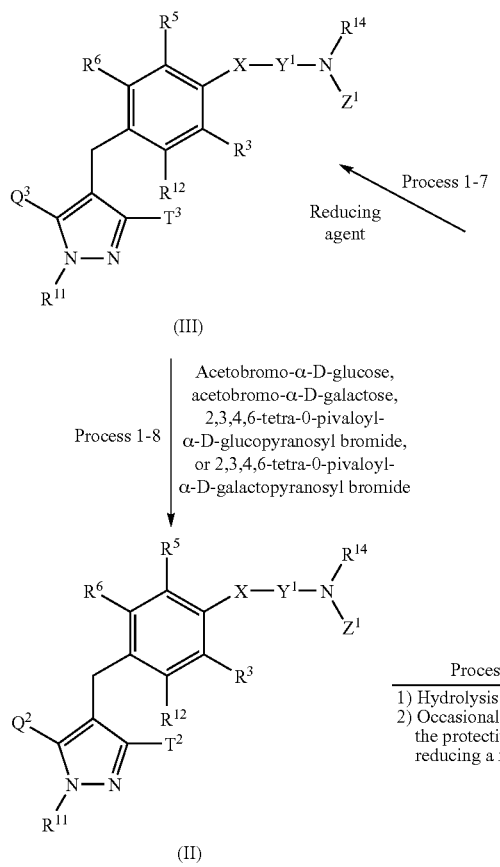

(III)

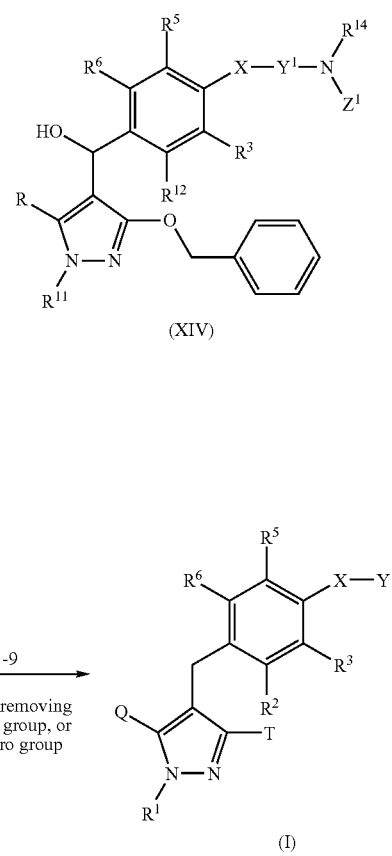

(XIV)

wherein $L^1$ represents a leaving group such as a halogen atom, a mesyloxy group, a tosyloxy group or the like; $L^2$ represents MgBr, MgCl, MgI, ZnI, ZnBr, ZnCl or a lithium atom; R represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; $R^0$ represents a $C_{1-6}$ alkyl group; one of $Q^3$ and $T^3$ represents a hydroxy group, the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group; and $R^1$, $R^2$, $R^3$, $R^4$, $R^5$, $R^6$, $R^{11}$, $R^{12}$ $R^{14}$, Q, $Q^2$, T, $T^2$, X, Y, $Y^1$, Z and $Z^1$ have the same meanings as defined above.

Process 1-1

A compound represented by the above general formula (VI) can be prepared by condensing a benzyl compound represented by the above general formula (IV) with a ketoacetate represented by the above general formula (V) in the presence of a base such as sodium hydride or potassium tert-butoxide in an inert solvent. As the inert solvent used in the reaction, for example, 1,2-dimethoxyethane, tetrahydrofuran, N,N-dimethylformamide, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 1-2

A benzylpyrazole derivative represented by the above general formula (III) can be prepared by condensing a compound represented by the above general formula (VI) with a hydrazine compound represented by the above general formula (VII) or a monohydrate thereof, or a salt thereof in the presence or absence of a base in an inert solvent, and introducing a hydroxy-protective group in the usual way as occasion demands. As the inert solvent used in the condensing reaction, for example, toluene, tetrahydrofuran, chloroform, methanol, ethanol, a mixed solvent thereof and the like can be illustrated, and as the base, for example, triethylamine, N,N-diisopropylethylamine, pyridine, sodium methoxide, sodium ethoxide and the like can be illustrated. The reaction temperature is usually from room temperature to reflux temperature, and the reaction time is usually from 1 hour to 1 day, varying based on a used starting material, solvent and reaction temperature. The obtained benzylpyrazole derivative represented by the above general formula (III) can be also used in the subsequent process after suitably converting into a salt thereof in the usual way.

Process 1-3

A compound represented by the above general formula (X) can be prepared by condensing dithiocarbonate ester compound represented by the above general formula (VIII) with a ketone compound represented by the above general formula (IX) in the presence of a base such as sodium amide in an inert solvent. As the inert solvent used in the reaction, for example, toluene and the like can be illustrated. The reaction temperature is usually from −20° C. to room temperature, and the reaction time is usually from 30 minutes to 1 day, varying based on a used starting material, solvent and reaction temperature.

Process 1-4

A benzyloxypyrazole derivative represented by the above general formula (XI) can be prepared by condensing a compound represented by the above general formula (X) with a hydrazine compound represented by the above general formula (VII) or a monohydrate thereof, or a salt thereof in the presence of a base such as triethylamine or N,N-diisopropylethylamine in an inert solvent, and introducing a hydroxy-protective group in the usual way as occasion demands. As the inert solvent used in the condensing reaction, for example, acetonitrile and the like can be illustrated. The reaction temperature is usually from 0° C. to reflux temperature, and the reaction time is usually from 1 hour to 1 day, varying based on a used starting material, solvent and reaction temperature.

Process 1-5

A pyrazole aldehyde derivative represented by the above general formula (XII) can be prepared by subjecting a compound represented by the above general formula (XI) to Vilsmeier reaction using phosphorus oxychloride and N,N-dimethylformamide in a various solvent. As the solvent used in the reaction, for example, N,N-dimethylformamide and the like can be illustrated. The reaction temperature is usually from 0° C. to reflux temperature, and the reaction time is usually from 30 minutes to 1 day, varying based on a used starting material, solvent and reaction temperature.

Process 1-6

A compound represented by the above general formula (XIV) can be prepared by condensing a compound represented by the above general formula (XII) with a Grignard reagent, a Reformatsky reagent or a lithium reagent represented by the above general formula (XIII) in an inert solvent. As the inert solvent used in the reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process 1-7

A benzylpyrazole derivative represented by the above general formula (III) can be prepared by subjecting a compound represented by the above general formula (XIV) to catalytic hydrogenation using a palladium catalyst such as palladium-carbon powder in the presence or absence of an acid such as hydrochloric acid in an inert solvent, and in case that a compound represented by the above general formula (XIV) has any sulfur atom, subjecting the resulting compound to acid treatment in an aqueous solution of trifluoroacetic acid and dimethyl sulfide usually at 0° C. to reflux temperature for 30 minutes to 1 day as occasion demands. As the solvent used in the catalytic hydrogenation, for example, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. The obtained benzylpyrazole derivative represented by the above general formula (III) can be also used in the subsequent process after suitably converting into a salt thereof in the usual way.

Process 1-8

[1] In case that one of $Q^3$ and $T^3$ is a $C_{1-6}$ alkyl group, a $C_{1-6}$ alkoxy-substituted ($C_{1-6}$ alkyl) group or a $C_{3-7}$ cycloalkyl group in a benzylpyrazole derivative represented by the above general formula (III), a corresponding compound represented by the above general formula (II) of the present invention can be prepared by subjecting a corresponding benzylpyrazole derivative represented by the above general formula (III) to glycosidation using acetobromo-β-D-glucose, acetobromo-α-D-galactose, 2,3,4,6-tetra-O-pivaloyl-α-D-glucopyranosyl bromide or 2,3,4,6-tetra-O-pivaloyl-α-D-galactopyranosyl bromide in the presence of a base such as silver carbonate, sodium hydride or the like in an inert solvent. As the inert solvent used in the reaction, for example, tetrahydrofuran, dimethoxyethane, N,N-dimethylformamide, a mixed solvent thereof and the like can be illustrated. The reaction temperature is usually from room temperature to reflux temperature, and the reaction time is usually from 1 hour to 1 day, varying based on a used starting material, solvent and reaction temperature.

[2] In case that one of $Q^3$ and $T^3$ is a halo($C_{1-6}$ alkyl) group in a benzylpyrazole derivative represented by the above general formula (III), a corresponding compound represented by the above general formula (II) of the present invention can be prepared by subjecting a corresponding benzylpyrazole derivative represented by the above general formula (III) to glycosidation using acetobromo-β-D-glucose, acetobromo-α-D-galactose, 2,3,4,6-tetra-O-pivaloyl-α-D-glucopyranosyl bromide or 2,3,4,6-tetra-O-pivaloyl-α-D-galactopyranosyl bromide in the presence of a base such as potassium carbonate or the like in an inert solvent. As the inert solvent used in the reaction, for example, tetrahydrofuran, acetonitrile, a mixed solvent thereof and the like can be illustrated. The reaction temperature is usually from room temperature to reflux temperature, and the reaction time is usually from 1 hour to 1 day, varying based on a used starting material, solvent and reaction temperature.

[3] In case that one of $Q^3$ and $T^3$ is a $C_{2-6}$ alkyl group, a $C_{1-6}$ alkoxy-substituted ($C_{1-6}$ alkyl) group or a $C_{3-7}$ cycloalkyl group in a benzylpyrazole derivative represented by the above general formula (III), a corresponding compound represented by the above general formula (II) of the present invention can be also prepared by subjecting a corresponding benzylpyrazole derivative represented by the above general formula (III) to glycosidation using acetobromo-α-D-glucose, acetobromo-α-D-galactose, 2,3,4,6-tetra-O-pivaloyl-α-D-glucopyranosyl bromide or 2,3,4,6-tetra-O-pivaloyl-α-D-galactopyranosyl bromide in the presence of a base such as sodium hydroxide, potassium hydroxide, potassium carbonate or the like and a phase transfer catalyst such as benzyltri(n-butyl)ammonium chloride, benzyltri-(n-butyl)ammonium bromide, tetra(n-butyl)ammonium hydrogen sulfate or the like in an inert solvent containing water. As the inert solvent used in the reaction, dichloromethane, toluene, benzotrifluoride, a mixed solvent thereof and the like can be illustrated. The reaction temperature is usually from 0° C. to reflux temperature, and the reaction time is usually from 30 minutes to 1 day, varying based on a used starting material, solvent and reaction temperature.

The obtained glycosidated benzylpyrazole derivative represented by the above general formula (II) can be also used in the subsequent process after suitably converting into a salt thereof and separating in the usual way.

Process 1-9

A pyrazole derivative represented by the above general formula (I) of the present invention can be prepared by subjecting a compound represented by the above general formula (II) to alkaline hydrolysis, and removing a protective group or subjecting a nitro group of the resulting compound to reduction as occasion demands. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. As mentioned above, in case of compounds having a protective group in $R^{11}$, $R^{12}$, $R^{14}$, $Y^1$ and/or $Z^1$ after the hydrolysis, the protective group can be suitably removed in the usual way. Furthermore, after the completion of the above reaction, compounds having a nitro group in $R^2$ represented by the above general formula (I) can be also derived into a corresponding compound having an amino group by catalytic reduction using a platinum catalyst such as platinum oxide in an inert solvent such as ethyl acetate at usually room temperature to reflux temperature for usually 30 minutes to 1 day in the usual way.

Among the compounds represented by the above general formula (III) as starting materials, there can be the following three tautomers in compounds wherein $R^{11}$ is a hydrogen atom, varying based on difference in the reaction conditions, and the compounds represented by the above general formula (III) include all the compounds:

alkoxy group on the ring, for example, can be prepared according to the following procedure:

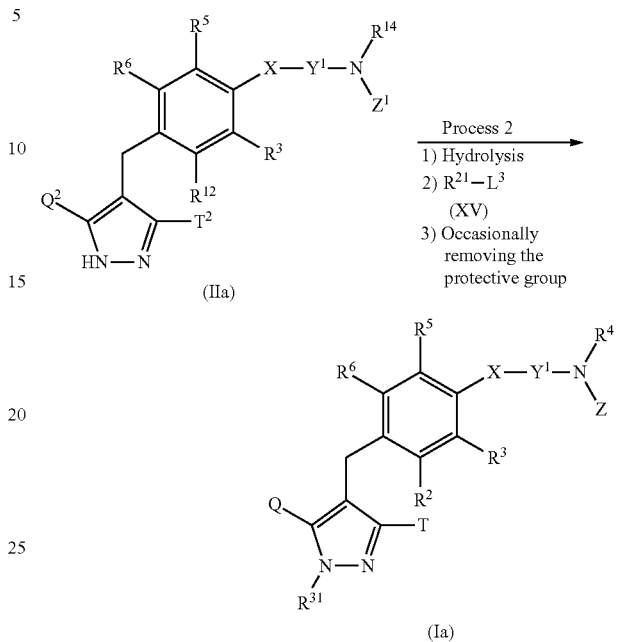

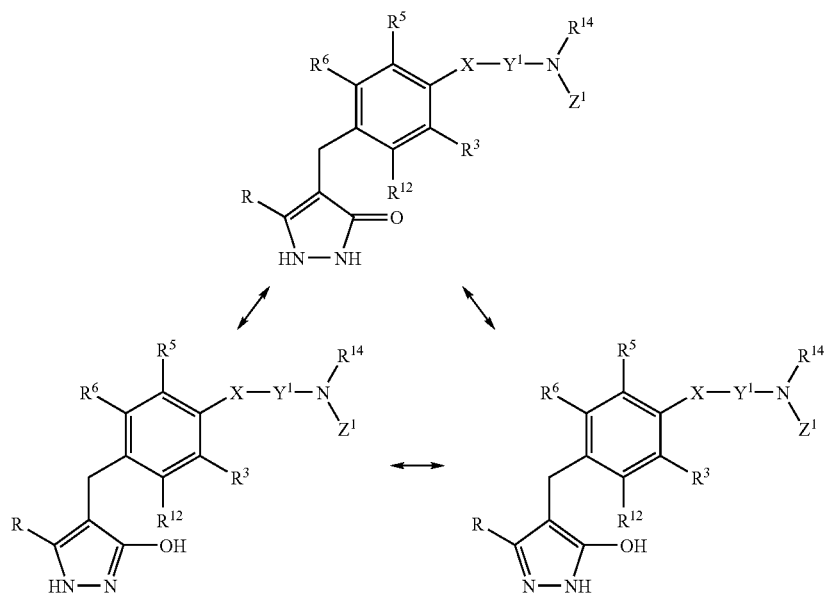

wherein R, $R^3$, $R^5$, $R^6$, $R^{12}$ $R^{14}$, X, $Y^1$ and $Z^1$ have the same meanings as defined above.

Of the compounds represented by the above general formula (I) of the present invention, a compound wherein $R^1$ represents a $C_{1-6}$ alkyl group, a $C_{2-6}$ alkenyl group, a hydroxy ($C_{2-6}$ alkyl) group, a $C_{3-7}$ cycloalkyl group, a $C_{3-7}$ cycloalkyl-substituted ($C_{1-6}$ alkyl) group or an aryl($C_{1-6}$ alkyl) group which may have the same or different 1 to 3 substituents selected from the group consisting of a halogen atom, a hydroxy group, an amino group, a $C_{1-6}$ alkyl group and a $C_{1-6}$ wherein $L^3$ represents a leaving group such as a halogen atom, a mesyloxy group, a tosyloxy group or the like; $R^{21}$ represents a $C_{1-6}$ alkyl group, a $C_{2-6}$ alkenyl group, a hydroxy($C_{2-6}$ alkyl) group which may have a protective group, a $C_{3-7}$ cycloalkyl group, a $C_{3-7}$ cycloalkyl-substituted ($C_{1-6}$ alkyl) group or an aryl($C_{1-6}$ alkyl) group which may have the same or different 1 to 3 substituents selected from the group consisting of a halogen atom, a hydroxy group which may have a protective group, an amino group which may have a protective group, a $C_{1-6}$ alkyl group and a $C_{1-6}$ alkoxy group on the ring; $R^{31}$ represents a $C_{1-6}$ alkyl group, a $C_{2-6}$ alkenyl group, a hydroxy ($C_{2-6}$ alkyl) group, a $C_{3-7}$ cycloalkyl group, a $C_{3-7}$ cycloalkyl-substituted ($C_{1-6}$ alkyl) group or an aryl($C_{1-6}$ alkyl) group which may have the same or different 1 to 3 substituents selected from the group consisting of a halogen atom, a hydroxy group, an amino group, a $C_{1-6}$ alkyl group and a $C_{2-6}$ alkoxy group on the ring; and $R^2$, $R^3$, $R^4$, $R^5$, $R^6$, $R^{12}$, $R^{14}$, Q, $Q^2$, T, $T^2$, X, Y, $Y^1$, Z and $Z^1$ have the same meanings as defined above.

Process 2

A pyrazole derivative represented by the above general formula (Ia) of the present invention can be prepared by subjecting a compound represented by the above general formula (IIa) to hydrolysis according to a similar method to that described in the above process 1-9 and N-alkylation using an alkylating agent represented by the above general formula (XV) in the presence of a base such as cesium carbonate or potassium carbonate in an inert solvent, and in case of compounds having a protective group, suitably removing the protective group in the usual way as occasion demands. As the inert solvent used in the N-alkylation, for example, acetonitrile, ethanol, 1,2-dimethoxyethane, tetrahydrofuran, N,N-dimethylformamide, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature.

Of the compounds represented by the above general formula (I) of the present invention, a compound wherein $R^1$, $R^4$ and Z represent a hydrogen atom, for example, can be also prepared according to the following procedure:

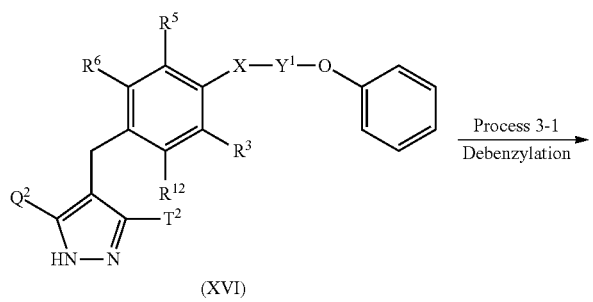

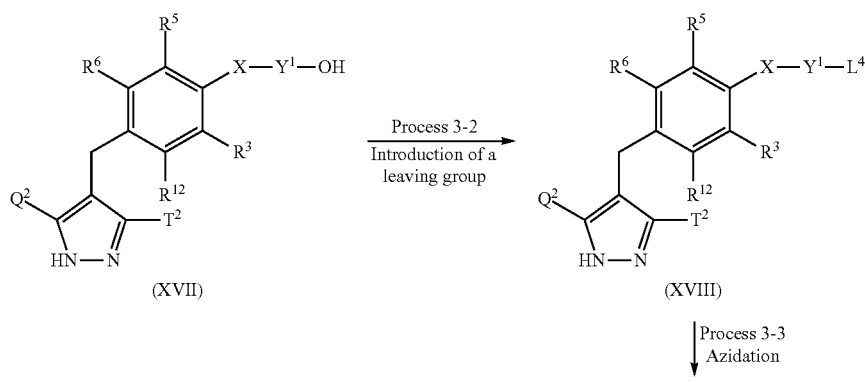

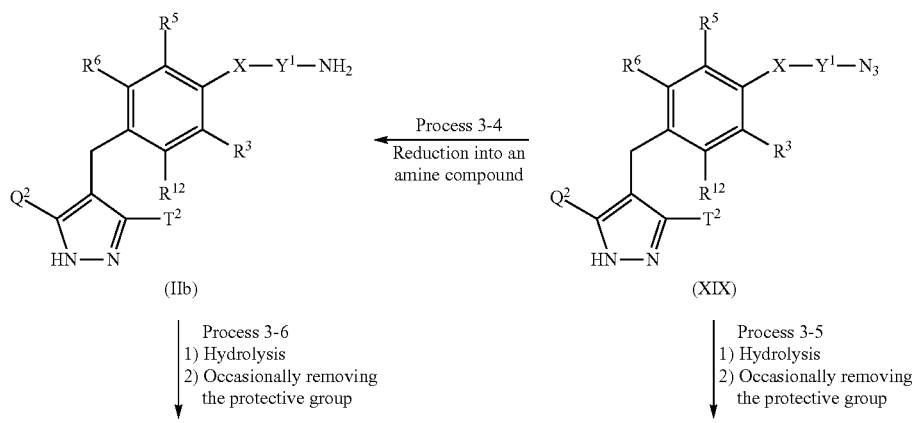

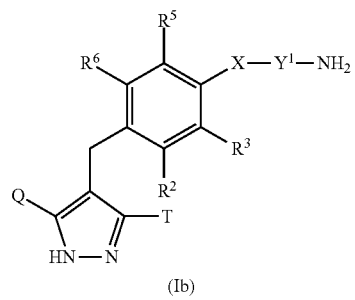

(Ib)

Process 3-7
Reduction into an
amine compound

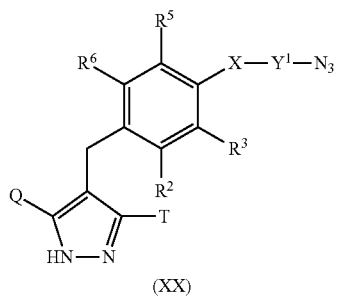

(XX)

wherein $L^4$ represents a leaving group such as a mesyloxy group, a tosyloxy group or the like; and $R^2$, $R^3$, $R^5R^6$, $R^{12}$, Q, $Q^2$, T, $T^2$, X, Y and $Y^1$ have the same meanings as defined above.

Process 3-1

A compound represented by the above general formula (XVII) can be prepared by subjecting a compound represented by the above general formula (XVI) to catalytic hydrogenation using a palladium catalyst such as palladium-carbon powder in an inert solvent to remove the benzyl group. As the solvent used in the catalytic hydrogenation, for example, methanol, ethanol, tetrahydrofuran, ethyl acetate, acetic acid, a mixed solvent thereof and the like can be illustrated. The reaction temperature is usually from 0° C. to reflux temperature, and the reaction time is usually from 1 hour to 2 days, varying based on a used starting material, solvent and reaction temperature.

Process 3-2

A compound represented by the above general formula (XVIII) can be prepared by introducing a leaving group into a compound represented by the above general formula (XVII) using an acid chloride such as mesyl chloride or tosyl chloride in the presence of a base such as triethylamine or N,N-diisopropylethylamine in an inert solvent. As the solvent used in the introducing reaction, for example, dichloromethane, ethyl acetate, tetrahydrofuran, pyridine, a mixed solvent thereof and the like can be illustrated. The reaction temperature is usually from 0° C. to room temperature, and the reaction time is usually from 30 minutes to 1 day, varying based on a used starting material, solvent and reaction temperature.

Process 3-3

A compound represented by the above general formula (XIX) can be prepared by subjecting a compound represented by the above general formula (XVIII) to azidation using an azidating agent such as sodium azide in an inert solvent. As the solvent used in the azidation, for example, dichloromethane, ethyl acetate, N,N-dimethylformamide, dimethyl sulfoxide, N-methylpyrrolidone, N,N-dimethylimidazolidinone, a mixed solvent thereof and the like can be illustrated. The reaction temperature is usually from room temperature to reflux temperature, and the reaction time is usually from 30 minutes to 1 day, varying based on a used starting material, solvent and reaction temperature.

Process 3-4

A compound represented by the above general formula (IIb) of the present invention can be prepared by subjecting a compound represented by the above general formula (XIX) to catalytic hydrogenation using a palladium catalyst such as palladium-carbon powder in an inert solvent. As the solvent used in the catalytic hydrogenation, for example, tetrahydrofuran, methanol, ethanol, ethyl acetate, a mixed solvent thereof and the like can be illustrated. The reaction temperature is usually from room temperature to reflux temperature, and the reaction time is usually from 30 minutes to 1 day, varying based on a used starting material, solvent and reaction temperature.

Process 3-5

A compound represented by the above general formula (XX) can be prepared by subjecting a compound represented by the above general formula (XIX) to alkaline hydrolysis, and removing the protective group in the usual way as occasion demands. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}$ and/or $Y^1$ after the hydrolysis, the protective group can be suitably removed in the usual way as the process 1-9.

Process 3-6

A pyrazole derivative represented by the above general formula (Ib) of the present invention can be prepared by subjecting a compound represented by the above general formula (IIb) to alkaline hydrolysis, and removing the protective group in the usual way as occasion demands. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}$ and/or $Y^1$ after the hydrolysis, the protective group can be suitably removed in the usual way as the process 1-9.

Process 3-7

A pyrazole derivative represented by the above general formula (Ib) of the present invention can be prepared by subjecting a compound represented by the above general formula (XX) to catalytic hydrogenation using a palladium catalyst such as palladium-carbon powder in an inert solvent. As the solvent used in the catalytic hydrogenation, for example, tetrahydrofuran, methanol, ethanol, ethyl acetate, a mixed solvent thereof and the like can be illustrated. The reaction temperature is usually from room temperature to reflux temperature, and the reaction time is usually from 30 minutes to 1 day, varying based on a used starting material, solvent and reaction temperature.

Of the compounds represented by the above general formula (I) of the present invention, a compound wherein $R^1$ and $R^4$ represent a hydrogen atom; and Z represents —$COR^C$, —$SO_2R^C$, —$CON(R^D)R^E$ or —$C(=NR^{2G})NHR^{2H}$, for example, can be prepared according to the following procedures:
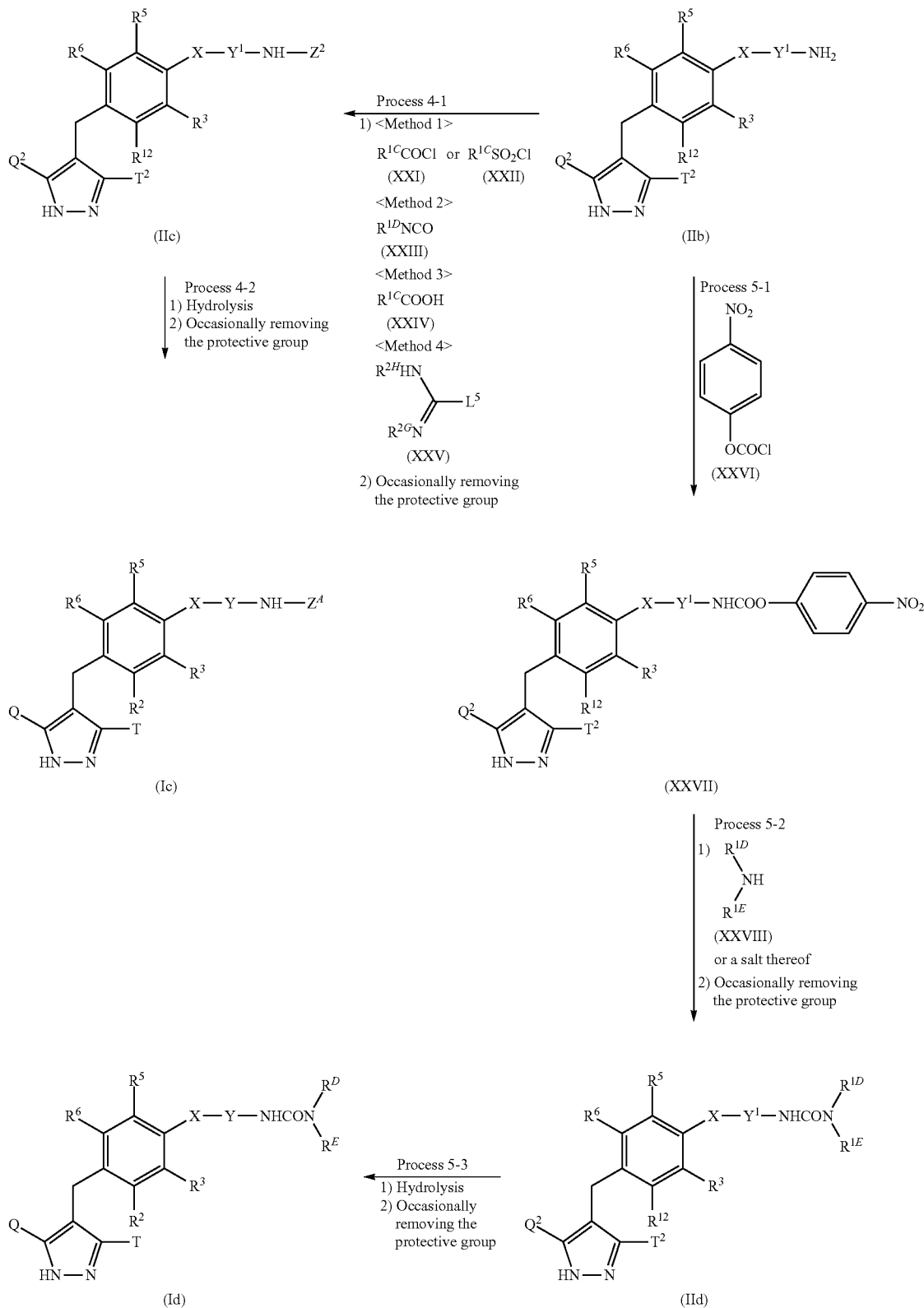

wherein $L^5$ represents a leaving group such as a pyrazolyl group, a methylthio group, a benzotriazolyl group or the like; $R^{2G}$ and $R^{2H}$ are the same or different, and each represents a hydrogen atom, a benzyloxycarbonyl group or a tert-butoxycarbonyl group; $Z^2$ represents $-COR^{1C}$, $SO_2R^{1C}$, $-CONHR^{1D}$ or $-C(=NR^{2G})NHR^{2H}$; $Z^A$ represents $-COR^C$, $-SO_2R^C$, $-CONHR^D$ or $-C(=NR^{2G})NHR^{2H}$; and $R^{1C}$, $R^{1D}$, $R^{1E}$, $R^2$, $R^3$, $R^5$, $R^6$, $R^{12}$, $R^D$, $R^E$, Q, $Q^2$, T, $T^2$, X, Y and $Y^1$ have the same meanings as defined above.

Process 4-1

A compound represented by the above general formula (IIc) can be prepared from a compound represented by the above general formula (IIb) by treating according to the following methods 1-4, and removing the protective group in the usual way as occasion demands.

<Method 1>

A compound represented by the above general formula (IIb) is allowed to react with an acid chloride represented by the above general formula (XXI) or (XXII) in the presence of a base such as triethylamine, N,N-diisopropylethylamine, pyridine or 1,8-diazabicyclo[5.4.0]unde-7-cene in an inert solvent such as dichloromethane, ethyl acetate, tetrahydrofuran, pyridine, acetonitrile or a mixed solvent thereof at usually 0° C. to reflux temperature for usually 30 minutes to 1 day.

<Method 2>

A compound represented by the above general formula (IIb) is allowed to react with an isocyanate compound represented by the above general formula (XXIII) in the presence or absence of a base such as triethylamine, N,N-diisopropylethylamine, pyridine or 1,8-diazabicyclo[5.4.0]unde-7-cene in an inert solvent such as dichloromethane, ethyl acetate, tetrahydrofuran, pyridine, acetonitrile, toluene or a mixed solvent thereof at usually 0° C. to reflux temperature for usually 30 minutes to 1 day.

<Method 3>

A compound represented by the above general formula (IIb) is allowed to react with a carboxylic acid compound represented by the above general formula (XXIV) after suitably adding 1-hydroxybenzotriazole as occasion demands in the presence of a condensing agent such as 1-ethyl-3-(3-dimethylaminopropyl)carbodiimide hydrochloride or dicyclohexylcarbodiimide and in the presence or absence of a base such as triethylamine or N,N-diisopropylethylamine in an inert solvent such as N,N-dimethylformamide, dichloromethane or a mixed solvent thereof at usually 0° C. to reflux temperature for usually 1 hour to 2 days.

<Method 4>

A compound represented by the above general formula (IIb) is allowed to react with a guanidylating reagent represented by the above general formula (XXV) such as N-(benzyloxycarbonyl)-1H-pyrazol-1-carboxamidine in an inert solvent such as tetrahydrofuran, methanol, ethanol, toluene, N,N-dimethylformamide or a mixed solvent thereof at usually room temperature to reflux temperature for usually 1 hour to 5 days.

Process 4-2

A pyrazole derivative represented by the above general formula (Ic) of the present invention can be prepared by subjecting a compound represented by the above general formula (IIc) to alkaline hydrolysis, and removing the protective group in the usual way as occasion demands. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}$, $Y^1$ and/or $Z^2$ after the hydrolysis, the protective group can be suitably removed 16 in the usual way as the process 1-9.

Process 5-1

An activated ester compound represented by the above general formula (XXVII) can be prepared by condensing a compound represented by the above general formula (IIb) with an agent for making an activated ester represented by the above formula (XXVI) in the presence of a base such as triethylamine, N,N-diisopropylethylamine, pyridine or 1,8-diazabicyclo-[5.4.0]unde-7-cene in an inert solvent. As the solvent used in the condensing reaction, for example, dichloromethane, tetrahydrofuran, ethyl acetate, acetonitrile, pyridine, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 5-2

An pyrazole derivative represented by the above general formula (IId) of the present invention can be prepared by condensing a compound represented by the above general formula (XXVII) with an amine compound represented by the above general formula (XXVIII) or a salt thereof in the presence or absence of a base such as triethylamine, N,N-diisopropylethylamine, pyridine, 1,8-diazabicyclo[5.4.0] unde-7-cene, sodium hydride, potassium tert-butoxide, potassium carbonate or cesium carbonate in an inert solvent, and removing the protective group in the usual way as occasion demands. As the solvent used in the condensing reaction, for example, dichloromethane, methanol, ethanol, tetrahydrofuran, ethyl acetate, acetonitrile, pyridine, N,N-dimethylformamide, a mixed solvent thereof and the like can be illustrated. The reaction temperature is usually from room temperature to reflux temperature, and the reaction time is usually from 30 minutes to 2 days, varying based on a used starting material, solvent and reaction temperature.

Process 5-3

A pyrazole derivative represented by the above general formula (Id) of the present invention can be prepared by subjecting a compound represented by the above general formula (IId) to alkaline hydrolysis, and removing the protective group in the usual way as occasion demands. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}$, $R^{1D}$, $R^{1E}$ and/or $Y^1$ after the hydrolysis, the protective group can be suitably removed in the usual way as the process 1-9.

Of the compounds represented by the above general formula (I) of the present invention, a compound wherein $R^1$ represents a hydrogen atom; and Z represents $R^B$, for example, can be also prepared according to the following procedures:

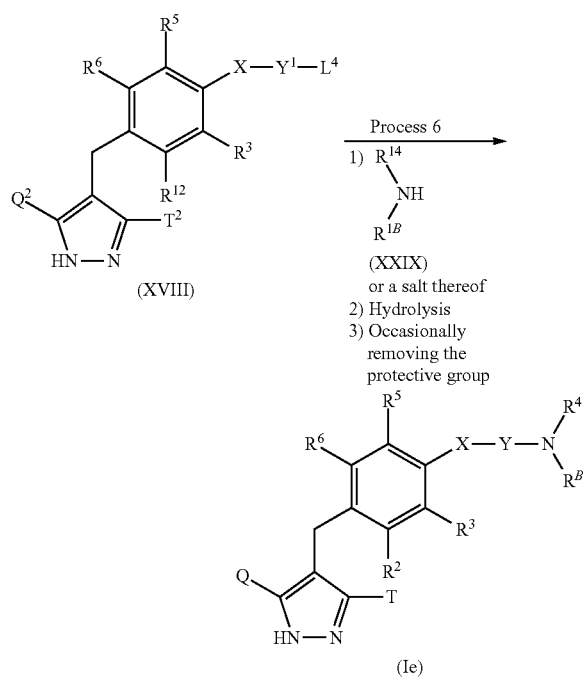

wherein $R^{14}, R^{1B}, R^2, R^3, R^4, R^5, R^6, R^{12}, R^B, L^4, Q, Q^2, T, T^2, X, Y$ and $Y^1$ have the same meanings as defined above.

Process 6

A pyrazole derivative represented by the above general formula (Ie) of the present invention can be prepared by condensing a compound represented by the above general formula (XVIII) with an amine compound represented by the above general formula (XXIX) or a salt thereof in the presence or absence of a base such as triethylamine, N,N-diisopropylethylamine, pyridine, 1,8-diazabicyclo[5.4.0]unde-7- cene, sodium hydride, potassium tert-butoxide, potassium carbonate or cesium carbonate in an inert solvent after adding sodium iodide as occasion demands, subjecting the resulting compound to alkaline hydrolysis, and removing the protective group in the usual way as occasion demands. As the solvent used in the condensing reaction, for example, acetonitrile, N,N-dimethylformamide, dimethyl sulfoxide, N-methylpyrrolidone, methanol, ethanol, 2-propanol, tetrahydrofuran, a mixed solvent thereof and the like can be illustrated. The reaction temperature is usually from room temperature to reflux temperature, and the reaction time is usually from 1 hour to 5 days, varying based on a used starting material, solvent and reaction temperature. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}, R^{14}, R^{1B}$ and/or $Y^1$ after the hydrolysis, the protective group can be suitably removed in the usual way as the process 1-9.

Of the compounds represented by the above general formula (I) of the present invention, a compound wherein $R^1$ represents a hydrogen atom; $R^4$ represent a $C_{1-6}$ alkyl group which may have the same or different 1 to 5 groups selected from the above substituent group (i); and Z represents a hydrogen atom, a $C_{1-6}$ alkyl group which may have the same or different 1 to 5 groups selected from the above substituent group (i), $-COR^C, -SO_2R^C, -CONHR^D$ or $-C(=NR^{2G})NHR^{2H}$, for example, can be also prepared according to the following procedures:

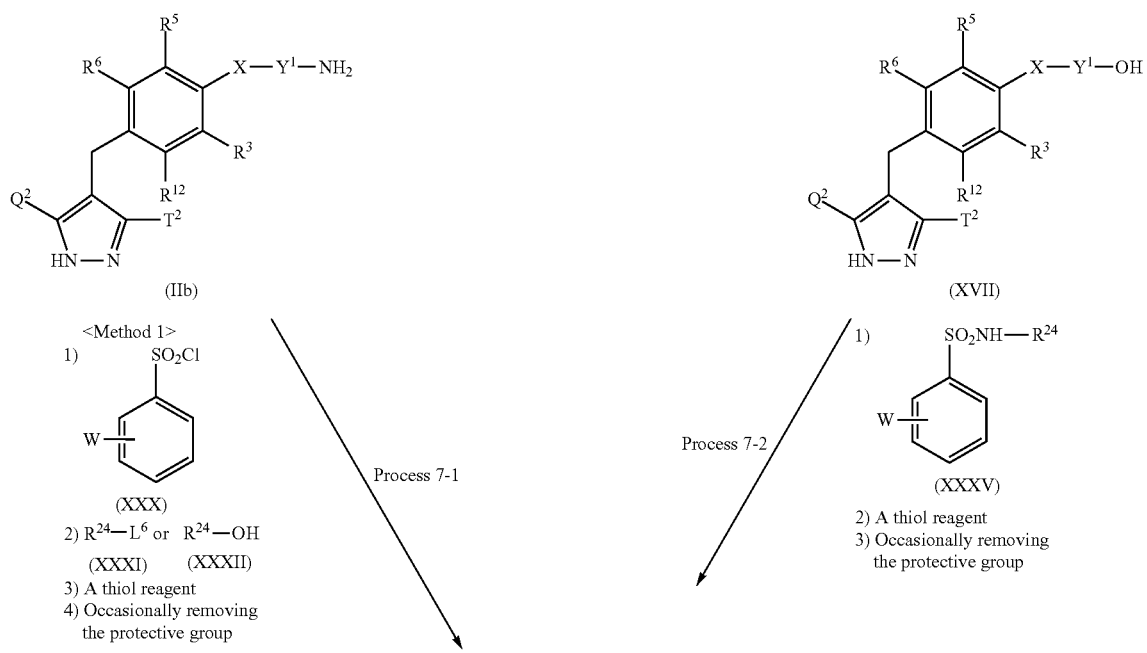

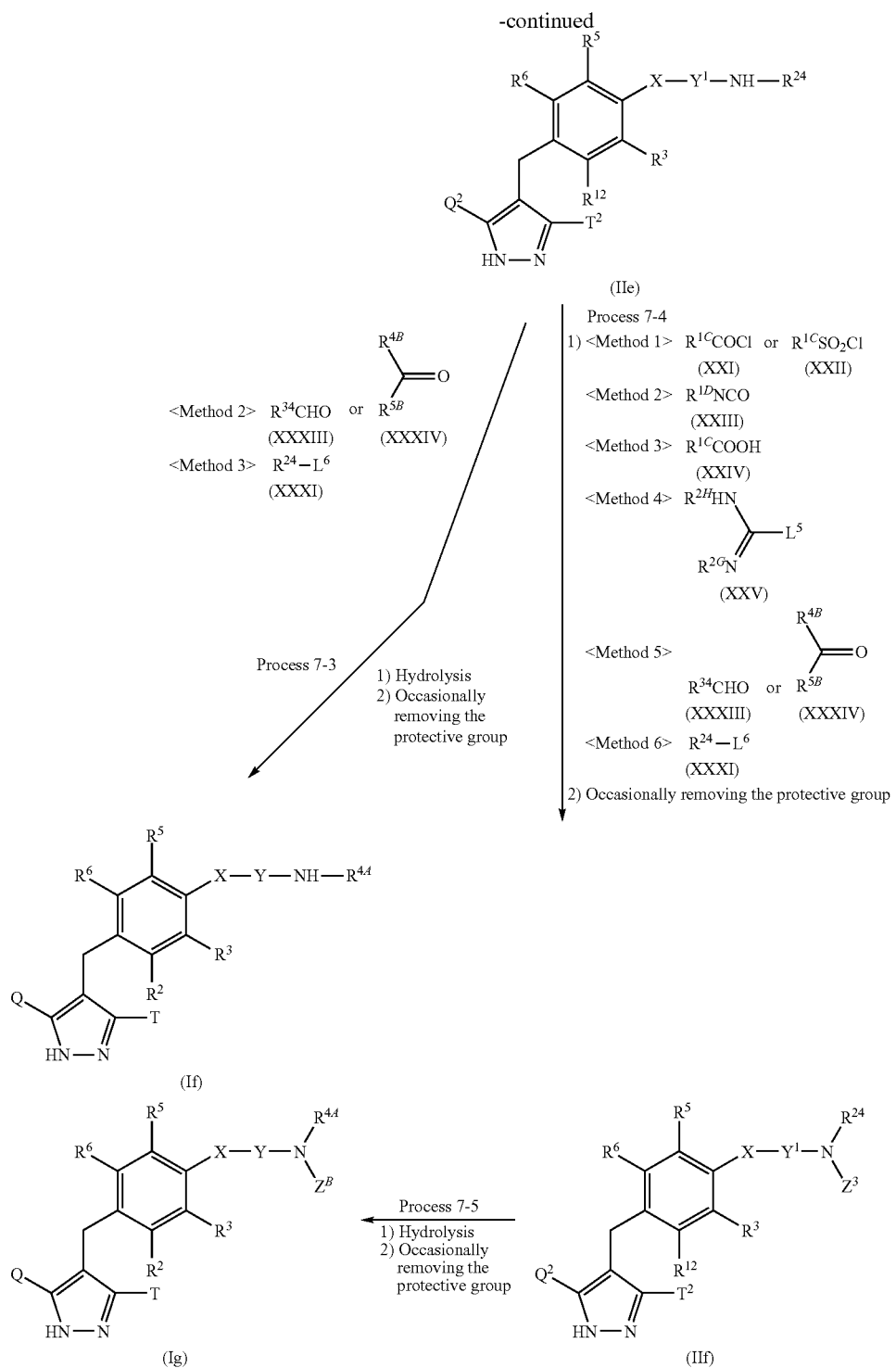

wherein $L^6$ represents a leaving group such as a halogen atom, a mesyloxy group, a tosyloxy group or the like; W represents a 2-nitro group, a 4-nitro group or a 2,4-dinitro group; $R^{24}$ represents a $C_{1-6}$ alkyl group which may have the same or different 1 to 5 groups selected from the above substituent group (ii); $R^{34}$ and the neighboring carbon atom form $R^{24}$ after reduction; both of $R^{4B}$ and $R^{5B}$ bind together with the neighboring carbon atom to form $R^{24}$ having a branched $C_{3-6}$ alkyl group after reduction; $R^{4A}$ represents a $C_{1-6}$ alkyl group which may have the same or different 1 to 5 groups selected from the above substituent group (i); $Z^3$ represents a $C_{1-6}$ alkyl group which may have the same or different 1 to 5 groups selected from the above substituent group (ii), —$COR^{1C}$, —$SO_2R^{1C}$, —$CONHR^{1D}$ or —$C(=NR^{2G})NHR^{2H}$; $Z^B$ represents a $C_{1-6}$ alkyl group which may have the same or different 1 to 5 groups selected from the above substituent group (i), —$COR^C$, —$SO_2R^C$, —$CONHR^D$ or —$C(=NR^{2G})NHR^{2H}$; and $L^5$, $R^{1C}$, $R^{1D}$, $R^{2G}$, $R^{2H}$, $R^2$, $R^3$, $R^5, R^6, R^{12}, Q, Q^2, T, T^2, X, Y$ and $Y^1$ have the same meanings as defined above.

Process 7-1

A compound represented by the above general formula (IIe) of the present invention can be prepared from a compound represented by the above general formula (IIb) by treating according to the following methods 1-3.

<Method 1>

1) A compound represented by the above general formula (IIb) is allowed to react with an acid chloride represented by the above general formula (XXX) in the presence of a base such as triethylamine, N,N-diisopropylethylamine, pyridine or 1,8-diazabicyclo[5.4.0]unde-7-cene in an inert solvent such as dichloromethane, ethyl acetate, tetrahydrofuran, pyridine, acetonitrile or a mixed solvent thereof at usually 0° C. to room temperature for usually 30 minutes to 1 day to obtain the corresponding sulfonamide compound.

2) The obtained sulfonamide compound is N-alkylated using an alkylating agent represented by the above general formula (XXXI) after adding sodium iodide as occasion demands in the presence of a base such as potassium carbonate, cesium carbonate or sodium hydride in an inert solvent such as N,N-dimethylformamide, acetone, tetrahydrofuran, acetonitrile or a mixed solvent thereof at usually room temperature to reflux temperature for usually 1 hour to 2 days, or the obtained sulfonamide compound is N-alkylated using an alcohol compound represented by the above general formula (XXXII) in the presence of a diester of an azodicarboxylic acid such as diethyl azodicarboxylate or diisopropyl azodicarboxylate, and triphenylphosphine in an inert solvent such as tetrahydrofuran, ethyl acetate, acetonitrile or a mixed solvent thereof at usually room temperature to reflux temperature for usually 30 minutes to 1 day to obtain the corresponding N,N-disubstituted sulfonamide compound.

3)-4) The obtained N,N-disubstituted sulfonamide compound is deprotected using a thiol reagent such as mercaptoacetic acid or thiophenol in the presence of a base such as cesium carbonate or potassium carbonate in an inert solvent such as N,N-dimethylformamide, acetonitrile or a mixed solvent thereof at usually room temperature to reflux temperature for usually 1 hour to 1 day to obtain the corresponding secondary amine compound, and the protective group is removed in the usual way as occasion demands.

<Method 2>

An aldehyde compound represented by the above general formula (XXXIII) or a ketone compound represented by the above general formula (XXXIV) is reductively aminated using a compound represented by the above general formula (IIb) in the presence of a reducing agent such as sodium cyanoborohydride or sodium triacetoxyborohydride in an inert solvent such as tetrahydrofuran, 1,2-dichloroethane, acetic acid or a mixed solvent thereof at usually room temperature to reflux temperature for usually 1 hour to 1 day.

<Method 3>

A compound represented by the above general formula (IIb) is N-alkylated using an alkylating agent represented by the above general formula (XXXI) after adding sodium iodide as occasion demands in the presence or absence of a base such as triethylamine, N,N-diisopropylethylamine, pyridine or 1,8-diazabicyclo-[5.4.0]unde-7-cene in an inert solvent such as acetonitrile, N,N-dimethylformamide, dimethyl sulfoxide, N-methylpyrrolidone, methanol, ethanol, 2-propanol or a mixed solvent thereof at usually room temperature to reflux temperature for usually 1 hour to 5 days.

Process 7-2

1) A sulfonamide compound represented by the above general formula (XXXV) is N-alkylated using a compound represented by the above general formula (XVII) in the presence of a diester of an azodicarboxylic acid such as diethyl azodicarboxylate or diisopropyl azodicarboxylate, and triphenylphosphine in an inert solvent such as tetrahydrofuran, ethyl acetate, acetonitrile or a mixed solvent thereof at usually room temperature to reflux temperature for usually 30 minutes to 1 day to obtain the corresponding N,N-disubstituted sulfonamide compound.

2)-3) The obtained N,N-disubstituted sulfonamide compound is deprotected using a thiol reagent such as mercaptoacetic acid or thiophenol in the presence of a base such as cesium carbonate or potassium carbonate in an inert solvent such as N,N-dimethylformamide, acetonitrile or a mixed solvent thereof at usually room temperature to reflux temperature for usually 1 hour to 1 day to obtain the corresponding secondary amine compound, and the protective group is removed in the usual way as occasion demands to prepare a prazole derivative represented by the above general formula (IIe) of the present invention.

Process 7-3

1)-2) A pyrazole derivative represented by the above general formula (If) of the present invention can be prepared by subjecting a compound represented by the above general formula (IIe) to alkaline hydrolysis, and removing the protective group in the usual way as occasion demands. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}$, $R^{24}$ and/or $Y^1$ after the hydrolysis, the protective group can be suitably removed in the usual way as the process 1-9.

Process 7-4

1)-2) A compound represented by the above general formula (IIf) of the present invention can be prepared from a compound represented by the above general formula (IIe) by treating according to the following methods 1-6, and removing the protective group in the usual way as occasion demands.

<Method 1>

A compound represented by the above general formula (IIe) is allowed to react with an acid chloride represented by the above general formula (XXI) or (XXII) in the presence of a base such as triethylamine, N,N-diisopropylethylamine, pyridine or 1,8-diazabicyclo[5.4.0]unde-7-cene in an inert solvent such as dichloromethane, ethyl acetate, tetrahydrofuran, pyridine, acetonitrile or a mixed solvent thereof at usually 0° C. to reflux temperature for usually 30 minutes to 1 day.

<Method 2>

A compound represented by the above general formula (IIe) is allowed to react with an isocyanate compound represented by the above general formula (XXIII) in the presence or absence of a base such as triethylamine, N,N-diisopropylethylamine, pyridine or 1,8-diazabicyclo[5.4.0]unde-7-cene in an inert solvent such as dichloromethane, ethyl acetate, tetrahydrofuran, pyridine, acetonitrile, toluene or a mixed solvent thereof at usually 0° C. to reflux temperature for usually 30 minutes to 1 day.

<Method 3>

A compound represented by the above general formula (IIe) is allowed to react with a carboxylic acid compound represented by the above general formula (XXIV) after suitably adding 1-hydroxybenzotriazole as occasion demands in the presence of a condensing agent such as 1-ethyl-3-(3-dimethylaminopropyl)carbodiimide hydrochloride or dicyclohexylcarbodiimide and in the presence or absence of a base such as triethylamine or N,N-diisopropylethylamine in an inert solvent such as N,N-dimethylformamide, dichloromethane or a mixed solvent thereof at usually 0° C. to reflux temperature for usually 1 hour to 2 days.

<Method 4>

A compound represented by the above general formula (IIe) is allowed to react with a guanidylating reagent represented by the above general formula (XXV) such as N-(benzyloxycarbonyl)-1H-pyrazol-1-carboxamidine in an inert solvent such as tetrahydrofuran, methanol, ethanol, toluene, N,N-dimethylformamide or a mixed solvent thereof at usually room temperature to reflux temperature for usually 1 hour to 5 days.

<Method 5>

An aldehyde compound represented by the above general formula (XXXIII) or a ketone compound represented by the above general formula (XXXIV) is reductively aminated using a compound represented by the above general formula (IIe) in the presence of a reducing agent such as sodium cyanoborohydride or sodium triacetoxyborohydride in an inert solvent such as tetrahydrofuran, 1,2-dichloroethane, acetic acid or a mixed solvent thereof at usually room temperature to reflux temperature for usually 1 hour to 1 day.

<Method 6>

A compound represented by the above general formula (IIe) is N-alkylated using an alkylating agent represented by the above general formula (XXXI) after adding sodium iodide as occasion demands in the presence or absence of a base such as triethylamine, N,N-diisopropylethylamine, pyridine or 1,8-diazabicyclo[5.4.0]unde-7-cene in an inert solvent such as acetonitrile, N,N-dimethylformamide, dimethyl sulfoxide, N-methylpyrrolidone, methanol, ethanol, 2-propanol or a mixed solvent thereof at usually room temperature to reflux temperature for usually 1 hour to 5 days.

Process 7-5

1)-2) A pyrazole derivative represented by the above general formula (Ig) of the present invention can be prepared by subjecting a compound represented by the above general formula (IIf) to alkaline hydrolysis, and removing the protective group in the usual way as occasion demands. As the solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}$, $R^{24}$, $Y^1$ and/or $Z^3$ after the hydrolysis, the protective group can be suitably removed in the usual way as the process 1-9.

Of the compounds represented by the above general formula (I) of the present invention, a compound wherein $R^1$ represents a hydrogen atom; X represents an oxygen atom; Y represents —$CH_2CH(OH)CH_2$—; and Z is $R^B$, for example, can be also prepared according to the following procedures:

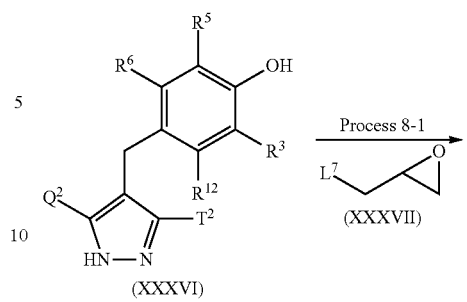

(XXXVI)

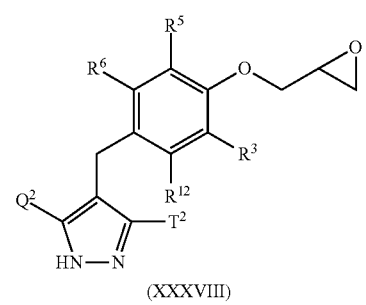

(XXXVIII)

Process 8-2
1) $R^{14}$
   $\diagdown$
   NH
   $\diagup$
   $R^{1B}$
   (XXIX)
   or a salt thereof
2) Hydrolysis
3) Occasionally removing the protective group

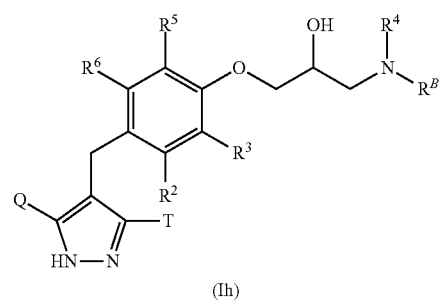

(Ih)

wherein $L^7$ represents a leaving group such as a halogen atom, a mesyloxy group, a tosyloxy group, a nosyloxy group or the like; and $R^{1B}$, $R^2$, $R^3$, $R^4$, $R^5$, $R^6$, $R^{12}$, $R^{14}$, $R^B$, Q, $Q^2$, T and $T^2$ have the same meanings as defined above.

Process 8-1

A compound represented by the above general formula (XXXVIII) can be prepared by subjecting a compound represented by the above general formula (XXXVI) to O-alkylation using an alkylating agent represented by the above general formula (XXXVII) after suitably adding a phase transfer catalyst such as tetra(n-butyl)ammonium bromide or the like as occasion demands in the presence of a base such as cesium carbonate, potassium carbonate, sodium hydride, sodium hydroxide, cesium fluoride or the like in an inert solvent. As the solvent used in the O-alkylation, N,N-dimethylformamide, acetone, tetrahydrofuran, chlorobenzene, dichloromethane, water, a mixed solvent thereof and the like can be illustrated. The reaction temperature is usually from room temperature to reflux temperature, and the reaction time is usually from 1 hour to 3 days, varying based on a used starting material, solvent and reaction temperature.

Process 8-2

An pyrazole derivative represented by the above general formula (Ih) of the present invention can be prepared by condensing a compound represented by the above general formula (XXXVIII) with an amine compound represented by the above general formula (XXIX) or a salt thereof in the presence or absence of a base such as triethylamine, N,N-diisopropylethylamine, pyridine, 1,8-diazabicyclo[5.4.0]unde-7-cene, sodium hydride, potassium tert-butoxide, potassium carbonate or cesium carbonate in an inert solvent, subjecting the resulting compound to alkaline hydrolysis, and removing the protective group in the usual way as occasion demands. As the solvent used in the condensing reaction, for example, acetonitrile, N,N-dimethylformamide, methanol, ethanol, tetrahydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature. As the solvent used in the hydrolysis, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{12}$, $R^{14}$ and/or $R^{1B}$ after the hydrolysis, the protective group can be suitably removed in the usual way as the process 1-9.

Of the compounds represented by the above general formula (I) of the present invention, a compound wherein $R^1$ and $R^4$ represents a hydrogen atom; and Z is —C(=NCN)N($R^7$)$R^8$, for example, can be also prepared according to the following procedures:

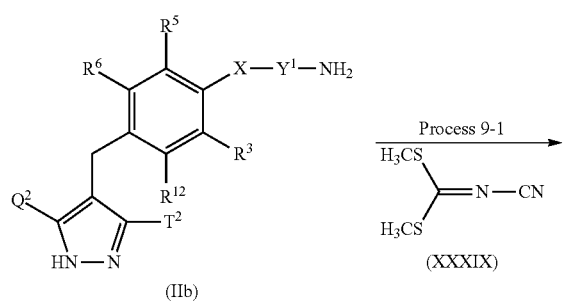

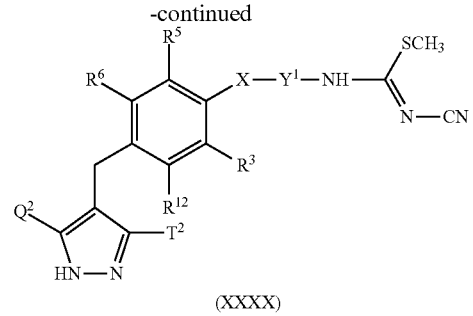

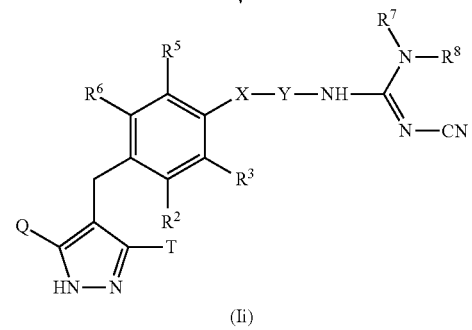

wherein $R^7$ and $R^8$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the above substituent group (i), or both of $R^7$ and $R^8$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group; and $R^{1B}$, $R^2$, $R^3$, $R^5$, $R^6$, $R^{12}$, $R^{14}$, Q, $Q^2$, T, $T^2$, X, Y and $Y^1$ have the same meanings as defined above.

Process 9-1

A compound represented by the above general formula (XXXX) can be prepared by condensing a compound represented by the above general formula (IIb) with an isothioureidating reagent represented by the above general formula (XXXIX) in an inert solvent. As the solvent used in the condensing reaction, for example, methanol, ethanol, 2-propanol, tetrahydrofuran, toluene, a mixed solvent thereof and the like can be illustrated. The reaction temperature is usually from room temperature to reflux temperature, and the reaction time is usually from 1 hour to 1 day, varying based on a used starting material, solvent and reaction temperature.

Process 9-2

A compound represented by the above general formula (II) of the present invention can be prepared by condensing a compound represented by the above general formula (XXXX) with an amine compound represented by the above general formula (XXIX) or a salt thereof in the presence or absence of a base such as triethylamine, N,N-diisopropylethylamine, pyridine, 1,8-diazabicyclo[5.4.0]unde-7-cene, sodium hydride, potassium tert-butoxide, potassium carbonate or cesium carbonate in an inert solvent, subjecting the resulting compound to alkaline hydrolysis, and removing the protective group in the usual way as occasion demands. As the solvent used in the condensing reaction, for example, methanol, ethanol, acetonitrile, 2-propanol, N,N-dimethylformamide, tetrahydrofuran, a mixed solvent thereof and the like can be illustrated. The reaction temperature is usually from room temperature to reflux temperature, and the reaction time is usually from 1 hour to 1 day, varying based on a used starting material, solvent and reaction temperature. As the solvent used in the hydrolysis, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. In case of compounds having a protective group in $R^{1B}$, $R^{12}$, $R^{14}$ and/or $Y^1$ after the hydrolysis, the protective group can be suitably removed in the usual way as the process 1-9.

In case of removing a protective group in the above production processes, methods other than those described above can be also carried out in the usual way.

The compounds represented by the above general formula (I) of the present invention obtained by the above production processes can be isolated and purified by conventional separation means such as fractional recrystallization, purification using chromatography, solvent extraction and solid phase extraction.

The pyrazole derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and salts with organic bases such as N-methyl-D-glucamine, N,N'-dibenzyletylenediamine, 2-aminoethanol, tris (hydroxymethyl)aminomethane, arginine, lysine and the like.

The compounds represented by the above general formula (I) of the present invention include their solvates with pharmaceutically acceptable solvents such as ethanol and water.

Of the pyrazole derivatives represented by the above general formula (I) of the present invention and the prodrugs thereof, there are two geometrical isomers in each compound having an unsaturated bond. In the present invention, either of cis(Z)-isomer or trans(E)-isomer can be employed.

Of the pyrazole derivatives represented by the above general formula (I) of the present invention and the prodrugs thereof, there are two optical isomers, R-isomer and S-isomer, in each compound having an asymmetric carbon atom excluding the glucopyranosyloxy moiety or the galactopyranosyloxy moiety. In the present invention, either of the isomers can be employed, and a mixture of both isomers can be also employed.

A prodrug of a compound represented by the above general formula (I) of the present invention can be prepared by introducing an appropriate group forming a prodrug into any one or more groups selected from a hydroxy group, an amino group and a cyclic amino group (e.g., a pyrazole ring, a piperazine ring) of the compound represented by the above general formula (I) using a corresponding reagent to produce a prodrug such as a halide compound or the like in the usual way, and then by suitably isolating and purifying in the usual way as occasion demands. As a group forming a prodrug used in a hydroxy group or an amino group, for example, a $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, an aryl($C_{2-7}$ alkoxycarbonyl) group, a $C_{1-6}$ alkoxy-substituted ($C_{2-7}$ alkoxycarbonyl) group or the like can be illustrated. As a group forming a prodrug used in a cyclic amino group, for example, a $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, an aryl($C_{2-7}$ alkoxycarbonyl) group, a $C_{1-6}$ alkoxy-substituted ($C_{2-7}$ alkoxycarbonyl) group, a ($C_{2-7}$ acyloxy)methyl group, a 1-($C_{2-7}$ acyloxy)ethyl group, a ($C_{2-7}$ alkoxycarbonyl)oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group or the like can be illustrated. The term "$C_{1-6}$ alkoxy-substituted ($C_{2-7}$ acyl) group" means the above $C_{2-7}$ acyl group substituted by the above $C_{1-6}$ alkoxy group; the term "$C_{2-7}$ alkoxycarbonyl-substituted ($C_{2-7}$ acyl) group" means the above $C_{2-7}$ acyl group substituted by the above $C_{2-7}$ alkoxycarbonyl group; the term "$C_{1-6}$ alkoxy-substituted ($C_{2-7}$ alkoxycarbonyl) group" means the above $C_{2-7}$ alkoxycarbonyl group substituted by the above $C_{1-6}$ alkoxy group; the term "($C_{2-7}$ acyloxy)methyl group" means a hydroxymethyl group O-substituted by the above $C_{2-7}$ acyl group; the term "1-($C_{2-7}$ acyloxy) ethyl group" means a 1-hydroxyethyl group O-substituted by the above $C_{2-7}$ acyl group; the term "($C_{2-7}$ alkoxycarbonyl) oxymethyl group" means a hydroxymethyl group substituted by the above $C_{2-7}$ alkoxycarbonyl group; and the term "1-[($C_{2-7}$ alkoxycarbonyl)oxy]ethyl group" means a 1-hydroxyethyl group O-substituted by the above $C_{2-7}$ alkoxycarbonyl group. In addition, the term "($C_{3-7}$ cycloalkyl)oxycarbonyl group" means a cyclic alkoxycarbonyl group having the above $C_{3-7}$ cycloalkyl group; the term "($C_{3-7}$ cycloalkyl)oxycarbonyloxymethyl group" means a hydroxymethyl group O-substituted by the above ($C_{3-7}$ cycloalkyl)oxycarbonyl group; and the term "1-[($C_{3-7}$ cycloalkyl)oxycarbonyloxy] ethyl group" means a 1-hydroxyethyl group O-substituted by the above ($C_{3-7}$ cycloalkyl)oxycarbonyl group. Furthermore, as a group forming a prodrug, a glucopyranosyl group or a galactopyranosyl group can be illustrated. For example, these groups are preferably introduced into the hydroxy group at the 4 or 6 position of the glucopyranosyl group or the galactopyranosyl group, and are more preferably introduced into the hydroxy group at the 4 or 6 position of the glucopyranosyl group.

The pyrazole derivatives represented by the above general formula (I) of the present invention, for example, showed a potent inhibitory activity in human SGLT1 in a human SGLT1 inhibitory activity confirmatory test as described below, and exerted an excellent inhibitory activity of blood glucose level increase in a confirmatory test of the inhibitory activity of blood glucose level increase in rat. Thus, the pyrazole derivatives represented by the above general formula (I) of the present invention exhibit an excellent SGLT1 inhibitory activity at the small intestine, and can remarkably inhibit blood glucose level increase and/or decrease blood galactose level by inhibiting or delaying glucose and galactose absorption. Therefore, a pharmaceutical composition comprising as an active ingredient a pyrazole derivative represented by the above general formula (I) of the present invention, a pharmaceutically acceptable salt and a prodrug thereof is extremely useful as an agent for inhibiting postprandial hypreglycemia, an agent for the inhibition of advancing impaired glucose tolerance (IGT) or impaired fasting glycemia (IFG) into diabetes in a subject, and an agent for the prevention or treatment of a disease associated with hyperglycemia such as diabetes, impaired glucose tolerance, impaired fasting glycemia, diabetic complications (e.g., retinopathy, neuropathy, nephropathy, ulcer, macroangiopathy), obesity, hyperinsulinemia, hyperlipidemia, hypercholesterolemia, hypertriglyceridemia, lipid metabolism disorder, atherosclerosis, hypertension, congestive heart failure, edema, hyperuricemia, gout or the like, which relates to SGLT1 activity at the small intestine, and an agent for the prevention or treatment of a disease associated with increasing blood galactose level such as galactosemia.

Furthermore, the compounds of the present invention can be suitably used in combination with at least one member selected from drugs other than SGLT2 inhibitors. Examples of the drugs which can be used in combination with the compounds of the present invention include an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, antidiarrhoics, cathartics, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route. A pharmaceutical combination comprising the compound of the present invention and the above drug(s) includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of coadministrated drugs other than SGLT1 inhibitors can be avoided or declined.

Concrete compounds as the drugs used for combination and preferable diseases to be treated are exemplified as follows. However, the present invention is not limited thereto, and the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100. T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, N,N-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia because of improving the disturbance of insulin signal transduction in peripheral tissues and enhancing glucose uptake into the tissues from the blood, leading to lowering of blood glucose level.

As glucose absorption inhibitors, compounds other than SGLT1 inhibitors, for example, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, impaired glucose tolerance, diabetic complications, obesity or hyperinsulinemia, and more preferably for impaired glucose tolerance because of inhibiting the gastrointestinal enzymatic digestion of carbohydrates contained in foods, and inhibiting or delaying the absorption of glucose into the body.

As biguanides, phenformin, buformin hydrochloride, metformin hydrochloride or the like are illustrated. Biguanides are used preferably for diabetes, impaired glucose tolerance, diabetic complications or hyperinsulinemia, and more preferably for diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. In addition, the insulin secretion enhancers include glucokinase activators such as RO-28-1675. Insulin secretion enhancers are used preferably for diabetes, impaired glucose tolerance or diabetic complications, and more preferably for diabetes or impaired glucose tolerance because of lowering blood glucose level by acting on pancreatic β-cells and enhancing the insulin secretion.

As SGLT2 inhibitors, T-1095 and compounds described in Japanese patent publications Nos. Hei10-237089 and 2001-288178, and International Publications Nos. WO01/16147, WO01/27128, WO01/68660, WO01/74834, WO01/74835, WO02/28872, WO02/36602, WO02/44192, WO02/53573 etc. are illustrated. SGLT2 inhibitors are used preferably for diabetes, impaired glucose tolerance, diabetic complications, obesity or hyperinsulinemia, and more preferably for diabetes, impaired glucose tolerance, obesity or hyperinsulinemia because of lowering blood glucose level by inhibiting the reabsorption of glucose at the kidney's proximal tubule.

As insulin or insulin analogues, human insulin, animal-derived insulin, human or animal-derived insulin analogues or the like are illustrated. These preparations are used preferably for diabetes, impaired glucose tolerance or diabetic complications, and more preferably for diabetes or impaired glucose tolerance.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, NVP-DPP728A, TSL-225, P-32/98 or the like are illustrated; as protein tyrosine phosphatase 1B inhibitors, PTP-112, OC-86839, PNU-177496 or the like are illustrated; as glycogen phosphorylase inhibitors, N,N-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated: as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 are used preferably for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors are preferably used for diabetic complications because of inhibiting aldose reductase and lowering excessive intracellular accumulation of sorbitol in accelated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride or the like are illustrated. Advanced glycation endproducts formation inhibitors are preferably used for diabetic complications because of inhibiting formation of advanced glycation endproducts which are accelated in continuous hyperglycemic condition in diabetes and declining of cellular damage.

As protein kinase C inhibitors, LY-333531, midostaurin or the like are illustrated. Protein kinase C inhibitors are preferably used for diabetic complications because of inhibiting of protein kinase C activity which is accelated in continuous hyperglycemic condition in diabetes.

As γ-aminobutyric acid receptor antagonists, topiramate or the like are illustrated; as sodium channel antagonists, mexiletine hydrochloride, oxcarbazepine or the like are illustrated; as transcrit factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecamine hydrochloride, levocarnitine chloride, levocarnitine, ST-261 or the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As antidiarrhoics or cathartics, polycarbophil calcium, albumin tannate, bismuth subnitrate or the like are illustrated. These drugs are preferably used for diarrhea, constipation or the like accompanying diabetes or the like.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering of blood triglyceride level.

As β$_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 or the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine- and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as $\gamma$-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated. Appetite suppressants are used preferably for diabetes, impaired glucose tolerance, diabetic complications, obesity, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists are preferably used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as α$_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents are preferably used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs are preferably used for hyperuricemia or gout.

In case of uses in combination with drugs other than SGLT2 inhibitors, for example, in the use for diabetes, the combination with at least one member of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a biguanide, an insulin secretion enhancer, a SGLT2 inhibitor and an insulin or insulin analogue is most preferable. Similarly, in the use for diabetic complications, the combination with at least one member of the group consisting of an insulin sensitivity enhancer, a glucose absorption inhibitor, abiguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced-glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, abiguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a SGLT2 inhibitor, a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry sirups, tablets, capsules, injections, solutions, ointments, suppositories, poultices and the like are illustrated, which are orally or parenterally administered. The pharmaceutical compositions of the present invention also include sustained release formulation including gastrointestinal mucoadhesive formulation (e.g., International publications Nos. WO99/10010, WO99/26606, and Japanese patent publication No. 2001-2567).

These pharmaceutical compositions can be prepared by admixing with or by diluting and dissolving with an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with conventional methods. In case of the uses of the compound of the present invention in combination with the drug(s) other than SGLT1 inhibitors, they can be prepared by formulating each active ingredient together or individually.

When the pharmaceutical compositions of the present invention are employed in the practical treatment, the dosage of a compound represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the uses of the compound of the present invention in combination with the drug(s) other than SGLT1 inhibitors, the dosage of the compound of the present invention can be decreased, depending on the dosage of the drug(s) other than SGLT1 inhibitors.

EXAMPLES

The present invention is further illustrated in more detail by way of the following Reference Examples, Examples and Test Examples. However, the present invention is not limited thereto.

Reference Example 1

2-Amino-2-methylpropionamide

To a solution of 2-benzyloxycarbonylamino-2-methylpropionic acid (1 g) in N,N-dimethylformamide (10 mL) were added 1-hydroxybenzotriazole (0.63 g), 1-ethyl-3-(3-dimethylaminopropyl)carbodiimide hydrochloride (1.21 g), triethylamine (1.76 mL) and 28% aqueous ammonia solution (2 mL), and the mixture was stirred at room temperature overnight. The reaction mixture was poured into water, and the resulting mixture was extracted with ethyl acetate. The organic layer was washed with 0.5 mol/L hydrochloric acid, water, 1 mol/L aqueous sodium hydroxide solution, water and brine successively, and dried over anhydrous sodium sulfate. The solvent was removed under reduced pressure to give 2-benzyloxycarbonylamino-2-methylpropionamide (0.26 g). This material was dissolved in methanol (5 mL). To the solution was added 10% palladium-carbon powder (30 mg), and the mixture was stirred at room temperature under a hydrogen atmosphere for 3 hours. The insoluble material was removed by filtration, and the filtrate was concentrated under reduced pressure to give the title compound (0.11 g).
$^1$H-NMR (DMSO-$d_6$) $\delta$ ppm:
1.15 (6H, s), 1.9 (2H, brs), 6.83 (1H, brs), 7.26 (1H, brs)

Reference Example 2

2-(2-Nitrobenzenesulfonylamino)acetoamide

To a suspension of glycinamide hydrochloride (0.11 g) and triethylamine (0.35 mL) in dichloromethane (3 mL) was added 2-nitrobenzenesulfonyl chloride (0.27 g), and the mixture was stirred at room temperature for 1 hour. The reaction mixture was poured into 0.5 mol/L hydrochloric acid, and the resulting mixture was extracted with ethyl acetate. The organic layer was washed with water and brine successively, and dried over anhydrous sodium sulfate. The solvent was removed under reduced pressure, and the residue was purified by column chromatography on silica gel (eluent: dichloromethane/methanol=20/1) to give the title compound (72 mg).
$^1$H-NMR (DMSO-$d_6$) $\delta$ ppm:
3.57 (2H, d, J=5.9 Hz), 7.1 (1H, brs), 7.33 (1H, brs), 7.8-7.9 (2H, m), 7.95-8.1 (2H, m), 8.16 (1H, t, J=5.9 Hz)

Reference Example 3

(S)-2-(2-Nitrobenzenesulfonylamino)propionamide

The title compound was prepared in a similar manner to that described in Reference Example 2 using L-alanine amide hydrochloride instead of glycinamide hydrochloride.
$^1$H-NMR (CD$_3$OD) $\delta$ ppm:
1.33 (3H, d, J=7.1 Hz), 4.03 (1H, q, J=7.1 Hz), 7.75-7.85 (2H, m), 7.85-7.9 (1H, m), 8.05-8.15 (1H, m)

Reference Example 4

2-Methyl-2-(2-nitrobenzenesulfonylamino)propionamide

The title compound was prepared in a similar manner to that described in Reference Example 2 using 2-amino-2-methylpropionamide instead of glycinamide hydrochloride.
$^1$H-NMR (DMSO-$d_6$) $\delta$ ppm:
1.32 (6H, s), 7.2-7.3 (2H, m), 7.8-7.9 (2H, m), 7.92 (1H, s), 7.95-8.0 (1H, m), 8.05-8.15 (1H, m)

Reference Example 5

3-(2-Nitrobenzenesulfonylamino)propionamide

The title compound was prepared in a similar manner to that described in Reference Example 2 using 3-aminopropionamide hydrochloride instead of glycinamide hydrochloride.

¹H-NMR (DMSO-d₆) δ ppm:
2.27 (2H, t, J=7.3 Hz), 3.0-3.15 (2H, m), 6.85 (1H, brs), 7.34 (1H, brs), 7.8-7.9 (2H, m), 7.95-8.05 (3H, m)

Reference Example 6

[4-(3-Benzyloxypropoxy)phenyl]methanol

To a solution of 4-hydroxybenzaldehyde (2.44 g) in N,N-dimethylformamide (20 mL) were added cesium carbonate (7.17 g), benzyl 3-bromopropyl ether (4.81 g) and a catalytic amount of sodium iodide, and the mixture was stirred at room temperature for 4 days. The reaction mixture was poured into water, and the resulting mixture was extracted with diethyl ether. The organic layer was washed with water, and dried over anhydrous magnesium sulfate. The solvent was removed under reduced pressure to give 4-(3-benzyloxypropoxy)benzaldehyde. This material was dissolved in ethanol (20 mL). To the solution was added sodium borohydride (757 mg), and the mixture was stirred at room temperature for 3 hours. To the reaction mixture was added methanol, and the resulting mixture was concentrated under reduced pressure. Water was added to the residue, and the mixture was extracted with diethyl ether. The organic layer was washed with a saturated aqueous sodium hydrogen carbonate solution, and dried over anhydrous magnesium sulfate. The solvent was removed under reduced pressure, and the residue was purified by column chromatography on silica gel (eluent: n-hexane/ethyl acetate=5/1-2/1) to give the title compound (5.17 g).
¹H-NMR (CDCl₃) δ ppm:
1.54 (1H, t, J=5.9 Hz), 2.05-2.15 (2H, m), 3.66 (2H, t, J=6.2 Hz), 4.09 (2H, t, J=6.2 Hz), 4.52 (2H, s), 4.61 (2H, d, J=5.9 Hz), 6.85-6.95 (2H, m), 7.2-7.35 (7H, m)

Reference Example 7

[4-(2-Benzyloxyethoxy)phenyl]methanol

The title compound was prepared in a similar manner to that described in Reference Example 6 using benzyl 2-bromoethyl ether instead of benzyl 3-bromopropyl ether.
¹H-NMR (CDCl₃) δ ppm:
1.53 (1H, t, J=5.8 Hz), 3.8-3.85 (2H, m), 4.1-4.2 (2H, m), 4.62 (2H, d, J=5.8 Hz), 4.64 (2H, s), 6.85-6.95 (2H, m), 7.25-7.4 (7H, m)

Reference Example 8

[4-(4-Benzyloxybutoxy)phenyl]methanol

The title compound was prepared in a similar manner to that described in Reference Example 6 using benzyl 4-bromobutyl ether instead of benzyl 3-bromopropyl ether.
¹H-NMR (CDCl₃) δ ppm:
1.52 (1H, t, J=5.6 Hz), 1.75-1.95 (4H, m), 3.54 (2H, t, J=6.1 Hz), 3.98 (2H, t, J=6.3 Hz), 4.52 (2H, s), 4.61 (2H, d, J=5.6 Hz), 6.8-6.9 (2H, m), 7.2-7.4 (7H, m)

Reference Example 9

[4-(3-Benzyloxypropoxy)-2-methylphenyl]methanol

To a solution of 4-bromo-3-methylphenol (2.5 g) in N,N-dimethylformamide (10 mL) were added cesium carbonate (4.79 g), benzyl 3-bromopropyl ether (2.48 mL) and a catalytic amount of sodium iodide, and the mixture was stirred at room temperature for 60 hours. The reaction mixture was poured into water, and the resulting mixture was extracted with diethyl ether. The organic layer was washed with water, and dried over anhydrous magnesium sulfate. The solvent was removed under reduced pressure to give 4-(3-benzyloxypropoxy)-1-bromo-2-methylbenzene. This material was dissolved in tetrahydrofuran (100 mL). To the solution was added n-butyl lithium (2.46 mol/L n-hexane solution, 6 mL) at −78° C. under an argon atmosphere, and the mixture was stirred for 5 minutes. To the reaction mixture was added N,N-dimethylformamide (2.57 mL), and the mixture was allowed to warm to 0° C. and stirred for 1 hour. The reaction mixture was poured into water, and the resulting mixture was extracted with diethyl ether. The organic layer was washed with water and brine successively, and dried over anhydrous magnesium sulfate. The solvent was removed under reduced pressure to give 4-(3-benzyloxypropoxy)-2-methylbenzaldehyde. This material was dissolved in ethanol (40 mL). To the solution was added sodium borohydride (506 mg), and the mixture was stirred at room temperature overnight. To the reaction mixture was added methanol, and the resulting mixture was concentrated under reduced pressure. Water was added to the residue, and the mixture was extracted with diethyl ether. The organic layer was washed with a saturated aqueous sodium hydrogen carbonate solution, and dried over anhydrous magnesium sulfate. The solvent was removed under reduced pressure, and the residue was purified by column chromatography on silica gel (eluent: n-hexane/ethyl acetate=5/1-1.5/1) to give the title compound (3.33 g).
¹H-NMR (CDCl₃) δ ppm:
1.37 (1H, t, J=5.7 Hz), 2.0-2.15 (2H, m), 2.36 (3H, s), 3.66 (2H, t, J=6.2 Hz), 4.08 (2H, t, J=6.3 Hz), 4.52 (2H, s), 4.63 (2H, d, J=5.7 Hz), 6.65-6.8 (2H, m), 7.15-7.4 (6H, m)

Reference Example 10

[4-(2-Benzyloxyethoxy)-2-methylphenyl]methanol

The title compound was prepared in a similar manner to that described in Reference Example 9 using benzyl 2-bromoethyl ether instead of benzyl 3-bromopropyl ether.
¹H-NMR (CDCl₃) δ ppm:
1.39 (1H, t, J=5.8 Hz), 2.35 (3H, s), 3.8-3.85 (2H, m), 4.1-4.2 (2H, m), 4.6-4.65 (4H, m), 6.73 (1H, dd, J=8.2 Hz, 2.6 Hz), 6.78 (1H, d, J=2.6 Hz), 7.22 (1H, d, J=8.2 Hz), 7.25-7.4 (5H, m)

Reference Example 11

4-{[4-(3-Benzyloxypropoxy)phenyl]methyl}-1,2-dihydro-5-isopropyl-3H-pyrazol-3-one To a solution of [4-(3-benzyloxypropoxy)phenyl]methanol (5.17 g) in tetrahydrofuran (25 mL) were added triethylamine (3.04 mL) and methanesulfonyl chloride (1.62 mL) under ice-cooling, and the mixture was stirred for 1 hour. The insoluble material was removed by filtration. The obtained solution of [4-(3-benzyloxypropoxy)phenyl]methyl mesylate in tetrahydrofuran was added to a suspension of sodium hydride (60%, 875 mg) and ethyl 4-methyl-3-oxopentanoate (3.3 g) in tetrahydrofuran (50 mL), and the mixture was heated for reflux for 8 hours. To the reaction mixture was added 1 mol/L hydrochloric acid, and the resulting mixture was extracted with diethyl ether. The organic layer was washed with water, and dried over anhydrous magnesium sulfate. The solvent was removed under reduced pressure. To a solution of the residue in toluene (10 mL) was added hydrazine monohydrate (2.76 mL), and the mixture was stirred at 100° C. overnight. The reaction mixture was purified by column chromatography on silica gel (eluent: dichloromethane/methanol=50/1-20/1) to give the title compound (5.22 g).

$^1$H-NMR (CDCl$_3$) δ ppm:
1.14 (6H, d, J=6.8 Hz), 2.0-2.1 (2H, m), 2.8-2.95 (1H, m), 3.6-3.7 (4H, m), 4.04 (2H, t, J=6.5 Hz), 4.51 (2H, s), 6.75-6.85 (2H, m), 7.05-7.15 (2H, m), 7.2-7.35 (5H, m)

Reference Example 12

4-{[4-(2-Benzyloxyethoxy)phenyl]methyl}-1,2-dihydro-5-isopropyl-3H-pyrazol-3-one The title compound was prepared in a similar manner to that described in Reference Example 11 using [4-(2-benzyloxyethoxy)phenyl]methanol instead of [4-(3-benzyloxypropoxy)phenyl]methanol.

$^1$H-NMR (CDCl$_3$) δ ppm:
1.14 (6H, d, J=7.3 Hz), 2.8-2.95 (1H, m), 3.66 (2H, s), 3.75-3.85 (2H, m), 4.05-4.15 (2H, m), 4.62 (2H, s), 6.75-6.85 (2H, m), 7.1-7.15 (2H, m), 7.25-7.4 (5H, m)

Reference Example 13

4-{[4-(4-Benzyloxybutoxy)phenyl]methyl}-1,2-dihydro-5-isopropyl-3H-pyrazol-3-one The title compound was prepared in a similar manner to that described in Reference Example 11 using [4-(4-benzyloxybutoxy)phenyl]methanol instead of [4-(3-benzyloxypropoxy)phenyl]methanol.

$^1$H-NMR (CDCl$_3$) δ ppm:
1.14 (6H, d, J=7.0 Hz), 1.7-1.9 (4H, m), 2.8-2.95 (1H, m), 3.53 (2H, t, J=6.1 Hz), 3.66 (2H, s), 3.93 (2H, t, J=6.3 Hz), 4.51 (2H, s), 6.7-6.8 (2H, m), 7.05-7.15 (2H, m), 7.2-7.35 (5H, m)

Reference Example 14

4-{[4-(3-Benzyloxypropoxy)-2-methylphenyl]methyl}-1,2-dihydro-5-isopropyl-3H-pyrazol-3-one The title compound was prepared in a similar manner to that described in Reference Example 11 using [4-(3-benzyloxypropoxy)-2-methylphenyl]methanol instead of [4-(3-benzyloxypropoxy)phenyl]methanol.

$^1$H-NMR (DMSO-d$_6$) δ ppm:
1.04 (6H, d, J=7.0 Hz), 1.9-2.0 (2H, m), 2.24 (3H, s), 2.65-2.8 (1H, m), 3.44 (2H, s), 3.56 (2H, t, J=6.4 Hz), 3.97 (2H, t, J=6.1 Hz), 4.47 (2H, s), 6.6 (1H, dd, J=8.6 Hz, 2.6 Hz), 6.69 (1H, d, J=2.6 Hz), 6.78 (1H, d, J=8.6 Hz), 7.2-7.35 (5H, m)

Reference Example 15

4-[(4-Benzyloxyphenyl)methyl]-1,2-dihydro-5-isopropyl-3H-pyrazol-3-one

The title compound was prepared in a similar manner to that described in Reference Example 11 using (4-benzyloxyphenyl)methanol instead of [4-(3-benzyloxypropoxy)phenyl]methanol.

$^1$H-NMR (DMSO-d$_6$) δ ppm:
1.06 (6H, d, J=6.8 Hz), 2.75-2.9 (1H, m), 3.5 (2H, s), 5.03 (2H, s), 6.85-6.9 (2H, m), 7.0-7.1 (2H, m), 7.25-7.45 (5H, m)

Reference Example 16

4-{[4-(2-Benzyloxyethoxy)-2-methylphenyl]methyl}-1,2-dihydro-5-isopropyl-3H-pyrazol-3-one The title compound was prepared in a similar manner to that described in Reference Example 11 using [4-(2-benzyloxyethoxy)-2-methylphenyl]methanol instead of [4-(3-benzyloxypropoxy)phenyl]methanol.

$^1$H-NMR (CDCl$_3$) δ ppm:
1.1 (6H, d, J=6.9 Hz), 2.3 (3H, s), 2.75-2.9 (1H, m), 3.6 (2H, s), 3.75-3.85 (2H, m), 4.05-4.15 (2H, m), 4.62 (2H, s), 6.64 (1H, dd, J=8.5 Hz, 2.5 Hz), 6.74 (1H, d, J=2.5 Hz), 6.94 (1H, d, J=8.5 Hz), 7.25-7.4 (5H, m)

Reference Example 17

3-(2,3,4,6-Tetra-O-acetyl-β-D-glucopyranosyloxy)-4-{[4-(3-benzyloxypropoxy)phenyl]methyl}-5-isopropyl-1H-pyrazole To a solution of 4-{[4-(3-benzyloxypropoxy)phenyl]methyl}-1,2-dihydro-5-isopropyl-3H-pyrazol-3-one (5.08 g), acetobromo-α-D-glucose (5.49 g) and benzyltri(n-butyl)ammonium chloride (2.08 g) in dichloromethane (40 mL) was added 5 mol/L aqueous sodium hydroxide solution (8 mL), and the mixture was stirred at room temperature for 3 hours. The reaction mixture was purified by column chromatography on aminopropylated silica gel (eluent: n-hexane/ethyl acetate=1/1-1/3-1/5). The purified material was further purified by column chromatography on silica gel (eluent: n-hexane/ethyl acetate=1/1-1/2-1/4) to give the title compound (2.75 g).

$^1$H-NMR (CDCl$_3$) δ ppm:
1.15 (6H, d, J=7.1 Hz), 1.87 (3H, s), 1.95-2.1 (11H, m), 2.85-2.95 (1H, m), 3.5-3.7 (4H, m), 3.8-3.9 (1H, m), 4.03 (2H, t, J=6.4 Hz), 4.15 (1H, dd, J=12.3 Hz, 2.4 Hz), 4.31 (1H, dd, J=12.3 Hz, 4.1 Hz), 4.51 (2H, s), 5.15-5.3 (3H, m), 5.55-5.65 (1H, m), 6.7-6.8 (2H, m), 7.0-7.05 (2H, m), 7.2-7.35 (5H, m)

Reference Example 18

3-(2,3,4,6-Tetra-O-acetyl-β-D-glucopyranosyloxy)-4-{[4-(2-benzyloxyethoxy)phenyl]methyl}-5-isopropyl-1H-pyrazole The title compound was prepared in a similar manner to that described in Reference Example 17 using 4-{[4-(2-benzyloxyethoxy)phenyl]methyl}-1,2-dihydro-5-isopropyl-3H-pyrazol-3-one instead of 4-{[4-(3-benzyloxypropoxy)phenyl]methyl}-1,2-dihydro-5-isopropyl-3H-pyrazol-3-one.

$^1$H-NMR (CDCl$_3$) δ ppm:
1.14 (6H, d, J=6.8 Hz), 1.88 (3H, s), 2.01 (3H, s), 2.03 (3H, s), 2.06 (3H, s), 2.8-2.95 (1H, m), 3.57 (1H, d, J=15.8 Hz), 3.63 (1H, d, J=15.8 Hz), 3.75-3.9 (3H, m), 4.05-4.2 (3H, m), 4.31 (1H, dd, J=12.4 Hz, 4.1 Hz), 4.62 (2H, s), 5.15-5.3 (3H, m), 5.55-5.6 (1H, m), 6.75-6.85 (2H, m), 7.0-7.05 (2H, m), 7.25-7.4 (5H, m)

Reference Example 19

3-(2,3,4,6-Tetra-O-acetyl-β-D-glucopyranosyloxy)-4-{[4-(4-benzyloxybutoxy)phenyl]methyl}-5-isopropyl-1H-pyrazole The title compound was prepared in a similar manner to that described in Reference Example 17 using 4-{[4-(4-benzyloxybutoxy)phenyl]methyl}-1,2-dihydro-5-isopropyl-3H-pyrazol-3-one instead of 4-{[4-(3-benzyloxypropoxy)phenyl]-methyl}-1,2-dihydro-5-isopropyl-3H-pyrazol-3-one.

$^1$H-NMR (CDCl$_3$) δ ppm:
1.15 (6H, d, J=6.7 Hz), 1.7-1.9 (7H, m), 2.01 (3H, s), 2.03 (3H, s), 2.06 (3H, s), 2.85-2.95 (1H, m), 3.5-3.6 (3H, m), 3.62 (1H, d, J=16.3 Hz), 3.8-3.9 (1H, m), 3.92 (2H, t, J=6.5 Hz), 4.1-4.2 (1H, m), 4.31 (1H, dd, J=12.3 Hz, 4.1 Hz), 4.51 (2H, s), 5.15-5.3 (3H, m), 5.55-5.65 (1H, m), 6.7-6.8 (2H, m), 6.95-7.05 (2H, m), 7.2-7.4 (5H, m)

Reference Example 20

3-(2,3,4,6-Tetra-O-acetyl-β-D-glucopyranosyloxy)-4-{[4-(3-benzyloxypropoxy)-2-methylphenyl]methyl}-5-isopropyl-1H-pyrazole The title compound was prepared in a similar manner to that described in Reference Example 17 using 4-{[4-(3-benzyloxypropoxy)-2-methylphenyl]methyl}-1,2-dihydro-5-isopropyl-3H-pyrazol-3-one instead of 4-{[4-(3-benzyloxypropoxy)phenyl]methyl}-1,2-dihydro-5-isopropyl-3H-pyrazol-3-one.

$^1$H-NMR (CDCl$_3$) δ ppm:
1.05-1.15 (6H, m), 1.8 (3H, s), 1.9-2.15 (11H, m), 2.25 (3H, s), 2.75-2.85 (1H, m), 3.49 (1H, d, J=16.4 Hz), 3.59 (1H, d, J=16.4 Hz), 3.64 (2H, t, J=6.3 Hz), 3.8-3.9 (1H, m), 4.0-4.05 (2H, m), 4.1-4.15 (1H, m), 4.3 (1H, dd, J=12.2 Hz, 4.1 Hz), 4.51 (2H, s), 5.15-5.3 (3H, m), 5.55 (1H, d, J=7.8 Hz), 6.57 (1H, dd, J=8.4 Hz, 2.6 Hz), 6.68 (1H, d, J=2.6 Hz), 6.79 (1H, d, J=8.4 Hz), 7.2-7.4 (5H, m)

Reference Example 21

3-(2,3,4,6-Tetra-O-acetyl-β-D-glucopyranosyloxy)-4-[(4-benzyloxyphenyl)methyl]-5-isopropyl-1H-pyrazole The title compound was prepared in a similar manner to that described in Reference Example 17 using 4-[(4-benzyloxyphenyl)methyl]-1,2-dihydro-5-isopropyl-3H-pyrazol-3-one instead of 4-{[4-(3-benzyloxypropoxy)phenyl]methyl}-1,2-dihydro-5-isopropyl-3H-pyrazol-3-one.

$^1$H-NMR (CDCl$_3$) δ ppm:
1.16 (6H, d, J=7.1 Hz), 1.85 (3H, s), 2.01 (3H, s), 2.03 (3H, s), 2.06 (3H, s), 2.85-2.95 (1H, m), 3.57 (1H, d, J=15.9 Hz), 3.63 (1H, d, J=15.9 Hz), 3.8-3.9 (1H, m), 4.1-4.2 (1H, m), 4.31 (1H, dd, J=12.6 Hz, 3.9 Hz), 5.02 (2H, s), 5.15-5.3 (3H, m), 5.55-5.65 (1H, m), 6.8-6.9 (2H, m), 7.0-7.1 (2H, m), 7.25-7.45 (5H, m)

Reference Example 22

3-(2,3,4,6-Tetra-O-acetyl-β-D-glucopyranosyloxy)-4-{[4-(2-benzyloxyethoxy)-2-methylphenyl]methyl}-5-isopropyl-1H-pyrazole The title compound was prepared in a similar manner to that described in Reference Example 17 using 4-{[4-(2-benzyloxyethoxy)-2-methylphenyl]methyl}-1,2-dihydro-5-isopropyl-3H-pyrazol-3-one instead of 4-{[4-(3-benzyloxypropoxy)phenyl]methyl}-1,2-dihydro-5-isopropyl-3H-pyrazol-3-one.

$^1$H-NMR (CDCl$_3$) δ ppm:
1.05-1.15 (6H, m), 1.81 (3H, s), 1.99 (3H, s), 2.02 (3H, s), 2.06 (3H, s), 2.25 (3H, s), 2.7-2.85 (1H, m), 3.5 (1H, d, J=16.6 Hz), 3.59 (1H, d, J=16.6 Hz), 3.75-3.9 (3H, m), 4.05-4.2 (3H, m), 4.3 (1H, dd, J=12.2 Hz, 4.1 Hz), 4.62 (2H, s), 5.1-5.3 (3H, m), 5.55 (1H, d, J=8.0 Hz), 6.6 (1H, dd, J=8.5 Hz, 2.5 Hz), 6.71 (1H, d, J=2.5 Hz), 6.8 (1H, d, J=8.5 Hz), 7.25-7.4 (5H, m)

Reference Example 23

3-(2,3,4,6-Tetra-O-acetyl-β-D-glucopyranosyloxy)-4-{[4-(3-hydroxypropoxy)phenyl]methyl}-5-isopropyl-1H-pyrazole 3-(2,3,4,6-Tetra-O-acetyl-β-D-glucopyranosyloxy)-4-{[4-(3-benzyloxypropoxy)phenyl]methyl}-5-isopropyl-1H-pyrazole (2.75 g) was dissolved in a mixed solvent of methanol (20 mL) and tetrahydrofuran (9 mL). To the solution was added 10% palladium-carbon powder (550 mg), and the mixture was stirred at room temperature under a hydrogen atmosphere for 4 hours. The insoluble material was removed by filtration, and the solvent of the filtrate was removed under reduced pressure to give the title compound (2.4 g).

$^1$H-NMR (CDCl$_3$) δ ppm:
1.1-1.2 (6H, m), 1.89 (3H, s), 1.95-2.1 (11H, m), 2.85-2.95 (1H, m), 3.58 (1H, d, J=16.3 Hz), 3.63 (1H, d, J=16.3 Hz), 3.8-3.9 (3H, m), 4.05-4.1 (2H, m), 4.13 (1H, dd, J=12.1 Hz, 2.1 Hz), 4.3 (1H, dd, J=12.1 Hz, 4.1 Hz), 5.15-5.3 (3H, m), 5.58 (1H, d, J=7.3 Hz), 6.7-6.8 (2H, m), 7.0-7.05 (2H, m)

Reference Example 24

3-(2,3,4,6-Tetra-O-acetyl-β-D-glucopyranosyloxy)-4-{[4-(2-hydroxyethoxy)phenyl]methyl}-5-isopropyl-1H-pyrazole The title compound was prepared in a similar manner to that described in Reference Example 23 using 3-(2,3,4,6-tetra-O-acetyl-β-D-glucopyranosyloxy)-4-{[4-(2-benzyloxyethoxy)phenyl]methyl}-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) δ ppm:
1.16 (6H, d, J=6.8 Hz), 1.89 (3H, s), 2.01 (3H, s), 2.03 (3H, s), 2.06 (3H, s), 2.85-2.95 (1H, m), 3.58 (1H, d, J=16.0 Hz), 3.63 (1H, d, J=16.0 Hz), 3.8-3.9 (1H, m), 3.9-4.0 (2H, m), 4.0-4.1 (2H, m), 4.1-4.2 (1H, m), 4.25-4.35 (1H, m), 5.15-5.3 (3H, m), 5.55-5.65 (1H, m), 6.75-6.85 (2H, m), 7.0-7.1 (2H, m)

Reference Example 25

3-(2,3,4,6-Tetra-O-acetyl-β-D-glucopyranosyloxy)-4-{[4-(4-hydroxybutoxy)phenyl]methyl}-5-isopropyl-1H-pyrazole The title compound was prepared in a similar manner to that described in Reference Example 23 using 3-(2,3,4,6-tetra-O-acetyl-β-D-glucopyranosyloxy)-4-{[4-(4-benzyloxybutoxy)phenyl]methyl}-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) 1 ppm:
1.1-1.2 (6H, m), 1.65-1.8 (2H, m), 1.8-1.95 (5H, m), 2.01 (3H, s), 2.03 (3H, s), 2.06 (3H, s), 2.85-2.95 (1H, m), 3.57 (1H, d, J=16.2 Hz), 3.63 (1H, d, J=16.2 Hz), 3.71 (2H, t, J=6.3 Hz), 3.8-3.9 (1H, m), 3.96 (2H, t, J=6.2 Hz), 4.14 (1H, dd, J=12.4 Hz, 2.4 Hz), 4.31 (1H, dd, J=12.4 Hz, 4.1 Hz), 5.15-5.3 (3H, m), 5.55-5.65 (1H, m), 6.7-6.8 (2H, m), 7.0-7.05 (2H, m)

Reference Example 26

3-(2,3,4,6-Tetra-O-acetyl-β-D-glucopyranosyloxy)-4-{[4-(3-hydroxypropoxy)-2-methylphenyl]methyl}-5-isopropyl-1H-pyrazole The title compound was prepared in a similar manner to that described in Reference Example 23 using 3-(2,3,4,6-tetra-O-acetyl-β-D-glucopyranosyloxy)-4-{[4-(3-benzyloxypropoxy)-2-methylphenyl]methyl}-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) δ ppm:
1.1-1.2 (6H, m), 1.83 (3H, s), 1.95-2.1 (11H, m), 2.26 (3H, s), 2.75-2.9 (1H, m), 3.5 (1H, d, J=16.5 Hz), 3.58 (1H, d, J=16.5 Hz), 3.75-3.9 (3H, m), 4.0-4.15 (3H, m), 4.28 (1H, dd, J=12.3 Hz, 4.1 Hz), 5.1-5.3 (3H, m), 5.55 (1H, d, J=7.9 Hz), 6.59 (1H, dd, J=8.3 Hz, 2.5 Hz), 6.69 (1H, d, J=2.5 Hz), 6.81 (1H, d, J=8.3 Hz)

Reference Example 27

3-(2,3,4,6-Tetra-O-acetyl-β-D-glucopyranosyloxy)-4-[(4-hydroxyphenyl)methyl]-5-isopropyl-1H-pyrazole The title compound was prepared in a similar manner to that described in Reference Example 23 using 3-(2,3,4,6-tetra-O-acetyl-β-D-glucopyranosyloxy)-4-[(4-benzyloxyphenyl)methyl]-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) δ ppm:
1.1-1.2 (6H, m), 1.89 (3H, s), 2.0 (3H, s), 2.02 (3H, s), 2.06 (3H, s), 2.85-3.0 (1H, m), 3.57 (1H, d, J=16.2 Hz), 3.61 (1H, d, J=16.2 Hz), 3.8-3.9 (1H, m), 4.05-4.2 (1H, m), 4.29 (1H, dd, J=12.5 Hz, 4.0 Hz), 4.91 (1H, brs), 5.15-5.3 (3H, m), 5.55-5.6 (1H, m), 6.65-6.75 (2H, m), 6.95-7.05 (2H, m)

Reference Example 28

3-(2,3,4,6-Tetra-O-acetyl-β-D-glucopyranosyloxy)-4-{[4-(2-hydroxyethoxy)-2-methylphenyl]methyl}-5-isopropyl-1H-pyrazole The title compound was prepared in a similar manner to that described in Reference Example 23 using 3-(2,3,4,6-tetra-O-acetyl-β-D-glucopyranosyloxy)-4-{[4-(2-benzyloxyethoxy)-2-methylphenyl]methyl}-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) δ ppm:
1.1-1.2 (6H, m), 1.83 (3H, s), 1.99 (3H, s), 2.02 (3H, s), 2.06 (3H, s), 2.26 (3H, s), 2.75-2.9 (1H, m), 3.51 (1H, d, J=16.9 Hz), 3.59 (1H, d, J=16.9 Hz), 3.8-3.85 (1H, m), 3.9-3.95 (2H, m), 4.0-4.1 (2H, m), 4.11 (1H, dd, J=12.5 Hz, 2.5 Hz), 4.28 (1H, dd, J=12.5 Hz, 4.1 Hz), 5.1-5.3 (3H, m), 5.55 (1H, d, J=7.9 Hz), 6.6 (1H, dd, J=8.3 Hz, 2.7 Hz), 6.71 (1H, d, J=2.7 Hz), 6.82 (1H, d, J=8.3 Hz)

Reference Example 29

3-(2,3,4,6-Tetra-O-acetyl-β-D-glucopyranosyloxy)-4-{[4-(3-azidopropoxy)phenyl]methyl}-5-isopropyl-1H-pyrazole To a solution of 3-(2,3,4,6-tetra-O-acetyl-β-D-glucopyranosyloxy)-4-{[4-(3-hydroxypropoxy)phenyl]methyl}-5-isopropyl-1H-pyrazole (2.21 g) in dichloromethane (35 mL) were added triethylamine (0.65 mL) and methanesulfonyl chloride (0.33 mL), and the mixture was stirred at room temperature overnight. The reaction mixture was poured into 0.5 mol/L hydrochloric acid, and the resulting mixture was extracted with ethylacetate. The organic layer was washed with water, and dried over anhydrous magnesium sulfate. The solvent was removed under reduced pressure to give 3-(2,3,4,6-tetra-O-acetyl-β-D-glucopyranosyloxy)-5-isopropyl-4-({4-[3-(methanesulfonyloxy)propoxy]phenyl}methyl)-1H-pyrazole. This material was dissolved in N,N-dimethylformamide (20 mL). To the solution was added sodium azide (0.46 g), and the mixture was stirred at 100° C. for 1.5 hours. The reaction mixture was poured into water, and the resulting mixture was extracted with ethylacetate. The organic layer was washed with water three times, and dried over anhydrous magnesium sulfate. The solvent was removed under reduced pressure, and the residue was purified by column chromatography on silica gel (eluent: n-hexane/ethyl acetate 1/1-1/3) to give the title compound (1.6 g).

$^1$H-NMR (CDCl$_3$) δ ppm:
1.1-1.2 (6H, m), 1.89 (3H, s), 1.95-2.1 (11H, m), 2.85-2.95 (1H, m), 3.5 (2H, t, J=6.7 Hz), 3.57 (1H, d, J=15.9 Hz), 3.63 (1H, d, J=15.9 Hz), 3.8-3.9 (1H, m), 4.0 (2H, t, J=5.9 Hz), 4.1-4.2 (1H, m), 4.31 (1H, dd, J=12.2 Hz, 4.2 Hz), 5.15-5.3 (3H, m), 5.55-5.65 (1H, m), 6.7-6.8 (2H, m), 7.0-7.1 (2H, m)

Reference Example 30

3-(2,3,4,6-Tetra-O-acetyl-β-D-glucopyranosyloxy)-4-{[4-(2-azidoethoxy)phenyl]methyl}-5-isopropyl-1H-pyrazole The title compound was prepared in a similar manner to that described in Reference Example 29 using 3-(2,3,4,6-tetra-O-acetyl-β-D-glucopyranosyloxy)-4-{[4-(2-hydroxyethoxy)phenyl]methyl}-5-isopropyl-1H-pyrazole instead of 3-(2,3,4,6-tetra-O-acetyl-β-D-glucopyranosyloxy)-4-{[4-(3-hydroxypropoxy)phenyl]methyl}-5-isopropyl-1H-pyrazole.

$^1$H-NMR (CDCl$_3$) δ ppm:
1.1-1.2 (6H, m), 1.89 (3H, s), 2.01 (3H, s), 2.03 (3H, s), 2.06 (3H, s), 2.85-2.95 (1H, m), 3.5-3.7 (4H, m), 3.8-3.9 (1H, m), 4.11 (2H, t, J=5.1 Hz), 4.14 (1H, dd, J=12.2 Hz, 2.2 Hz), 4.31 (1H, dd, J=12.2 Hz, 4.0 Hz), 5.15-5.3 (3H, m), 5.55-5.65 (1H, m), 6.75-6.85 (2H, m), 7.0-7.1 (2H, m)

Reference Example 31

3-(2,3,4,6-Tetra-O-acetyl-β-D-glucopyranosyloxy)-4-{[4-(4-azidobutoxy)phenyl]methyl}-5-isopropyl-1H-pyrazole The title compound was prepared in a similar manner to that described in Reference Example 29 using 3-(2,3,4,6-tetra-O-acetyl-β-D-glucopyranosyloxy)-4-{[4-(4-hydroxybutoxy)phenyl]methyl}-5-isopropyl-1H-pyrazole instead of 3-(2,3,4,6-tetra-O-acetyl-β-D-glucopyranosyloxy)-4-{[4-(3-hydroxypropoxy)phenyl]methyl}-5-isopropyl-1H-pyrazole.

$^{1}$H-NMR (CDCl$_3$) δ ppm:
1.1-1.2 (6H, m), 1.7-1.95 (7H, m), 2.01 (3H, s), 2.03 (3H, s), 2.06 (3H, s), 2.85-2.95 (1H, m), 3.35 (2H, t, J=6.8 Hz), 3.57 (1H, d, J=16.0 Hz), 3.63 (1H, d, J=16.0 Hz), 3.8-3.9 (1H, m), 3.94 (2H, t, J=6.0 Hz), 4.14 (1H, dd, J=12.6 Hz, 2.5 Hz), 4.31 (1H, dd, J=12.6 Hz, 4.1 Hz), 5.15-5.3 (3H, m), 5.55-5.65 (1H, m), 6.7-6.8 (2H, m), 7.0-7.1 (2H, m)

Reference Example 32

3-(2,3,4,6-Tetra-O-acetyl-β-D-glucopyranosyloxy)-4-{[4-(3-azidopropoxy)-2-methylphenyl]methyl}-5-isopropyl-1H-pyrazole The title compound was prepared in a similar manner to that described in Reference Example 29 using 3-(2,3,4,6-tetra-O-acetyl-β-D-glucopyranosyloxy)-4-{[4-(3-hydroxypropoxy)-2-methylphenyl]methyl}-5-isopropyl-1H-pyrazole instead of 3-(2,3,4,6-tetra-O-acetyl-β-D-glucopyranosyloxy)-4-{[4-(3-hydroxypropoxy)phenyl]methyl}-5-isopropyl-1H-pyrazole.

$^{1}$H-NMR (CDCl$_3$) δ ppm:
1.05-1.15 (6H, m), 1.81 (3H, s), 1.95-2.1 (11H, m), 2.26 (3H, s), 2.75-2.9 (1H, m), 3.45-3.55 (3H, m), 3.59 (1H, d, J=16.5 Hz), 3.8-3.9 (1H, m), 3.95-4.05 (2H, m), 4.05-4.15 (1H, m), 4.29 (1H, dd, J=12.6 Hz, 4.1 Hz), 5.1-5.3 (3H, m), 5.55 (1H, d, J=7.9 Hz), 6.57 (1H, dd, J=8.7 Hz, 2.6 Hz), 6.68 (1H, d, J=2.6 Hz), 6.8 (1H, d, J=8.7 Hz)

Reference Example 33

3-(2,3,4,6-Tetra-O-acetyl-β-D-glucopyranosyloxy)-4-{[4-(2-azidoethoxy)-2-methylphenyl]methyl}-5-isopropyl-1H-pyrazole The title compound was prepared in a similar manner to that described in Reference Example 29 using 3-(2,3,4,6-tetra-O-acetyl-β-D-glucopyranosyloxy)-4-{[4-(2-hydroxyethoxy)-2-methylphenyl]methyl}-5-isopropyl-1H-pyrazole instead of 3-(2,3,4,6-tetra-O-acetyl-β-D-glucopyranosyloxy)-4-{[4-(3-hydroxypropoxy)phenyl]methyl}-5-isopropyl-1H-pyrazole.

$^{1}$H-NMR (CDCl$_3$) δ ppm:
1.05-1.2 (6H, m), 1.82 (3H, s), 2.0 (3H, s), 2.02 (3H, s), 2.06 (3H, s), 2.27 (3H, s), 2.75-2.9 (1H, m), 3.45-3.65 (4H, m), 3.8-3.9 (1H, m), 4.05-4.15 (3H, m), 4.29 (1H, dd, J=12.2 Hz, 4.2 Hz), 5.1-5.3 (3H, m), 5.56 (1H, d, J=7.7 Hz), 6.6 (1H, dd, J=8.3 Hz, 2.6 Hz), 6.71 (1H, d, J=2.6 Hz), 6.82 (1H, d, J=8.3 Hz)

Example 1

3-(2,3,4,6-Tetra-O-acetyl-β-D-glucopyranosyloxy)-4-{[4-(3-aminopropoxy)phenyl]methyl}-5-isopropyl-1H-pyrazole To a solution of 3-(2,3,4,6-tetra-O-acetyl-β-D-glucopyranosyloxy)-4-{[4-(3-azidopropoxy)phenyl]methyl}-5-isopropyl-1H-pyrazole (1.6 g) in tetrahydrofuran (25 mL) was added 10% palladium-carbon powder (300 mg), and the mixture was stirred at room temperature under a hydrogen atmosphere for 2 hours. The insoluble material was removed by filtration, and the solvent of the filtrate was removed under reduced pressure to give the title compound (1.5 g).

$^{1}$H-NMR (CD$_3$OD) δ ppm:
1.1-1.2 (6H, m), 1.85-2.0 (8H, m), 2.01 (3H, s), 2.02 (3H, s), 2.8-3.0 (3H, m), 3.6 (2H, s), 3.9-4.0 (1H, m), 4.01 (2H, t, J=6.0 Hz), 4.11 (1H, dd, J=12.4 Hz, 2.5 Hz), 4.29 (1H, dd, J=12.4 Hz, 3.9 Hz), 5.05-5.15 (2H, m), 5.25-5.35 (1H, m), 5.48 (1H, d, J=8.2 Hz), 6.75-6.85 (2H, m), 7.0-7.05 (2H, m)

Example 2

3-(2,3,4,6-Tetra-O-acetyl-β-D-glucopyranosyloxy)-4-{[4-(2-aminoethoxy)phenyl]methyl}-5-isopropyl-1H-pyrazole The title compound was prepared in a similar manner to that described in Example 1 using 3-(2,3,4,6-tetra-O-acetyl-β-D-glucopyranosyloxy)-4-{[4-(2-azidoethoxy)phenyl]methyl}-5-isopropyl-1H-pyrazole instead of 3-(2,3,4,6-tetra-O-acetyl-β-D-glucopyranosyloxy)-4-{[4-(3-azidopropoxy)phenyl]methyl}-5-isopropyl-1H-pyrazole.

$^{1}$H-NMR (CDCl$_3$) δ ppm:
1.16 (6H, d, J=6.9 Hz), 1.89 (3H, s), 2.01 (3H, s), 2.03 (3H, s), 2.06 (3H, s), 2.85-2.95 (1H, m), 3.05 (2H, t, J=5.0 Hz), 3.57 (1H, d, J=16.0 Hz), 3.63 (1H, d, J=16.0 Hz), 3.8-3.9 (1H, m), 3.94 (2H, t, J=5.0 Hz), 4.1-4.2 (1H, m), 4.25-4.35 (1H, m), 5.15-5.3 (3H, m), 5.5-5.65 (1H, m), 6.75-6.8 (2H, m), 7.0-7.1 (2H, m)

Example 3

3-(2,3,4,6-Tetra-O-acetyl-β-D-glucopyranosyloxy)-4-{[4-(4-aminobutoxy)phenyl]methyl}-5-isopropyl-1H-pyrazole The title compound was prepared in a similar manner to that described in Example 1 using 3-(2,3,4,6-tetra-O-acetyl-β-D-glucopyranosyloxy)-4-{[4-(4-azidobutoxy)phenyl]methyl}-5-isopropyl-1H-pyrazole instead of 3-(2,3,4,6-tetra-O-acetyl-β-D-glucopyranosyloxy)-4-{[4-(3-azidopropoxy)phenyl]methyl}-5-isopropyl-1H-pyrazole.

$^{1}$H-NMR (CDCl$_3$) δ ppm:
1.15 (6H, d, J=6.8 Hz), 1.5-1.65 (2H, m), 1.7-1.85 (2H, m), 1.88 (3H, s), 2.01 (3H, s), 2.03 (3H, s), 2.06 (3H, s), 2.76 (2H, t, J=7.1 Hz), 2.85-2.95 (1H, m), 3.56 (1H, d, J=15.7 Hz), 3.62 (1H, d, J=15.7 Hz), 3.8-3.9 (1H, m), 3.92 (2H, t, J=6.5 Hz), 4.1-4.2 (1H, m), 4.31 (1H, dd, J=12.2 Hz, 4.1 Hz), 5.15-5.3 (3H, m), 5.55-5.65 (1H, m), 6.7-6.8 (2H, m), 6.95-7.05 (2H, m)

Example 4

3-(2,3,4,6-Tetra-O-acetyl-β-D-glucopyranosyloxy)-4-{[4-(3-aminopropoxy)-2-methylphenyl]methyl}-5-isopropyl-1H-pyrazole The title compound was prepared in a similar manner to that described in Example 1 using 3-(2,3,4,6-tetra-O-acetyl-β-D-glucopyranosyloxy)-4-{[4-(3-azidopropoxy)-2-methylphenyl]methyl}-5-isopropyl-1H-pyrazole instead of 3-(2,3,4,6-tetra-O-acetyl-β-D-glucopyranosyloxy)-4-{[4-(3-azidopropoxy)phenyl]methyl}-5-isopropyl-1H-pyrazole.

$^{1}$H-NMR (CDCl$_3$) δ ppm:
1.05-1.15 (6H, m), 1.82 (3H, s), 1.85-1.95 (2H, m), 1.99 (3H, s), 2.02 (3H, s), 2.06 (3H, s), 2.25 (3H, s), 2.75-2.95 (3H, m), 3.5 (1H, d, J=16.5 Hz), 3.58 (1H, d, J=16.5 Hz), 3.75-3.9 (1H, m), 3.9-4.05 (2H, m), 4.05-4.2 (1H, m), 4.29 (1H, dd, J=12.6 Hz, 4.0 Hz), 5.1-5.3 (3H, m), 5.5-5.6 (1H, m), 6.58 (1H, dd, J=8.4 Hz, 2.7 Hz), 6.68 (1H, d, J=2.7 Hz), 6.8 (1H, d, J=8.4 Hz)

Example 5

3-(2,3,4,6-Tetra-O-acetyl-β-D-glucopyranosyloxy)-4-{[4-(2-aminoethoxy)-2-methylphenyl]methyl}-5-isopropyl-1H-pyrazole The title compound was prepared in a similar manner to that described in Example 1 using 3-(2,3,4,6-tetra-O-acetyl-β-D-glucopyranosyloxy)-4-{[4-(2-azidoethoxy)-2-methylphenyl]methyl}-5-isopropyl-1H-pyrazole instead of 3-(2,3,4,6-tetra-O-acetyl-β-D-glucopyranosyloxy)-4-{[4-(3-azidopropoxy)phenyl]methyl}-5-isopropyl-1H-pyrazole.

$^1$H-NMR (CDCl$_3$) δ ppm:
1.05-1.15 (6H, m), 1.82 (3H, s), 2.0 (3H, s), 2.02 (3H, s), 2.06 (3H, s), 2.26 (3H, s), 2.75-2.85 (1H, m), 3.0-3.1 (2H, m), 3.5 (1H, d, J=16.3 Hz), 3.59 (1H, d, J=16.3 Hz), 3.8-3.9 (1H, m), 3.9-4.0 (2H, m), 4.12 (1H, dd, J=12.4 Hz, 2.4 Hz), 4.29 (1H, dd, J=12.4 Hz, 4.0 Hz), 5.15-5.3 (3H, m), 5.55 (1H, d, J=7.9 Hz), 6.59 (1H, dd, J=8.5 Hz, 2.6 Hz), 6.7 (1H, d, J=2.6 Hz), 6.81 (1H, d, J=8.5 Hz)

Example 6

4-{[4-(3-Aminopropoxy)phenyl]methyl}-3-(β-D-glucopyranosyloxy)-5-isopropyl-1H-pyrazole To a solution of 3-(2,3,4,6-tetra-O-acetyl-β-D-glucopyranosyloxy)-4-{[4-(3-aminopropoxy)phenyl]methyl}-5-isopropyl-1H-pyrazole (0.1 g) in methanol (2 mL) was added sodium methoxide (28% methanol solution, 0.062 mL), and the mixture was stirred at room temperature for 30 minutes. The reaction mixture was concentrated under reduced pressure, and the residue was purified by solid phase extraction on ODS (washing solvent: distilled water, eluent: methanol) to give the title compound (57 mg).

$^1$H-NMR (CD$_3$OD) δ ppm:
1.05-1.15 (6H, m), 1.8-1.95 (2H, m), 2.8 (2H, t, J=7.0 Hz), 2.85-2.95 (1H, m), 3.25-3.45 (4H, m), 3.6-3.8 (3H, m), 3.8-3.9 (1H, m), 3.99 (2H, t, J=6.0 Hz), 5.0-5.1 (1H, m), 6.7-6.85 (2H, m), 7.05-7.15 (2H, m)

Example 7

4-{[4-(2-Aminoethoxy)phenyl]methyl}-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-{[4-(2-aminoethoxy)phenyl]methyl}-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.15 (6H, m), 2.8-2.95 (1H, m), 2.96 (2H, t, J=5.4 Hz), 3.25-3.45 (4H, m), 3.6-3.7 (2H, m), 3.73 (1H, d, J=15.9 Hz), 3.8-3.9 (1H, m), 3.95 (2H, t, J=5.4 Hz), 5.05-5.1 (1H, m), 6.75-6.85 (2H, m), 7.05-7.15 (2H, m)

Example 8

4-{[4-(4-Aminobutoxy)phenyl]methyl}-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-{[4-(4-aminobutoxy)phenyl]methyl}-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.2 (6H, m), 1.55-1.7 (2H, m), 1.7-1.85 (2H, m), 2.67 (2H, t, J=7.1 Hz), 2.8-2.95 (1H, m), 3.25-3.45 (4H, m), 3.6-3.7 (2H, m), 3.73 (1H, d, J=15.7 Hz), 3.8-3.9 (1H, m), 3.93 (2H, t, J=6.3 Hz), 5.0-5.15 (1H, m), 6.7-6.85 (2H, m), 7.05-7.15 (2H, m)

Example 9

4-{[4-(3-Aminopropoxy)-2-methylphenyl]methyl}-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-{[4-(3-aminopropoxy)-2-methylphenyl]methyl}-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.2 (6H, m), 1.85-2.0 (2H, m), 2.29 (3H, s), 2.7-2.9 (3H, m), 3.25-3.45 (4H, m), 3.55-3.75 (3H, m), 3.75-3.85 (1H, m), 4.0 (2H, t, J=5.9 Hz), 4.95-5.1 (1H, m), 6.62 (1H, dd, J=8.4 Hz, 2.5 Hz), 6.71 (1H, d, J=2.5 Hz), 6.85 (1H, d, J=8.4 Hz)

Example 10

3-(β-D-Glucopyranosyloxy)-5-isopropyl-4-({4-[3-(methanesulfonylamino)propoxy]phenyl}methyl)-1H-pyrazole To a solution of 3-(2,3,4,6-tetra-O-acetyl-β-D-glucopyranosyloxy)-4-{[4-(3-aminopropoxy)phenyl]methyl}-5-isopropyl-1H-pyrazole (0.36 g) in dichloromethane (6 mL) were added triethylamine (0.2 mL) and methanesulfonyl chloride (0.05 mL), and the mixture was stirred at room temperature overnight. The reaction mixture was poured into 0.5 mol/L hydrochloric acid, and the resulting mixture was extracted with ethylacetate. The organic layer was washed with water, and dried over anhydrous magnesium sulfate. The solvent was removed under reduced pressure, and the residue was purified by column chromatography on silica gel (eluent: n-hexane/ethyl acetate=1/3-ethyl acetate) to give 3-(2,3,4,6-tetra-O-acetyl-β-D-glucopyranosyloxy)-5-isopropyl-4-({4-[3-(methanesulfonylamino)propoxy]phenyl}methyl)-1H-pyrazole (255 mg). This material was dissolved in methanol (6 mL). To the solution was added sodium methoxide (28% methanol solution, 0.11 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (0.16 g).

$^1$H-NMR (CD$_3$OD) δ ppm:
1.05-1.15 (6H, m), 1.9-2.05 (2H, m), 2.8-2.95 (4H, m), 3.24 (2H, t, J=7.0 Hz), 3.3-3.45 (4H, m), 3.6-3.7 (2H, m), 3.73 (1H, d, J=16.0 Hz), 3.8-3.9 (1H, m), 4.01 (2H, t, J=6.1 Hz), 5.0-5.15 (1H, m), 6.75-6.85 (2H, m), 7.05-7.15 (2H, m)

Example 11

3-(β-D-Glucopyranosyloxy)-5-isopropyl-4-({4-[2-(methanesulfonylamino)ethoxy]phenyl}methyl)-1H-pyrazole The title compound was prepared in a similar manner to that described in Example 10 using 3-(2,3,4,6-tetra-O-acetyl-β-D-glucopyranosyloxy)-4-{[4-(2-aminoethoxy)phenyl]-methyl}-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.15 (6H, m), 2.8-2.95 (1H, m), 2.97 (3H, s), 3.25-3.45 (6H, m), 3.6-3.7 (2H, m), 3.74 (1H, d, J=15.9 Hz), 3.8-3.9 (1H, m), 4.03 (2H, t, J=5.4 Hz), 5.0-5.15 (1H, m), 6.8-6.85 (2H, m), 7.05-7.15 (2H, m)

Example 12

4-[(4-{(3-[N—(Carbamoylmethyl)-N-(methanesulfonyl)amino]-propoxy}-2-methylphenyl)methyl]-3-(β-D-glucopyranosyloxy)-5-isopropyl-1H-pyrazole The title compound was prepared in a similar manner to that described in Example 10 using 3-(2,3,4,6-tetra-O-acetyl-β-D-glucopyranosyloxy)-4-({4-[3-(carbamoylmethylamino)propoxy]-2-methylphenyl}methyl)-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.15 (6H, m), 1.95-2.1 (2H, m), 2.29 (3H, s), 2.75-2.85 (1H, m), 3.0 (3H, s), 3.25-3.4 (4H, m), 3.46 (2H, t, J=7.1 Hz), 3.6-3.75 (3H, m), 3.75-3.85 (1H, m), 3.95-4.05 (4H, m), 4.95-5.05 (1H, m), 6.62 (1H, dd, J=8.3 Hz, 2.7 Hz), 6.72 (1H, d, J=2.7 Hz), 6.85 (1H, d, J=8.3 Hz)

Example 13

4-({4-[3-(2-Aminoacetylamino)propoxy]phenyl}methyl)-3-(β-D-glucopyranosyloxy)-5-isopropyl-1H-pyrazole To a solution of 3-(2,3,4,6-tetra-O-acetyl-β-D-glucopyranosyloxy)-4-{[4-(3-aminopropoxy)phenyl]methyl}-5-isopropyl-1H-pyrazole (0.1 g) in N,N-dimethylformamide (1 mL) were added 2-benzyloxycarbonylaminoacetic acid (51 mg), 1-hydroxybenzotriazole (33 mg) and 1-ethyl-3-(3-dimethylaminopropyl)carbodiimide hydrochloride (93 mg), and the mixture was stirred at room temperature overnight. The reaction mixture was poured into water, and the resulting mixture was extracted with ethyl acetate. The organic layer was washed with water, a saturated aqueous sodium hydrogen carbonate solution, water and brine successively, dried over anhydrous magnesium sulfate and concentrated under reduced pressure. The residue was purified by column chromatography on silica gel (eluent: ethyl acetate-dichloromethane/methanol=30/1-20/1) to give 3-(2,3,4,6-tetra-O-acetyl-β-D-glucopyranosyloxy)-4-[(4-{3-[2-(benzyloxycarbonylamino)acetylamino]propoxy}phenyl)methyl]-5-isopropyl-1H-pyrazole (46 mg). This material was dissolved in methanol (3 mL). To the solution was added 10% palladium-carbon powder (20 mg), and the mixture was stirred at room temperature under a hydrogen atmosphere for 1.5 hours. The insoluble material was removed by filtration, and the solvent of the filtrate was removed under reduced pressure to give 3-(2,3,4,6-tetra-O-acetyl-β-D-glucopyranosyloxy)-4-({4-[3-(2-aminoacetylamino)propoxy]phenyl}methyl)-5-isopropyl-1H-pyrazole (34 mg). This material was dissolved in methanol (3 mL). To the solution was added sodium methoxide (28% methanol solution, 0.01 mL), and the mixture was stirred at room temperature for 30 minutes. The reaction mixture was concentrated under reduced pressure, and the residue was purified by solid phase extraction on ODS (washing solvent: distilled water, eluent: methanol) to give the title compound (23 mg).

$^1$H-NMR (CD$_3$OD) δ ppm:
1.1-1.15 (6H, m), 1.9-2.0 (2H, m), 2.85-2.95 (1H, m), 3.23 (2H, s), 3.25-3.45 (6H, m), 3.6-3.7 (2H, m), 3.73 (1H, d, J=16.0 Hz), 3.8-3.9 (1H, m), 3.98 (2H, t, J=6.1 Hz), 5.0-5.1 (1H, m), 6.75-6.85 (2H, m), 7.05-7.15 (2H, m)

Example 14

4-[(4-{3-[(S)-2-Aminopropionylamino]propoxy}phenyl)methyl]-3-(β-D-glucopyranosyloxy)-5-isopropyl-1H-pyrazole The title compound was prepared in a similar manner to that described in Example 13 using (S)-2-(benzyloxycarbonylamino)propionic acid instead of 2-benzyloxycarbonylaminoacetic acid.

$^1$H-NMR (CD$_3$OD) δ ppm:
1.05-1.2 (6H, m), 1.24 (3H, d, J=6.9 Hz), 1.9-2.0 (2H, m), 2.8-2.95 (1H, m), 3.25-3.45 (7H, m), 3.6-3.8 (3H, m), 3.8-3.9 (1H, m), 3.98 (2H, t, J=6.0 Hz), 5.0-5.15 (1H, m), 6.75-6.85 (2H, m), 7.0-7.15 (2H, m)

Example 15

4-({4-[3-(3-Aminopropionylamino)propoxy]phenyl}methyl)-3-(β-D-glucopyranosyloxy)-5-isopropyl-1H-pyrazole The title compound was prepared in a similar manner to that described in Example 13 using 3-(benzyloxycarbonylamino)propionic acid instead of 2-benzyloxycarbonylaminoacetic acid.

$^1$H-NMR (CD$_3$OD) δ ppm:
1.05-1.2 (6H, m), 1.85-2.0 (2H, m), 2.33 (2H, t, J=6.6 Hz), 2.75-2.95 (3H, m), 3.25-3.45 (6H, m), 3.6-3.7 (2H, m), 3.73 (1H, d, J=16.0 Hz), 3.8-3.9 (1H, m), 3.97 (2H, t, J=6.0 Hz), 5.0-5.1 (1H, m), 6.7-6.85 (2H, m), 7.05-7.15 (2H, m)

Example 16

4-[(4-(3-[(S)-2-Amino-3-hydroxypropionylamino]propoxy)phenyl)methyl]-3-(β-D-glucopyranosyloxy)-5-isopropyl-1H-pyrazole The title compound was prepared in a similar manner to that described in Example 13 using (S)-2-benzyloxycarbonylamino-3-hydroxypropionic acid instead of 2-benzyloxycarbonylaminoacetic acid.

$^1$H-NMR (CD$_3$OD) δ ppm:
1.05-1.2 (6H, m), 1.9-2.0 (2H, m), 2.8-2.95 (1H, m), 3.25-3.45 (7H, m), 3.55-3.7 (4H, m), 3.73 (1H, d, J=15.6 Hz), 3.8-3.9 (1H, m), 3.99 (2H, t, J=6.2 Hz), 5.0-5.15 (1H, m), 6.75-6.85 (2H, m), 7.05-7.15 (2H, m)

Example 17

4-[(4-{3-[(S)-2-Amino-3-(1H-imidazol-4-yl)propionylamino]-propoxy}phenyl)methyl]-3-(β-D-glucopyranosyloxy)-5-isopropyl-1H-pyrazole The title compound was prepared in a similar manner to that described in Example 13 using (S)-2-benzyloxycarbonylamino-3-(1H-imidazol-4-yl)propionic acid instead of 2-benzyloxycarbonylaminoacetic acid.

$^1$H-NMR (CD$_3$OD) δ ppm:
1.1-1.2 (6H, m), 1.8-1.95 (2H, m), 2.7-3.0 (3H, m), 3.25-3.45 (6H, m), 3.5-3.55 (1H, m), 3.6-3.7 (2H, m), 3.73 (1H, d, J=15.7 Hz), 3.8-3.95 (3H, m), 5.0-5.15 (1H, m), 6.75-6.85 (3H, m), 7.05-7.15 (2H, m), 7.54 (1H, s)

Example 18

4-[(4-{3-[2-Amino-2-(methyl)propionylamino]propoxy}phenyl)methyl]-3-(β-D-glucopyranosyloxy)-5-isopropyl-1H-pyrazole The title compound was prepared in a similar manner to that described in Example 13 using 2-benzyloxycarbonylamino-2-methylpropionic acid instead of 2-benzyloxycarbonylaminoacetic acid.

$^1$H-NMR (CD$_3$OD) δ ppm:
1.05-1.2 (6H, m), 1.29 (6H, s), 1.9-2.0 (2H, m), 2.8-2.95 (1H, m), 3.25-3.45 (6H, m), 3.6-3.7 (2H, m), 3.73 (1H, d, J=16.1 Hz), 3.8-3.9 (1H, m), 3.98 (2H, t, J=6.1 Hz), 5.0-5.15 (1H, m), 6.75-6.85 (2H, m), 7.05-7.2 (2H, m)

Example 19

3-(β-D-Glucopyranosyloxy)-5-isopropyl-4-{[4-(3-{3-[2-(morpholin-4-yl)ethyl]ureido}propoxy)phenyl]methyl}-1H-pyrazole To a solution of 3-(2,3,4,6-tetra-O-acetyl-β-D-glucopyranosyloxy)-4-{[4-(3-aminopropoxy)phenyl]methyl}-5-isopropyl-1H-pyrazole (97 mg) in dichloromethane (3 mL) were added triethylamine (0.035 mL) and 4-nitrophenyl chloroformate (35 mg), and the mixture was stirred at room temperature for 1 hour. To the reaction mixture was added 4-(2-aminoethyl)morpholine (41 mg), and the mixture was stirred at room temperature overnight. The reaction mixture was poured into water, and the resulting mixture was extracted with ethyl acetate. The organic layer was washed with water, a saturated aqueous sodium hydrogen carbonate solution, water and brine successively, dried over anhydrous magnesium sulfate and concentrated under reduced pressure. The residue was purified by column chromatography on silica gel (eluent: ethyl acetate-dichloromethane/methanol=10/1-5/1) to give 3-(2,3,4,6-tetra-O-acetyl-β-D-glucopyranosyloxy)-5-isopropyl-4-{[4-(3-{3-[2-(morpholin-4-yl)ethyl]ureido}propoxy)phenyl]-methyl}-1H-pyrazole (58 mg). This material was dissolved in methanol (3 mL). To the solution was added sodium methoxide (28% methanol solution, 0.03 mL), and the mixture was stirred at room temperature for 30 minutes. The reaction mixture was concentrated under reduced pressure, and the residue was purified by solid phase extraction on ODS (washing solvent: distilled water, eluent: methanol) to give the title compound (39 mg).

$^1$H-NMR (CD$_3$OD) δ ppm:
1.10-1.15 (6H, m), 1.85-1.95 (2H, m), 2.35-2.5 (6H, m), 2.85-2.95 (1H, m), 3.2-3.45 (8H, m), 3.6-3.7 (6H, m), 3.73 (1H, d, J=15.9 Hz), 3.8-3.9 (1H, m), 3.97 (2H, t, J=6.2 Hz), 5.0-5.1 (1H, m), 6.75-6.85 (2H, m), 7.05-7.15 (2H, m)

Example 20

3-(β-D-Glucopyranosyloxy)-5-isopropyl-4-{[4-(3-{3-[2-(dimethylamino)ethyl]ureido}propoxy)phenyl]methyl}-1H-pyrazole The title compound was prepared in a similar manner to that described in Example 19 using N,N-dimethylethylenediamine instead of 4-(2-aminoethyl)morpholine.

$^1$H-NMR (CD$_3$OD) δ ppm:
1.1-1.15 (6H, m), 1.85-1.95 (2H, m), 2.26 (6H, s), 2.43 (2H, t, J=6.7 Hz), 2.85-2.95 (1H, m), 3.2-3.4 (8H, m), 3.6-3.7 (2H, m), 3.73 (1H, d, J=15.9 Hz), 3.8-3.9 (1H, m), 3.97 (2H, t, J=6.0 Hz), 5.0-5.1 (1H, m), 6.75-6.85 (2H, m), 7.05-7.15 (2H, m)

Example 21

3-(β-D-Glucopyranosyloxy)-4-{[4-(3-{3-[2-hydroxy-1-(hydroxymethyl)-1-(methyl)ethyl]ureido}propoxy)phenyl]-methyl}-5-isopropyl-1H-pyrazole The title compound was prepared in a similar manner to that described in Example 19 using 2-amino-2-methyl-1,3-propanediol instead of 4-(2-aminoethyl)morpholine.

$^1$H-NMR (CD$_3$OD) δ ppm:
1.05-1.2 (9H, m), 1.8-1.95 (2H, m), 2.8-2.95 (1H, m), 3.2-3.45 (6H, m), 3.5-3.8 (7H, m), 3.8-3.9 (1H, m), 3.97 (2H, t, J=6.1 Hz), 5.0-5.15 (1H, m), 6.75-6.85 (2H, m), 7.05-7.15 (2H, m)

Example 22

3-(β-D-Glucopyranosyloxy)-4-{[4-(3-{3-[2-hydroxy-1-(hydroxymethyl)ethyl]ureido}propoxy)phenyl]methyl}-5-isopropyl-1H-pyrazole The title compound was prepared in a similar manner to that described in Example 19 using 2-amino-1,3-propanediol instead of 4-(2-aminoethyl)morpholine.

$^1$H-NMR (CD$_3$OD) δ ppm:
1.05-1.15 (6H, m), 1.85-1.95 (2H, m), 2.8-2.95 (1H, m), 3.25-3.45 (6H, m), 3.5-3.75 (8H, m), 3.8-3.9 (1H, m), 3.97 (2H, t, J=6.2 Hz), 5.0-5.1 (1H, m), 6.75-6.85 (2H, m), 7.05-7.15 (2H, m)

Example 23

3-(β-D-Glucopyranosyloxy)-4-[(4-{3-[3-(2-hydroxyethyl)ureido]propoxy}phenyl)methyl]-5-isopropyl-1H-pyrazole The title compound was prepared in a similar manner to that described in Example 19 using 2-aminoethanol instead of 4-(2-aminoethyl)morpholine.

$^1$H-NMR (CD$_3$OD) δ ppm:
1.05-1.2 (6H, m), 1.85-1.95 (2H, m), 2.85-2.95 (1H, m), 3.21 (2H, t, J=5.6 Hz), 3.25-3.45 (6H, m), 3.55 (2H, t, J=5.6 Hz), 3.6-3.7 (2H, m), 3.73 (1H, d, J=16.1 Hz), 3.8-3.9 (1H, m), 3.97 (2H, t, J=6.2 Hz), 5.0-5.1 (1H, m), 6.75-6.85 (2H, m), 7.05-7.15 (2H, m)

Example 24

3-(β-D-Glucopyranosyloxy)-4-{[4-(3-{3-[2-hydroxy-1,1-di(methyl)ethyl]ureido}propoxy)phenyl]methyl}-5-isopropyl-1H-pyrazole The title compound was prepared in a similar manner to that described in Example 19 using 2-amino-2-methyl-1-propanol instead of 4-(2-aminoethyl)morpholine.

$^1$H-NMR (CD$_3$OD) δ ppm:
1.1-1.5 (6H, m), 1.22 (6H, s), 1.85-1.95 (2H, m), 2.8-2.95 (1H, m), 3.24 (2H, t, J=6.6 Hz), 3.25-3.45 (4H, m), 3.5 (2H, s), 3.6-3.7 (2H, m), 3.73 (1H, d, J=15.8 Hz), 3.8-3.9 (1H, m), 3.96 (2H, t, J=6.2 Hz), 5.0-5.1 (1H, m), 6.75-6.85 (2H, m), 7.05-7.15 (2H, m)

Example 25

3-(β-D-Glucopyranosyloxy)-5-isopropyl-4-{[4-(3-{3-[2-(pyrrolidin-1-yl)ethyl]ureido}propoxy)phenyl]methyl}-1H-pyrazole The title compound was prepared in a similar manner to that described in Example 19 using 1-(2-aminoethyl)pyrrolidine instead of 4-(2-aminoethyl)morpholine.

$^1$H-NMR (CD$_3$OD) δ ppm:
1.05-1.2 (6H, m), 1.75-1.85 (4H, m), 1.85-1.95 (2H, m), 2.5-2.65 (6H, m), 2.85-2.95 (1H, m), 3.2-3.45 (8H, m), 3.6-3.7 (2H, m), 3.73 (1H, d, J=15.8 Hz), 3.8-3.9 (1H, m), 3.97 (2H, t, J=6.0 Hz), 5.0-5.1 (1H, m), 6.75-6.85 (2H, m), 7.05-7.15 (2H, m)

Example 26

3-(β-D-Glucopyranosyloxy)-4-{[4-(3-{3-[2-hydroxy-1,1-bis(hydroxymethyl)ethyl]ureido}propoxy)phenyl]methyl}-5-isopropyl-1H-pyrazole The title compound was prepared in a similar manner to that described in Example 19 using tris(hydroxymethyl)aminomethane instead of 4-(2-aminoethyl)morpholine.

$^1$H-NMR (CD$_3$OD) δ ppm:
1.05-1.2 (6H, m), 1.85-1.95 (2H, m), 2.8-2.95 (1H, m), 3.2-3.45 (6H, m), 3.55-3.7 (8H, m), 3.73 (1H, d, J=16.0 Hz), 3.8-3.9 (1H, m), 3.97 (2H, t, J=6.1 Hz), 5.0-5.1 (1H, m), 6.75-6.85 (2H, m), 7.05-7.15 (2H, m)

Example 27

3-(β-D-Glucopyranosyloxy)-4-{[4-(3-{[4-(2-hydroxyethyl)piperazin-1-yl]carbonylamino}propoxy)-2-methylphenyl]-methyl}-5-isopropyl-1H-pyrazole The title compound was prepared in a similar manner to that described in Example 19 using 3-(2,3,4,6-tetra-O-acetyl-β-D-glucopyranosyloxy)-4-{[4-(3-aminopropoxy)-2-methylphenyl]methyl}-5-isopropyl-1H-pyrazole and 1-(2-hydroxyethyl)piperazine instead of 3-(2,3,4,6-tetra-O-acetyl-β-D-glucopyranosyloxy)-4-{[4-(3-aminopropoxy)phenyl]methyl}-5-isopropyl-1H-pyrazole and 4-(2-aminoethyl)morpholine, respectively.

$^1$H-NMR (CD$_3$OD) δ ppm:
1.05-1.15 (6H, m), 1.85-2.0 (2H, m), 2.29 (3H, s), 2.4-2.55 (6H, m), 2.75-2.85 (1H, m), 3.25-3.45 (10H, m), 3.55-3.75 (5H, m), 3.75-3.85 (1H, m), 3.96 (2H, t, J=6.1 Hz), 4.95-5.05 (1H, m), 6.61 (1H, dd, J=8.5 Hz, 2.6 Hz), 6.7 (1H, d, J=2.6 Hz), 6.85 (1H, d, J=8.5 Hz)

Example 28

3-(β-D-Glucopyranosyloxy)-4-{[4-(3-{3-[2-hydroxy-1-(hydroxymethyl)-1-(methyl)ethyl]ureido}propoxy)-2-methylphenyl]methyl}-5-isopropyl-1H-pyrazole The title compound was prepared in a similar manner to that described in Example 19 using 3-(2,3,4,6-tetra-O-acetyl-β-D-glucopyranosyloxy)-4-{[4-(3-aminopropoxy)-2-methylphenyl]methyl}-5-isopropyl-1H-pyrazole and 2-amino-2-methyl-1,3-propanediol instead of 3-(2,3,4,6-tetra-O-acetyl-β-D-glucopyranosyloxy)-4-{[4-(3-aminopropoxy)phenyl]methyl}-5-isopropyl-1H-pyrazole and 4-(2-aminoethyl)morpholine, respectively.

$^1$H-NMR (CD$_3$OD) δ ppm:
1.05-1.15 (6H, m), 1.19 (3H, s), 1.85-1.95 (2H, m), 2.29 (3H, s), 2.75-2.85 (1H, m), 3.2-3.4 (6H, m), 3.5-3.75 (7H, m), 3.75-3.85 (1H, m), 3.96 (2H, t, J=6.2 Hz), 4.95-5.05 (1H, m), 6.62 (1H, dd, J=8.6 Hz, 2.5 Hz), 6.71 (1H, d, J=2.5 Hz), 6.85 (1H, d, J=8.6 Hz)

Example 29

3-(β-D-Glucopyranosyloxy)-4-{[4-(3-(3-[2-hydroxy-1,1-di(methyl)ethyl]ureido)propoxy)-2-methylphenyl]methyl}-5-isopropyl-1H-pyrazole The title compound was prepared in a similar manner to that described in Example 19 using 3-(2,3,4,6-tetra-O-acetyl-β-D-glucopyranosyloxy)-4-{[4-(3-aminopropoxy)-2-methylphenyl]methyl}-5-isopropyl-1H-pyrazole and 2-amino-2-methyl-1-propanol instead of 3-(2,3,4,6-tetra-O-acetyl-β-D-glucopyranosyloxy)-4-{[4-(3-aminopropoxy)phenyl]methyl}-5-isopropyl-1H-pyrazole and 4-(2-aminoethyl)morpholine, respectively.

$^1$H-NMR (CD$_3$OD) δ ppm:
1.05-1.15 (6H, m), 1.23 (6H, s), 1.8-1.95 (2H, m), 2.29 (3H, s), 2.75-2.85 (1H, m), 3.24 (2H, t, J=6.8 Hz), 3.25-3.4 (4H, m), 3.5 (2H, s), 3.55-3.75 (3H, m), 3.75-3.85 (1H, m), 3.96 (2H, t, J=6.2 Hz), 4.95-5.05 (1H, m), 6.62 (1H, dd, J=8.5 Hz, 2.6 Hz), 6.71 (1H, d, J=2.6 Hz), 6.85 (1H, d, J=8.5 Hz)

Example 30

3-(β-D-Glucopyranosyloxy)-4-[(4-(3-[3-(2-hydroxyethyl)ureido]propoxy)-2-methylphenyl)methyl]-5-isopropyl-1H-pyrazole The title compound was prepared in a similar manner to that described in Example 19 using 3-(2,3,4,6-tetra-O-acetyl-β-D-glucopyranosyloxy)-4-{[4-(3-aminopropoxy)-2-methylphenyl]methyl}-5-isopropyl-1H-pyrazole and 2-aminoethanol instead of 3-(2,3,4,6-tetra-O-acetyl-β-D-glucopyranosyloxy)-4-{[4-(3-aminopropoxy)phenyl]methyl}-5-isopropyl-1H-pyrazole and 4-(2-aminoethyl)morpholine, respectively.

$^1$H-NMR (CD$_3$OD) δ ppm:
1.05-1.15 (6H, m), 1.85-1.95 (2H, m), 2.29 (3H, s), 2.75-2.85 (1H, m), 3.22 (2H, t, J=5.7 Hz), 3.25-3.4 (6H, m), 3.55 (2H, t, J=5.7 Hz), 3.6-3.75 (3H, m), 3.75-3.85 (1H, m), 3.96 (2H, t, J=6.2 Hz), 4.95-5.05 (1H, m), 6.62 (1H, dd, J=8.2 Hz, 2.4 Hz), 6.71 (1H, d, J=2.4 Hz), 6.85 (1H, d, J=8.2 Hz)

Example 31

4-{[4-(2-{3-[1-Carbamoyl-1-(methyl)ethyl] ureido}ethoxy)-2-methylphenyl]methyl}-3-(β-D-glucopyranosyloxy)-5-isopropyl-1H-pyrazole The title compound was prepared in a similar manner to that described in Example 19 using 3-(2,3,4,6-tetra-O-acetyl-β-D-glucopyranosyloxy)-4-{[4-(2-aminoethoxy)-2-methylphenyl]methyl}-5-isopropyl-1H-pyrazole and 2-amino-2-methylpropionamide instead of 3-(2,3,4,6-tetra-O-acetyl-β-D-glucopyranosyloxy)-4-{[4-(3-aminopropoxy)phenyl]methyl}-5-isopropyl-1H-pyrazole and 4-(2-aminoethyl)morpholine, respectively.

¹H-NMR (CD₃OD) δ ppm:
1.05-1.15 (6H, m), 1.44 (6H, s), 2.29 (3H, s), 2.75-2.85 (1H, m), 3.25-3.4 (4H, m), 3.44 (2H, t, J=5.3 Hz), 3.55-3.75 (3H, m), 3.75-3.85 (1H, m), 3.95 (2H, t, J=5.3 Hz), 4.95-5.05 (1H, m), 6.63 (1H, dd, J=8.5 Hz, 2.6 Hz), 6.72 (1H, d, J=2.6 Hz), 6.86 (1H, d, J=8.5 Hz)

Example 32

3-(β-D-Glucopyranosyloxy)-4-{[4-(2-{3-[2-hydroxy-1-(hydroxymethyl)-1-(methyl)ethyl]ureido}ethoxy)-2-methylphenyl]methyl}-5-isopropyl-1H-pyrazole The title compound was prepared in a similar manner to that described in Example 19 using 3-(2,3,4,6-tetra-O-acetyl-β-D-glucopyranosyloxy)-4-{[4-(2-aminoethoxy)-2-methylphenyl]methyl}-5-isopropyl-1H-pyrazole and 2-amino-2-methyl-1,3-propanediol instead of 3-(2,3,4,6-tetra-O-acetyl-β-D-glucopyranosyloxy)-4-{[4-(3-aminopropoxy)phenyl]methyl}-5-isopropyl-1H-pyrazole and 4-(2-aminoethyl)morpholine, respectively.

¹H-NMR (CD₃OD) δ ppm:
1.05-1.15 (6H, m), 1.2 (3H, s), 2.29 (3H, s), 2.75-2.85 (1H, m), 3.25-3.4 (4H, m), 3.43 (2H, t, J=5.3 Hz), 3.5-3.75 (7H, m), 3.75-3.85 (1H, m), 3.94 (2H, t, J=5.3 Hz), 4.95-5.05 (1H, m), 6.63 (1H, dd, J=8.3 Hz, 2.7 Hz), 6.73 (1H, d, J=2.7 Hz), 6.86 (1H, d, J=8.3 Hz)

Example 33

3-(β-D-Glucopyranosyloxy)-4-{[4-(2-{3-[2-hydroxy-1,1-di(methyl)ethyl]ureido}ethoxy)-2-methylphenyl]methyl}-5-isopropyl-1H-pyrazole The title compound was prepared in a similar manner to that described in Example 19 using 3-(2,3,4,6-tetra-O-acetyl-β-D-glucopyranosyloxy)-4-{[4-(2-aminoethoxy)-2-methylphenyl]methyl}-5-isopropyl-1H-pyrazole and 2-amino-2-methyl-1-propanol instead of 3-(2,3,4,6-tetra-O-acetyl-β-D-glucopyranosyloxy)-4-{[4-(3-aminopropoxy)phenyl]methyl}-5-isopropyl-1H-pyrazole and 4-(2-aminoethyl)morpholine, respectively.

¹H-NMR (CD₃OD) δ ppm:
1.05-1.15 (6H, m), 1.23 (6H, s), 2.29 (3H, s), 2.75-2.85 (1H, m), 3.25-3.4 (4H, m), 3.42 (2H, t, J=5.3 Hz), 3.52 (2H, s), 3.55-3.75 (3H, m), 3.75-3.85 (1H, m), 3.94 (2H, t, J=5.3 Hz), 4.95-5.05 (1H, m), 6.63 (1H, dd, J=8.3 Hz, 2.5 Hz), 6.72 (1H, d, J=2.5 Hz), 6.86 (1H, d, J=8.3 Hz)

Example 34

3-(2,3,4,6-Tetra-O-acetyl-β-D-glucopyranosyloxy)-4-[(4-{3-[4-(2-hydroxyethyl)piperazin-1-yl]propoxy}-2-methylphenyl)methyl]-5-isopropyl-1H-pyrazole To a solution of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole (0.29 g) in dichloromethane (5 mL) were added triethylamine (0.08 mL) and methanesulfonyl chloride (0.04 mL), and the mixture was stirred at room temperature overnight. The reaction mixture was poured into 0.5 mol/L hydrochloric acid, and the resulting mixture was extracted with ethyl acetate. The organic layer was washed with water, and dried over anhydrous magnesium sulfate. The solvent was removed under reduced pressure to give 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole. This material was dissolved in N,N-dimethylformamide (3 mL). To the solution was added 1-(2-hydroxyethyl)piperazine (0.13 g), and the mixture was stirred at 60° C. for 9 hours. The reaction mixture was poured into water, and the resulting mixture was extracted with ethyl acetate. The organic layer was washed with water twice, and dried over anhydrous magnesium sulfate. The solvent was removed under reduced pressure, and the residue was purified by column chromatography on silica gel (eluent: ethyl acetate-dichloromethane/methanol=10/1-5/1) to give the title compound (91 mg).

¹H-NMR (CDCl₃) δ ppm:
1.05-1.2 (6H, m), 1.81 (3H, s), 1.9-2.0 (5H, m), 2.02 (3H, s), 2.07 (3H, s), 2.26 (3H, s), 2.3-2.75 (12H, m), 2.75-2.9 (1H, m), 3.49 (1H, d, J=16.4 Hz), 3.55-3.7 (3H, m), 3.8-3.9 (1H, m), 3.9-4.0 (2H, m), 4.1-4.2 (1H, m), 4.3 (1H, dd, J=12.3 Hz, 3.8 Hz), 5.15-5.3 (3H, m), 5.55 (1H, d, J=8.3 Hz), 6.57 (1H, dd, J=8.6 Hz, 2.7 Hz), 6.68 (1H, d, J=2.7 Hz), 6.79 (1H, d, J=8.6 Hz)

Example 35

3-(β-D-Glucopyranosyloxy)-4-[(4-{3-[4-(2-hydroxyethyl)piperazin-1-yl]propoxy}-2-methylphenyl)methyl]-5-isopropyl-1H-pyrazole The title compound was prepared in a similar manner to that described in Example 6 using 3-(2,3,4,6-tetra-O-acetyl-β-D-glucopyranosyloxy)-4-[(4-{3-[4-(2-hydroxyethyl)piperazin-1-yl]propoxy}-2-methylphenyl)methyl]-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

¹H-NMR (CD₃OD) δ ppm:
1.05-1.15 (6H, m), 1.85-2.0 (2H, m), 2.28 (3H, s), 2.3-2.85 (13H, m), 3.25-3.4 (4H, m), 3.6-3.75 (5H, m), 3.75-3.85 (1H, m), 3.96 (2H, t, J=6.2 Hz), 4.95-5.1 (1H, m), 6.6 (1H, dd, J=8.5 Hz, 2.4 Hz), 6.69 (1H, d, J=2.4 Hz), 6.84 (1H, d, J=8.5 Hz)

Reference Example 34

3-(2,3,4,6-Tetra-O-acetyl-β-D-glucopyranosyloxy)-4-[(4-{3-[N'-(cyano)-S-(methyl)isothioureido]propoxy}phenyl)methyl]-5-isopropyl-1H-pyrazole To a solution of 3-(2,3,4,6-tetra-O-acetyl-β-D-glucopyranosyloxy)-4-{[4-(3-aminopropoxy)phenyl]methyl}-5-isopropyl-1H-pyrazole (0.19 g) in 2-propanol (2 mL) was added S,S'-dimethyl-N-cyanodithioiminocarbonate (57 mg), and the mixture was stirred at room temperature for 4 hours. The reaction mixture was purified by column chromatography on silica gel (eluent: n-hexane/ethyl acetate=1/1-dichloromethane/methanol=20/1) to give the title compound (0.19 g).

$^1$H-NMR (CD$_3$OD) δ ppm:

1.1-1.2 (6H, m), 1.91 (3H, s), 1.97 (3H, s), 2.0-2.1 (8H, m), 2.56 (3H, s), 2.85-3.0 (1H, m), 3.5-3.65 (4H, m), 3.9-4.05 (3H, m), 4.11 (1H, dd, J=12.4 Hz, 2.3 Hz), 4.29 (1H, dd, J=12.4 Hz, 4.0 Hz), 5.05-5.15 (2H, m), 5.25-5.35 (1H, m), 5.48 (1H, d, J=8.0 Hz), 6.75-6.85 (2H, m), 7.0-7.1 (2H, m)

Example 36

4-({4-[3-(2-Cyano-3-methylguanidino)propoxy]phenyl}methyl)-3-(β-D-glucopyranosyloxy)-5-isopropyl-1H-pyrazole Methylamine (40% methanol solution, 2 mL) was added to 3-(2,3,4,6-tetra-O-acetyl-β-D-glucopyranosyloxy)-4-[(4-{3-[N'-(cyano)-S-(methyl)isothioureido]propoxy}phenyl)methyl]-5-isopropyl-1H-pyrazole (40 mg), and the mixture was stirred at room temperature overnight. The reaction mixture was concentrated under reduced pressure, and the residue was dissolved in methanol (2 mL). To the solution was added sodium methoxide (28% methanol solution, 0.02 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (18 mg).

$^1$H-NMR (CD$_3$OD) δ ppm:

1.1-1.15 (6H, m), 1.95-2.05 (2H, m) 2.76 (3H, s), 2.85-2.95 (1H, m), 3.25-3.45 (6H, m), 3.6-3.7 (2H, m), 3.73 (1H, d, J=16.2 Hz), 3.8-3.9 (1H, m), 4.0 (2H, t, J=5.9 Hz), 5.05-5.1 (1H, m), 6.75-6.85 (2H, m), 7.05-7.15 (2H, m)

Example 37

4-[(4-{3-[2-Cyano-3-(2-hydroxyethyl)guanidino]propoxy}phenyl)methyl]-3-(β-D-glucopyranosyloxy)-5-isopropyl-1H-pyrazole To a solution of 3-(2,3,4,6-tetra-O-acetyl-β-D-glucopyranosyloxy)-4-[(4-{3-[N'-(cyano)-S-(methyl)isothioureido]propoxy}phenyl)methyl]-5-isopropyl-1H-pyrazole (30 mg) in methanol (1 mL) was added 2-aminoethanol (0.5 mL), and the mixture was stirred at 50° C. overnight. After cooling to room temperature, to the reaction mixture was added sodium methoxide (28% methanol solution, 0.02 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (15 mg).

$^1$H-NMR (CD$_3$OD) δ ppm:

1.05-1.2 (6H, m), 1.95-2.05 (2H, m), 2.8-2.95 (1H, m), 3.25-3.45 (6H, m), 3.5-3.7 (6H, m), 3.73 (1H, d, J=15.8 Hz), 3.8-3.9 (1H, m), 4.0 (2H, t, J=5.9 Hz), 5.0-5.1 (1H, m), 6.75-6.85 (2H, m), 7.05-7.15 (2H, m)

Example 38

3-(β-D-Glucopyranosyloxy)-5-isopropyl-4-({4-[3-(sulfamoylamino)propoxy]phenyl}methyl)-1H-pyrazole To a solution of chlorosulfonyl isocyanate (0.022 mL) in acetonitrile (1 mL) was added water (0.005 mL), and the mixture was stirred at room temperature for 10 minutes. This reaction mixture was added to a solution of 3-(2,3,4,6-tetra-O-acetyl-β-D-glucopyranosyloxy)-4-{[4-(3-aminopropoxy)phenyl]-methyl}-5-isopropyl-1H-pyrazole (51 mg) and triethylamine (0.052 mL) in dichloromethane (2 mL), and the mixture was stirred at room temperature overnight. The reaction mixture was poured into water, and the resulting mixture was extracted with ethyl acetate. The organic layer was washed with brine, and dried over anhydrous sodium sulfate. The solvent was removed under reduced pressure, and the residue was purified by column chromatography on silica gel (eluent: dichloromethane/methanol=30/1) to give 3-(2,3,4,6-tetra-O-acetyl-β-D-glucopyranosyloxy)-5-isopropyl-4-({4-[3-(sulfamoylamino)propoxy]phenyl}methyl)-1H-pyrazole (18 mg). This material was dissolved in methanol (2 mL). To the solution was added sodium methoxide (28% methanol solution, 0.01 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (3 mg).

$^1$H-NMR (CD$_3$OD) δ ppm:

1.05-1.2 (6H, m), 1.95-2.05 (2H, m), 2.8-2.95 (1H, m), 3.21 (2H, t, J=6.8 Hz), 3.25-3.45 (4H, m), 3.6-3.8 (3H, m), 3.84 (1H, d, J=11.6 Hz), 4.02 (2H, t, J=6.0 Hz), 5.0-5.15 (1H, m), 6.75-6.85 (2H, m), 7.05-7.15 (2H, m)

Example 39

3-(2,3,4,6-Tetra-O-acetyl-β-D-glucopyranosyloxy)-4-({4-[3-(carbamoylmethylamino)propoxy]-2-methylphenyl}methyl)-5-isopropyl-1H-pyrazole To a solution of 3-(2,3,4,6-tetra-O-acetyl-β-D-glucopyranosyloxy)-4-{[4-(3-hydroxypropoxy)-2-methylphenyl]-methyl}-5-isopropyl-1H-pyrazole (98 mg) in tetrahydrofuran (2 mL) were added 2-(2-nitrobenzenesulfonylamino)acetoamide (40 mg), triphenylphosphine (45 mg) and diethyl azodicarboxylate (40% toluene solution, 0.1 mL), and the mixture was stirred at room temperature overnight. The reaction mixture was purified by column chromatography on silica gel (eluent: ethyl acetate-dichloromethane/methanol=10/1) to give 3-(2,3,4,6-tetra-O-acetyl-β-D-glucopyranosyloxy)-5-isopropyl-4-[(4-(3-[N-(2-nitrobenzenesulfonyl)-N-(carbamoylmethyl)amino]propoxy)-2-methylphenyl)methyl]-1H-pyrazole (92 mg). This material was dissolved in acetonitrile (1 mL). To the solution were added cesium carbonate (0.14 g) and thiophenol (0.012 mL), and the mixture was stirred at room temperature for 1 hour. The reaction mixture was poured into water, and the resulting mixture was extracted with ethyl acetate. The organic layer was washed with brine, and dried over sodium sulfate. The solvent was removed under reduced pressure, and the residue was purified by column chromatography on silica gel (eluent: dichloromethane/methanol=10/1-5/1) to give the title compound (57 mg).

¹H-NMR (CD₃OD) δ ppm:
1.1-1.15 (6H, m), 1.83 (3H, s), 1.9-2.05 (11H, m), 2.26 (3H, s), 2.75-2.9 (3H, m), 3.28 (2H, s), 3.53 (1H, d, J=16.1 Hz), 3.58 (1H, d, J=16.1 Hz), 3.85-3.95 (1H, m), 4.01 (2H, t, J=6.3 Hz), 4.06 (1H, dd, J=12.4 Hz, 2.3 Hz), 4.27 (1H, dd, J=12.4 Hz, 4.2 Hz), 5.0-5.15 (2H, m), 5.2-5.3 (1H, m), 5.43 (1H, d, J=8.0 Hz), 6.61 (1H, dd, J=8.5 Hz, 2.6 Hz), 6.71 (1H, d, J=2.6 Hz), 6.77 (1H, d, J=8.5 Hz)

Example 40

3-(2,3,4,6-Tetra-O-acetyl-β-D-glucopyranosyloxy)-4-({4-[3-(carbamoylmethylamino)propoxy]phenyl}methyl)-5-isopropyl-1H-pyrazole The title compound was prepared in a similar manner to that described in Example 39 using 3-(2,3,4,6-tetra-O-acetyl-β-D-glucopyranosyloxy)-4-{[4-(3-hydroxypropoxy)phenyl]-methyl}-5-isopropyl-1H-pyrazole instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole.

¹H-NMR (CD₃OD) δ ppm:
1.1-1.2 (6H, m), 1.85-2.0 (8H, m), 2.01 (3H, s), 2.02 (3H, s), 2.78 (2H, t, J=6.9 Hz), 2.85-3.0 (1H, m), 3.27 (2H, s), 3.59 (2H, s), 3.9-4.0 (1H, m), 4.01 (2H, t, J=6.2 Hz), 4.11 (1H, dd, J=12.5 Hz, 2.3 Hz), 4.3 (1H, dd, J=12.5 Hz, 4.0 Hz), 5.05-5.15 (2H, m), 5.25-5.35 (1H, m), 5.47 (1H, d, J=8.4 Hz), 6.75-6.85 (2H, m), 7.0-7.05 (2H, m)

Example 41

3-(2,3,4,6-Tetra-O-acetyl-β-D-glucopyranosyloxy)-4-[(4-{3-[(S)-1-(carbamoyl)ethylamino]propoxy}phenyl)methyl]-5-isopropyl-1H-pyrazole The title compound was prepared in a similar manner to that described in Example 39 using 3-(2,3,4,6-tetra-O-acetyl-β-D-glucopyranosyloxy)-4-{[4-(3-hydroxypropoxy)phenyl]-methyl}-5-isopropyl-1H-pyrazole and (S)-2-(2-nitrobenzenesulfonylamino)propionamide instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-(2-nitrobenzenesulfonylamino)acetoamide, respectively.

¹H-NMR (CD₃OD) δ ppm:
1.1-1.2 (6H, m), 1.27 (3H, d, J=6.9 Hz), 1.85-2.0 (8H, m), 2.01 (3H, s), 2.02 (3H, s), 2.65-2.8 (2H, m), 2.85-3.0 (1H, m), 3.59 (2H, s), 3.9-4.05 (3H, m), 4.11 (1H, dd, J=12.5 Hz, 2.2 Hz), 4.3 (1H, dd, J=12.5 Hz, 3.9 Hz), 5.05-5.15 (2H, m), 5.25-5.35 (1H, m), 5.48 (1H, d, J=7.8 Hz), 6.75-6.85 (2H, m), 7.0-7.05 (2H, m)

Example 42

3-(2,3,4,6-Tetra-O-acetyl-β-D-glucopyranosyloxy)-4-[(4-{3-[1-carbamoyl-1-(methyl)ethylamino]propoxy}phenyl)methyl]-5-isopropyl-1H-pyrazole The title compound was prepared in a similar manner to that described in Example 39 using 3-(2,3,4,6-tetra-O-acetyl-β-D-glucopyranosyloxy)-4-{[4-(3-hydroxypropoxy)phenyl]-methyl}-5-isopropyl-1H-pyrazole and 2-methyl-2-(2-nitrobenzenesulfonylamino)propionamide instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-(2-nitrobenzenesulfonylamino)acetoamide, respectively.

¹H-NMR (CD₃OD) δ ppm:
1.1-1.2 (6H, m), 1.31 (6H, s), 1.85-2.0 (8H, m), 2.01 (3H, s), 2.02 (3H, s), 2.6-2.8 (2H, m), 2.85-3.0 (1H, m), 3.59 (2H, s), 3.9-4.0 (1H, m), 4.02 (2H, t, J=6.1 Hz), 4.11 (1H, dd, J=12.5 Hz, 2.6 Hz), 4.3 (1H, dd, J=12.5 Hz, 4.1 Hz), 5.05-5.15 (2H, m), 5.25-5.35 (1H, m), 5.48 (1H, d, J=8.2 Hz), 6.75-6.85 (2H, m), 7.0-7.05 (2H, m)

Example 43

3-(2,3,4,6-Tetra-O-acetyl-β-D-glucopyranosyloxy)-4-({4-[2-(carbamoylmethylamino)ethoxy]-2-methylphenyl}methyl)-5-isopropyl-1H-pyrazole The title compound was prepared in a similar manner to that described in Example 39 using 3-(2,3,4,6-tetra-O-acetyl-β-D-glucopyranosyloxy)-4-{[4-(2-hydroxyethoxy)-2-methylphenyl]methyl}-5-isopropyl-1H-pyrazole instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole.

¹H-NMR (CD₃OD) δ ppm:
1.05-1.15 (6H, m), 1.83 (3H, s), 1.96 (3H, s), 2.0 (3H, s), 2.02 (3H, s), 2.26 (3H, s), 2.75-2.9 (1H, m), 2.96 (2H, t, J=5.2 Hz), 3.32 (2H, s), 3.53 (1H, d, J=16.6 Hz), 3.59 (1H, d, J=16.6 Hz), 3.85-3.95 (1H, m), 4.03 (2H, t, J=5.2 Hz), 4.06 (1H, dd, J=12.3 Hz, 52.0 Hz), 4.27 (1H, dd, J=12.3 Hz, 4.2 Hz), 5.0-5.15 (2H, m), 5.2-5.35 (1H, m), 5.43 (1H, d, J=8.0 Hz), 6.64 (1H, dd, J=8.5 Hz, 2.3 Hz), 6.74 (1H, d, J=2.3 Hz), 6.78 (1H, d, J=8.5 Hz)

Example 44

3-(2,3,4,6-Tetra-O-acetyl-β-D-glucopyranosyloxy)-4-[(4-{2-[2-(carbamoyl)ethylamino]ethoxy}-2-methylphenyl)methyl]-5-isopropyl-1H-pyrazole The title compound was prepared in a similar manner to that described in Example 39 using 3-(2,3,4,6-tetra-O-acetyl-β-D-glucopyranosyloxy)-4-{[4-(2-hydroxyethoxy)-2-methylphenyl]methyl}-5-isopropyl-1H-pyrazole and 3-(2-nitrobenzenesulfonylamino)propionamide instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-(2-nitrobenzenesulfonylamino)acetoamide, respectively.

¹H-NMR (CD₃OD) δ ppm:
1.05-1.15 (6H, m), 1.83 (3H, s), 1.96 (3H, s), 2.0 (3H, s), 2.02 (3H, s), 2.26 (3H, s), 2.47 (2H, t, J=6.7 Hz), 2.75-2.9 (1H, m), 2.9-3.05 (4H, m), 3.53 (1H, d, J=16.4 Hz), 3.59 (1H, d, J=16.4 Hz), 3.85-3.95 (1H, m), 4.0-4.1 (3H, m), 4.27 (1H, dd, J=12.5 Hz, 4.1 Hz), 5.0-5.15 (2H, m), 5.25-5.35 (1H, m), 5.43 (1H, d, J=8.2 Hz), 6.64 (1H, dd, J=8.3 Hz, 2.6 Hz), 6.75 (1H, d, J=2.6 Hz), 6.79 (1H, d, J=8.3 Hz)

Example 45

4-({4-[3-(Carbamoylmethylamino)propoxy]-2-methylphenyl}methyl)-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-({4-[3-(carbamoylmethylamino)propoxy]-2-methylphenyl}methyl)-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.15 (6H, m), 1.85-2.0 (2H, m), 2.28 (3H, s), 2.7-2.85 (3H, m), 3.24 (2H, s), 3.25-3.4 (4H, m), 3.6-3.75 (3H, m), 3.75-3.85 (1H, m), 4.01 (2H, t, J=6.1 Hz), 4.95-5.05 (1H, m), 6.62 (1H, dd, J=8.4 Hz, 2.4 Hz), 6.71 (1H, d, J=2.4 Hz), 6.85 (1H, d, J=8.4 Hz)

Example 46

4-({4-[3-(Carbamoylmethylamino)propoxy]phenyl}methyl)-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-({4-[3-(carbamoylmethylamino)propoxy]phenyl}methyl)-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.2 (6H, m), 1.85-2.0 (2H, m), 2.75 (2H, t, J=6.9 Hz), 2.8-2.95 (1H, m), 3.25 (2H, s), 3.3-3.45 (4H, m), 3.6-3.7 (2H, m), 3.73 (1H, d, J=16.3 Hz), 3.8-3.9 (1H, m), 4.02 (2H, t, J=6.0 Hz), 5.0-5.1 (1H, m), 6.75-6.85 (2H, m), 7.05-7.15 (2H, m)

Example 47

4-[(4-{3-[(S)-1-(Carbamoyl)ethylamino]propoxy}phenyl)methyl]-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-[(4-{3-[(S)-1-(carbamoyl)ethylamino]propoxy}phenyl)methyl]-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.2 (6H, m), 1.26 (3H, d, J=7.0 Hz), 1.85-2.0 (2H, m), 2.6-2.75 (2H, m), 2.8-2.95 (1H, m), 3.19 (1H, q, J=7.0 Hz), 3.25-3.45 (4H, m), 3.6-3.7 (2H, m), 3.73 (1H, d, J=16.0 Hz), 3.8-3.9 (1H, m), 4.0 (2H, t, J=6.2 Hz), 5.0-5.15 (1H, m), 6.75-6.85 (2H, m), 7.05-7.15 (2H, m)

Example 48

4-[(4-{3-[1-Carbamoyl-1-(methyl)ethylamino]propoxy}phenyl)methyl]-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-[(4-{3-[1-carbamoyl-1-(methyl)ethylamino]propoxy}phenyl)methyl]-5-isopropyl-1H-pyrazole instead of 3-(2,3,4,6-tetra-O-acetyl-β-D-glucopyranosyloxy)-4-({4-(3-aminopropoxy)phenyl)methyl}-5-isopropyl-1H-pyrazole.

$^1$H-NMR (CD$_3$OD) δ ppm:
1.05-1.2 (6H, m), 1.29 (6H, s), 1.85-1.95 (2H, m), 2.65 (2H, t, J=7.1 Hz), 2.8-2.95 (1H, m), 3.25-3.45 (4H, m), 3.6-3.7 (2H, m), 3.73 (1H, d, J=15.9 Hz), 3.8-3.9 (1H, m), 4.02 (2H, t, J=5.9 Hz), 5.0-5.1 (1H, m), 6.75-6.85 (2H, m), 7.05-7.15 (2H, m)

Example 49

4-({4-[2-(Carbamoylmethylamino)ethoxy]-2-methylphenyl}methyl)-3-(1-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-({4-[2-(carbamoylmethylamino)ethoxy]-2-methylphenyl}methyl)-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.15 (6H, m), 2.29 (3H, s), 2.75-2.85 (1H, m), 2.94 (2H, t, J=5.2 Hz), 3.25-3.4 (6H, m), 3.6-3.75 (3H, m), 3.75-3.85 (1H, m), 4.02 (2H, t, J=5.2 Hz), 4.95-5.1 (1H, m), 6.64 (1H, dd, J=8.4 Hz, 2.5 Hz), 6.74 (1H, d, J=2.5 Hz), 6.86 (1H, d, J=8.4 Hz)

Example 50

4-[(4-(2-[(2-(Carbamoyl)ethylamino]ethoxy)-2-methylphenyl)methyl]-3-(1-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-[(4-{2-[2-(carbamoyl)ethylamino]-ethoxy}-2-methylphenyl)methyl]-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.15 (6H, m), 2.29 (3H, s), 2.44 (2H, t, J=6.8 Hz), 2.7-2.85 (1H, m), 2.9 (2H, t, J=6.8 Hz), 2.95 (2H, t, J=5.1 Hz), 3.25-3.4 (4H, m), 3.6-3.75 (3H, m), 3.75-3.85 (1H, m), 4.03 (2H, t, J=5.1 Hz), 4.95-5.05 (1H, m), 6.64 (1H, dd, J=8.5 Hz, 2.4 Hz), 6.74 (1H, d, J=2.4 Hz), 6.86 (1H, d, J=8.5 Hz)

Example 51

4-[(4-{3-[1-Carbamoyl-1-(methyl)ethylamino]propoxy}-2-methylphenyl)methyl]-3-(β-D-glucopyranosyloxy)-5-isopropyl-1H-pyrazole To a solution of 3-(2,3,4,6-tetra-O-acetyl-β-D-glucopyranosyloxy)-4-{[4-(3-hydroxypropoxy)-2-methylphenyl]-methyl}-5-isopropyl-1H-pyrazole (0.25 g) in tetrahydrofuran (2 mL) were added 2-methyl-2-(2-nitrobenzenesulfonylamino) propionamide (0.14 g), triphenylphosphine (0.12 g) and diethyl azodicarboxylate (40% toluene solution, 0.26 mL), and the mixture was stirred at room temperature overnight. The reaction mixture was purified by column chromatography on silica gel (eluent: n-hexane/ethyl acetate=1/4-dichloromethane/methanol=20/1) to give 3-(2,3,4,6-tetra-O-acetyl-β-D-glucopyranosyloxy)-5-isopropyl-4-{[4-(3-{N-(2-nitrobenzenesulfonyl)-N-[1-carbamoyl-1-(methyl)ethyl]amino}propoxy)-2-methylphenyl]-methyl}-1H-pyrazole (0.32 g). This material was dissolved in acetonitrile (3 mL). To the solution were added cesium carbonate (0.46 g) and thiophenol (0.038 mL), and the mixture was stirred at room temperature for 1 hour. The reaction mixture was poured into water, and the resulting mixture was extracted with ethyl acetate. The organic layer was washed with water and brine successively, and dried over anhydrous sodium sulfate. The solvent was removed under reduced pressure, and the residue was purified by column chromatography on silica gel (eluent: n-hexane/ethyl acetate=1/5-dichloromethane/methanol=15/1-10/1) to give 3-(2,3,4,6-tetra-O-acetyl-β-D-glucopyranosyloxy)-4-[(4-(3-[1-carbamoyl-1-(methyl)ethylamino]propoxy)-2-methylphenyl)methyl]-5-isopropyl-1H-pyrazole (20 mg). This material was dissolved in methanol (1 mL). To the solution was added sodium methoxide (28% methanol solution, 0.01 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (11 mg).

$^1$H-NMR (CD$_3$OD) δ ppm:
1.05-1.15 (6H, m), 1.29 (6H, s), 1.85-1.95 (2H, m), 2.29 (3H, s), 2.65 (2H, t, J=6.9 Hz), 2.75-2.85 (1H, m), 3.25-3.4 (4H, m), 3.55-3.75 (3H, m), 3.75-3.85 (1H, m), 4.01 (2H, t, J=6.1 Hz), 4.95-5.05 (1H, m), 6.61 (1H, dd, J=8.5 Hz, 2.6 Hz), 6.7 (1H, d, J=2.6 Hz), 6.85 (1H, d, J=8.5 Hz)

Example 52

4-[(4-{3-[2-(Carbamoyl)ethylamino]propoxy}-2-methylphenyl)methyl]-3-(β-D-glucopyranosyloxy)-5-isopropyl-1H-pyrazole The title compound was prepared in a similar manner to that described in Example 51 using 3-(2-nitrobenzenesulfonylamino)propionamide instead of 2-methyl-2-(2-nitrobenzenesulfonylamino)propionamide.

$^1$H-NMR (CD$_3$OD) δ ppm:
1.05-1.15 (6H, m), 1.85-2.0 (2H, m), 2.29 (3H, s), 2.42 (2H, t, J=6.9 Hz), 2.7-2.9 (5H, m), 3.25-3.4 (4H, m), 3.6-3.75 (3H, m), 3.75-3.85 (1H, m), 3.99 (2H, t, J=6.2 Hz), 4.95-5.05 (1H, m), 6.62 (1H, dd, J=8.4 Hz, 2.4 Hz), 6.71 (1H, d, J=2.4 Hz), 6.85 (1H, d, J=8.4 Hz)

Example 53

3-(β-D-Glucopyranosyloxy)-4-[(4-{(R)-2-hydroxy-3-[2-hydroxy-1-(hydroxymethyl)-1-(methyl)ethylamino]propoxy)phenyl)methyl]-5-isopropyl-1H-pyrazole A mixture of 3-(2,3,4,6-tetra-O-acetyl-β-D-glucopyranosyloxy)-4-[(4-hydroxyphenyl)methyl]-5-isopropyl-1H-pyrazole (0.55 g), (R)-1-(3-nitrobenzenesulfonyloxy)-2,3-epoxypropane (0.38 g) and cesium carbonate (0.57 g) in N,N-dimethylformamide (5 mL) was stirred at room temperature for 24 hours. The reaction mixture was poured into water, and the resulting mixture was extracted with ethyl acetate. The organic layer was washed with water and brine successively, and dried over anhydrous magnesium sulfate. The solvent was removed under reduced pressure, and the residue was purified by column chromatography on silica gel (eluent: n-hexane/ethyl acetate 10=2/1) to give 3-(2,3,4,6-tetra-O-acetyl-β-D-glucopyranosyloxy)-4-({4-[(R)-2,3-epoxypropoxy]phenyl}methyl)-5-isopropyl-1H-pyrazole (0.4 g). This material (43 mg) was dissolved in ethanol (1.5 mL). To the solution was added 2-amino-2-methyl-1,3-propanediol (51 mg), and the mixture was stirred at 75° C. for 14 hours. To the reaction mixture was added 1 mol/L aqueous sodium hydroxide solution (0.28 mL), and the mixture was stirred at room temperature for 1 hour. The reaction mixture was directly purified by preparative reverse phase column chromatography (Shiseido CAPCELL PAK UG120 ODS, 5 μm, 120 Å, 20×50 mm, flow rate 30 mL/minute linear gradient, water/methanol=90/10-10/90) to give the title compound (12 mg).

$^1$H-NMR (CD$_3$OD) δ ppm:
1.0 (3H, s), 1.05-1.15 (6H, m), 2.68 (1H, dd, J=11.6 Hz, 8.1 Hz), 2.78 (1H, dd, J=11.6 Hz, 3.8 Hz), 2.8-2.95 (1H, m), 3.25-3.55 (8H, m), 3.6-3.7 (2H, m), 3.73 (1H, d, J=16.1 Hz), 3.8-4.0 (4H, m), 5.0-5.1 (1H, m), 6.75-6.85 (2H, m), 7.05-7.15 (2H, m)

Example 54

3-(β-D-Glucopyranosyloxy)-4-({4-[(R)-2-hydroxy-3-(2-hydroxyethylamino)propoxy]phenyl}methyl)-5-isopropyl-1H-pyrazole The title compound was prepared in a similar manner to that described in Example 53 using 2-aminoethanol instead of 2-amino-2-methyl-1,3-propanediol.

$^1$H-NMR (CD$_3$OD) δ ppm:
1.05-1.2 (6H, m), 2.65-2.95 (5H, m), 3.25-3.45 (4H, m), 3.6-3.8 (5H, m), 3.8-3.9 (1H, m), 3.91 (2H, d, J=5.4 Hz), 4.0-4.1 (1H, m), 5.0-5.1 (1H, m), 6.75-6.85 (2H, m), 7.05-7.15 (2H, m)

Example 55

3-(β-D-Glucopyranosyloxy)-4-{[4-(3-guanidinopropoxy)-2-methylphenyl]methyl}-5-isopropyl-1H-pyrazole To a solution of 3-(2,3,4,6-tetra-O-acetyl-β-D-glucopyranosyloxy)-4-{[4-(3-aminopropoxy)-2-methylphenyl]methyl}-5-isopropyl-1H-pyrazole (70 mg) in tetrahydrofuran (3 mL) was added N-(benzyloxycarbonyl)-1H-pyrazole-1-carboxamidine (0.27 g), and the mixture was stirred at 60° C. for 20 hours. The reaction mixture was concentrated under reduced pressure, and the residue was purified by column chromatography on silica gel (eluent: n-hexane/ethyl acetate=1/1-ethyl acetate-ethyl acetate/ethanol=10/1) to give 3-(2,3,4,6-tetra-O-acetyl-β-D-glucopyranosyloxy)-4-({4-[3-(N'-benzyloxycarbonylguanidino)propoxy]-2-methylphenyl}methyl)-5-isopropyl-1H-pyrazole (50 mg). This material was dissolved in methanol (1 mL). To the solution was added sodium methoxide (28% methanol solution, 0.01 mL), and the mixture was stirred at room temperature for 1 hour. The reaction mixture was concentrated under reduced pressure, and the residue was purified by solid phase extraction on ODS (washing solvent: distilled water, eluent: methanol) to give 4-({4-[3-(N'-benzyloxycarbonylguanidino)propoxy]-2-methylphenyl}methyl)-3-(β-D-glucopyranosyloxy)-5-isopropyl-1H-pyrazole (35 mg). This material was dissolved in methanol (2 mL). To the solution was added 10% palladium-carbon powder (15 mg), and the mixture was stirred at room temperature under a hydrogen atmosphere for 2 hours. The insoluble material was removed by filtration, and the solvent of the filtrate was removed under reduced pressure to give the title compound (27 mg).

$^1$H-NMR (CD$_3$OD) δ ppm:
1.05-1.2 (6H, m), 1.95-2.05 (2H, m), 2.29 (3H, s), 2.75-2.9 (1H, m), 3.25-3.45 (6H, m), 3.55-3.75 (3H, m), 3.75-3.85 (1H, m), 4.01 (2H, t, J=5.7 Hz), 4.95-5.05 (1H, m), 6.64 (1H, dd, J=8.6 Hz, 2.5 Hz), 6.73 (1H, d, J=2.5 Hz), 6.87 (1H, d, J=8.6 Hz)

Example 56

3-(β-D-Glucopyranosyloxy)-4-{[4-(2-guanidinoethoxy)-2-methylphenyl]methyl}-5-isopropyl-1H-pyrazole The title compound was prepared in a similar manner to that described in Example 55 using 3-(2,3,4,6-tetra-O-acetyl-β-D-glucopyranosyloxy)-4-{[4-(2-aminoethoxy)-2-methylphenyl]methyl}-5-isopropyl-1H-pyrazole instead of 3-(2,3,4,6-tetra-O-acetyl-β-D-glucopyranosyloxy)-4-{[4-(3-aminopropoxy)-2-methylphenyl]methyl}-5-isopropyl-1H-pyrazole.

$^1$H-NMR (CD$_3$OD) δ ppm:
1.05-1.15 (6H, m), 2.3 (3H, s), 2.75-2.9 (1H, m), 3.25-3.4 (4H, m), 3.55 (2H, t, J=5.0 Hz), 3.6-3.75 (3H, m), 3.75-3.85 (1H, m), 4.06 (2H, t, J=5.0 Hz), 5.02 (1H, d, J=7.0 Hz), 6.65 (1H, dd, J=8.5 Hz, 2.6 Hz), 6.75 (1H, d, J=2.6 Hz), 6.88 (1H, d, J=8.5 Hz)

Example 57

3-(β-D-Glucopyranosyloxy)-4-[(4-(3-[2-hydroxy-1,1-di(methyl)ethylamino]propoxy)-2-methylphenyl)methyl]-5-isopropyl-1H-pyrazole To a solution of 3-(2,3,4,6-tetra-O-acetyl-β-D-glucopyranosyloxy)-4-{[4-(3-hydroxypropoxy)-2-methylphenyl]-methyl}-5-isopropyl-1H-pyrazole (1 g) in dichloromethane (16 mL) were added triethylamine (0.29 mL) and methanesulfonyl chloride (0.15 mL), and the mixture was stirred at room temperature for 3 hours. The reaction mixture was poured into 0.5 mol/L hydrochloric acid, and the resulting mixture was extracted with ethylacetate. The organic layer was washed with water, and dried over anhydrous magnesium sulfate. The solvent was removed under reduced pressure to give 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole (1.12 g). The obtained 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole (0.2 g) was dissolved in a mixed solvent of acetonitrile (2 mL) and ethanol (2 mL). To the solution were added 2-amino-2-methyl-1-propanol (0.25 g) and a catalytic amount of sodium iodide, and the mixture was stirred at 60° C. for 2 days. The reaction mixture was concentrated under reduced pressure, and the residue was dissolved in methanol (3 mL). To the solution was added sodium methoxide (28% methanol solution, 0.16 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (0.13 g).

$^1$H-NMR (CD$_3$OD) δ ppm:
1.0-1.15 (12H, m), 1.85-2.0 (2H, m), 2.29 (3H, s), 2.65-2.85 (3H, m), 3.25-3.4 (6H, m), 3.6-3.75 (3H, m), 3.75-3.85 (1H, m), 4.0 (2H, t, J=5.6 Hz), 4.95-5.05 (1H, m), 6.62 (1H, dd, J=8.5 Hz, 2.6 Hz), 6.71 (1H, d, J=2.6 Hz), 6.85 (1H, d, J=8.5 Hz)

Example 58

3-(β-D-Glucopyranosyloxy)-4-({4-[3-(2-hydroxyethylamino)propoxy]-2-methylphenyl}methyl)-5-isopropyl-1H-pyrazole The title compound was prepared in a similar manner to that described in Example 57 using 2-aminoethanol instead of 2-amino-2-methyl-1-propanol.

$^1$H-NMR (CD$_3$OD) δ ppm:
1.05-1.15 (6H, m), 1.9-2.0 (2H, m), 2.29 (3H, s), 2.7-2.85 (5H, m), 3.25-3.4 (4H, m), 3.55-3.75 (5H, m), 3.75-3.85 (1H, m), 4.0 (2H, t, J=5.9 Hz), 4.95-5.05 (1H, m), 6.62 (1H, dd, J=8.5 Hz, 2.5 Hz), 6.71 (1H, d, J=2.5 Hz), 6.85 (1H, d, J=8.5 Hz)

Example 59

3-(β-D-Glucopyranosyloxy)-4-[(4-(3-[2-hydroxy-1-(hydroxymethyl)ethylamino]propoxy)-2-methylphenyl)methyl]-5-isopropyl-1H-pyrazole The title compound was prepared in a similar manner to that described in Example 57 using 2-amino-1,3-propanediol instead of 2-amino-2-methyl-1-propanol.

$^1$H-NMR (CD$_3$OD) δ ppm:
1.05-1.15 (6H, m), 1.9-2.0 (2H, m), 2.29 (3H, s), 2.65-2.9 (4H, m), 3.25-3.4 (4H, m), 3.54 (2H, dd, J=11.1 Hz, 5.8 Hz), 3.55-3.75 (5H, m), 3.75-3.85 (1H, m), 4.01 (2H, t, J=6.0 Hz), 4.95-5.05 (1H, m), 6.62 (1H, dd, J=8.6 Hz, 2.5 Hz), 6.72 (1H, d, J=2.5 Hz), 6.85 (1H, d, J=8.6 Hz)

Example 60

3-(β-D-Glucopyranosyloxy)-4-[(4-{3-[2-hydroxy-1-(hydroxymethyl)ethylamino]propoxy}phenyl)methyl]-5-isopropyl-1H-pyrazole The title compound was prepared in a similar manner to that described in Example 57 using 3-(2,3,4,6-tetra-O-acetyl-β-D-glucopyranosyloxy)-4-{[4-(3-hydroxypropoxy)phenyl]-methyl}-5-isopropyl-1H-pyrazole and 2-amino-1,3-propanediol instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-amino-2-methyl-1-propanol, respectively.

$^1$H-NMR (CD$_3$OD) δ ppm:
1.05-1.2 (6H, m), 1.9-2.0 (2H, m), 2.65-2.75 (1H, m), 2.8-2.95 (3H, m), 3.25-3.45 (4H, m), 3.54 (2H, dd, J=11.2 Hz, 5.9 Hz), 3.55-3.7 (4H, m), 3.73 (1H, d, J=15.8 Hz), 3.8-3.9 (1H, m), 4.02 (2H, t, J=6.1 Hz), 5.0-5.15 (1H, m), 6.75-6.85 (2H, m), 7.05-7.15 (2H, m)

Example 61

3-(β-D-Glucopyranosyloxy)-4-[(4-(3-[2-hydroxy-1,1-di(methyl)ethylamino]propoxy)phenyl)methyl]-5-isopropyl-1H-pyrazole The title compound was prepared in a similar manner to that described in Example 57 using 3-(2,3,4,6-tetra-O-acetyl-β-D-glucopyranosyloxy)-4-[4-{3-hydroxypropoxy)phenyl]-methyl}-5-isopropyl-1H-pyrazole instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole.

$^1$H-NMR (CD$_3$OD) δ ppm:
1.0-1.15 (12H, m), 1.85-2.0 (2H, m), 2.65-2.8 (2H, m), 2.8-2.95 (1H, m), 3.25-3.45 (6H, m), 3.6-3.8 (3H, m), 3.8-3.9 (1H, m), 3.95-4.05 (2H, m), 5.0-5.15 (1H, m), 6.75-6.85 (2H, m), 7.05-7.15 (2H, m)

Example 62

3-(β-D-Glucopyranosyloxy)-4-[(4-{2-[2-hydroxy-1-(hydroxymethyl)ethylamino]ethoxy}-2-methylphenyl)methyl]-5-isopropyl-1H-pyrazole The title compound was prepared in a similar manner to that described in Example 57 using 3-(2,3,4,6-tetra-O-acetyl-β-D-glucopyranosyloxy)-4-{[4-(2-hydroxyethoxy)-2-methylphenyl]methyl}-5-isopropyl-1H-pyrazole and 2-amino-1,3-propanediol instead of 3-(2,3,4,6-tetra-O-acetyl-β-D-glucopyranosyloxy)-4-{[4-(3-hydroxypropoxy)-2-methylphenyl]-methyl}-5-isopropyl-1H-pyrazole and 2-amino-2-methyl-1-propanol, respectively.

$^1$H-NMR (CD$_3$OD) δ ppm:
1.05-1.15 (6H, m), 2.29 (3H, s), 2.7-2.85 (2H, m), 3.04 (2H, t, J=5.2 Hz), 3.25-3.4 (4H, m), 3.55 (2H, dd, J=11.2 Hz, 5.8 Hz), 3.6-3.75 (5H, m), 3.75-3.85 (1H, m), 4.06 (2H, t, J=5.2 Hz), 4.95-5.1 (1H, m), 6.65 (1H, dd, J=8.5 Hz, 2.7 Hz), 6.75 (1H, d, J=2.7 Hz), 6.87 (1H, d, J=8.5 Hz)

Example 63

3-(β-D-Glucopyranosyloxy)-4-({4-[2-(2-hydroxyethylamino)ethoxy]-2-methylphenyl}methyl)-5-isopropyl-1H-pyrazole The title compound was prepared in a similar manner to that described in Example 57 using 3-(2,3,4,6-tetra-O-acetyl-β-D-glucopyranosyloxy)-4-{[4-(2-hydroxyethoxy)-2-methylphenyl]methyl}-5-isopropyl-1H-pyrazole and 2-aminoethanol instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-amino-2-methyl-1-propanol, respectively.

$^1$H-NMR (CD$_3$OD) δ ppm:
1.05-1.15 (6H, m), 2.29 (3H, s), 2.75-2.85 (3H, m), 2.99 (2H, t, J=5.2 Hz), 3.25-3.4 (4H, m), 3.6-3.75 (5H, m), 3.75-3.85 (1H, m), 4.05 (2H, t. J=5.2 Hz), 4.95-5.1 (1H, m), 6.65 (1H, dd, J=8.4 Hz, 2.4 Hz), 6.74 (1H, d, J=2.4 Hz), 6.87 (1H, d, J=8.4 Hz)

Example 64

3-(β-D-Glucopyranosyloxy)-5-isopropyl-4-({4-[3-(3-pyridyl-methylamino)propoxy]phenyl}methyl)-1H-pyrazole The title compound was prepared in a similar manner to that described in Example 57 using 3-(2,3,4,6-tetra-O-acetyl-β-D-glucopyranosyloxy)-4-{[4-(3-hydroxypropoxy)phenyl]methyl}-5-isopropyl-1H-pyrazole and 3-picolylamine instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-amino-2-methyl-1-propanol, respectively.

$^1$H-NMR (CD$_3$OD) δ ppm:
1.05-1.15 (6H, m), 1.9-2.0 (2H, m), 2.77 (2H, t, J=7.2 Hz), 2.8-2.95 (1H, m), 3.25-3.45 (4H, m), 3.6-3.7 (2H, m), 3.73 (1H, d, J=16.3 Hz), 3.75-3.9 (3H, m), 4.0 (2H, t, J=6.0 Hz), 5.0-5.1 (1H, m), 6.7-6.8 (2H, m), 7.05-7.15 (2H, m), 7.35-7.45 (1H, m), 7.8-7.85 (1H, m), 8.4-8.45 (1H, m), 8.5-8.55 (1H, m)

Example 65

4-{[4-(2-Aminoethoxy)-2-methylphenyl]methyl}-3-(β-D-glucopyranosyloxy)-5-isopropyl-1H-pyrazole The title compound was prepared in a similar manner to that described in Example 6 using 3-(2,3,4,6-tetra-O-acetyl-β-D-glucopyranosyloxy)-4-{[4-(2-aminoethoxy)-2-methylphenyl]methyl}-5-isopropyl-1H-pyrazole instead of 3-(2,3,4,6-tetra-O-acetyl-β-D-glucopyranosyloxy)-4-{[4-(3-aminopropoxy)phenyl]methyl}-5-isopropyl-1H-pyrazole.

$^1$H-NMR (CD$_3$OD) δ ppm:
1.05-1.15 (6H, m), 2.29 (3H, s), 2.7-2.85 (1H, m), 2.99 (2H, t, J=5.2 Hz), 3.25-3.4 (4H, m), 3.55-3.75 (3H, m), 3.75-3.85 (1H, m), 3.97 (2H, t, J=5.2 Hz), 4.95-5.05 (1H, m), 6.64 (1H, dd, J=8.6 Hz, 2.7 Hz), 6.74 (1H, d, J=2.7 Hz), 6.86 (1H, d, J=8.6 Hz)

Example 66

3-(β-D-Glucopyranosyloxy)-4-({4-[3-(3-hydroxypropylamino)propoxy]-2-methylphenyl}methyl)-5-isopropyl-1H-pyrazole The title compound was prepared in a similar manner to that described in Example 57 using 3-amino-1-propanol instead of 2-amino-2-methyl-1-propanol.

$^1$H-NMR (CD$_3$OD) δ ppm:
1.05-1.15 (6H, m), 1.7-1.8 (2H, m), 1.9-2.0 (2H, m), 2.29 (3H, s), 2.65-2.85 (5H, m), 3.25-3.4 (4H, m), 3.55-3.75 (5H, m), 3.75-3.85 (1H, m), 3.99 (2H, t, J=6.1 Hz), 4.95-5.05 (1H, m), 6.61 (1H, dd, J=8.5 Hz, 2.5 Hz), 6.7 (1H, d, J=2.5 Hz), 6.85 (1H, d, J=8.5 Hz)

Example 67

3-(β-D-Glucopyranosyloxy)-4-[(4-{3-[2-hydroxy-1-(hydroxymethyl)-1-(methyl)ethylamino]propoxy}-2-methylphenyl)methyl]-5-isopropyl-1H-pyrazole The title compound was prepared in a similar manner to that described in Example 57 using 2-amino-2-methyl-1,3-propanediol instead of 2-amino-2-methyl-1-propanol.

$^1$H-NMR (CD$_3$OD) δ ppm:
1.01 (3H, s), 1.05-1.15 (6H, m), 1.85-2.0 (2H, m), 2.29 (3H, s), 2.7-2.85 (3H, m), 3.25-3.4 (4H, m), 3.4-3.55 (4H, m), 3.6-3.75 (3H, m), 3.75-3.85 (1H, m), 4.01 (2H, t, J=6.0 Hz), 4.95-5.05 (1H, m), 6.62 (1H, dd, J=8.3 Hz, 2.6 Hz), 6.72 (1H, d, J=2.6 Hz), 6.84 (1H, d, J=8.3 Hz)

Example 68

3-(β-D-Glucopyranosyloxy)-4-[(4-(2-[2-hydroxy-1-(hydroxymethyl)-1-(methyl)ethylamino]ethoxy)-2-methylphenyl)methyl]-5-isopropyl-1H-pyrazole The title compound was prepared in a similar manner to that described in Example 57 using 3-(2,3,4,6-tetra-O-acetyl-β-D-glucopyranosyloxy)-4-{[4-(2-hydroxyethoxy)-2-methylphenyl]methyl}-5-isopropyl-1H-pyrazole and 2-amino-2-methyl-1,3-propanediol instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-amino-2-methyl-1-propanol, respectively.

$^1$H-NMR (CD$_3$OD) δ ppm:
1.01 (3H, s), 1.05-1.15 (6H, m), 2.29 (3H, s), 2.7-2.85 (1H, m), 2.92 (2H, t, J=5.3 Hz), 3.25-3.4 (4H, m), 3.4-3.55 (4H, m), 3.6-3.75 (3H, m), 3.75-3.85 (1H, m), 4.02 (2H, t, J=5.3 Hz), 4.95-5.05 (1H, m), 6.64 (1H, dd, J=8.4 Hz, 2.7 Hz), 6.74 (1H, d, J=2.7 Hz), 6.86 (1H, d, J=8.4 Hz)

Example 69

3-(β-D-Glucopyranosyloxy)-4-[(4-(3-[2-hydroxy-1, 1-bis(hydroxymethyl)ethylamino]propoxy)phenyl) methyl]-5-isopropyl-1H-pyrazole The title compound was prepared in a similar manner to that described in Example 57 using 3-(2,3,4,6-tetra-O-acetyl-β-D-glucopyranosyloxy)-4-{[4-(3-hydroxypropoxy)phenyl]-methyl}-5-isopropyl-1H-pyrazole and tris(hydroxymethyl)aminomethane instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-amino-2-methyl-1-propanol, respectively.
$^1$H-NMR (CD$_3$OD) δ ppm:
1.05-1.2 (6H, m), 1.85-2.0 (2H, m), 2.75-2.95 (3H, m), 3.25-3.4 (4H, m), 3.56 (6H, s), 3.6-3.75 (3H, m), 3.8-3.9 (1H, m), 4.02 (2H, t, J=6.1 Hz), 5.0-5.1 (1H, m), 6.75-6.85 (2H, m), 7.05-7.15 (2H, m)

Example 70

3-(β-D-Glucopyranosyloxy)-4-({4-[2-(3-hydroxypropylamino)ethoxy]-2-methylphenyl}methyl)-5-isopropyl-1H-pyrazole The title compound was prepared in a similar manner to that described in Example 57 using 3-(2,3,4,6-tetra-O-acetyl-β-D-glucopyranosyloxy)-4-{[4-(2-hydroxyethoxy)-2-methylphenyl]methyl}-5-isopropyl-1H-pyrazole and 3-amino-1-propanol instead of 3-(2,3,4,6-tetra-O-acetyl-β-D-glucopyranosyloxy)-4-{[4-(3-hydroxypropoxy)-2-methylphenyl]-methyl}-5-isopropyl-1H-pyrazole and 2-amino-2-methyl-1-propanol, respectively.
$^1$H-NMR (CD$_3$OD) δ ppm:
1.05-1.15 (6H, m), 1.7-1.8 (2H, m), 2.29 (3H, s), 2.65-2.85 (3H, m), 2.94 (2H, t, J=5.2 Hz), 3.25-3.4 (4H, m), 3.55-3.75 (5H, m), 3.75-3.85 (1H, m), 4.03 (2H, t, J=5.2 Hz), 4.95-5.05 (1H, m), 6.64 (1H, dd, J=8.1 Hz, 2.4 Hz), 6.74 (1H, d, J=2.4 Hz), 6.86 (1H, d, J=8.1 Hz)

Example 71

3-(β-D-Glucopyranosyloxy)-4-[(4-{3-[2-hydroxy-1,1-bis(hydroxymethyl)ethylamino]propoxy}-2-methylphenyl)methyl]-5-isopropyl-1H-pyrazole The title compound was prepared in a similar manner to that described in Example 57 using tris(hydroxymethyl)aminomethane instead of 2-amino-2-methyl-1-propanol.
$^1$H-NMR (CD$_3$OD) δ ppm:
1.05-1.15 (6H, m), 1.85-1.95 (2H, m), 2.28 (3H, s), 2.75-2.85 (3H, m), 3.25-3.4 (4H, m), 3.56 (6H, s), 3.6-3.75 (3H, m), 3.75-3.85 (1H, m), 4.01 (2H, t, J=6.0 Hz), 4.95-5.05 (1H, m), 6.62 (1H, dd, J=8.5 Hz, 2.5 Hz), 6.71 (1H, d, J=2.5 Hz), 6.84 (1H, d, J=8.5 Hz)

Reference Example 35

2-[2-Amino-2-(methyl)propionylamino]ethanol

To a solution of 2-benzyloxycarbonylamino-2-(methyl)propionic acid (1 g) in tetrahydrofuran (5 mL) was added 1,1'-carbonylbis-1H-imidazole (889 mg), and the mixture was stirred at room temperature for 1 hour. To the reaction mixture was added 2-aminoethanol (0.38 mL), and the mixture was stirred at room temperature for 2 hours. The reaction mixture was purified by column chromatography on silica gel (eluent: dichloromethane/methanol=20/1) to give 2-[2-benzyloxycarbonylamino-2-(methyl)propionylamino]ethanol (973 mg). This material was dissolved in methanol (5 mL). To the solution was added 10% palladium-carbon powder (200 mg), and the mixture was stirred at room temperature under a hydrogen atmosphere overnight. The insoluble material was removed by filtration, and the solvent of the filtrate was removed under reduced pressure to give the title compound (505 mg).
$^1$H-NMR (CD$_3$OD) δ ppm:
1.31 (6H, s), 3.25-3.35 (2H, m), 3.6 (2H, t, J=5.7 Hz)

Reference Example 36

4-Methyl-1-[2-amino-2-(methyl)propionyl]piperazine

The title compound was prepared in a similar manner to that described in Reference Example 35 using 1-methylpiperazine instead of 2-aminoethanol.
$^1$H-NMR (DMSO-d$_6$) δ ppm:
1.24 (6H, s), 1.83 (2H, brs), 2.16 (3H, s), 2.26 (4H, t, J=5.0 Hz), 3.5-3.95 (4H, br)

Reference Example 37

2-[2-Amino-2-(methyl)propionylamino]-2-methyl-1-propanol

The title compound was prepared in a similar manner to that described in Reference Example 35 using 2-amino-2-methyl-1-propanol instead of 2-aminoethanol.
$^1$H-NMR (CD$_3$OD) δ ppm:
1.28 (12H, s), 3.55 (2H, s)

Reference Example 38

3-[2-Amino-2-(methyl)propionylamino]-1-propanol

The title compound was prepared in a similar manner to that described in Reference Example 35 using 3-amino-1-propanol instead of 2-aminoethanol.
$^1$H-NMR (DMSO-d$_6$) δ ppm:
1.16 (6H, s), 1.5-1.6 (2H, m), 1.89 (2H, brs), 3.05-3.15 (2H, m), 3.35-3.45 (2H, m), 4.43 (1H, t, J=5.3 Hz), 7.8-7.95 (1H, br)

Reference Example 39

N-[2-Amino-2-(methyl)propionyl]morpholine

The title compound was prepared in a similar manner to that described in Reference Example 35 using morpholine instead of 2-aminoethanol.
$^1$H-NMR (DMSO-d$_6$) δ ppm:
1.25 (6H, s), 1.75-2.3 (2H, br), 3.45-3.6 (4H, m), 3.65-3.95 (4H, br)

Example 72

3-(β-D-Glucopyranosyloxy)-4-[(4-{3-[1-(2-hydroxyethylcarbamoyl)-1-(methyl)ethylamino] propoxy}phenyl)methyl]-5-isopropyl-1H-pyrazole To a solution of 3-(2,3,4,6-tetra-O-acetyl-β-D-glucopyranosyloxy)-4-{[4-(3-hydroxypropoxy)phenyl]methyl}-5-isopropyl-1H-pyrazole (0.77 g) in dichloromethane (5 mL) were added triethylamine (0.26 mL) and methanesulfonylchloride (0.12 mL), and the mixture was stirred at room temperature for 30 minutes. The reaction mixture was poured into 0.5 mol/L hydrochloric acid, and the resulting mixture was extracted with ethyl acetate. The organic layer was washed with water and brine, and dried over anhydrous sodium sulfate. The solvent was removed under reduced pressure to give 3-(2,3,4,6-tetra-O-acetyl-β-D-glucopyranosyloxy)-5-isopropyl-4-({4-[3-(methanesulfonyloxy)propoxy]phenyl}methyl)-1H-pyrazole (0.85 g). The obtained 3-(2,3,4,6-tetra-O-acetyl-β-D-glucopyranosyloxy)-5-isopropyl-4-({4-[(3-(methanesulfonyloxy)propoxy]phenyl}-methyl)-1H-pyrazole (0.2 g) was dissolved in a mixed solvent of acetonitrile (1.5 mL) and ethanol (1.5 mL). To the solution were added 2-[2-amino-2-(methyl)propionylamino]ethanol (0.25 g) and a catalytic amount of sodium iodide, and the mixture was stirred at 60° C. for 4 days. The reaction mixture was concentrated under reduced pressure, and the residue was purified by column chromatography on silica gel (eluent: dichloromethane/methanol=20/1-10/1) to give 3-(2,3,4,6-tetra-O-acetyl-β-D-glucopyranosyloxy)-4-[(4-(3-[1-(2-hydroxyethylcarbamoyl)-1-(methyl)ethylamino]propoxy)phenyl)methyl]-5-isopropyl-1H-pyrazole (0.13 g). This material was dissolved in methanol (3 mL). To the solution was added sodium methoxide (28% methanol solution, 0.05 mL), and the mixture was stirred at room temperature for 3 hours. The reaction mixture was concentrated under reduced pressure, and the residue was purified by solid phase extraction on ODS (washing solvent: distilled water, eluent: methanol) to give the title compound (93 mg).

$^1$H-NMR (CD$_3$OD) δ ppm:
1.05-1.15 (6H, m), 1.28 (6H, s), 1.8-1.95 (2H, m), 2.63 (2H, t, J=6.9 Hz), 2.85-2.95 (1H, m), 3.2-3.4 (6H, m), 3.55 (2H, t, J=5.8 Hz), 3.6-3.9 (4H, m), 4.03 (2H, t, J=6.2 Hz), 5.0-5.1 (1H, m), 6.7-6.85 (2H, m), 7.0-7.15 (2H, m)

Example 73

3-(β-D-Glucopyranosyloxy)-4-{[4-(3-{1-[(4-methylpiperazin-1-yl)carbonyl]-1-(methyl)ethylamino}propoxy)phenyl]methyl}-5-isopropyl-1H-pyrazole The title compound was prepared in a similar manner to that described in Example 72 using 4-methyl-1-[2-amino-2-(methyl)propionyl]piperazine instead of 2-[2-amino-2-(methyl)propionylamino]ethanol.

$^1$H-NMR (CD$_3$OD) δ ppm:
1.1-1.15 (6H, m), 1.34 (6H, s), 1.8-1.95 (2H, m), 2.19 (3H, s), 2.3-2.4 (4H, m), 2.66 (2H, t, J=6.3 Hz), 2.8-2.95 (1H, m), 3.3-3.4 (4H, m), 3.55-4.15 (10H, m), 5.0-5.15 (1H, m), 6.7-6.8 (2H, m), 7.05-7.15 (2H, m)

Example 74

3-(β-D-Glucopyranosyloxy)-4-{[4-(3-{1-[2-hydroxy-1,1-di(methyl)ethylcarbamoyl]-1-(methyl)ethylamino}propoxy)phenyl]methyl}-5-isopropyl-1H-pyrazole The title compound was prepared in a similar manner to that described in Example 72 using 2-[2-amino-2-(methyl)propionylamino]-2-methyl-1-propanol instead of 2-[2-amino-2-(methyl)propionylamino]ethanol.

$^1$H-NMR (CD$_3$OD) δ ppm:
1.1-1.15 (6H, m), 1.24 (6H, s), 1.25 (6H, s), 1.85-1.95 (2H, m), 2.64 (2H, t, J=6.9 Hz), 2.8-2.95 (1H, m), 3.3-3.45 (4H, m), 3.48 (2H, s), 3.6-3.9 (4H, m), 4.03 (2H, t, J=6.1 Hz), 5.05-5.1 (1H, m), 6.75-6.8 (2H, m), 7.05-7.15 (2H, m)

Example 75

3-(β-D-Glucopyranosyloxy)-4-[(4-{3-[1-(3-hydroxypropylcarbamoyl)-1-(methyl)ethylamino]propoxy}phenyl)methyl]-5-isopropyl-1H-pyrazole The title compound was prepared in a similar manner to that described in Example 72 using 3-[2-amino-2-(methyl)propionylamino]-1-propanol instead of 2-[2-amino-2-(methyl)propionylamino]ethanol.

$^1$H-NMR (CD$_3$OD) δ ppm:
1.1-1.15 (6H, m), 1.27 (6H, s), 1.55-1.7 (2H, m), 1.85-1.95 (2H, m), 2.62 (2H, t, J=6.8 Hz), 2.8-2.95 (1H, m), 3.23 (2H, t, J=6.7 Hz), 3.3-3.4 (4H, m), 3.53 (2H, t, J=6.2 Hz), 3.6-3.85 (4H, m), 4.03 (2H, t, J=6.0 Hz), 5.0-5.1 (1H, m), 6.75-6.85 (2H, m), 7.05-7.15 (2H, m)

Example 76

3-(β-D-Glucopyranosyloxy)-4-{[4-(3-{1-[(morpholin-4-yl)carbonyl]-1-(methyl)ethylamino}propoxy)phenyl]methyl}-5-isopropyl-1H-pyrazole The title compound was prepared in a similar manner to that described in Example 72 using N-[2-amino-2-(methyl)propionyl]morpholine instead of 2-[2-amino-2-(methyl)propionylamino]ethanol.

$^1$H-NMR (CD$_3$OD) δ ppm:
1.05-1.15 (6H, m), 1.35 (6H, s), 1.8-1.95 (2H, m), 2.6-2.75 (2H, m), 2.8-2.95 (1H, m), 3.3-3.4 (4H, m), 3.45-4.15 (14H, m), 5.0-5.15 (1H, m), 6.7-6.8 (2H, m), 7.05-7.15 (2H, m)

Example 77

3-(β-D-Glucopyranosyloxy)-4-[(4-{2-[3-(2-hydroxyethyl)-2-methanesulfonylguanidino]ethoxy}-2-methylphenyl)methyl]-5-isopropyl-1H-pyrazole To a solution of dichlorophenoxymethane (1 g) in acetonitrile (10 mL) was added methanesulfonamide (0.39 g) under ice-cooling, and the mixture was stirred at room temperature for 48 hours. The reaction mixture was poured into a saturated aqueous sodium hydrogen carbonate solution, and the resulting mixture was extracted with ethyl acetate. The organic layer was washed with water and brine, and dried over anhydrous magnesium sulfate. The solvent was removed under reduced pressure to give 1-(N-methanesulfonylamino)-1,1-diphenoxymethane (0.95 g). To a solution of 3-(2,3,4,6-tetra-O-acetyl-β-D-glucopyranosyloxy)-4-{[4-(2-aminoethoxy)-2-methylphenyl]methyl}-5-isopropyl-1H-pyrazole (50 mg) in tetrahydrofuran (1 mL) was added 1-(N-methanesulfonylamino)-1,1-diphenoxymethane (26 mg) under ice-cooling, and the mixture was stirred at room temperature for 1 hour. To the reaction mixture was added 2-aminoethanol (49 mg), and the mixture was stirred at 60° C. overnight. The reaction mixture was concentrated under reduced pressure, and the residue was dissolved in methanol (2 mL). To the solution was added sodium methoxide (28% methanol solution, 0.008 mL), and the mixture was stirred at room temperature for 3 hours. To the reaction mixture was added acetic acid (0.01 mL). The resulting mixture was concentrated under reduced pressure, and the residue was purified by solid phase extraction on ODS (washing solvent: distilled water, eluent: methanol) to give the title compound (38 mg).

¹H-NMR (CD₃OD) δ ppm:
1.05-1.15 (6H, m), 2.28 (3H, s), 2.75-2.85 (1H, m), 2.9 (3H, s), 3.25-3.4 (6H, m), 3.6 (2H, t, J=5.3 Hz), 3.6-3.75 (5H, m), 3.8 (1H, d, J=12.0 Hz), 4.05 (2H, t, J=5.3 Hz), 4.95-5.05 (1H, m), 6.65 (1H, dd, J=8.1 Hz, 2.4 Hz), 6.76 (1H, d, J=2.4 Hz), 6.86 (1H, d, J=8.1 Hz)

Example 78

4-[(4-{3-[(S)-5-Benzyloxycarbonylamino-1-(carbamoyl)pentylamino]propoxy}-2-methylphenyl)methyl]-3-(β-D-glucopyranosyloxy)-5-isopropyl-1H-pyrazole The title compound was prepared in a similar manner to that described in Example 72 using 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and (S)-2-amino-6-(benzyloxycarbonylamino)hexanamide instead of 3-(2,3,4,6-tetra-O-acetyl-β-D-glucopyranosyloxy)-4-{[4-(3-hydroxypropoxy)phenyl]methyl}-5-isopropyl-1H-pyrazole and 2-[2-amino-2-(methyl)propionylamino]ethanol, respectively.

¹H-NMR (CD₃OD) δ ppm:
1.05-1.15 (6H, m), 1.3-1.45 (2H, m), 1.45-1.7 (4H, m), 1.85-2.0 (2H, m), 2.28 (3H, s), 2.6-2.85 (3H, m), 3.05-3.15 (3H, m), 3.25-3.4 (4H, m), 3.6-3.7 (3H, m), 3.75-3.85 (1H, m), 3.99 (2H, t, J=6.0 Hz), 4.95-5.1 (3H, m), 6.61 (1H, dd, J=8.4 Hz, 2.5 Hz), 6.7 (1H, d, J=2.5 Hz), 6.84 (1H, d, J=8.4 Hz), 7.2-7.4 (5H, m)

Example 79

4-[(4-(3-[(S)-5-Amino-1-(carbamoyl)pentylamino]propoxy)-2-methylphenyl)methyl]-3-(β-D-glucopyranosyloxy)-5-isopropyl-1H-pyrazole To a solution of 4-[(4-{3-[(S)-5-benzyloxycarbonylamino-1-(carbamoyl)pentylamino]propoxy}-2-methylphenyl)methyl]-3-(β-D-glucopyranosyloxy)-5-isopropyl-1H-pyrazole (0.17 g) in methanol (4 mL) was added 10% palladium-carbon powder (30 mg), and the mixture was stirred at room temperature under a hydrogen atmosphere for 1 hour. The insoluble material was removed by filtration, and the filtrate was concentrated under reduced pressure to give the title compound (0.13 g).

¹H-NMR (CD₃OD) δ ppm:
1.05-1.15 (6H, m), 1.3-1.7 (6H, m), 1.85-2.0 (2H, m), 2.29 (3H, s), 2.6-2.9 (5H, m), 3.08 (1H, t, J=6.6 Hz), 3.25-3.4 (4H, m), 3.6-3.75 (3H, m), 3.75-3.85 (1H, m), 4.0 (2H, t, J=6.1 Hz), 5.01 (1H, d, J=7.0 Hz), 6.61 (1H, dd, J=8.4 Hz, 2.6 Hz), 6.7 (1H, d, J=2.6 Hz), 6.84 (1H, d, J=8.4 Hz)

Example 80

4-[(4-(3-[(S)-2,5-Diaminopentanoylamino]propoxy)-2-methylphenyl)methyl]-3-(β-D-glucopyranosyloxy)-5-isopropyl-1H-pyrazole The title compound was prepared in a similar manner to that described in Example 13 using 3-(2,3,4,6-tetra-O-acetyl-β-D-glucopyranosyloxy)-4-{[4-(3-aminopropoxy)-2-methylphenyl]methyl}-5-isopropyl-1H-pyrazole and (S)-2,5-bis(benzyloxycarbonylamino)pentanoic acid instead of 3-(2,3,4,6-tetra-O-acetyl-β-D-glucopyranosyloxy)-4-{[4-(3-aminopropoxy)phenyl]methyl}-5-isopropyl-1H-pyrazole and 2-benzyloxycarbonylaminoacetic acid, respectively.

¹H-NMR (CD₃OD) δ ppm:
1.05-1.15 (6H, m), 1.35-1.75 (4H, m), 1.9-2.0 (2H, m), 2.29 (3H, s), 2.59 (2H, t, J=6.9 Hz), 2.75-2.9 (1H, m), 3.2-3.5 (7H, m), 3.55-3.75 (3H, m), 3.75-3.85 (1H, m), 3.97 (2H, t, J=6.0 Hz), 5.01 (1H, d, J=7.3 Hz), 6.62 (1H, dd, J=8.5 Hz, 2.3 Hz), 6.72 (1H, d, J=2.3 Hz), 6.85 (1H, d, J=8.5 Hz)

Reference Example 40

1-Benzyloxycarbonyl-4-[2-carboxy-2-(methyl)propionyl]-piperazine

To a solution of diethyl dimethylmalonate (3 g) in ethanol (5 mL) was added a solution of sodium hydroxide (0.64 g) in water (2 mL), and the mixture was stirred at room temperature for 5 days. The reaction mixture was concentrated under reduced pressure, and the residue was acidified by addition of 2 mol/L hydrochloric acid. The resulting mixture was extracted with ethyl acetate. The extract was washed with brine, and dried over anhydrous magnesium sulfate. The solvent was removed under reduced pressure to give mono-ethyl dimethylmalonate (2.43 g).

To a solution of the obtained mono-ethyl dimethylmalonate (1 g) in N,N-dimethylformamide (20 mL) were added 1-(benzyloxycarbonyl)piperazine (1.38 g), 1-hydroxybenzotriazole (0.93 g), triethylamine (1.31 mL) and 1-ethyl-3-(3-dimethylaminopropyl)carbodiimide hydrochloride (2.4 g), and the mixture was stirred at room temperature for 2 days. The reaction mixture was poured into water, and the resulting mixture was extracted with diethyl ether. The extract was washed with a saturated aqueous sodium hydrogen carbonate solution, water and brine, and dried over anhydrous magnesium sulfate. The solvent was removed under reduced pressure, and the residue was purified by column chromatography on silica gel (eluent: n-hexane/ethyl acetate=4/1-2/1) to give 1-benzyloxycarbonyl-4-[2-ethoxycarbonyl-2-(methyl)propionyl]piperazine (1.77 g). This material was dissolved in ethanol (5 mL). To the solution was added 2 mol/L aqueous sodium hydroxide solution (2.93 mL), and the mixture was stirred at 55° C. overnight. The reaction mixture was poured into water, and the resulting mixture was washed with diethyl ether. The aqueous layer was acidified by addition of 2 mol/L hydrochloric acid, and the mixture was extracted with diethyl ether. The extract was washed with brine, and dried over anhydrous magnesium sulfate. The solvent was removed under reduced pressure to give the title compound (0.28 g).

¹H-NMR (CDCl₃) δ ppm:
1.48 (6H, s), 3.25-3.7 (8H, m), 5.14 (2H, s), 7.3-7.4 (5H, m)

Example 81

3-(β-D-Glucopyranosyloxy)-5-isopropyl-4-{[4-(2-{2-methyl-2-[(piperazin-1-yl)carbonyl]propionylamino}ethoxy)-2-methylphenyl]methyl}-1H-pyrazole The title compound was prepared in a similar manner to that described in Example 13 using 3-(2,3,4,6-tetra-O-acetyl-β-D-glucopyranosyloxy)-4-{[4-(2-aminoethoxy)-2-methylphenyl]methyl}-5-isopropyl-1H-pyrazole and 1-benzyloxycarbonyl-4-[2-carboxy-2-(methyl)propionyl]piperazine instead of 3-(2,3,4,6-tetra-O-acetyl-β-D-glucopyranosyloxy)-4-{[4-(3-aminopropoxy)phenyl]methyl}-5-isopropyl-1H-pyrazole and 2-benzyloxycarbonylaminoacetic acid, respectively.

¹H-NMR (CD₃OD) δ ppm:
1.1-1.2 (6H, m), 1.37 (6H, s), 2.3 (3H, s), 2.35-2.9 (5H, m), 3.1-3.75 (13H, m), 3.81 (1H, d, J=11.5 Hz), 4.02 (2H, t, J=5.4 Hz), 5.02 (1H, d, J=7.4 Hz), 6.62 (1H, dd, J=8.4 Hz, 2.5 Hz), 6.72 (1H, d, J=2.5 Hz), 6.86 (1H, d, J=8.4 Hz)

Reference Example 41

N,N-Dimethyl-N'-(2-nitrobenzenesulfonyl)-1,3-diaminopropane

To a solution of N,N-dimethyl-1,3-diaminopropane (0.92 g) and triethylamine (0.95 mL) in dichloromethane (10 mL) was added 2-nitrobenzenesulfonyl chloride (1 g), and the mixture was stirred at room temperature overnight. The reaction mixture was purified by column chromatography on silica gel (eluent: dichloromethane/methanol=10/1) to give the title compound (1.26 g).
¹H-NMR (CDCl₃) δ ppm:
1.7-1.8 (2H, m), 2.28 (6H, s), 2.46 (2H, t, J=5.9 Hz), 3.15-3.25 (2H, m), 7.65-7.75 (2H, m), 7.8-7.85 (1H, m), 8.05-8.15 (1H, m)

Reference Example 42

Methyl 3-(2-nitrobenzenesulfonylamino)propionate

The title compound was prepared in a similar manner to that described in Reference Example 2 using methyl 3-aminopropionate hydrochloride instead of glycinamide hydrochloride.
¹H-NMR (CDCl₃) δ ppm:
2.61 (2H, t, J=6.2 Hz), 3.37 (2H, q, J=6.2 Hz), 3.69 (3H, s), 5.96 (1H, t, J=6.2 Hz), 7.7-7.8 (2H, m), 7.85-7.9 (1H, m), 8.1-8.2 (1H, m)

Reference Example 43

4-Methyl-1-[3-(2-nitrobenzenesulfonylamino)propionyl]-piperazine

To a solution of methyl 3-(2-nitrobenzenesulfonylamino) propionate (6.15 g) in ethanol (20 mL)-methanol (5 mL) was added 5 mol/L aqueous sodium hydroxide solution (20 mL), and the mixture was stirred at room temperature overnight. The reaction mixture was acidified by addition of 2 mol/L hydrochloric acid (55 mL), and the resulting mixture was extracted with ethylacetate. The extract was washed with water and brine, and dried over anhydrous sodium sulfate. The solvent was removed under reduced pressure, and the residue was treated with n-hexane and ethylacetate. The precipitated crystals were collected by filtration, washed with n-hexane and dried under reduced pressure to give 3-(2-nitrobenzenesulfonylamino)propionic acid (5.83 g). To a solution of the obtained 3-(2-nitrobenzenesulfonylamino)propionic acid (0.5 g) in tetrahydrofuran (5 mL) was added 1,1'-carbonylbis-1H-imidazole (0.35 g), and the mixture was stirred at room temperature for 2 hours. To the reaction mixture was added 1-methylpiperazine (0.46 g), and the mixture was stirred at 50° C. for 3 days. The reaction mixture was concentrated under reduced pressure, and the residue was purified by column chromatography on aminopropylated silica gel (eluent: dichloromethane/methanol 40/1) to give the title compound (0.61 g).
¹H-NMR (CDCl₃) δ ppm:
2.25-2.4 (7H, m), 2.61 (2H, t, J=5.7 Hz), 3.3-3.45 (4H, m), 3.55-3.65 (2H, m), 7.65-7.75 (2H, m), 7.8-7.9 (1H, m), 8.1-8.15 (1H, m)

Reference Example 44

4-Benzyl-1-[3-(2-nitrobenzenesulfonylamino)propionyl]-piperazine

The title compound was prepared in a similar manner to that described in Reference Example 43 using 1-benzylpiperazine instead of 1-methylpiperazine.
¹H-NMR (CDCl₃) δ ppm:
2.35-2.45 (4H, m), 2.59 (2H, t, J=5.8 Hz), 3.3-3.45 (4H, m), 3.52 (2H, s), 3.55-3.65 (2H, m), 7.2-7.35 (5H, m), 7.65-7.75 (2H, m), 7.8-7.9 (1H, m), 8.05-8.15 (1H, m)

Reference Example 45

4-(2-Hydroxyethyl)-1-[3-(2-nitrobenzenesulfonylamino)propionyl]piperazine

The title compound was prepared in a similar manner to that described in Reference Example 43 using 1-(2-hydroxyethyl)piperazine instead of 1-methylpiperazine.
¹H-NMR (CDCl₃) δ ppm:
2.4-2.65 (8H, m), 3.37 (2H, t, J=5.8 Hz), 3.43 (2H, t, J=5.0 Hz), 3.55-3.7 (4H, m), 7.7-7.75 (2H, m), 7.8-7.9 (1H, m), 8.1-8.15 (1H, m)

Reference Example 46

4-(2-Acetoxyethyl)-1-[3-(2-nitrobenzenesulfonylamino)propionyl]piperazine

To a solution of 4-(2-hydroxyethyl)-1-[3-(2-nitrobenzenesulfonylamino)propionyl]piperazine (1.15 g) and pyridine (1.47 mL) in dichloromethane (10 mL) was added acetic anhydride (1.72 mL), and the mixture was stirred at room temperature overnight. The reaction mixture was poured into water, and the resulting mixture was extracted with ethylacetate. The extract was washed with water and brine, and dried over anhydrous sodium sulfate. The solvent was removed under reduced pressure, and the residue was purified by column chromatography on silica gel (eluent: n-hexane/ethyl acetate=1/2-dichloromethane/methanol=10/1) to give the title compound (0.38 g).
¹H-NMR (CDCl₃) δ ppm:
2.07 (3H, s), 2.4-2.55 (4H, m), 2.55-2.7 (4H, m), 3.3-3.45 (4H, m), 3.55-3.65 (2H, m), 4.05-4.15 (2H, m), 6.34 (1H, t, J=6.5 Hz), 7.7-7.75 (2H, m), 7.8-7.9 (1H, m), 8.1-8.15 (1H, m)

Example 82

3-(β-D-Glucopyranosyloxy)-5-isopropyl-4-[(4-{3-[3-(dimethylamino)propylamino]propoxy}-2-methylphenyl)methyl]-1H-pyrazole The title compound was prepared in a similar manner to that described in Example 51 using N,N-dimethyl-N'-(2-nitrobenzenesulfonyl)-1,3-diaminopropane instead of 2-methyl-2-(2-nitrobenzenesulfonylamino)propionamide.
¹H-NMR (CD₃OD) δ ppm:
1.05-1.15 (6H, m), 1.6-1.75 (2H, m), 1.85-2.0 (2H, m), 2.22 (6H, s), 2.29 (3H, s), 2.3-2.4 (2H, m), 2.61 (2H, t, J=7.4 Hz), 2.7-2.85 (3H, m), 3.25-3.4 (4H, m), 3.6-3.75 (3H, m), 3.75-3.85 (1H, m), 3.99 (2H, t, J=6.0 Hz), 4.95-5.1 (1H, m), 6.61 (1H, dd, J=8.2 Hz, 2.5 Hz), 6.7 (1H, d, J=2.5 Hz), 6.85 (1H, d, J=8.2 Hz)

Example 83

3-(β-D-Glucopyranosyloxy)-5-isopropyl-4-[(4-{3-[2-(methoxycarbonyl)ethylamino]propoxy}-2-methylphenyl)methyl]-1H-pyrazole The title compound was prepared in a similar manner to that described in Example 51 using methyl 3-(2-nitrobenzenesulfonylamino)propionate instead of 2-methyl-2-(2-nitrobenzenesulfonylamino)propionamide.

$^1$H-NMR (CD$_3$OD) δ ppm:
1.05-1.15 (6H, m), 1.95-2.05 (2H, m), 2.29 (3H, s), 2.64 (2H, t, J=6.5 Hz), 2.75-2.85 (1H, m), 2.9-3.1 (4H, m), 3.25-3.4 (4H, m), 3.6-3.7 (6H, m), 3.75-3.85 (1H, m), 4.03 (2H, t, J=6.0 Hz), 5.0-5.05 (1H, m), 6.64 (1H, dd, J=8.3 Hz, 2.3 Hz), 6.73 (1H, d, J=2.3 Hz), 6.87 (1H, d, J=8.3 Hz)

Example 84

3-(1-D-Glucopyranosyloxy)-5-isopropyl-4-{[4-(3-(2-[(4-methylpiperazin-1-yl)carbonyl]ethylamino) propoxy)-2-methylphenyl]methyl}-1H-pyrazole The title compound was prepared in a similar manner to that described in Example 51 using 4-methyl-1-[3-(2-nitrobenzenesulfonylamino)propionyl]piperazine instead of 2-methyl-2-(2-nitrobenzenesulfonylamino)propionamide.

$^1$H-NMR (CD$_3$OD) δ ppm:
1.05-1.15 (6H, m), 1.9-2.0 (2H, m), 2.29 (6H, s), 2.35-2.45 (4H, m), 2.6 (2H, t, J=6.6 Hz), 2.75-2.9 (5H, m), 3.3-3.4 (4H, m), 3.5-3.7 (7H, m), 3.8-3.85 (1H, m), 4.0 (2H, t, J=6.0 Hz), 5.0-5.05 (1H, m), 6.62 (1H, dd, J=8.4 Hz, 2.5 Hz), 6.72 (1H, d, J=2.5 Hz), 6.85 (1H, d, J=8.4 Hz)

Example 85

3-(β-D-Glucopyranosyloxy)-4-({4-[3-(2-{[4-(2-hydroxyethyl)piperazin-1-yl]carbonyl}ethylamino) propoxy]-2-methylphenyl}methyl)-5-isopropyl-1H-pyrazole The title compound was prepared in a similar manner to that described in Example 51 using 4-(2-acetoxyethyl)-1-[3-(2-nitrobenzenesulfonylamino)propionyl]piperazine instead of 2-methyl-2-(2-nitrobenzenesulfonylamino)propionamide.

$^1$H-NMR (CD$_3$OD) δ ppm:
1.05-1.15 (6H, m), 1.9-2.0 (2H, m), 2.29 (3H, s), 2.46 (2H, t, J=5.1 Hz), 2.5-2.55 (4H, m), 2.6 (2H, t, J=6.6 Hz), 2.75-2.9 (5H, m), 3.25-3.4 (4H, m), 3.5-3.7 (9H, m), 3.75-3.85 (1H, m), 4.0 (2H, t, J=6.0 Hz), 4.95-5.05 (1H, m), 6.62 (1H, dd, J=8.4 Hz, 2.6 Hz), 6.72 (1H, d, J=2.6 Hz), 6.85 (1H, d, J=8.4 Hz)

Example 86

3-(β-D-Glucopyranosyloxy)-5-isopropyl-4-{[4-(3-{2-[(piperazin-1-yl)carbonyl]ethylamino}propoxy)-2-methylphenyl]methyl}-1H-pyrazole 3-(β-D-Glucopyranosyloxy)-5-isopropyl-4-{[4-(3-{2-[(4-benzylpiperazin-1-yl)carbonyl]ethylamino}propoxy)-2-methylphenyl]methyl}-1H-pyrazole was prepared in a similar manner to that described in Example 51 using 4-benzyl-1-[3-(2-nitrobenzenesulfonylamino)propionyl]piperazine instead of 2-methyl-2-(2-nitrobenzenesulfonylamino)propionamide. Then the title compound was prepared in a similar manner to that described in Example 79 using this material instead of 4-[(4-{3-[(S)-5-benzyloxycarbonylamino-1-(carbamoyl)pentylamino]propoxy}-2-methylphenyl)methyl]-3-(β-D-glucopyranosyloxy)-5-isopropyl-1H-pyrazole.

$^1$H-NMR (CD$_3$OD) δ ppm:
1.05-1.15 (6H, m), 1.9-2.0 (2H, m), 2.29 (3H, s), 2.59 (2H, t, J=6.6 Hz), 2.7-2.9 (9H, m), 3.3-3.4 (4H, m), 3.45-3.55 (4H, m), 3.6-3.7 (3H, m), 3.75-3.85 (1H, m), 4.0 (2H, t, J=6.0 Hz), 4.95-5.05 (1H, m), 6.62 (1H, dd, J=8.4 Hz, 2.3 Hz), 6.72 (1H, d, J=2.3 Hz), 6.85 (1H, d, J=8.4 Hz)

Example 87

3-(β-D-Glucopyranosyloxy)-4-[(4-(3-[2-(2-hydroxyethylcarbamoyl)ethylamino]propoxy)-2-methylphenyl)methyl]-5-isopropyl-1H-pyrazole To a solution of 3-benzyloxycarbonylaminopropionic acid (1 g) in tetrahydrofuran (10 mL) was added 1,1'-carbonylbis-1H-imidazole (0.94 g), and the mixture was stirred at room temperature for 1 hour. To the reaction mixture was added 2-aminoethanol (0.81 mL), and the mixture was stirred at room temperature for 1 hour. The reaction mixture was poured into water, and the resulting mixture was extracted with ethylacetate. The extract was washed with 0.5 mol/L hydrochloric acid, water and brine successively, and dried over anhydrous sodium sulfate. The solvent was removed under reduced pressure, and the residue was washed with a mixed solvent of n-hexane and ethyl acetate (2/1), and dried under reduced pressure to give 2-[3-(benzyloxycarbonylamino)propionylamino]ethanol (0.25 g). The obtained 2-[3-(benzyloxycarbonylamino)propionylamino]-ethanol (50 mg) was dissolved in methanol (3 mL). To the solution was added 10% palladium-carbon powder (20 mg), and the mixture was stirred at room temperature under a hydrogen atmosphere for 2 hours. The insoluble material was removed by filtration, and the filtrate was concentrated under reduced pressure to give 2-(3-aminopropionylamino)ethanol (24 mg). To a solution of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole (0.81 g) and triethylamine (0.21 mL) in dichloromethane (6 mL) was added methanesulfonyl chloride (0.11 mL), and the mixture was stirred at room temperature for 1 hour. The reaction mixture was poured into 0.5 mol/L hydrochloric acid, and the resulting mixture was extracted with ethylacetate. The extract was washed with water and brine, and dried over anhydrous sodium sulfate. The solvent was removed under reduced pressure to give 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole (0.89 g). To a solution of the obtained 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole (50 mg) in acetonitrile (1 mL)-ethanol (1 mL) were added 2-(3-aminopropionylamino)ethanol described above (23 mg) and sodium iodide (11 mg), and the mixture was stirred at 60° C. for 3 days. The reaction mixture was concentrated under reduced pressure, and the residue was purified by column chromatography on silica gel (eluent: dichloromethane/methanol=10/1-5/1) to give 3-(2,3,4,6-tetra-O-acetyl-β-D-glucopyranosyloxy)-4-[(4-{3-[2-(2-hydroxyethylcarbamoyl)ethylamino]propoxy}-2-methylphenyl)methyl]-5-isopropyl-1H-pyrazole (42 mg). This material was dissolved in methanol (3 mL). To the solution was added sodium methoxide (28% methanol solution, 0.03 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (18 mg).

$^1$H-NMR (CD$_3$OD) δ ppm:
1.05-1.15 (6H, m), 1.9-2.0 (2H, m). 2.29 (3H, s), 2.41 (2H, t, J=6.7 Hz), 2.7-2.9 (5H, m), 3.25-3.4 (6H, m), 3.57 (2H, t, J=5.7 Hz), 3.6-3.7 (3H, m), 3.75-3.85 (1H, m), 3.99 (2H, t, J=6.1 Hz), 4.95-5.05 (1H, m), 6.62 (1H, dd, J=8.4 Hz, 2.5 Hz), 6.71 (1H, d, J=2.5 Hz), 6.85 (1H, d, J=8.4 Hz)

Example 88

3-(β-D-Glucopyranosyloxy)-4-[(4-{3-[2-(3-hydroxypropylcarbamoyl)ethylamino]propoxy}-2-methylphenyl)methyl]-5-isopropyl-1H-pyrazole The title compound was prepared in a similar manner to that described in Example 87 using 3-amino-1-propanol instead of 2-aminoethanol.

$^1$H-NMR (CD$_3$OD) δ ppm:
1.05-1.15 (6H, m), 1.65-1.75 (2H, m), 1.9-2.0 (2H, m), 2.29 (3H, s), 2.4 (2H, t, J=6.8 Hz), 2.75-2.9 (5H, m), 3.24 (2H, t, J=6.9 Hz), 3.25-3.4 (4H, m), 3.56 (2H, t, J=6.3 Hz), 3.6-3.7 (3H, m), 3.75-3.85 (1H, m), 3.99 (2H, t, J=6.1 Hz), 4.95-5.05 (1H, m), 6.62 (1H, dd, J=8.4 Hz, 2.5 Hz), 6.71 (1H, d, J=2.5 Hz), 6.85 (1H, d, J=8.4 Hz)

Example 89

3-(β-D-Glucopyranosyloxy)-4-{[4-(3-{2-[2-hydroxy-1-(hydroxymethyl)ethylcarbamoyl]ethylamino}propoxy)-2-methylphenyl]methyl}-5-isopropyl-1H-pyrazole The title compound was prepared in a similar manner to that described in Example 87 using 2-amino-1,3-propanediol instead of 2-aminoethanol.

$^1$H-NMR (CD$_3$OD) δ ppm:
1.05-1.15 (6H, m), 1.9-2.0 (2H, m), 2.29 (3H, s), 2.44 (2H, t, J=6.7 Hz), 2.75-2.85 (3H, m), 2.88 (2H, t, J=6.7 Hz), 3.25-3.4 (4H, m), 3.55-3.7 (7H, m), 3.75-3.85 (1H, m), 3.9-3.95 (1H, m), 4.0 (2H, t, J=6.1 Hz), 4.95-5.05 (1H, m), 6.62 (1H, dd, J=8.4 Hz, 2.5 Hz), 6.71 (1H, d, J=2.5 Hz), 6.85 (1H, d, J=8.4 Hz)

Example 90

3-(β-D-Glucopyranosyloxy)-4-{[4-(3-{2-[2-hydroxy-1-(hydroxymethyl)-1-(methyl)ethylcarbamoyl]ethylamino}propoxy)-2-methylphenyl]methyl}-5-isopropyl-1H-pyrazole The title compound was prepared in a similar manner to that described in Example 87 using 2-amino-2-methyl-1,3-propanediol instead of 2-aminoethanol.

$^1$H-NMR (CD$_3$OD) δ ppm:
1.05-1.15 (6H, m), 1.22 (3H, s), 1.9-2.0 (2H, m), 2.29 (3H, s), 2.4 (2H, t, J=6.5 Hz), 2.75-2.9 (5H, m), 3.25-3.4 (4H, m), 3.55-3.75 (7H, m), 3.75-3.85 (1H, m), 3.99 (2H, t, J=6.0 Hz), 4.95-5.05 (1H, m), 6.62 (1H, dd, J=8.4 Hz, 2.4 Hz), 6.71 (1H, d, J=2.4 Hz), 6.85 (1H, d, J=8.4 Hz)

Example 91

3-(β-D-Glucopyranosyloxy)-4-{[4-(3-{2-[2-hydroxy-1,1-bis(hydroxymethyl)ethylcarbamoyl]ethylamino}propoxy)-2-methylphenyl]methyl}-5-isopropyl-1H-pyrazole The title compound was prepared in a similar manner to that described in Example 87 using tris(hydroxymethyl)aminomethane instead of 2-aminoethanol.

$^1$H-NMR (CD$_3$OD) δ ppm:
1.05-1.15 (6H, m), 1.9-2.0 (2H, m), 2.29 (3H, s), 2.44 (2H, t, J=6.4 Hz), 2.75-2.9 (5H, m), 3.25-3.4 (4H, m), 3.6-3.75 (9H, m), 3.75-3.85 (1H, m), 4.0 (2H, t, J=6.0 Hz), 4.95-5.05 (1H, m), 6.62 (1H, dd, J=8.4 Hz, 2.2 Hz), 6.71 (1H, d, J=2.2 Hz), 6.85 (1H, d, J=8.4 Hz)

Reference Example 47

3-(2,3,4,6-Tetra-O-acetyl-β-D-galactopyranosyloxy)-4-{[4-(3-benzyloxypropoxy)-2-methylphenyl]methyl}-5-isopropyl-1H-pyrazole The title compound was prepared in a similar manner to that described in Reference Example 17 using 4-{[4-(3-benzyloxypropoxy)-2-methylphenyl]methyl}-1,2-dihydro-5-isopropyl-3H-pyrazol-3-one and acetobromo-α-D-galactose instead of 4-{[4-(3-benzyloxypropoxy)phenyl]methyl}-1,2-dihydro-5-isopropyl-3H-pyrazol-3-one and acetobromo-α-D-glucose, respectively.

$^1$H-NMR (CDCl$_3$) δ ppm:
1.05-1.15 (6H, m), 1.81 (3H, s), 1.98 (3H, s), 2.0-2.1 (5H, m), 2.22 (3H, s), 2.26 (3H, s), 2.75-2.85 (1H, m), 3.5 (1H, d, J=16.5 Hz), 3.55-3.7 (3H, m), 4.0-4.1 (3H, m), 4.1-4.2 (2H, m), 4.52 (2H, s), 5.07 (1H, dd, J=10.3 Hz, 3.3 Hz), 5.35-5.45 (2H, m), 5.52 (1H, d, J=7.8 Hz), 6.58 (1H, dd, J=8.4 Hz, 2.7 Hz), 6.69 (1H, d, J=2.7 Hz), 6.79 (1H, d, J=8.4 Hz), 7.2-7.35 (5H, m)

Reference Example 48

3-(2,3,4,6-Tetra-O-acetyl-β-D-galactopyranosyloxy)-4-{[4-(3-hydroxypropoxy)-2-methylphenyl]methyl}-5-isopropyl-1H-pyrazole The title compound was prepared in a similar manner to that described in Reference Example 23 using 3-(2,3,4,6-tetra-O-acetyl-β-D-galactopyranosyloxy)-4-{[4-(3-benzyloxypropoxy)-2-methylphenyl]methyl}-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) δ ppm:
1.1-1.2 (6H, m), 1.83 (3H, s), 1.95-2.05 (8H, m), 2.16 (3H, s), 2.27 (3H, s), 2.75-2.85 (1H, m), 3.51 (1H, s, J=16.6 Hz), 3.61 (1H, d, J=16.6 Hz), 3.8-3.9 (2H, m), 4.0-4.2 (5H, m), 5.07 (1H, dd, J=10.4 Hz, 3.5 Hz), 5.35-5.45 (2H, m), 5.51 (1H, d, J=8.2 Hz), 6.6 (1H, dd, J=8.5 Hz, 2.7 Hz), 6.7 (1H, d, J=2.7 Hz), 6.81 (1H, d, J=8.5 Hz)

Reference Example 49

3-Benzylaminopropionamide

To a solution of acrylamide (32 g) in ethanol (450 mL) was added benzylamine (59 mL), and the mixture was stirred at 60° C. overnight. The reaction mixture was concentrated under reduced pressure, and the residue was purified by column chromatography on silica gel (eluent: n-hexane/ethyl acetate=1/1-dichloromethane/methanol=50/1) to give the title compound (73.2 g).

$^1$H-NMR (CDCl$_3$) δ ppm:
2.35-2.45 (2H, m), 2.9-2.95 (2H, m), 3.81 (2H, s), 5.15-5.6 (1H, br), 7.2-7.65 (6H, m)

Example 92

3-(2,3,4,6-Tetra-O-acetyl-β-D-galactopyranosyloxy)-4-[(4-{3-[N-benzyl-N-(2-carbamoylethyl)amino] propoxy}-2-methylphenyl)methyl]-5-isopropyl-1H-pyrazole To a solution of 3-(2,3,4,6-tetra-O-acetyl-β-D-galactopyranosyloxy)-4-{[4-(3-hydroxypropoxy)-2-methylphenyl]methyl}-5-isopropyl-1H-pyrazole (0.1 g) and triethylamine (0.026 mL) in dichloromethane (3 mL) was added methanesulfonyl chloride (0.013 mL), and the mixture was stirred at room temperature for 1 hour. The reaction mixture was poured into 0.5 mol/L hydrochloric acid, and the resulting mixture was extracted with ethylacetate. The extract was washed with water and brine, and dried over anhydrous sodium sulfate. The solvent was removed under reduced pressure to give 3-(2,3,4,6-tetra-O-acetyl-β-D-galactopyranosyloxy)-5-isopropyl-4-({4-[3-(methanesulfonyloxy)propoxy]-2-methylphenyl}methyl)-1H-pyrazole (0.11 g). This material was dissolved in a solution of acetonitrile (2 mL) and methanol (2 mL). To the solution were added 3-benzylaminopropionamide (46 mg) and sodium iodide (24 mg), and the mixture was stirred at 60° C. for 3 days. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: dichloromethane/methanol=20/1-10/1) to give the title compound (78 mg).

$^1$H-NMR (CDCl$_3$) δ ppm:
1.05-1.15 (6H, m), 1.83 (3H, s), 1.9-2.0 (5H, m), 2.02 (3H, s), 2.15 (3H, s), 2.26 (3H, s), 2.39 (2H, t, J=6.1 Hz), 2.67 (2H, t, J=7.0 Hz), 2.7-2.85 (3H, m), 3.5 (1H, d, J=16.6 Hz), 3.55-3.65 (3H, m), 3.91 (2H, t, J=6.1 Hz), 4.0-4.1 (1H, m), 4.1-4.2 (2H, m), 5.07 (1H, dd, J=10.4 Hz, 3.5 Hz), 5.21 (1H, brs), 5.35-5.45 (2H, m), 5.53 (1H, d, J=8.2 Hz), 6.53 (1H, dd, J=8.6 Hz, 2.4 Hz), 6.63 (1H, d, J=2.4 Hz), 6.79 (1H, d, J=8.6 Hz), 7.2-7.35 (5H, m), 7.44 (1H, brs)

Example 93

3-(2,3,4,6-Tetra-O-acetyl-β-D-glucopyranosyloxy)-4-[(4-{3-[N-benzyl-N-(2-carbamoylethyl)amino] propoxy}-2-methylphenyl)methyl]-5-isopropyl-1H-pyrazole The title compound was prepared in a similar manner to that described in Example 92 using 3-(2,3,4,6-tetra-O-acetyl-β-D-glucopyranosyloxy)-4-{[4-(3-hydroxypropoxy)-2-methylphenyl]methyl}-5-isopropyl-1H-pyrazole instead of 3-(2,3,4,6-tetra-O-acetyl-β-D-galactopyranosyloxy)-4-{[4-(3-hydroxypropoxy)-2-methylphenyl]methyl}-5-isopropyl-1H-pyrazole.

$^1$H-NMR (CDCl$_3$) δ ppm:
1.1-1.15 (6H, m), 1.82 (3H, s), 1.9-2.1 (11H, m), 2.25 (3H, s), 2.39 (2H, t, J=6.1 Hz), 2.66 (2H, t, J=7.2 Hz), 2.7-2.9 (3H, m), 3.49 (1H, d, J=16.2 Hz), 3.58 (1H, d, J=16.2 Hz), 3.62 (2H, s), 3.8-3.95 (3H, m), 4.05-4.15 (1H, m), 4.29 (1H, dd, J=12.2 Hz, 4.0 Hz), 5.15-5.3 (4H, m), 5.56 (1H, d, J=7.6 Hz), 6.52 (1H, dd, J=8.2 Hz, 2.7 Hz), 6.62 (1H, d, J=2.7 Hz), 6.79 (1H, d, J=8.2 Hz), 7.2-7.35 (5H, m), 7.47 (1H, brs)

Example 94

4-[(4-{3-[2-(Carbamoyl)ethylamino]propoxy}-2-methylphenyl)methyl]-3-(β-D-galactopyranosyloxy)-5-isopropyl-1H-pyrazole To a solution of 3-(2,3,4,6-tetra-O-acetyl-β-D-galactopyranosyloxy)-4-[(4-{3-[N-benzyl-N-(2-carbamoylethyl)amino]propoxy}-2-methylphenyl)methyl]-5-isopropyl-1H-pyrazole (75 mg) in methanol (3 mL) was added 10% palladium-carbon powder (20 mg), and the mixture was stirred at room temperature under a hydrogen atmosphere for 2.5 hours. The insoluble material was removed by filtration, and the filtrate was concentrated under reduced pressure to give 4-[(4-{3-[2-(carbamoyl)ethylamino]propoxy}-2-methylphenyl)methyl]-3-(2,3,4,6-tetra-O-acetyl-β-D-galactopyranosyloxy)-5-isopropyl-1H-pyrazole (66 mg). This material was dissolved in methanol (3 mL). To the solution was added sodium methoxide (28% methanol solution, 0.03 mL), and the mixture was stirred at room temperature for 1 hour. To the reaction mixture was added acetic acid (0.04 mL), and the resulting mixture was concentrated under reduced pressure. The residue was purified by solid phase extraction on ODS (washing solvent: distilled water, eluent: methanol) to give the title compound (43 mg).

$^1$H-NMR (CD$_3$OD) δ ppm:
1.05-1.15 (6H, m), 1.9-2.0 (2H, m), 2.28 (3H, s), 2.42 (2H, t, J=6.8 Hz), 2.7-2.9 (5H, m), 3.49 (1H, dd, J=9.7 Hz, 3.2 Hz), 3.55-3.8 (6H, m), 3.85 (1H, d, J=3.2 Hz), 3.99 (2H, t, J=6.1 Hz), 5.0-5.05 (1H, m), 6.61 (1H, dd, J=8.4 Hz, 2.5 Hz), 6.7 (1H, d, J=2.5 Hz), 6.85 (1H, d, J=8.4 Hz)

Example 95

4-[(4-{3-[N-Benzyl-N-(2-carbamoylethyl)amino] propoxy}-2-methylphenyl)methyl]-3-(β-D-glucopyranosyloxy)-5-isopropyl-1H-pyrazole To a solution of 3-(2,3,4,6-tetra-O-acetyl-β-D-glucopyranosyloxy)-4-[(4-{3-[N-benzyl-N-(2-carbamoylethyl)amino] propoxy}-2-methylphenyl)methyl]-5-isopropyl-1H-pyrazole (45.3 g) in methanol (400 mL) was added sodium methoxide (28% methanol solution, 2.2 mL), and the mixture was stirred at room temperature for 1 hour. The reaction mixture was concentrated under reduced pressure, and the residue was purified by column chromatography on silica gel (eluent: dichloromethane/methanol=5/1-4/1) to give the title compound (33.2 g).

$^1$H-NMR (CD$_3$OD) δ ppm:
1.05-1.15 (6H, m), 1.85-1.95 (2H, m), 2.28 (3H, s), 2.4 (2H, t, J=6.9 Hz), 2.55-2.65 (2H, m), 2.75-2.85 (3H, m), 3.25-3.4 (4H, m), 3.55-3.75 (5H, m), 3.75-3.85 (1H, m), 3.92 (2H, t, J=6.2 Hz), 4.95-5.05 (1H, m), 6.55 (1H, dd, J=8.5 Hz, 2.8 Hz), 6.62 (1H, d, J=2.8 Hz), 6.83 (1H, d, J=8.5 Hz), 7.15-7.35 (5H, m)

Reference Example 50

(4-Benzyloxy-2-methylphenyl)methanol

The title compound was prepared in a similar manner to that described in Reference Example 9 using benzyl bromide instead of benzyl 3-bromopropyl ether.

$^1$H-NMR (CDCl$_3$) δ ppm:
1.37 (1H, t, J=5.8 Hz), 2.36 (3H, s), 4.64 (2H, d. J=5.8 Hz). 5.06 (2H, s), 6.79 (1H, dd, J=8.4 Hz, 2.4 Hz), 6.84 (1H, d, J=2.4 Hz), 7.23 (1H, d, J=8.4 Hz), 7.25-7.45 (5H, m)

Reference Example 51

[4-Benzyloxy-2-(tetrahydro-4H-pyran-4-yloxy)phenyl]methanol

To a solution of tetrahydro-4H-pyran-4-ol (3.62 g) and triethylamine (5.6 mL) in tetrahydrofuran (35 mL) was added methanesulfonyl chloride (2.93 mL) under ice-cooling, and the mixture was stirred at room temperature for 1 hour. The insoluble material was removed by filtration. To the filtrate were added N,N-dimethylformamide (70 mL), 4-benzyloxy-2-hydroxybenzaldehyde (5.39 g) and cesium carbonate (23 g), and the mixture was stirred at 80° C. for 12 hours. The reaction mixture was poured into water, and the resulting mixture was extracted with diethyl ether. The extract was washed with water and brine, and dried over anhydrous magnesium sulfate. The solvent was removed under reduced pressure, and the residue was purified by column chromatography on silica gel (eluent: n-hexane/ethyl acetate=4/1-2/1) to give 4-benzyloxy-2-(tetrahydro-4H-pyran-4-yloxy)benzaldehyde (4.58 g). This material was dissolved in ethanol (70 mL). To the solution was added sodium borohydride (0.28 g) under ice-cooling, and the mixture was stirred at room temperature for 3 hours. To the reaction mixture was added methanol, and the resulting mixture was concentrated under reduced pressure. A saturated aqueous sodium hydrogen carbonate solution was added to the residue, and the mixture was extracted with diethyl ether. The extract was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane/ethyl acetate=3/1-1/1) to give the title compound (4.45 g).
$^1$H-NMR (CDCl$_3$) δ ppm:
1.75-1.85 (2H, m), 1.95-2.05 (2H, m), 2.11 (1H, t, J=6.3 Hz), 3.5-3.65 (2H, m), 3.9-4.0 (2H, m), 4.45-4.55 (1H, m), 4.63 (2H, d, J=6.3 Hz), 5.05 (2H, s), 6.5-6.6 (2H, m), 7.19 (1H, d, J=7.7 Hz), 7.3-7.45 (5H, m)

Reference Example 52

4-[(4-Benzyloxy-2-methylphenyl)methyl]-1,2-dihydro-5-isopropyl-3H-pyrazol-3-one

The title compound was prepared in a similar manner to that described in Reference Example 11 using (4-benzyloxy-2-methylphenyl)methanol instead of [4-(3-benzyloxypropoxy)phenyl]methanol.
$^1$H-NMR (DMSO-d$_6$) δ ppm:
1.04 (6H, d, J=6.8 Hz), 2.24 (3H, s), 2.65-2.8 (1H, m), 3.44 (2H, s), 5.02 (2H, s), 6.69 (1H, dd, J=8.7 Hz, 2.4 Hz), 6.75-6.85 (2H, m), 7.25-7.45 (5H, m)

Reference Example 53

4-{[4-Benzyloxy-2-(tetrahydro-4H-pyran-4-yloxy)phenyl]-methyl}-1,2-dihydro-5-isopropyl-3H-pyrazol-3-one The title compound was prepared in a similar manner to that described in Reference Example 11 using [4-benzyloxy-2-(tetrahydro-4H-pyran-4-yloxy)phenyl]methanol instead of [4-(3-benzyloxypropoxy)phenyl]methanol.
$^1$H-NMR (CDCl$_3$) δ ppm:
1.16 (6H, d, J=7.1 Hz), 1.75-1.9 (2H, m), 1.95-2.1 (2H, m), 2.9-3.05 (1H, m), 3.5-3.6 (2H, m), 3.64 (2H, s), 3.9-4.05 (2H, m), 4.4-4.5 (1H, m), 5.0 (2H, s), 6.45-6.55 (2H, m), 7.0 (1H, d, J=8.4 Hz), 7.25-7.45 (5H, m)

Reference Example 54

4-[(4-Benzyloxy-2-methylphenyl)methyl]-5-isopropyl-3-(2,3,4,6-tetra-O-pivaloyl-β-D-glucopyranosyloxy)-1H-pyrazole The title compound was prepared in a similar manner to that described in Reference Example 17 using 4-[(4-benzyloxy-2-methylphenyl)methyl]-1,2-dihydro-5-isopropyl-3H-pyrazol-3-one and 2,3,4,6-tetra-O-pivaloyl-α-D-glucopyranosyl bromide (Kunz, H.; Harreus, A. Liebigs Ann. Chem. 1982, 41-48 Velarde, S.; Urbina, J.; Pena, M. R. J. Org. Chem. 1996, 61, 9541-9545) instead of 4-{[4-(3-benzyloxypropoxy)phenyl]methyl}-1,2-dihydro-5-isopropyl-3H-pyrazol-3-one and acetobromo-α-D-glucose, respectively.
$^1$H-NMR (CDCl$_3$) δ ppm:
1.04 (9H, s), 1.05-1.2 (33H, m), 2.27 (3H, s), 2.7-2.85 (1H, m), 3.45-3.6 (2H, m), 3.8-3.9 (1H, m), 4.11 (1H, dd, J=12.6 Hz, 4.8 Hz), 4.17 (1H, dd, J=12.6 Hz, 1.8 Hz), 5.0 (2H, s), 5.15-5.3 (2H, m), 5.37 (1H, t, J=9.5 Hz), 5.65 (1H, d, J=7.8 Hz), 6.64 (1H, dd, J=8.4 Hz, 2.8 Hz), 6.77 (1H, d, J=2.8 Hz), 6.83 (1H, d, J=8.4 Hz), 7.25-7.45 (5H, m)

Reference Example 55

4-{[4-Benzyloxy-2-(tetrahydro-4H-pyran-4-yloxy)phenyl]-methyl}-5-isopropyl-3-(2,3,4,6-tetra-O-pivaloyl-β-D-glucopyranosyloxy)-1H-pyrazole The title compound was prepared in a similar manner to that described in Reference Example 17 using 4-{[4-benzyloxy-2-(tetrahydro-4H-pyran-4-yloxy)phenyl]methyl}-1,2-dihydro-5-isopropyl-3H-pyrazol-3-one and 2,3,4,6-tetra-O-pivaloyl-α-D-glucopyranosyl bromide instead of 4-{[4-(3-benzyloxypropoxy)phenyl]methyl}-1,2-dihydro-5-isopropyl-3H-pyrazol-3-one and acetobromo-α-D-glucose, respectively.
$^1$H-NMR (CDCl$_3$) δ ppm:
1.0-1.2 (42H, m), 1.7-1.85 (2H, m), 1.95-2.05 (2H, m), 2.85-2.95 (1H, m), 3.5-3.65 (4H, m), 3.8-3.9 (1H, m), 3.9-4.0 (2H, m), 4.12 (1H, dd, J=12.4 Hz, 5.1 Hz), 4.19 (1H, dd, J=12.4 Hz, 1.8 Hz), 4.4-4.5 (1H, m), 4.99 (2H, s), 5.15-5.3 (2H, m), 5.36 (1H, t, J=9.4 Hz), 5.66 (1H, d, J=8.0 Hz), 6.42 (1H, dd, J=8.3 Hz, 2.3 Hz), 6.47 (1H, d, J=2.3 Hz), 6.86 (1H, d, J=8.3 Hz), 7.25-7.45 (5H, m)

Reference Example 56

1-(2-Benzyloxyethyl)-4-[(4-benzyloxy-2-methylphenyl)methyl]-5-isopropyl-3-(2,3,4,6-tetra-O-pivaloyl-β-D-glucopyranosyloxy)-1H-pyrazole To a solution of 4-[(4-benzyloxy-2-methylphenyl)methyl]-5-isopropyl-3-(2,3,4,6-tetra-O-pivaloyl-β-D-glucopyranosyloxy)-1H-pyrazole (2 g) in N,N-dimethylacetoamide (36 mL) were added sodium hydride (55%, 0.26 g) and benzyl 2-bromoethyl ether (0.76 mL) under ice-cooling, and the mixture was stirred at room temperature for 2 hours. The reaction mixture was poured into water, and the resulting mixture was extracted with diethyl ether. The extract was washed with water twice and brine, and dried over anhydrous magnesium sulfate. The solvent was removed under reduced pressure, and the residue was purified by column chromatography on silica gel (eluent: n-hexane/ethyl acetate=4/1) to give the title compound (0.89 g).

$^1$H-NMR (CDCl$_3$) δ ppm:
1.0-1.2 (42H, m), 2.28 (3H, s), 2.95-3.05 (1H, m), 3.52 (1H, d, J=17.0 Hz), 3.57 (1H, d, J=17.0 Hz), 3.75-3.85 (3H, m), 4.0-4.2 (4H, m), 4.46 (1H, d, J=12.1 Hz), 4.49 (1H, d, J=12.1 Hz), 4.99 (2H, s), 5.1-5.2 (2H, m), 5.34 (1H, t, J=9.5 Hz), 5.61 (1H, d, J=8.1 Hz), 6.6 (1H, dd, J=8.5 Hz, 2.6 Hz), 6.73 (1H, d, J=8.5 Hz), 6.77 (1H, d, J=2.6 Hz), 7.2-7.45 (10H, m)

Reference Example 57

4-[(4-Benzyloxy-2-methylphenyl)methyl]-1-(3-benzyloxypropyl)-5-isopropyl-3-(2,3,4,6-tetra-O-pivaloyl-β-D-glucopyranosyloxy)-1H-pyrazole The title compound was prepared in a similar manner to that described in Reference Example 56 using benzyl 3-bromopropyl ether instead of benzyl 2-bromoethyl ether.

$^1$H-NMR (CDCl$_3$) δ ppm:
1.03 (9H, s), 1.05-1.2 (33H, m), 2.05-2.15 (2H, m), 2.28 (3H, s), 2.9-3.0 (1H, m), 3.45-3.6 (4H, m), 3.7-3.8 (1H, m), 3.95-4.1 (3H, m), 4.12 (1H, dd, J=12.0 Hz, 1.9 Hz), 4.51 (2H, s), 5.0 (2H, s), 5.1-5.2 (2H, m), 5.33 (1H, t, J=9.5 Hz), 5.61 (1H, d, J=8.2 Hz), 6.61 (1H, dd, J=8.3 Hz, 2.7 Hz). 6.72 (1H, d, J=8.3 Hz), 6.77 (1H, d, J=2.7 Hz), 7.2-7.5 (10H, m)

Reference Example 58

4-[(4-Hydroxy-2-methylphenyl)methyl]-5-isopropyl-3-(2,3,4,6-tetra-O-pivaloyl-β-D-glucopyranosyloxy)-1H-pyrazole 4-[(4-Benzyloxy-2-methylphenyl)methyl]-5-isopropyl-3-(2,3,4,6-tetra-O-pivaloyl-O-D-glucopyranosyloxy)-1H-pyrazole (5 g) was dissolved in tetrahydrofuran (18 mL). To the solution was added 10% palladium-carbon powder (500 mg), and the mixture was stirred at room temperature under a hydrogen atmosphere for 3 hours. The insoluble material was removed by filtration, and the solvent of the filtrate was removed under reduced pressure to give the title compound (4.45 g).

$^1$H-NMR (CDCl$_3$) δ ppm:
1.0-1.2 (42H, m), 2.24 (3H, s), 2.7-2.85 (1H, m), 3.52 (2H, s), 3.8-3.9 (1H, m), 4.09 (1H, dd, J=12.4 Hz, 4.7 Hz), 4.15 (1H, dd, J=12.4 Hz, 1.9 Hz), 4.6 (1H, s), 5.15-5.25 (2H, m), 5.36 (1H, t, J=9.2 Hz), 5.65 (1H, d, J=8.0 Hz), 6.5 (1H, dd, J=8.3 Hz, 2.9 Hz), 6.61 (1H, d, J=2.9 Hz), 6.78 (1H, d, J=8.3 Hz)

Reference Example 59

1-(2-Hydroxyethyl)-4-[(4-hydroxy-2-methylphenyl)methyl]-5-isopropyl-3-(2,3,4,6-tetra-O-pivaloyl-β-D-glucopyranosyloxy)-1H-pyrazole The title compound was prepared in a similar manner to that described in Reference Example 58 using 1-(2-benzyloxyethyl)-4-[(4-benzyloxy-2-methylphenyl)methyl]-5-isopropyl-3-(2,3,4,6-tetra-O-pivaloyl-β-D-glucopyranosyloxy)-1H-pyrazole instead of 4-[(4-benzyloxy-2-methylphenyl)methyl]-5-isopropyl-3-(2,3,4,6-tetra-O-pivaloyl-β-D-glucopyranosyloxy)-1H-pyrazole.

$^1$H-NMR (CDCl$_3$) δ ppm:
1.0-1.2 (42H, m), 2.26 (3H, s), 2.9-3.0 (1H, m), 3.51 (1H, d, J=17.0 Hz), 3.55 (1H, d, J=17.0 Hz), 3.75-3.9 (2H, m), 3.9-4.0 (2H, m), 4.0-4.15 (4H, m), 4.61 (1H, s), 5.15-5.25 (2H, m), 5.35 (1H, t, J=9.4 Hz), 5.53 (1H, d, J=8.1 Hz), 6.48 (1H, dd, J=8.4 Hz, 2.7 Hz), 6.61 (1H, d, J=2.7 Hz), 6.67 (1H, d, J=8.4 Hz)

Reference Example 60

4-[(4-Hydroxy-2-methylphenyl)methyl]-1-(3-hydroxypropyl)-5-isopropyl-3-(2,3,4,6-tetra-O-pivaloyl-β-D-glucopyranosyloxy)-1H-pyrazole The title compound was prepared in a similar manner to that described in Reference Example 58 using 4-[(4-benzyloxy-2-methylphenyl)methyl]-1-(3-benzyloxypropyl)-5-isopropyl-3-(2,3,4,6-tetra-O-pivaloyl-β-D-glucopyranosyloxy)-1H-pyrazole instead of 4-[(4-benzyloxy-2-methylphenyl)methyl]-5-isopropyl-3-(2,3,4,6-tetra-O-pivaloyl-β-D-glucopyranosyloxy)-1H-pyrazole.

$^1$H-NMR (CDCl$_3$) δ ppm:
1.03 (9H, s), 1.05-1.15 (24H, m), 1.19 (9H, s), 1.9-2.0 (2H, m), 2.25 (3H, s), 2.9-3.0 (1H, m), 3.5 (1H, d, J=17.3 Hz), 3.54 (1H, d, J=17.3 Hz), 3.6-3.7 (2H, m), 3.8-3.9 (1H, m), 3.93 (1H, t, J=6.4 Hz), 4.1-4.2 (3H, m), 4.22 (1H, dd, J=12.6 Hz, 1.7 Hz), 4.51 (1H, s), 5.15-5.25 (2H, m), 5.35 (1H, t, J=9.4 Hz), 5.52 (1H, d, J=8.1 Hz), 6.48 (1H, dd, J=8.3 Hz, 2.4 Hz), 6.61 (1H, d, J=2.4 Hz), 6.66 (1H, d, J=8.3 Hz)

Reference Example 61

4-{[4-Hydroxy-2-(tetrahydro-4H-pyran-4-yloxy)phenyl]-methyl}-5-isopropyl-3-(2,3,4,6-tetra-O-pivaloyl-β-D-glucopyranosyloxy)-1H-pyrazole The title compound was prepared in a similar manner to that described in Reference Example 58 using 4-{[4-benzyloxy-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole instead of 4-[(4-benzyloxy-2-methylphenyl)methyl]-5-isopropyl-3-(2,3,4,6-tetra-O-pivaloyl-β-D-glucopyranosyloxy)-1H-pyrazole.

$^1$H-NMR (CDCl$_3$) δ ppm:
1.0-1.2 (42H, m), 1.75-1.9 (2H, m), 1.95-2.1 (2H, m), 2.8-2.95 (1H, m), 3.52 (1H, d, J=16.5 Hz), 3.55-3.65 (3H, m), 3.8-3.9 (1H, m), 3.9-4.05 (2H, m), 4.05-4.2 (2H, m), 4.4-4.5 (1H, m), 5.14 (1H, brs), 5.15-5.3 (2H, m), 5.3-5.4 (1H, m), 5.65 (1H, d, J=8.1 Hz), 6.22 (1H, dd, J=8.2 Hz, 2.3 Hz), 6.37 (1H, d, J=2.3 Hz), 6.78 (1H, d, J=8.2 Hz)

Reference Example 62

4-{[4-(3-Chloropropoxy)-2-methylphenyl]methyl}-5-isopropyl-3-(2,3,4,6-tetra-O-pivaloyl-β-D-glucopyranosyloxy)-1H-pyrazole To a solution of 4-[(4-hydroxy-2-methylphenyl)methyl]-5-isopropyl-3-(2,3,4,6-tetra-O-pivaloyl-β-D-glucopyranosyloxy)-1H-pyrazole (8.58 g), 1-bromo-3-chloropropane (2.85 mL) and tetra(n-butyl)ammonium bromide (1.86 g) in tetrahydrofuran (43 mL) was added 5 mol/L aqueous sodium hydroxide solution (5.76 mL), and the mixture was stirred at room temperature overnight. The reaction mixture was poured into 1 mol/L hydrochloric acid, and the resulting mixture was extracted with diethyl ether. The extract was washed with 1 mol/L hydrochloric acid, water and brine successively, and dried over anhydrous sodium sulfate. The solvent was removed under reduced pressure, and the residue was dissolved in n-hexane (15 mL)-diisopropyl ether (5 mL) under reflux condition. The solution was cooled to room temperature, and n-hexane (25 mL) was added to the solution. The precipitated crystals were collected by filtration, and the crystals were washed with n-hexane and dried under reduced pressure to give the title compound (6.06 g).

$^1$H-NMR (CDCl$_3$) δ ppm:
1.0-1.2 (42H, m), 2.15-2.25 (2H, m), 2.27 (3H, s), 2.7-2.85 (1H, m), 3.51 (1H, d, J=16.7 Hz), 3.53 (1H, d, J=16.7 Hz), 3.73 (2H, t, J=6.4 Hz), 3.8-3.9 (1H, m), 4.05 (2H, t, J=5.9 Hz), 4.11 (1H, dd, J=12.4 Hz, 4.7 Hz), 4.17 (1H, dd, J=12.4 Hz, 1.9 Hz), 5.15-5.3 (2H, m), 5.3-5.4 (1H, m), 5.65 (1H, d, J=8.1 Hz), 6.57 (1H, dd, J=8.4 Hz, 2.7 Hz), 6.68 (1H, d, J=2.7 Hz), 6.83 (1H, d, J=8.4 Hz)

Reference Example 63

4-{[4-(3-Chloropropoxy)-2-methylphenyl]methyl}-1-(2-hydroxyethyl)-5-isopropyl-3-(2,3,4,6-tetra-O-pivaloyl-β-D-glucopyranosyloxy)-1H-pyrazole To a solution of 1-(2-hydroxyethyl)-4-[(4-hydroxy-2-methylphenyl)methyl]-5-isopropyl-3-(2,3,4,6-tetra-O-pivaloyl-β-D-glucopyranosyloxy)-1H-pyrazole (0.69 g), 1-bromo-3-chloropropane (0.22 mL) and tetra(n-butyl)ammonium bromide (0.14 g) in tetrahydrofuran (8 mL) was added 5 mol/L aqueous sodium hydroxide solution (0.43 mL), and the mixture was stirred at room temperature overnight. The reaction mixture was poured into 0.5 mol/L hydrochloric acid, and the resulting mixture was extracted with diethylether. The extract was washed with water and brine successively, and dried over anhydrous magnesium sulfate. The solvent was removed under reduced pressure, and the residue was purified by column chromatography on silica gel (eluent: n-hexane/ethyl acetate=1/1) to give the title compound (0.56 g).

$^1$H-NMR (CDCl$_3$) δ ppm:
1.0-1.2 (42H, m), 2.15-2.25 (2H, m), 2.28 (3H, s), 2.9-3.0 (1H, m), 3.52 (1H, d, J=16.9 Hz), 3.57 (1H, d, J=16.9 Hz), 3.73 (2H, t, J=6.2 Hz), 3.75-4.0 (4H, m), 4.0-4.15 (6H, m), 5.15-5.25 (2H, m), 5.35 (1H, t, J=9.6 Hz), 5.54 (1H, d, J=8.1 Hz), 6.56 (1H, dd, J=8.5 Hz, 2.5 Hz), 6.69 (1H, d, J=2.5 Hz), 6.72 (1H, d, J=8.5 Hz)

Reference Example 64

4-{[4-(3-Chloropropoxy)-2-methylphenyl]methyl}-1-(3-hydroxypropyl)-5-isopropyl-3-(2,3,4,6-tetra-O-pivaloyl-β-D-glucopyranosyloxy)-1H-pyrazole The title compound was prepared in a similar manner to that described in Reference Example 63 using 4-[(4-hydroxy-2-methylphenyl)methyl]-1-(3-hydroxypropyl)-5-isopropyl-3-(2,3,4,6-tetra-O-pivaloyl-β-D-glucopyranosyloxy)-1H-pyrazole instead of 1-(2-hydroxyethyl)-4-[(4-hydroxy-2-methylphenyl)methyl]-5-isopropyl-3-(2,3,4,6-tetra-O-pivaloyl-β-D-glucopyranosyloxy)-1H-pyrazole.

$^1$H-NMR (CDCl$_3$) δ ppm:
1.02 (9H, s), 1.05-1.15 (24H, m), 1.19 (9H, s), 1.9-2.0 (2H, m), 2.15-2.25 (2H, m), 2.28 (3H, s), 2.9-3.0 (1H, m), 3.51 (1H, d, J=16.9 Hz), 3.55 (1H, d, J=16.9 Hz), 3.6-3.7 (2H, m), 3.73 (2H, t, J=6.3 Hz), 3.8-3.9 (1H, m), 3.96 (1H, t, J=6.4 Hz), 4.05 (2H, t, J=5.9 Hz), 4.1-4.2 (3H, m), 4.23 (1H, dd, J=12.6 Hz, 1.7 Hz), 5.15-5.25 (2H, m), 5.35 (1H, t, J=9.4 Hz), 5.52 (1H, d, J=8.1 Hz), 6.55 (1H, dd, J=8.4 Hz, 2.6 Hz), 6.69 (1H, d, J=2.6 Hz), 6.71 (1H, d, J=8.4 Hz)

Reference Example 65

4-{[4-(3-Chloropropoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole The title compound was prepared in a similar manner to that described in Reference Example 63 using 4-{[4-hydroxy-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole instead of 1-(2-hydroxyethyl)-4-[(4-hydroxy-2-methylphenyl)methyl]-5-isopropyl-3-(2,3,4,6-tetra-O-pivaloyl-β-D-glucopyranosyloxy)-1H-pyrazole.

$^1$H-NMR (CDCl$_3$) δ ppm:
1.0-1.2 (42H, m), 1.75-1.9 (2H, m), 2.0-2.1 (2H, m), 2.15-2.25 (2H, m), 2.85-2.95 (1H, m), 3.5-3.65 (4H, m), 3.73 (2H, t, J=6.4 Hz), 3.8-3.9 (1H, m), 3.9-4.1 (4H, m), 4.13 (1H, dd, J=12.4 Hz, 4.8 Hz), 4.19 (1H, dd, J=12.4 Hz, 1.9 Hz), 4.4-4.55 (1H, m), 5.15-5.3 (2H, m), 5.3-5.4 (1H, m), 5.66 (1H, d, J=8.1 Hz), 6.34 (1H, dd, J=8.4 Hz, 2.4 Hz), 6.41 (1H, d, J=2.4 Hz), 6.86 (1H, d, J=8.4 Hz)

Reference Example 66

3-[N-Benzyloxycarbonyl-N-(3-bromopropyl)amino] propionamide

To a solution of acrylamide (2 g) in ethanol (30 mL) was added 3-amino-1-propanol (3.23 mL), and the mixture was stirred at room temperature for 3 hours. The reaction mixture was concentrated under reduced pressure. To the residue were added tetrahydrofuran (30 mL) and N-(benzyloxycarbonyloxy)succinimide (14 g), and the mixture was stirred at room temperature overnight. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: dichloromethane/methanol=40/1-20/1-5/1) to give 3-[N-benzyloxycarbonyl-N-(3-hydroxypropyl)amino]propionamide (3.51 g). To a solution of the obtained 3-[N-benzyloxycarbonyl-N-(3-hydroxypropyl)amino]propionamide (0.5 g) and carbon tetrabromide (0.65 g) in dichloromethane (5 mL) was added triphenylphosphine (1.03 g) under ice-cooling, and the mixture was stirred at room temperature for 2 hours. The reaction mixture was poured into water, and the resulting mixture was extracted with ethylacetate. The extract was washed with water and brine, and dried over anhydrous sodium sulfate. The solvent was removed under reduced pressure, and the residue was purified by column chromatography on silica gel (eluent: n-hexane/ethyl acetate=1/4-dichloromethane/methanol=10/1) to give the title compound (0.41 g).

$^1$H-NMR (CD$_3$OD) δ ppm:
2.0-2.2 (2H, m), 2.4-2.55 (2H, m), 3.35-3.5 (4H, m), 3.56 (2H, t, J=6.9 Hz), 5.12 (2H, s), 7.25-7.45 (5H, m)

Example 96

4-[(4-{3-[N-Benzyloxycarbonyl-N-(2-carbamoylethyl)amino]-propoxy}-2-methylphenyl)methyl]-5-isopropyl-3-(2,3,4,6-tetra-O-pivaloyl-β-D-glucopyranosyloxy)-1H-pyrazole To a solution of 4-[(4-hydroxy-2-methylphenyl)methyl]-5-isopropyl-3-(2,3,4,6-tetra-O-pivaloyl-β-D-glucopyranosyloxy)-1H-pyrazole (0.4 g), 3-[N-benzyloxycarbonyl-N-(3-bromopropyl)amino]propionamide (0.28 g) and tetra(n-butyl)ammonium bromide (87 mg) in dichloromethane (4 mL) was added 5 mol/L aqueous sodium hydroxide solution (0.32 mL), and the mixture was stirred at room temperature overnight. The reaction mixture was poured into 1 mol/L hydrochloric acid, and the resulting mixture was extracted with diethylether. The extract was washed with 1 mol/L hydrochloric acid, water and brine, and dried over anhydrous magnesium sulfate. The solvent was removed under reduced pressure, and the residue was purified by column chromatography on silica gel (eluent: n-hexane/ethyl acetate=1/3-1/6) to give the title compound (0.42 g).

$^1$H-NMR (CD$_3$OD) δ ppm:
1.0-1.2 (42H, m), 1.9-2.05 (2H, m), 2.25 (3H, s), 2.4-2.55 (2H, m), 2.75-2.85 (1H, m), 3.45-3.65 (6H, m), 3.85-4.0 (3H, m), 4.08 (1H, dd, J=12.5 Hz, 1.9 Hz), 4.16 (1H, dd, J=12.5 Hz, 4.4 Hz), 4.95-5.2 (4H, m), 5.35-5.45 (1H, m), 5.58 (1H, d, J=7.9 Hz), 6.45-6.75 (2H, m), 6.8 (1H, d, J=8.4 Hz), 7.25-7.4 (5H, m)

Example 97

4-{[4-{3-[N-Benzyloxycarbonyl-N-(2-carbamoyl-ethyl)amino]-propoxy}-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole The title compound was prepared in a similar manner to that described in Example 96 using 4-{[4-hydroxy-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole instead of 4-[(4-hydroxy-2-methylphenyl)methyl]-5-isopropyl-3-(2,3,4,6-tetra-O-pivaloyl-β-D-glucopyranosyloxy)-1H-pyrazole.

$^1$H-NMR (CD$_3$OD) δ ppm:
1.0-1.2 (42H, m), 1.7-1.85 (2H, m), 1.9-2.15 (4H, m), 2.4-2.55 (2H, m), 2.85-2.95 (1H, m), 3.35-3.65 (8H, m), 3.85-4.0 (5H, m), 4.11 (1H, dd, J=12.5 Hz, 1.9 Hz), 4.18 (1H, dd, J=12.5 Hz, 4.4 Hz), 4.45-4.6 (1H, m), 5.05-5.2 (4H, m), 5.35-5.4 (1H, m), 5.57 (1H, d, J=8.2 Hz), 6.2-6.6 (2H, m), 6.8 (1H, d, J=8.4 Hz), 7.2-7.45 (5H, m)

Example 98

4-{[4-(3-[N-Benzyl-N-(2-carbamoylethyl)amino]propoxy}-2-methylphenyl)methyl]-5-isopropyl-3-(2,3,4,6-tetra-O-pivaloyl-β-D-glucopyranosyloxy)-1H-pyrazole A mixture of 4-{[4-(3-chloropropoxy)-2-methylphenyl]methyl}-5-isopropyl-3-(2,3,4,6-tetra-O-pivaloyl-β-D-glucopyranosyloxy)-1H-pyrazole (1.34 g), 3-benzylaminopropionamide (0.73 g), sodium iodide (0.24 g), ethanol (6 mL) and acetonitrile (6 mL) was stirred at 70° C. for 2 days. To the reaction mixture was added sodium iodide (0.2 g), and the mixture was further stirred at 75° C. for 24 hours. The reaction mixture was poured into 1 mol/L hydrochloric acid, and the resulting mixture was extracted with ethyl acetate. The extract was washed with water, a saturated aqueous sodium hydrogen carbonate solution and brine, and dried over anhydrous sodium sulfate. The solvent was removed under reduced pressure, and the residue was purified by column chromatography on silica gel (eluent: n-hexane/ethyl acetate=1/5–dichloromethane/methanol=15/1) to give the title compound (0.97 g).

$^1$H-NMR (CD$_3$OD) δ ppm:
1.0-1.2 (42H, m), 1.85-1.95 (2H, m), 2.26 (3H, s), 2.4 (2H, t, J=6.9 Hz), 2.62 (2H, t, J=6.9 Hz), 2.75-2.9 (3H, m), 3.52 (1H, d, J=16.4 Hz), 3.56 (1H, d, J=16.4 Hz), 3.62 (2H, s), 3.85-3.95 (3H, m), 4.08 (1H, dd, J=12.4 Hz, 1.8 Hz), 4.16 (1H, dd, J=12.4 Hz, 4.4 Hz), 5.05-5.2 (2H, m), 5.35-5.45 (1H, m), 5.58 (1H, d, J=8.1 Hz), 6.52 (1H, dd, J=8.5 Hz, 2.5 Hz), 6.61 (1H, d, J=2.5 Hz), 6.79 (1H, d, J=8.5 Hz), 7.15-7.35 (5H, m)

Example 99

4-[(4-{3-[N-Benzyl-N-(2-carbamoylethyl)amino]propoxy}-2-methylphenyl)methyl]-1-(2-hydroxyethyl)-5-isopropyl-3-(2,3,4,6-tetra-O-pivaloyl-β-D-glucopyranosyloxy)-1H-pyrazole The title compound was prepared in a similar manner to that described in Example 98 using 4-{[4-(3-chloropropoxy)-2-methylphenyl]methyl}-1-(2-hydroxyethyl)-5-isopropyl-3-(2,3,4,6-tetra-O-pivaloyl-β-D-glucopyranosyloxy)-1H-pyrazole instead of 4-{[4-(3-chloropropoxy)-2-methylphenyl]methyl}-5-isopropyl-3-(2,3,4,6-tetra-O-pivaloyl-β-D-glucopyranosyloxy)-1H-pyrazole.

$^1$H-NMR (CD$_3$OD) δ ppm:
1.0-1.2 (42H, m), 1.85-1.95 (2H, m), 2.28 (3H, s), 2.4 (2H, t, J=7.1 Hz), 2.62 (2H, t, J=7.0 Hz), 2.8 (2H, t, J=7.1 Hz), 3.05-3.15 (1H, m), 3.5-3.65 (4H, m), 3.8-3.95 (5H, m), 4.0-4.2 (4H, m), 5.0-5.2 (2H, m), 5.36 (1H, t, J=9.5 Hz), 5.59 (1H, d, J=7.8 Hz), 6.5 (1H, dd, J=8.5 Hz, 2.7 Hz), 6.62 (1H, d, J=2.7 Hz), 6.7 (1H, d, J=8.5 Hz), 7.15-7.4 (5H, m)

Example 100

4-[(4-{3-[N-Benzyl-N-(2-carbamoylethyl)amino]propoxy}-2-methylphenyl)methyl]-1-(3-hydroxypropyl)-5-isopropyl-3-(2,3,4,6-tetra-O-pivaloyl-β-D-glucopyranosyloxy)-1H-pyrazole The title compound was prepared in a similar manner to that described in Example 98 using 4-{[4-(3-chloropropoxy)-2-methylphenyl]methyl}-1-(3-hydroxypropyl)-5-isopropyl-3-(2,3,4,6-tetra-O-pivaloyl-β-D-glucopyranosyloxy)-1H-pyrazole instead of 4-{[4-(3-chloropropoxy)-2-methylphenyl]methyl}-5-isopropyl-3-(2,3,4,6-tetra-O-pivaloyl-β-D-glucopyranosyloxy)-1H-pyrazole.

$^1$H-NMR (CD$_3$OD) δ ppm:
1.0-1.2 (42H, m), 1.85-2.05 (4H, m), 2.28 (3H, s), 2.4 (2H, t, J=7.0 Hz), 2.62 (2H, t, J=7.0 Hz), 2.8 (2H, t, J=7.0 Hz), 3.0-3.1 (1H, m), 3.5-3.65 (6H, m), 3.85-3.95 (3H, m), 4.0-4.2 (4H, m), 5.0-5.2 (2H, m), 5.37 (1H, t, J=9.4 Hz), 5.6 (1H, d, J=7.7 Hz), 6.5 (1H, dd, J=8.4 Hz, 2.6 Hz), 6.62 (1H, d, J=2.6 Hz), 6.67 (1H, d, J=8.4 Hz), 7.15-7.35 (5H, m)

Example 101

4-{[4-(3-[1-Carbamoyl-1-(methyl)ethylamino]propoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole The title compound was prepared in a similar manner to that described in Example 98 using 4-{[4-(3-chloropropoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole and 2-amino-2-methylpropionamide instead of 4-{[4-(3-chloropropoxy)-2-methylphenyl]methyl}-5-isopropyl-3-(2,3,4,6-tetra-O-pivaloyl-β-D-glucopyranosyloxy)-1H-pyrazole and 3-benzylaminopropionamide, respectively.

$^1$H-NMR (CD$_3$OD) δ ppm:
1.05-1.2 (42H, m), 1.32 (6H, s), 1.7-1.85 (2H, m), 1.85-2.1 (4H, m), 2.69 (2H, t, J=7.0 Hz), 2.85-2.95 (1H, m), 3.53 (1H, d, J=16.6 Hz), 3.55-3.7 (3H, m), 3.85-4.05 (5H, m), 4.11 (1H, dd, J=12.4 Hz, 1.6 Hz), 4.18 (1H, dd, J=12.4 Hz, 4.3 Hz), 4.55-4.65 (1H, m), 5.05-5.2 (2H, m), 5.3-5.4 (1H, m), 5.56 (1H, d, J=8.2 Hz), 6.38 (1H, dd, J=8.4 Hz, 2.2 Hz), 6.53 (1H, d, J=2.2 Hz), 6.81 (1H, d, J=8.4 Hz)

Example 102

4-[(4-(3-[2-(Carbamoyl)ethylamino]propoxy)-2-methylphenyl)methyl]-5-isopropyl-3-(2,3,4,6-tetra-O-pivaloyl-β-D-glucopyranosyloxy)-1H-pyrazole To a solution of 4-[(4-{3-[N-benzyl-N-(2-carbamoylethyl)amino]propoxy}-2-methylphenyl)methyl]-5-isopropyl-3-(2,3,4,6-tetra-O-pivaloyl-β-D-glucopyranosyloxy)-1H-pyrazole (0.96 g) in tetrahydrofuran (5 mL) was added 10% palladium-carbon powder (0.1 g), and the mixture was stirred at room temperature under a hydrogen atmosphere overnight. The insoluble material was removed by filtration, and the filtrate was concentrated under reduced pressure to give the title compound (0.87 g).

$^1$H-NMR (CD$_3$OD) δ ppm:
1.05-1.2 (42H, m), 1.9-2.0 (2H, m), 2.27 (3H, s), 2.43 (2H, t, J=6.8 Hz), 2.75-2.9 (5H, m), 3.53 (1H, d, J=16.4 Hz), 3.56 (1H, d, J=16.4 Hz), 3.9-4.05 (3H, m), 4.08 (1H, dd, J=12.4 Hz, 1.8 Hz), 4.16 (1H, dd, J=12.4 Hz, 4.4 Hz), 5.05-5.2 (2H, m), 5.35-5.45 (1H, m), 5.58 (1H, d, J=8.1 Hz), 6.59 (1H, dd, J=8.4 Hz, 2.6 Hz), 6.7 (1H, d, J=2.6 Hz), 6.81 (1H, d, J=8.4 Hz)

Example 103

4-[(4-{3-[2-(Carbamoyl)ethylamino]propoxy}-2-methylphenyl)methyl]-1-(2-hydroxyethyl)-5-isopropyl-3-(2,3,4,6-tetra-O-pivaloyl-β-D-glucopyranosyloxy)-1H-pyrazole The title compound was prepared in a similar manner to that described in Example 102 using 4-[(4-{3-[N-benzyl-N-(2-carbamoylethyl)amino]propoxy}-2-methylphenyl)methyl]-1-(2-hydroxyethyl)-5-isopropyl-3-(2,3,4,6-tetra-O-pivaloyl-β-D-glucopyranosyloxy)-1H-pyrazole instead of 4-[(4-{3-[N-benzyl-N-(2-carbamoylethyl)amino]propoxy}-2-methylphenyl)methyl]-5-isopropyl-3-(2,3,4,6-tetra-O-pivaloyl-β-D-glucopyranosyloxy)-1H-pyrazole.

$^1$H-NMR (CD$_3$OD) δ ppm:
1.05-1.2 (42H, m), 1.85-2.0 (2H, m), 2.29 (3H, s), 2.42 (2H, t, J=6.9 Hz), 2.77 (2H, t, J=7.1 Hz), 2.85 (2H, t, J=6.9 Hz), 3.05-3.2 (1H, m), 3.56 (1H, d, J=16.8 Hz), 3.61 (1H, d, J=16.8 Hz), 3.8-4.2 (9H, m), 5.0-5.2 (2H, m), 5.37 (1H, t, J=9.4 Hz), 5.59 (1H, d, J=8.0 Hz), 6.56 (1H, dd, J=8.4 Hz, 2.5 Hz), 6.65-6.75 (2H, m)

Example 104

4-[(4-{3-[2-(Carbamoyl)ethylamino]propoxy}-2-methylphenyl)methyl]-1-(3-hydroxypropyl)-5-isopropyl-3-(2,3,4,6-tetra-O-pivaloyl-β-D-glucopyranosyloxy)-1H-pyrazole The title compound was prepared in a similar manner to that described in Example 102 using 4-[(4-{3-[N-benzyl-N-(2-carbamoylethyl)amino]propoxy}-2-methylphenyl)methyl]-1-(3-hydroxypropyl)-5-isopropyl-3-(2,3,4,6-tetra-O-pivaloyl-β-D-glucopyranosyloxy)-1H-pyrazole instead of 4-[(4-{3-[N-benzyl-N-(2-carbamoylethyl)amino]propoxy}-2-methylphenyl)methyl]-5-isopropyl-3-(2,3,4,6-tetra-O-pivaloyl-β-D-glucopyranosyloxy)-1H-pyrazole.

$^1$H-NMR (CD$_3$OD) δ ppm:
1.0-1.2 (42H, m), 1.9-2.05 (4H, m), 2.29 (3H, s), 2.44 (2H, t, J=6.8 Hz), 2.81 (2H, t, J=7.1 Hz), 2.88 (2H, t, J=6.8 Hz), 3.0-3.15 (1H, m), 3.5-3.65 (4H, m), 3.85-4.2 (7H, m), 5.0-5.2 (2H, m), 5.37 (1H, t, J=9.5 Hz), 5.6 (1H, d, J=8.4 Hz), 6.57 (1H, dd, J=8.3 Hz, 2.3 Hz), 6.65-6.75 (2H, m)

Example 105

4-{[4-{3-[2-(Carbamoyl)ethylamino]propoxy}-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole The title compound was prepared in a similar manner to that described in Example 102 using 4-{[4-(3-[N-benzyloxycarbonyl-N-(2-carbamoylethyl)amino]propoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole instead of 4-[(4-(3-[N-benzyl-N-(2-carbamoylethyl)amino]propoxy)-2-methylphenyl)methyl]-5-isopropyl-3-(2,3,4,6-tetra-O-pivaloyl-β-D-glucopyranosyloxy)-1H-pyrazole.

$^1$H-NMR (CD$_3$OD) δ ppm:
1.0-1.2 (42H, m), 1.7-1.85 (2H, m), 2.0-2.1 (2H, m), 2.1-2.2 (2H, m), 2.67 (2H, t, J=6.2 Hz), 2.85-2.95 (1H, m), 3.2-3.35 (4H, m), 3.54 (1H, d, J=16.5 Hz), 3.55-3.7 (3H, m), 3.9-4.0 (3H, m), 4.05-4.15 (3H, m), 4.19 (1H, dd, J=12.4 Hz, 4.4 Hz), 4.55-4.65 (1H, m), 5.05-5.2 (2H, m), 5.35-5.45 (1H, m), 5.58 (1H, d, J=8.1 Hz), 6.43 (1H, dd, J=8.4 Hz, 2.3 Hz), 6.64 (1H, d, J=2.3 Hz), 6.84 (1H, d, J=8.4 Hz)

Example 106

4-[(4-{3-[2-(Carbamoyl)ethylamino]propoxy}-2-methylphenyl)methyl]-3-(β-D-glucopyranosyloxy)-1-(3-hydroxypropyl)-5-isopropyl-1H-pyrazole To a solution of 4-[(4-{3-[2-(carbamoyl)ethylamino]-propoxy}-2-methylphenyl)methyl]-1-(3-hydroxypropyl)-5-isopropyl-3-(2,3,4,6-tetra-O-pivaloyl-β-D-glucopyranosyloxy)-1H-pyrazole (0.3 g) in methanol (6 mL) was added sodium methoxide (28% methanol solution, 0.25 mL), and the mixture was stirred at 50° C. overnight. The reaction mixture was concentrated under reduced pressure, and the residue was purified by solid phase extraction on ODS (washing solvent: distilled water, eluent: methanol) to give the title compound (0.16 g).

$^1$H-NMR (CD$_3$OD) δ ppm:
1.1-1.2 (6H, m), 1.9-2.05 (4H, m), 2.3 (3H, s), 2.42 (2H, t, J=6.8 Hz), 2.77 (2H, t, J=7.1 Hz), 2.84 (2H, t, J=6.8 Hz), 3.0-3.15 (1H, m), 3.2-3.4 (4H, m), 3.55-3.75 (5H, m), 3.8 (1H, dd, J=12.1 Hz, 2.1 Hz), 3.99 (2H, t, J=6.2 Hz), 4.11 (2H, t, J=7.2 Hz), 5.03 (1H, d, J=7.6 Hz), 6.6 (1H, dd, J=8.3 Hz, 2.6 Hz), 6.72 (1H, d, J=2.6 Hz), 6.74 (1H, d, J=8.3 Hz)

Example 107

4-[(4-(3-[2-(Carbamoyl)ethylamino]propoxy)-2-methylphenyl)methyl]-3-(β-D-glucopyranosyloxy)-1-(2-hydroxyethyl)-5-isopropyl-1H-pyrazole The title compound was prepared in a similar manner to that described in Example 106 using 4-[(4-{3-[2-(carbamoyl)

ethylamino]propoxy}-2-methylphenyl)methyl]-1-(2-hydroxyethyl)-5-isopropyl-3-(2,3,4,6-tetra-O-pivaloyl-β-D-glucopyranosyloxy)-1H-pyrazole instead of 4-[(4-{3-[2-(carbamoyl)ethylamino]propoxy}-2-methylphenyl)methyl]-1-(3-hydroxypropyl)-5-isopropyl-3-(2,3,4,6-tetra-O-pivaloyl-β-D-glucopyranosyloxy)-1H-pyrazole.

$^1$H-NMR (CD$_3$OD) δ ppm:
1.1-1.2 (6H, m), 1.85-2.0 (2H, m), 2.3 (3H, s), 2.41 (2H, t, J=6.8 Hz), 2.77 (2H, t, J=7.1 Hz), 2.84 (2H, t, J=6.8 Hz), 3.05-3.2 (1H, m), 3.2-3.4 (4H, m), 3.6-3.75 (3H, m), 3.79 (1H, dd, J=12.0 Hz, 2.2 Hz), 3.85 (2H, t, J=5.7 Hz), 3.99 (2H, t, J=6.0 Hz), 4.09 (2H, t, J=5.7 Hz), 5.06 (1H, d, J=7.7 Hz), 6.6 (1H, dd, J=8.4 Hz, 2.7 Hz), 6.72 (1H, d, J=2.7 Hz), 6.77 (1H, d, J=8.4 Hz)

Example 108

4-{[4-{3-[1-Carbamoyl-1-(methyl)ethylamino]propoxy}-2-(tetrahydro-4H-pyran-4-yloxy)phenyl]methyl}-3-(β-D-glucopyranosyloxy)-5-isopropyl-1H-pyrazole The title compound was prepared in a similar manner to that described in Example 106 using 4-{[4-{3-[1-carbamoyl-1-(methyl)ethylamino]propoxy}-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole instead of 4-[(4-(3-[2-(carbamoyl)ethylamino]propoxy)-2-methylphenyl)methyl]-1-(3-hydroxypropyl)-5-isopropyl-3-(2,3,4,6-tetra-O-pivaloyl-β-D-glucopyranosyloxy)-1H-pyrazole.

$^1$H-NMR (CD$_3$OD) δ ppm:
1.05-1.2 (6H, m), 1.29 (6H, s), 1.7-1.85 (2H, m), 1.85-1.95 (2H, m), 1.95-2.1 (2H, m) 2.64 (2H, t, J=6.9 Hz), 2.8-2.95 (1H, m), 3.25-3.45 (4H, m), 3.55-3.75 (5H, m), 3.8-3.9 (1H, m), 3.9-4.05 (4H, m), 4.5-4.65 (1H, m), 5.0-5.1 (1H, m), 6.4 (1H, dd, J=8.4 Hz, 2.0 Hz), 6.53 (1H, d, J=2.0 Hz), 6.9 (1H, d, J=8.4 Hz)

Example 109

4-{[4-{3-[2-(Carbamoyl)ethylamino]propoxy}-2-(tetrahydro-4H-pyran-4-yloxy)phenyl]methyl}-3-(β-D-glucopyranosyloxy)-5-isopropyl-1H-pyrazole The title compound was prepared in a similar manner to that described in Example 106 using 4-{[4-{3-[2-(carbamoyl)ethylamino]propoxy}-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole instead of 4-[(4-{3-[2-(carbamoyl)ethylamino]propoxy}-2-methylphenyl)methyl]-1-(3-hydroxypropyl)-5-isopropyl-3-(2,3,4,6-tetra-O-pivaloyl-β-D-glucopyranosyloxy)-1H-pyrazole.

$^1$H-NMR (CD$_3$OD) δ ppm:
1.05-1.15 (6H, m), 1.7-1.85 (2H, m), 1.9-2.1 (4H, m), 2.43 (2H, t, J=6.8 Hz), 2.79 (2H, t, J=7.0 Hz), 2.8-2.95 (3H, m), 3.25-3.4 (4H, m), 3.55-3.75 (5H, m), 3.8-3.85 (1H, m), 3.9-4.05 (4H, m), 4.55-4.65 (1H, m), 5.0-5.1 (1H, m), 6.41 (1H, dd, J=8.4 Hz, 2.4 Hz), 6.54 (1H, d, J=2.4 Hz), 6.9 (1H, d, J=8.4 Hz)

Example 110

4-[(4-{3-[N-Benzyl-N-(2-carbamoylethyl)amino]propoxy}-2-methylphenyl)methyl]-3-(β-D-glucopyranosyloxy)-5-isopropyl-1H-pyrazole To a solution of 4-[(4-{3-[N-benzyl-N-(2-carbamoylethyl)amino]propoxy}-2-methylphenyl)methyl]-5-isopropyl-3-(2,3,4,6-tetra-O-pivaloyl-β-D-glucopyranosyloxy)-1H-pyrazole (1.25 g) in methanol (13 mL) was added sodium methoxide (28% methanol solution, 0.25 mL), and the mixture was stirred at 50° C. for 6 hours. The reaction mixture was concentrated under reduced pressure, and the residue was purified by column chromatography on silica gel (eluent: dichloromethane/methanol=10/1-5/1) to give the title compound (0.5 g).

$^1$H-NMR (CD$_3$OD) δ ppm:
1.05-1.15 (6H, m), 1.85-1.95 (2H, m), 2.28 (3H, s), 2.4 (2H, t, J=6.9 Hz), 2.55-2.65 (2H, m), 2.75-2.85 (3H, m), 3.25-3.4 (4H, m), 3.55-3.75 (5H, m), 3.75-3.85 (1H, m), 3.92 (2H, t, J=6.2 Hz), 4.95-5.05 (1H, m), 6.55 (1H, dd, J=8.5 Hz, 2.8 Hz). 6.62 (1H, d, J=2.8 Hz), 6.83 (1H, d, J=8.5 Hz), 7.15-7.35 (5H, m)

Example 111

4-[(4-{3-[2-(Carbamoyl)ethylamino]propoxy}-2-methylphenyl)methyl]-3-(β-D-glucopyranosyloxy)-5-isopropyl-1H-pyrazole 4-[(4-{3-[N-Benzyl-N-(2-carbamoylethyl)amino]-propoxy}-2-methylphenyl)methyl]-3-(β-D-glucopyranosyloxy)-5-isopropyl-1H-pyrazole (0.5 g) was dissolved in methanol (8 mL). To the solution was added 10% palladium-carbon powder (0.1 g), and the mixture was stirred at room temperature under a hydrogen atmosphere for 3 hours. The insoluble material was removed by filtration, and the filtrate was concentrated under reduced pressure. A part (0.1 g) of the residue was dissolved in a mixed solvent of methanol (1 mL) and ethyl acetate (1.5 mL). To the solution was added a seed crystal, and the mixture was stirred at room temperature for 3 days. The precipitated crystals were collected by filtration. The crystals were washed with a mixed solvent of methanol and ethyl acetate (2/3), and dried under reduced pressure to give the title compound (85 mg).

$^1$H-NMR (CD$_3$OD) δ ppm:
1.05-1.15 (6H, m), 1.85-2.0 (2H, m), 2.29 (3H, s), 2.42 (2H, t, J=6.9 Hz), 2.7-2.9 (5H, m), 3.25-3.4 (4H, m), 3.6-3.75 (3H, m), 3.75-3.85 (1H, m), 3.99 (2H, t, J=6.2 Hz), 4.95-5.05 (1H, m). 6.62 (1H, dd, J=8.4 Hz, 2.4 Hz), 6.71 (1H, d, J=2.4 Hz), 6.85 (1H, d, J=8.4 Hz)

melting point: 191-193° C.

Example 112

4-[(4-{(S)-3-[2-(Carbamoyl)ethylamino]-2-hydroxypropoxy}-2-methylphenyl)methyl]-3-(β-D-glucopyranosyloxy)-5-isopropyl-1H-pyrazole To a suspension of 4-[(4-hydroxy-2-methylphenyl)methyl]-5-isopropyl-3-(2,3,4,6-tetra-O-pivaloyl-β-D-glucopyranosyloxy)-1H-pyrazole (0.3 g) and potassium carbonate (84 mg) in N,N-dimethylformamide (3 mL) were added (S)-1-(p-toluenesulfonyloxy)-2,3-epoxypropane (0.1 g) and a catalytic amount of cesium fluoride, and the mixture was stirred at room temperature overnight. The reaction mixture was poured into a saturated aqueous ammonium chloride solution, and the resulting mixture was extracted with ethylacetate. The extract was washed with a saturated aqueous sodium hydrogen carbonate solution and brine, and dried over anhydrous sodium sulfate. The solvent was removed under reduced pressure, and the residue was dissolved in methanol (5 mL). To the solution was added 3-benzylamino-propionamide (0.14 g), and the mixture was stirred at 50° C. overnight. The reaction mixture was concentrated under reduced pressure, and the residue was purified by column chromatography on silica gel (eluent: n-hexane/ethyl acetate=1/2-dichloromethane/methanol=10/1) to give 4-[(4-{(S)-3-[N-benzyl-N-(2-carbamoylethyl)amino]-2-hydroxypropoxy}-2-methylphenyl)methyl]-5-isopropyl-3-(2,3,4,6-tetra-O-pivaloyl-β-D-glucopyranosyloxy)-1H-pyrazole (0.23 g). This material was dissolved in methanol (5 mL). To the solution was added 10% palladium-carbon powder (0.1 g), and the mixture was stirred at room temperature under a hydrogen atmosphere for 4 days. The insoluble material was removed by filtration, and the filtrate was concentrated under reduced pressure. The residue was dissolved in methanol (5 mL). To the solution was added sodium methoxide (28% methanol solution, 0.085 mL), and the mixture was stirred at 50° C. overnight. The reaction mixture was concentrated under reduced pressure, and the residue was purified by solid phase extraction on ODS (washing solvent: distilled water, eluent: methanol) and preparative reverse phase column chromatography (Shiseido CAPCELL PAK UG120 ODS, 5 μm, 120 Å, 20×50 mm, flow rate 30 mL/minute linear gradient, water/methanol=90/10-10/90) successively to give the title compound (23 mg).

$^1$H-NMR (CD$_3$OD) δ ppm:
1.05-1.15 (6H, m), 2.29 (3H, s), 2.43 (2H, t, J=6.7 Hz), 2.65-2.95 (5H, m), 3.25-3.4 (4H, m), 3.6-3.7 (3H, m), 3.75-3.85 (1H, m), 3.9 (2H, d, J=5.3 Hz), 3.95-4.05 (1H, m), 4.95-5.05 (1H, m), 6.64 (1H, dd, J=8.4 Hz, 2.4 Hz), 6.74 (1H, d, J=2.4 Hz), 6.86 (1H, d, J=8.4 Hz)

Example 113

4-[(4-{(R)-3-[2-(Carbamoyl)ethylamino]-2-hydroxypropoxy}-2-methylphenyl)methyl]-3-(β-D-glucopyranosyloxy)-5-isopropyl-1H-pyrazole The title compound was prepared in a similar manner to that described in Example 112 using (R)-1-(p-toluenesulfonyloxy)-2,3-epoxypropane instead of (S)-1-(p-toluenesulfonyloxy)-2,3-epoxypropane.

$^1$H-NMR (CD$_3$OD) δ ppm:
1.05-1.15 (6H, m), 2.29 (3H, s), 2.43 (2H, t, J=6.7 Hz), 2.65-2.95 (5H, m), 3.25-3.4 (4H, m), 3.6-3.7 (3H, m), 3.75-3.85 (1H, m), 3.9 (2H, d, J=5.3 Hz), 4.0-4.05 (1H, m), 4.95-5.05 (1H, m), 6.64 (1H, dd, J=8.4 Hz, 2.5 Hz), 6.74 (1H, d, J=2.5 Hz), 6.86 (1H, d, J=8.4 Hz)

Reference Example 67

Benzyl 3-benzylaminopropionate

To a solution of benzyl acrylate (2 g) in ethanol (15 mL) was added benzylamine (1.75 mL), and the mixture was stirred at room temperature overnight. The reaction mixture was concentrated under reduced pressure, and the residue was purified by column chromatography on silica gel (eluent: n-hexane/ethyl acetate=2/1-1/1) to give the title compound (2.91 g).

$^1$H-NMR (CDCl$_3$) δ ppm:
2.59 (2H, t, J=6.5 Hz), 2.92 (2H, t, J=6.5 Hz), 3.79 (2H, s), 5.13 (2H, s), 7.2-7.4 (10H, m)

Example 114

4-{[4-(3-{2-[(S)-1-Carbamoyl-2-hydroxyethylcarbamoyl]ethylamino}propoxy)-2-methylphenyl]methyl}-3-(β-D-glucopyranosyloxy)-5-isopropyl-1H-pyrazole To a solution of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole (1 g) and triethylamine (0.29 mL) in dichloromethane (10 mL) was added methanesulfonyl chloride (0.13 mL), and the mixture was stirred at room temperature for 1 hour. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure to give 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole (1.12 g). This material was dissolved in acetonitrile (7 mL)-ethanol (7 mL). To the solution were added benzyl 3-benzylaminopropionate (1.27 g) and sodium iodide (240 mg), and the mixture was stirred at 60° C. for 2 days. The reaction mixture was poured into water, and the resulting mixture was extracted with ethylacetate. The extract was washed with water and brine, and dried over anhydrous sodium sulfate. The solvent was removed under reduced pressure, and the residue was purified by column chromatography on silica gel (eluent: dichloromethane/methanol=30/1-20/1) to give 3-(2,3,4,6-tetra-O-acetyl-β-D-glucopyranosyloxy)-4-[(4-{3-[N-benzyl-N-(2-benzyloxycarbonylethyl)amino]propoxy}-2-methylphenyl)methyl]-5-isopropyl-1H-pyrazole (1.3 g). This material was dissolved in methanol (10 mL). To the solution was added 10% palladium-carbon powder (0.65 g), and the mixture was stirred at room temperature under a hydrogen atmosphere overnight. The insoluble material was removed by filtration, and the filtrate was concentrated under reduced pressure to give 3-(2,3,4,6-tetra-O-acetyl-β-D-glucopyranosyloxy)-4-({4-[3-(2-carboxyethylamino)propoxy]-2-methylphenyl}methyl)-5-isopropyl-1H-pyrazole (0.95 g). This material was dissolved in 1,4-dioxane (10 mL). To the solution were added sodium hydrogen carbonate (0.45 g) and water (10 mL), and the mixture was stirred for 15 minutes. To the reaction mixture was added benzyloxycarbonyl chloride (0.23 mL), and the mixture was stirred at room temperature overnight. To the reaction mixture was added benzyloxycarbonyl chloride (0.23 mL), and the mixture was stirred at room temperature for 3 hours. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure to give 3-(2,3,4,6-tetra-O-acetyl-β-D-glucopyranosyloxy)-4-[(4-{3-[N-benzyloxycarbonyl-N-(2-carboxyethyl)amino]propoxy}-2-methylphenyl)methyl]-5-isopropyl-1H-pyrazole (0.86 g). To a solution of the obtained 3-(2,3,4,6-tetra-O-acetyl-β-D-glucopyranosyloxy)-4-[(4-{3-[N-benzyloxycarbonyl-N-(2-carboxyethyl)amino]-propoxy}-2-methylphenyl)methyl]-5-isopropyl-1H-pyrazole (0.17 g) in N,N-dimethylformamide (3 mL) were added L-serine amide hydrochloride (37 mg), 1-hydroxybenzotriazole (30 mg), 1-ethyl-3-(3-dimethylaminopropyl)carbodiimide hydrochloride (77 mg) and triethylamine (0.11 mL), and the mixture was stirred at room temperature for 8 hours. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: dichloromethane/methanol=20/1-10/1) to give 3-(2,3,4,6-tetra-O-acetyl-β-D-glucopyranosyloxy)-4-({4-[3-(N-benzyloxycarbonyl-N-{2-[(S)-1-carbamoyl-2-hydroxyethylcarbamoyl]ethyl}amino)propoxy]-2-methylphenyl}methyl)-5-isopropyl-1H-pyrazole (81 mg). This material was dissolved in methanol (5 mL). To the solution was added 10% palladium-carbon powder (10 mg), and the mixture was stirred at room temperature under a hydrogen atmosphere for 3 hours. The insoluble material was removed by filtration, and the filtrate was concentrated under reduced pressure. The residue was dissolved in methanol (4 mL). To the solution was added sodium methoxide (28% methanol solution, 0.02 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (38 mg).

$^1$H-NMR (CD$_3$OD) δ ppm:
1.0-1.2 (6H, m), 1.85-2.0 (2H, m), 2.28 (3H, s), 2.4-2.55 (2H, m), 2.7-2.95 (5H, m), 3.25-3.4 (4H, m), 3.55-3.85 (6H, m), 3.99 (2H, t, J=6.1 Hz), 4.35-4.45 (1H, m), 4.95-5.05 (1H, m), 6.61 (1H, dd, J=8.4 Hz, 2.2 Hz), 6.71 (1H, d, J=2.2 Hz), 6.84 (1H, d, J=8.4 Hz)

Example 115

4-[(4-{3-[2-(Carbamoylmethylcarbamoyl)ethylamino]propoxy}-2-methylphenyl)methyl]-3-(β-D-glucopyranosyloxy)-5-isopropyl-1H-pyrazole The title compound was prepared in a similar manner to that described in Example 114 using glycinamide hydrochloride instead of L-serine amide hydrochloride.

$^1$H-NMR (CD$_3$OD) δ ppm:
1.05-1.15 (6H, m), 1.9-2.0 (2H, m), 2.29 (3H, s), 2.46 (2H, t, J=6.6 Hz), 2.7-2.85 (3H, m), 2.88 (2H, t, J=6.6 Hz), 3.3-3.4 (4H, m), 3.6-3.7 (3H, m), 3.75-3.85 (3H, m), 3.99 (2H, t, J=6.1 Hz), 5.0-5.05 (1H, m), 6.61 (1H, dd, J=8.4 Hz, 2.5 Hz), 6.71 (1H, d, J=2.5 Hz), 6.85 (1H, d, J=8.4 Hz)

Example 116

4-{[4-(3-{2-[(S)-1-(Carbamoyl)ethylcarbamoyl]ethylamino}propoxy)-2-methylphenyl]methyl}-3-(β-D-glucopyranosyloxy)-5-isopropyl-1H-pyrazole The title compound was prepared in a similar manner to that described in Example 114 using L-alanine amide hydrochloride instead of L-serine amide hydrochloride.

$^1$H-NMR (CD$_3$OD) δ ppm:
1.05-1.15 (6H, m), 1.33 (3H, d, J=7.2 Hz), 1.9-2.0 (2H, m), 2.29 (3H, s), 2.35-2.5 (2H, m), 2.7-2.9 (5H, m), 3.3-3.4 (4H, m), 3.6-3.7 (3H, m), 3.75-3.85 (1H, m), 3.99 (2H, t, J=6.1 Hz), 4.32 (1H, q, J=7.2 Hz), 4.95-5.05 (1H, m), 6.61 (1H, dd, J=8.4 Hz, 2.3 Hz), 6.71 (1H, d, J=2.3 Hz), 6.85 (1H, d, J=8.4 Hz)

Example 117

4-{[4-(3-{2-[(S)-5-Amino-1-(carbamoyl)pentylcarbamoyl]-ethylamino}propoxy)-2-methylphenyl]methyl}-3-(β-D-glucopyranosyloxy)-5-isopropyl-1H-pyrazole The title compound was prepared in a similar manner to that described in Example 114 using (S)-2-amino-6-(benzyloxycarbonylamino)hexanamide hydrochloride instead of L-serine amide hydrochloride.

$^1$H-NMR (CD$_3$OD) δ ppm:
1.05-1.2 (6H, m), 1.25-2.0 (8H, m), 2.29 (3H, s), 2.35-2.55 (2H, m), 2.63 (2H, t, J=7.0 Hz), 2.7-2.95 (5H, m), 3.25-3.4 (4H, m), 3.55-3.75 (3H, m), 3.75-3.85 (1H, m), 3.99 (2H, t, J=6.0 Hz), 4.25-4.35 (1H, m), 4.95-5.05 (1H, m), 6.62 (1H, dd, J=8.4 Hz, 2.2 Hz), 6.71 (1H, d. J=2.2 Hz), 6.84 (1H, d, J=8.4 Hz)

Reference Example 68

Benzyl 3-amino-2,2-di(methyl)propionate

To a solution of 3-amino-2,2-dimethyl-1-propanol (5 g) in methanol (50 mL) was added di-tert-butyl dicarbonate (12.7 g), and the mixture was stirred at room temperature overnight. The reaction mixture was concentrated under reduced pressure. The residue (solid) was treated with n-hexane-diethyl ether and collected by filtration, washed with n-hexane and dried under reduced pressure to give 3-(tert-butoxycarbonylamino)-2,2-dimethyl-1-propanol (7.48 g). To this material were added carbon tetrachloride (40 mL), acetonitrile (40 mL), water (48 mL), sodium periodate (38.8 g) and ruthenium trichloride-n hydrate (1 g) successively, and the mixture was stirred at room temperature overnight. The reaction mixture was diluted with water, and the resulting mixture was extracted with ethyl acetate. The organic layer was washed with water and brine. To the organic layer was added a saturated aqueous potassium carbonate solution, and the aqueous layer was separated. The aqueous layer was acidified with 2 mol/L hydrochloric acid, and the mixture was extracted with ethyl acetate. The extract was washed with water and brine, and dried over anhydrous magnesium sulfate. The solvent was removed under reduced pressure to give 3-(tert-butoxycarbonylamino)-2,2-di(methyl)propionic acid (2.78 g). This material was dissolved in N,N-dimethylformamide (30 mL). To the solution were added potassium carbonate (3.54 g) and benzyl bromide (2.28 mL), and the mixture was stirred at room temperature overnight. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=2/1) to give benzyl 3-(tert-butoxycarbonylamino)-2,2-di(methyl)propionate (2.72 g). To this material was added hydrochloric acid (4 mol/L 1,4-dioxane solution, 10 mL), and the mixture was stirred at room temperature for 3 days. The reaction mixture was concentrated under reduced pressure. To the residue was added a saturated aqueous sodium hydrogen carbonate solution, and the mixture was extracted with ethyl acetate. The extract was washed with water and brine, and dried over anhydrous sodium sulfate. The solvent was removed under reduced pressure to give the title compound (1.61 g).

$^1$H-NMR (DMSO-d$_6$) δ ppm:
1.09 (6H, s), 1.35-1.7 (2H, br), 2.63 (2H, s), 5.09 (2H, s), 7.25-7.45 (5H, m)

Example 118

3-(β-D-Glucopyranosyloxy)-5-isopropyl-4-{[4-(3-{2-[(piperazin-1-yl)carbonyl]-2-(methyl)propylamino}propoxy)-2-methylphenyl]methyl}-1H-pyrazole To a solution of 3-(2,3,4,6-tetra-O-acetyl-β-D-glucopyranosyloxy)-4-{[4-(3-hydroxypropoxy)-2-methylphenyl]-methyl}-5-isopropyl-1H-pyrazole (1 g) and triethylamine (0.25 mL) in dichloromethane (5 mL) was added methanesulfonyl chloride (0.13 mL), and the mixture was stirred at room temperature for 1 hour. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure to give 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole (1.12 g). The obtained 3-(2,3,4,6-tetra-O-acetyl-β-D-glucopyranosyloxy)-5-isopropyl-4-({4-[3-(methanesulfonyloxy)propoxy]-2-methylphenyl}methyl)-1H-pyrazole (0.36 g) was dissolved in 2-propanol (2 mL)-acetonitrile (2 mL). To the solution were added benzyl 3-amino-2,2-di(methyl)propionate (0.26 g) and sodium iodide (75 mg), and the mixture was stirred at 60° C. for 2 days. The reaction mixture was poured into water, and the resulting mixture was extracted with ethylacetate. The extract was washed with water and brine, and dried over anhydrous sodium sulfate. The solvent was removed under reduced pressure, and the residue was purified by column chromatography on silica gel (eluent: n-hexane/ethyl acetate=1/5-dichloromethane/methanol=20/1) to give 3-(2,3,4,6-tetra-O-acetyl-β-D-glucopyranosyloxy)-4-[(4-{3-[2-benzyloxycarbonyl-2-(methyl)propylamino]propoxy}-2-methylphenyl)methyl]-5-isopropyl-1H-pyrazole (0.35 g). This material was dissolved in methanol (5 mL). To the solution was added 10% palladium-carbon powder (0.1 g), and the mixture was stirred at room temperature under a hydrogen atmosphere for 5 hours. The insoluble material was removed by filtration, and the filtrate was concentrated under reduced pressure to give 3-(2,3,4,6-tetra-O-acetyl-β-D-glucopyranosyloxy)-4-[(4-{3-[2-carboxy-2-(methyl)propylamino]propoxy}-2-methylphenyl)methyl]-5-isopropyl-1H-pyrazole (0.31 g). This material was dissolved in tetrahydrofuran (4 mL). To the solution were added triethylamine (0.094 mL) and N-(benzyloxycarbonyloxy)succinimide (64 mg), and the mixture was stirred at room temperature overnight. The reaction mixture was poured into 0.5 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: dichloromethane/methanol=20/1) to give 3-(2,3,4,6-tetra-O-acetyl-β-D-glucopyranosyloxy)-4-{[4-(3-{N-benzyloxycarbonyl-N-[2-carboxy-2-(methyl)propyl]amino}propoxy)-2-methylphenyl]methyl}-5-isopropyl-1H-pyrazole (0.3 g). To a solution of the obtained 3-(2,3,4,6-tetra-O-acetyl-β-D-glucopyranosyloxy)-4-{[4-(3-{N-benzyloxycarbonyl-N-[2-carboxy-2-(methyl)propyl]amino}propoxy)-2-methylphenyl]methyl}-5-isopropyl-1H-pyrazole (0.1 g) in N,N-dimethylformamide (2 mL) were added 1-benzylpiperazine (26 mg), 1-hydroxybenzotriazole (17 mg), 1-ethyl-3-(3-dimethylaminopropyl)carbodiimide hydrochloride (44 mg) and triethylamine (0.064 mL), and the mixture was stirred at room temperature for 6 hours. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: dichloromethane/methanol=40/1) to give 3-(2,3,4,6-tetra-O-acetyl-β-D-glucopyranosyloxy)-4-{[4-(3-{N-benzyloxycarbonyl-N-[2-(4-benzylpiperazin-1-yl)carbonyl-2-(methyl)propyl]amino}propoxy)-2-methylphenyl]methyl}-5-isopropyl-1H-pyrazole (45 mg). This material was dissolved in tetrahydrofuran (4 mL). To the solution was added 10% palladium-carbon powder (20 mg), and the mixture was stirred at room temperature under a hydrogen atmosphere overnight. To the reaction mixture was added methanol (2 mL), and the mixture was stirred at room temperature under a hydrogen atmosphere for 5 hours. The insoluble material was removed by filtration, and the filtrate was concentrated under reduced pressure. The residue was dissolved in methanol (2 mL). To the solution was added sodium methoxide (28% methanol solution, 0.02 mL), and the mixture was stirred at room temperature for 1 hour. The reaction mixture was concentrated under reduced pressure, and the residue was purified by solid phase extraction on ODS (washing solvent: distilled water, eluent: methanol) and preparative reverse phase column chromatography (Shiseido CAPCELL PAK UG120 ODS, 5 μm, 120 Å, 20×50 mm, flow rate 30 mL/minute linear gradient, water/methanol=90/10-10/90) successively to give the title compound (12 mg).

$^1$H-NMR (CD$_3$OD) δ ppm:
1.05-1.2 (6H, m), 1.29 (6H, s). 1.85-2.0 (2H, m), 2.3 (3H, s), 2.65-2.9 (9H, m), 3.25-3.4 (4H, m), 3.5-3.75 (7H, m), 3.75-3.85 (1H, m), 4.0 (2H, t, J=5.8 Hz), 5.0-5.1 (1H, m), 6.62 (1H, dd, J=8.4 Hz, 2.0 Hz), 6.72 (1H, d, J=2.0 Hz), 6.84 (1H, d, J=8.4 Hz)

Example 119

4-{[4-(3-{2-[(S)-1-Carbamoyl-2-hydroxyethylcarbamoyl]-2-(methyl)propylamino}propoxy)-2-methylphenyl]methyl}-3-(β-D-glucopyranosyloxy)-5-isopropyl-1H-pyrazole The title compound was prepared in a similar manner to that described in Example 118 using L-serine amide hydrochloride instead of 1-benzylpiperazine.

$^1$H-NMR (CD$_3$OD) δ ppm:
1.05-1.15 (6H, m), 1.17 (3H, s), 1.19 (3H, s), 1.9-2.0 (2H, m), 2.28 (3H, s), 2.7 (2H, s), 2.75-2.85 (3H, m), 3.25-3.4 (4H, m), 3.6-3.7 (3H, m), 3.76 (1H, dd, J=11.1 Hz, 4.7 Hz), 3.8-3.9 (2H, m), 4.0 (2H, t, J=6.1 Hz), 4.35-4.4 (1H, m), 4.95-5.05 (1H, m), 6.61 (1H, dd, J=8.4 Hz, 2.3 Hz), 6.71 (1H, d, J=2.3 Hz), 6.84 (1H, d, J=8.4 Hz)

Example 120 3-(β-D-Glucopyranosyloxy)-5-isopropyl-4-{[4-(3-{2-[(4-methylpiperazin-1-yl)carbonyl]-2-(methyl)propylamino}propoxy)-2-methylphenyl]methyl}-1H-pyrazole The title compound was prepared in a similar manner to that described in Example 118 using 1-methylpiperazine instead of 1-benzylpiperazine.

$^1$H-NMR (CD$_3$OD) δ ppm:
1.05-1.15 (6H, m), 1.29 (6H, s), 1.85-2.0 (2H, m), 2.26 (3H, s), 2.29 (3H, s), 2.3-2.45 (4H, m), 2.6-2.85 (5H, m), 3.25-3.4 (4H, m), 3.55-3.75 (7H, m), 3.75-3.85 (1H, m), 3.99 (2H, t, J=6.0 Hz), 4.95-5.05 (1H, m), 6.61 (1H, dd, J=8.4 Hz, 2.5 Hz), 6.71 (1H, d, J=2.5 Hz), 6.84 (1H, d, J=8.4 Hz)

Example 121

3-(β-D-Glucopyranosyloxy)-4-[(4-{3-[2-{[4-(2-hydroxyethyl)piperazin-1-yl]carbonyl}-2-(methyl)propylamino]propoxy}-2-methylphenyl)methyl]-5-isopropyl-1H-pyrazole The title compound was prepared in a similar manner to that described in Example 118 using 1-(2-hydroxyethyl)piperazine instead of 1-benzylpiperazine.

$^1$H-NMR (CD$_3$OD) δ ppm:
1.05-1.15 (6H, m), 1.29 (6H, s), 1.85-2.0 (2H, m), 2.29 (3H, s), 2.4-2.55 (6H, m), 2.65-2.85 (5H, m), 3.25-3.4 (4H, m), 3.55-3.75 (9H, m), 3.75-3.85 (1H, m), 3.99 (2H, t, J=5.8 Hz), 5.0-5.05 (1H, m), 6.61 (1H, dd, J=8.3 Hz, 1.9 Hz), 6.71 (1H, d, J=1.9 Hz), 6.85 (1H, d, J=8.3 Hz)

Reference Example 69

Benzyl 3-amino-3-methylbutyrate

To a suspension of 3,3-dimethylacrylic acid (1.3 g) and potassium carbonate (2.07 g) in N,N-dimethylformamide (15 mL) was added benzyl bromide (1.19 mL), and the mixture was stirred at room temperature for 4 hours. The reaction mixture was poured into water, and the resulting mixture was extracted with diethyl ether. The extract was washed with water and brine, and dried over anhydrous sodium sulfate. The solvent was removed under reduced pressure, and the residue was dissolved in 2-propanol (20 mL). An ammonia gas was bubbled into the solution at −15° C. until saturation, and the mixture was stirred at 80° C. overnight. The reaction mixture was concentrated under reduced pressure, and the residue was purified by column chromatography on silica gel (eluent: dichloromethane/methanol 15/1-7/1) to give the title compound (0.31 g).

$^1$H-NMR (DMSO-d$_6$) δ ppm:
1.08 (6H, s), 1.78 (2H, brs), 2.38 (2H, s), 5.08 (2H, s), 7.3-7.4 (5H, m)

Example 122

3-(β-D-Glucopyranosyloxy)-4-[(4-{3-[2-{[4-(2-hydroxyethyl)piperazin-1-yl]carbonyl}-1,1-di(methyl)ethylamino]propoxy}-2-methylphenyl)methyl]-5-isopropyl-1H-pyrazole A mixture of 4-{[4-(3-chloropropoxy)-2-methylphenyl]methyl}-5-isopropyl-3-(2,3,4,6-tetra-O-pivaloyl-β-D-glucopyranosyloxy)-1H-pyrazole (1 g) and sodium iodide (0.27 g) in acetonitrile (5 mL) was heated for reflux for 10 hours. After cooling to 60° C., to the reaction mixture was added a solution of benzyl 3-amino-3-methylbutyrate (0.31 g) in 2-propanol (5 mL), and the mixture was stirred at 55° C. for 6 days. The reaction mixture was concentrated under reduced pressure, and the residue was dissolved in ethyl acetate-water. The organic layer was separated. The organic layer was washed with water and brine, and dried over anhydrous sodium sulfate. The solvent was removed under reduced pressure, and the residue was purified by column chromatography on silica gel (eluent: n-hexane/ethyl acetate=1/2-dichloromethane/methanol=20/1) to give 4-[(4-{3-[2-benzyloxycarbonyl-1,1-di(methyl)ethylamino]propoxy}-2-methylphenyl)methyl]-5-isopropyl-3-(2,3,4,6-tetra-O-pivaloyl-β-D-glucopyranosyloxy)-1H-pyrazole (0.63 g). This material was dissolved in methanol (5 mL). To the solution was added 10% palladium-carbon powder (65 mg), and the mixture was stirred at room temperature under a hydrogen atmosphere overnight. The insoluble material was removed by filtration, and the filtrate was concentrated under reduced pressure to give 4-[(4-{3-[2-carboxy-1,1-di(methyl)ethylamino]propoxy}-2-methylphenyl)methyl]-5-isopropyl-3-(2,3,4,6-tetra-O-pivaloyl-β-D-glucopyranosyloxy)-1H-pyrazole (0.52 g). To a solution of 4-[(4-{3-[2-carboxy-1,1-di(methyl)ethylamino]propoxy}-2-methylphenyl)methyl]-5-isopropyl-3-(2,3,4,6-tetra-O-pivaloyl-β-D-glucopyranosyloxy)-1H-pyrazole (0.1 g) in N,N-dimethylformamide (2 mL) were added 1-(2-hydroxyethyl)piperazine (19 mg), 1-hydroxybenzotriazole (17 mg), 1-ethyl-3-(3-dimethylaminopropyl)carbodiimide hydrochloride (43 mg) and triethylamine (0.062 mL), and the mixture was stirred at room temperature for 20 hours. The reaction mixture was poured into water, and the resulting mixture was extracted with ethyl acetate. The extract was washed with water and brine, and dried over anhydrous sodium sulfate. The solvent was removed under reduced pressure, and the residue was dissolved in methanol (3 mL). To the solution was added sodium methoxide (286 methanol solution, 0.1 mL), and the mixture was stirred at 50° C. overnight. The reaction mixture was concentrated under reduced pressure, and the residue was purified by solid phase extraction on ODS (washing solvent: distilled water, eluent: methanol) and preparative reverse phase column chromatography (Shiseido CAPCELL PAK UG120 ODS, 5 μm, 120 Å, 20×50 mm, flowrate 30 mL/minute linear gradient, water/methanol=90/10-10/90) successively to give the title compound (13 mg).

MS (ESI, m/z): 678 [M+H]$^+$
$^1$H-NMR (CD$_3$OD) δ ppm:
1.05-1.15 (6H, m), 1.18 (6H, s), 1.85-2.0 (2H, m), 2.29 (3H, s), 2.42 (2H, t, J=5.0 Hz), 2.45-2.55 (6H, m), 2.71 (2H, t, J=7.0 Hz), 2.75-2.9 (1H, m), 3.25-3.4 (4H, m), 3.5-3.75 (9H, m), 3.75-3.85 (1H, m), 3.99 (2H, t, J=6.0 Hz), 4.95-5.05 (1H, m), 6.62 (1H, dd, J=8.4 Hz, 2.5 Hz), 6.72 (1H, d, J=2.5 Hz), 6.85 (1H, d, J=8.4 Hz)

Example 123

4-{[4-(3-{2-[(S)-1-Carbamoyl-2-hydroxyethylcarbamoyl]-1,1-di(methyl)ethylamino}propoxy)-2-methylphenyl]methyl}-3-(β-D-glucopyranosyloxy)-5-isopropyl-1H-pyrazole The title compound was prepared in a similar manner to that described in Example 122 using L-serine amide hydrochloride instead of 1-(2-hydroxyethyl)piperazine.

MS (ESI, m/z): 652 [M+H]$^+$
$^1$H-NMR (CD$_3$OD) δ ppm:
1.05-1.15 (6H, m), 1.19 (6H, s), 1.85-2.0 (2H, m), 2.2-2.5 (5H, m), 2.7-2.95 (3H, m), 3.25-3.4 (4H, m), 3.55-3.9 (6H, m), 4.01 (2H, t, J=6.1 Hz), 4.35-4.45 (1H, m), 4.95-5.05 (1H, m), 6.62 (1H, dd, J=8.3 Hz, 2.3 Hz), 6.72 (1H, d, J=2.3 Hz), 6.85 (1H, d, J=8.3 Hz)

Example 124

4-{[4-(3-{2-[(S)-5-Amino-1-(carbamoyl)pentylcarbamoyl]-1,1-di(methyl)ethylamino}propoxy)-2-methylphenyl]methyl}-3-(β-D-glucopyranosyloxy)-5-isopropyl-1H-pyrazole 4-{[4-(3-{2-[(S)-5-Benzyloxycarbonylamino-1-(carbamoyl)pentylcarbamoyl]-1,1-di(methyl)ethylamino}propoxy)-2-methylphenyl]methyl}-3-(β-D-glucopyranosyloxy)-5-isopropyl-1H-pyrazole was prepared in a similar manner to that described in Example 122 using 2-amino-6-(benzyloxycarbonylamino)hexanamide hydrochloride instead of 1-(2-hydroxyethyl)piperazine, and the title compound was prepared in a similar manner to that described in Example 79 using this material instead of 4-[(4-{3-[(S)-5-benzyloxycarbonylamino-1-(carbamoyl)pentylamino]propoxy}-2-methylphenyl)methyl]-3-(β-D-glucopyranosyloxy)-5-isopropyl-1H-pyrazole.

MS (ESI, m/z): 693 [M+H]$^+$
$^1$H-NMR (CD$_3$OD) δ ppm:
1.05-1.15 (6H, m), 1.17 (6H, s), 1.25-1.85 (6H, m), 1.85-2.0 (2H, m), 2.2-2.45 (5H, m), 2.55-2.9 (5H, m), 3.25-3.4 (4H, m), 3.6-3.75 (3H, m), 3.75-3.85 (1H, m), 4.02 (2H, t, J=5.8 Hz), 4.25-4.35 (1H, m), 4.95-5.05 (1H, m), 6.63 (1H, dd, J=8.4 Hz, 2.3 Hz), 6.72 (1H, d, J=2.3 Hz), 6.85 (1H, d, J=8.4 Hz)

Example 125

3-(β-D-Glucopyranosyloxy)-5-isopropyl-4-{[4-(3-{2-[(piperazin-1-yl)carbonyl]-1,1-di(methyl)ethylamino}propoxy)-2-methylphenyl]methyl}-1H-pyrazole 4-{[4-(3-{2-[(4-Benzylpiperazin-1-yl)carbonyl]-1,1-di(methyl)ethylamino}propoxy)-2-methylphenyl]methyl}-3-(β-D-glucopyranosyloxy)-5-isopropyl-1H-pyrazole was prepared in a similar manner to that described in Example 122 using 1-benzylpiperazine instead of 1-(2-hydroxyethyl)piperazine, and the title compound was prepared in a similar manner to that described in Example 79 using this material instead of 4-[(4-{3-[(S)-5-benzyloxycarbonylamino-1-(carbamoyl)pentylamino]propoxy}-2-methylphenyl)methyl]-3-(β-D-glucopyranosyloxy)-5-isopropyl-1H-pyrazole.

MS (ESI, m/z): 634 [M+H]+
$^1$H-NMR (CD$_3$OD) δ ppm:
1.05-1.15 (6H, m), 1.19 (6H, s), 1.85-2.0 (2H, m), 2.29 (3H, s), 2.52 (2H, s), 2.6-2.9 (7H, m), 3.25-3.4 (4H, m), 3.4-3.55 (4H, m), 3.6-3.75 (3H, m), 3.75-3.85 (1H, m), 3.99 (2H, t, J=6.0 Hz), 4.95-5.05 (1H, m), 6.62 (1H, dd, J=8.4 Hz, 2.5 Hz), 6.72 (1H, d, J=2.5 Hz), 6.84 (1H, d, J=8.4 Hz)

Reference Example 70

3-Aminobutyramide

To a mixture of 3-aminobutyric acid (0.52 g), 2 mol/L aqueous sodium hydroxide solution (10 mL) and tetrahydrofuran (10 mL) was added benzyloxycarbonyl chloride (1.07 mL), and the mixture was stirred at room temperature overnight. The reaction mixture was poured into 2 mol/L hydrochloric acid, and the resulting mixture was extracted with ethylacetate. The extract was washed with water and brine, and dried over anhydrous sodium sulfate. The solvent was removed under reduced pressure. The residue (solid) was treated with n-hexane. The crystals were collected by filtration, washed with n-hexane and dried under reduced pressure to give 3-benzyloxycarbonylaminobutyric acid (0.59 g). This material was dissolved in tetrahydrofuran (5 mL). To the solution was added 1,1'-carbonylbis-1H-imidazole (0.59 g), and the mixture was stirred at room temperature for 1 hour. To the reaction mixture was added 28% aqueous ammonia solution (5 mL), and the mixture was stirred at room temperature for 1 hour. The reaction mixture was diluted with diethylether. The insoluble material was collected by filtration, washed with water and diethyl ether, and dried under reduced pressure to give 3-benzyloxycarbonylaminobutyramide (0.54 g). The obtained 3-benzyloxycarbonylaminobutyramide (76 mg) was dissolved in methanol (3 mL). To the solution was added 10% palladium-carbon powder (20 mg), and the mixture was stirred at room temperature under a hydrogen atmosphere for 2 hours. The insoluble material was removed by filtration, and the filtrate was concentrated under reduced pressure to give the title compound (32 mg).

$^1$H-NMR (CD$_3$OD) δ ppm:
1.14 (3H, d, J=6.6 Hz), 2.2-2.35 (2H, m), 3.25-3.35 (1H, m)

Reference Example 71

3-Amino-2-methylpropionamide

The title compound was prepared in a similar manner to that described in Reference Example 70 using 3-amino-2-methylpropionic acid instead of 3-aminobutyric acid.
$^1$H-NMR (CD$_3$OD) δ ppm:
1.13 (3H, d, J=6.9 Hz), 2.4-2.5 (1H, m), 2.6-2.7 (1H, m), 2.8-2.9 (1H, m)

Reference Example 72

3-Amino-2,2-di(methyl)propionamide

To a solution of 3-amino-2,2-dimethyl-1-propanol (2 g) in tetrahydrofuran (20 mL) was added N-(benzyloxycarbonyloxy)succinimide (7.25 g), and the mixture was stirred at room temperature overnight. The reaction mixture was poured into water, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=3/1-1/1) to give 3-benzyloxycarbonylamino-2,2-dimethyl-1-propanol (4.6 g) To this material were added carbon tetrachloride (40 mL), acetonitrile (40 mL), water (48 mL), sodium periodate (11.6 g) and ruthenium trichloride (0.2 g) successively, and the mixture was stirred at room temperature overnight. To the reaction mixture were added sodium periodate (11.6 g) and ruthenium trichloride (0.2 g), and the mixture was stirred at room temperature for 3 days. The reaction mixture was diluted with water, and the resulting mixture was extracted with ethyl acetate. The extract was dried over anhydrous sodium sulfate. The solvent was removed under reduced pressure, and the residue was dissolved in a saturated aqueous potassium carbonate solution. The solution was washed with ethyl acetate, and the aqueous layer was acidified with 2 mol/L hydrochloric acid. The mixture was extracted with ethyl acetate, and the extract was washed with water and brine, and dried over anhydrous sodium sulfate. The solvent was removed under reduced pressure to give 3-benzyloxycarbonylamino-2,2-di(methyl)propionic acid (3.6 g). This material was dissolved in tetrahydrofuran (25 mL). To the solution was added 1,1'-carbonylbis-1H-imidazole (3.39 g), and the mixture was stirred at room temperature for 1 hour. To the reaction mixture was added 28% aqueous ammonia solution (25 mL), and the mixture was stirred at room temperature for 1 hour. The reaction mixture was diluted with water, and the resulting mixture was extracted with ethylacetate. The extract was washed with 1 mol/L hydrochloric acid, water and brine, and dried over anhydrous sodium sulfate. The solvent was removed under reduced pressure to give 3-benzyloxycarbonylamino-2,2-di(methyl)propionamide (3.35 g). The obtained 3-benzyloxycarbonylamino-2,2-di(methyl)propionamide (0.13 g) was dissolved in methanol (5 mL). To the solution was added 10% palladium-carbon powder (30 mg), and the mixture was stirred at room temperature under a hydrogen atmosphere for 2 hours. The insoluble material was removed by filtration, and the filtrate was concentrated under reduced pressure to give the title compound (61 mg).

$^1$H-NMR (DMSO-d$_6$) δ ppm:
1.0 (6H, s), 1.4-2.0 (2H, br), 2.52 (2H, s), 6.69 (1H, brs), 7.36 (1H, brs)

151

Examples 126-137

The compounds described in Tables 1-2 were prepared in a similar manner to that described in Example 57 or Example 72 using the corresponding starting materials.

TABLE 1

| Example No. | Structure | $^1$H-NMR (CD$_3$OD) δ ppm: |
|---|---|---|
| Example 126 | 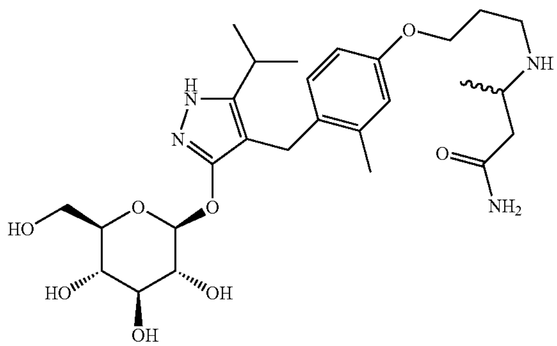 | 1.05-1.2(9H, m), 1.9-2.0(2H, m), 2.25(1H, dd J = 14.6 Hz, 6.5 Hz), 2.29 (3H, s), 2.39(1H, dd, J = 14.6 Hz, 6.5 Hz), 2.7-2.9(3H, m), 3.05-3.15 (1H, m), 3.25-3.4(4H, m), 3.6-3.7 (3H, m), 3.75-3.85(1H, m), 4.0(2H, t, J = 6.0 Hz), 4.95-5.05(1H, m), 6.62 (1H, dd, J = 8.4 Hz, 2.3 Hz), 6.71(1H, d, J = 2.3 Hz), 6.85(1H, d, J = 8.4 Hz) |
| Example 127 | 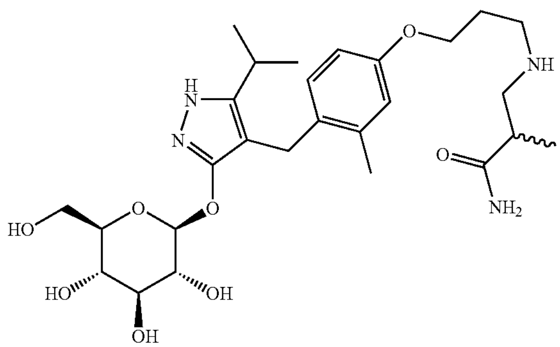 | 1.05-1.2(9H, m), 1.9-2.0(2H, m), 2.29(3H, s), 2.5-2.65(2H, m), 2.7-2.9(4H, m), 3.25-3.4(4H, m), 3.6-3.7(3H, m), 3.75-3.85(1H, m), 3.95-4.05(2H, m), 4.95-5.05(1H, m), 6.62(1H, dd, J = 8.3 Hz, 2.3 Hz), 6.71(1H, d, J = 2.3 Hz), 6.85(1H, d, J = 8.3 Hz) |
| Example 128 | 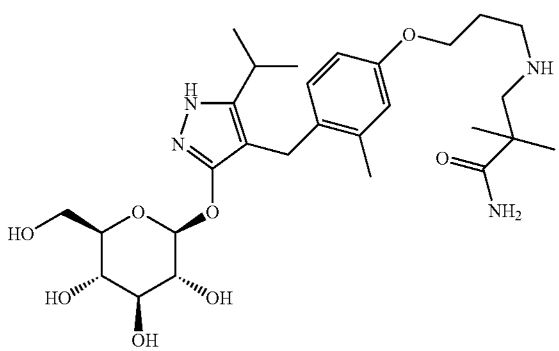 | 1.05-1.15(6H, m), 1.17(6H, s), 1.9-2.0(2H, m), 2.29(3H, s), 2.66 (2H, s), 2.75-2.85(3H, m), 3.25-3.4 (4H, m), 3.6-3.7(3H, m), 3.75-3.85 (1H, m), 4.0(2H, t, J = 6.0 Hz), 4.95-5.05(1H, m), 6.61(1H, dd, J = 8.4 Hz, 2.6 Hz), 6.7(1H, d, J = 2.6 Hz), 6.85(1H, d, J = 8.4 Hz) |
| Example 129 | 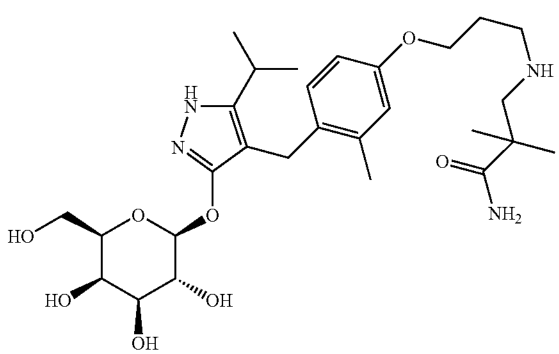 | 1.05-1.15(6H, m), 1.16(6H, s), 1.85-2.0(2H, m), 2.28(3H, s), 2.65 (2H, s), 2.7-2.85(3H, m), 3.49(1H, dd, J = 9.7 Hz, 3.2 Hz), 3.55-3.8(6H, m), 3.85(1H, d, J = 3.2 Hz), 3.99(2H, t, J = 6.0 Hz), 5.03(1H, d, J = 7.9 Hz), 6.61(1H, dd, J = 8.4 Hz, 2.3 Hz), 6.7 (1H, d, J = 2.3 Hz), 6.85(1H, d, J = 8.4 Hz) |

TABLE 1-continued

| Example No. | Structure | $^1$H-NMR (CD$_3$OD) δ ppm: |
|---|---|---|
| Example 130 | 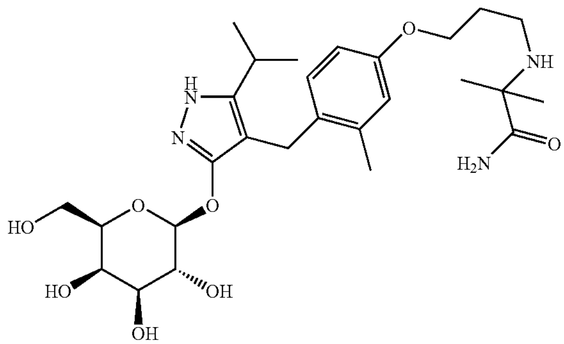 | 1.05-1.2(6H, m), 1.29(6H, s), 1.85-1.95(2H, m), 2.28(3H, s), 2.65 (2H, t, J = 7.0 Hz), 2.75-2.85(1H, m), 3.49(1H, dd, J = 9.7 Hz, 3.2 Hz), 3.55-3.8(6H, m), 3.84(1H, d, J = 3.2 Hz), 4.01(2H, t, J = 6.1 Hz), 5.03(1H, d, J = 7.7 Hz), 6.61(1H, dd, J = 8.4 Hz, 2.4 Hz), 6.7(1H, d, J = 2.4 Hz), 6.85(1H, d, J = 8.4 Hz) |
| Example 131 | 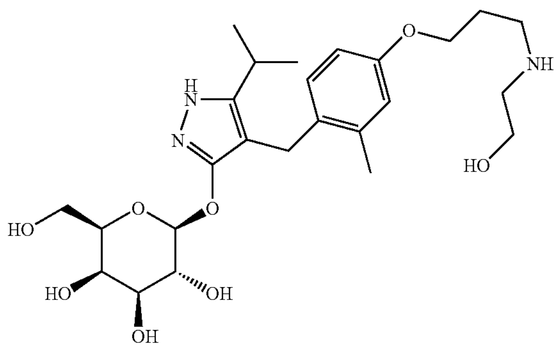 | 1.05-1.15(6H, m), 1.9-2.0(2H, m), 2.28(3H, s), 2.65-2.85(5H, m), 3.49 (1H, dd, J = 9.8 Hz, 3.6 Hz), 3.55-3.8 (8H, m), 3.8-3.9(1H, m), 3.99(2H, t, J = 6.1 Hz), 5.03(1H, d, J = 7.9 Hz), 6.61(1H, dd, J = 8.4 Hz, 2.6 Hz), 6.71 (1H, d, J = 2.6 Hz), 6.85(1H, d, J = 8.4 Hz) |

TABLE 2

| Example No. | Structure | $^1$H-NMR (CD$_3$OD) δ ppm: |
|---|---|---|
| Example 132 | 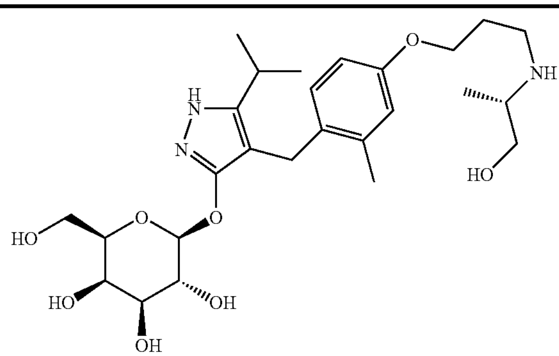 | 1.03(3H, d, J = 6.4 Hz), 1.05-1.15 (6H, m), 1.85-2.0(2H, m), 2.28(3H, s), 2.65-2.95(4H, m), 3.38(1H, dd, J = 10.6 Hz, 7.3 Hz), 3.45-3.8 (8H, m), 3.84(1H, d, J = 3.3 Hz), 3.9-4.1(2H, m), 5.03(1H, d, J = 8.0 Hz), 6.61(1H, dd, J = 8.5 Hz, 2.6 Hz), 6.71(1H, d, J = 2.6 Hz), 6.85 (1H, d, J = 8.5 Hz) |
| Example 133 | 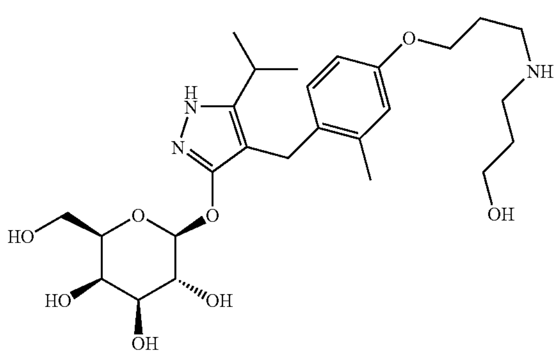 | 1.05-1.15(6H, m), 1.65-1.8(2H, m), 1.9-2.0(2H, m), 2.28(3H, s), 2.65-2.85(5H, m), 3.49(1H, dd, J = 9.7 Hz, 3.5 Hz), 3.55-3.8(8H, m), 3.84(1H, d, J = 3.5 Hz), 3.99(2H, t, J = 6.3 Hz), 5.03(1H, d, J = 7.8 Hz), 6.61(1H, dd, J = 8.5 Hz, 2.7 Hz), 6.7 (1H, d, J = 2.7 Hz), 6.85(1H, d, J = 8.5 Hz) |

TABLE 2-continued
| Example No. | Structure | $^1$H-NMR (CD$_3$OD) δ ppm: |
|---|---|---|
| Example 134 | 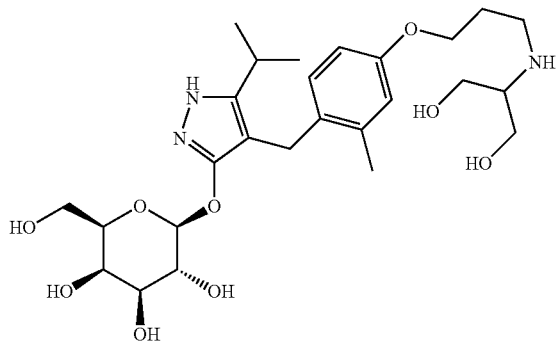 | 1.05-1.15(6H, m), 1.9-2.0(2H, m), 2.28(3H, s), 2.65-2.9(4H, m), 3.45-3.8(11H, m), 3.8-3.9(1H, m), 4.0(2H, t, J = 6.1 Hz), 5.03(1H, d, J = 7.8 Hz), 6.61(1H, dd, J = 8.4 Hz, 2.7 Hz), 6.71(1H, d, J = 2.7 Hz), 6.84 (1H, d, J = 8.4 Hz) |
| Example 135 | 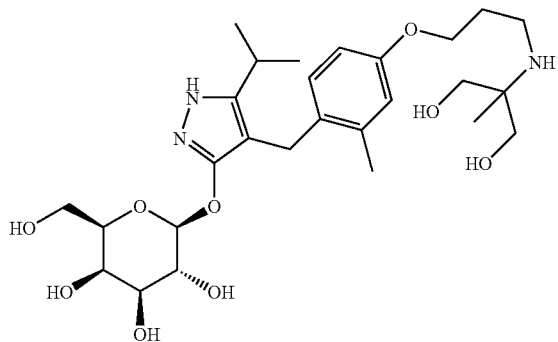 | 0.99(3H, s), 1.05-1.15(6H, m), 1.85-1.95(2H, m), 2.28(3H, s), 2.7-2.85(3H, m), 3.46(4H, s), 3.49 (1H, dd, J = 9.6 Hz, 3.1 Hz), 3.55-3.8 (6H, m), 3.84(1H, d, J = 3.1 Hz), 4.0 (2H, t, J = 6.1 Hz), 5.03(1H, d, J = 7.9 Hz), 6.61(1H, dd, J = 8.3 Hz, 2.6 Hz), 6.71(1H, d, J = 2.6 Hz), 6.84 (1H, d, J = 8.3 Hz) |
| Example 136 | 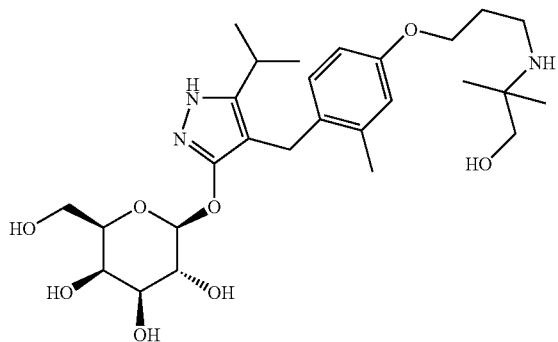 | 1.04(6H, s), 1.05-1.15(6H, m), 1.85-2.0(2H, m), 2.28(3H, s), 2.65-2.85(3H, m), 3.36(2H, s), 3.49(1H, dd, J = 9.8 Hz, 3.6 Hz), 3.55-3.8(6H, m), 3.8-3.9(1H, m), 3.99(2H, t, J = 6.1 Hz), 5.03(1H, d, J = 7.8 Hz), 6.61(1H, dd, J = 8.3 Hz, 2.4 Hz), 6.71(1H, d, J = 2.4 Hz), 6.85 (1H, d, J = 8.3 Hz) |
| Example 137 | 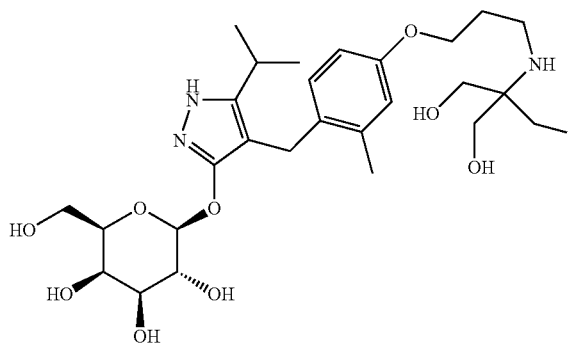 | 1.05-1.15(6H, m), 1.85-2.0(2H, m), 2.28(3H, s), 2.7-2.9(3H, m), 3.45-3.8(13H, m), 3.8-3.9(1H, m), 4.01(2H, t, J = 6.1 Hz), 5.03(1H, d, J = 7.8 Hz), 6.61(1H, dd, J = 8.6 Hz, 2.4 Hz), 6.71(1H, d, J = 2.4 Hz), 6.85 (1H, d, J = 8.6 Hz) |

Reference Example 73

3-(2,3,4,6-Tetra-O-acetyl-β-D-galactopyranosyloxy)-4-{[4-(3-azidopropoxy)-2-methylphenyl]methyl}-5-isopropyl-1H-pyrazole The title compound was prepared in a similar manner to that described in Reference Example 29 using 3-(2,3,4,6-tetra-O-acetyl-β-D-galactopyranosyloxy)-4-{[4-(3-hydroxypropoxy)-2-methylphenyl]methyl}-5-isopropyl-1H-pyrazole instead of 3-(2,3,4,6-tetra-O-acetyl-β-D-glucopyranosyloxy)-4-{[4-(3-hydroxypropoxy)phenyl]methyl}-5-isopropyl-1H-pyrazole.

$^1$H-NMR (CDCl$_3$) δ ppm:
1.05-1.2 (6H, m), 1.82 (3H, s), 1.95-2.1 (8H, m), 2.16 (3H, s), 2.27 (3H, s), 2.75-2.85 (1H, m), 3.45-3.55 (3H, m), 3.61 (1H, d, J=16.3 Hz), 3.95-4.1 (3H, m), 4.1-4.2 (2H, m), 5.07 (1H, dd, J=10.4 Hz, 3.5 Hz), 5.35-5.45 (2H, m), 5.52 (1H, d, J=8.2 Hz), 6.58 (1H, dd, J=8.3 Hz, 2.6 Hz), 6.69 (1H, d, J=2.6 Hz), 6.81 (1H, d, J=8.3 Hz)

Reference Example 74

4-{[4-(3-Azidopropoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole To a solution of 4-{[4-(3-chloropropoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole (0.3 g) in N,N-dimethylformamide (5 mL) was added sodium azide (43 mg), and the mixture was stirred at 80° C. for 3 hours. To the reaction mixture was added water, and the precipitated crystals were collected by filtration. The crystals were washed with water and n-hexane, and dried under reduced pressure to give the title compound (0.3 g).

$^1$H-NMR (CDCl$_3$) δ ppm:
1.0-1.2 (42H, m), 1.75-1.9 (2H, m), 1.95-2.1 (4H, m), 2.85-2.95 (1H, m), 3.45-3.65 (6H, m), 3.8-3.9 (1H, m), 3.95-4.05 (4H, m), 4.1-4.25 (2H, m), 4.4-4.55 (1H, m), 5.15-5.3 (2H, m), 5.36 (1H, t, J=9.2 Hz), 5.67 (1H, d, J=8.0 Hz), 6.33 (1H, dd, J=8.5 Hz, 2.4 Hz), 6.4 (1H, d, J=2.4 Hz), 6.86 (1H, d, J=8.5 Hz)

Example 138

3-(2,3,4,6-Tetra-O-acetyl-β-D-galactopyranosyloxy)-4-{[4-(3-aminopropoxy)-2-methylphenyl]methyl}-5-isopropyl-1H-pyrazole The title compound was prepared in a similar manner to that described in Example 1 using 3-(2,3,4,6-tetra-O-acetyl-β-D-galactopyranosyloxy)-4-{[4-(3-azidopropoxy)-2-methylphenyl]methyl}-5-isopropyl-1H-pyrazole instead of 3-(2,3,4,6-tetra-O-acetyl-β-D-glucopyranosyloxy)-4-{[4-(3-azidopropoxy)phenyl]methyl}-5-isopropyl-1H-pyrazole.

$^1$H-NMR (CD$_3$OD) δ ppm:
1.05-1.15 (6H, m), 1.84 (3H, s), 1.85-2.0 (8H, m), 2.14 (3H, s), 2.27 (3H, s), 2.75-2.9 (3H, m), 3.53 (1H, d, J=16.5 Hz), 3.59 (1H, d, J=16.5 Hz), 4.0 (2H, t, J=6.2 Hz), 4.05-4.2 (3H, m), 5.1-5.2 (1H, m), 5.2-5.3 (1H, m) 5.35-5.45 (2H, m), 6.61 (1H, dd, J=8.3 Hz, 2.3 Hz), 6.71 (1H, d, J=2.3 Hz), 6.78 (1H, d, J=8.3 Hz)

Example 139

4-{[4-(3-Aminopropoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole The title compound was prepared in a similar manner to that described in Example 1 using 4-{[4-(3-azidopropoxy)-2-(tetrahydro-4H-pyran-4-yloxy)phenyl]methyl}-5-isopropyl-3-(2,3,4,6-tetra-O-pivaloyl-β-D-glucopyranosyloxy)-1H-pyrazole instead of 3-(2,3,4,6-tetra-O-acetyl-β-D-glucopyranosyloxy)-4-{[4-(3-azidopropoxy)phenyl]methyl}-5-isopropyl-1H-pyrazole.

$^1$H-NMR (CDCl$_3$) δ ppm:
1.0-1.2 (42H, m), 1.75-1.95 (4H, m), 1.95-2.1 (2H, m), 2.8-3.0 (3H, m), 3.5-3.7 (4H, m), 3.8-3.9 (1H, m), 3.9-4.05 (4H, m), 4.05-4.25 (2H, m), 4.4-4.55 (1H, m), 5.15-5.3 (2H, m), 5.36 (1H, t, J=9.3 Hz), 5.67 (1H, d, J=7.4 Hz), 6.3-6.45 (2H, m), 6.85 (1H, d, J=8.6 Hz)

Example 140

3-(β-D-Glucopyranosyloxy)-4-{[4-(2-{3-[2-hydroxy-1,1-bis(hydroxymethyl)ethyl]ureido}ethoxy)-2-methylphenyl]methyl}-5-isopropyl-1H-pyrazole To a solution of 3-(2,3,4,6-tetra-O-acetyl-β-D-glucopyranosyloxy)-4-{[4-(2-aminoethoxy)-2-methylphenyl]methyl}-5-isopropyl-1H-pyrazole (60 mg) in dichloromethane (3 mL) were added triethylamine (0.016 mL) and 4-nitrophenyl chloroformate (21 mg), and the mixture was stirred at room temperature for 1 hour. To the reaction mixture were added tris(hydroxymethyl)aminomethane (35 mg) and methanol (3 mL), and the mixture was stirred at room temperature for 3 hours. The reaction mixture was poured into water, and the resulting mixture was extracted with ethyl acetate. The organic layer was washed with water and brine, and dried over anhydrous magnesium sulfate. The solvent was removed under reduced pressure, and the residue was purified by column chromatography on silica gel (eluent: dichloromethane/methanol=10/1-6/1) to give 3-(2,3,4,6-tetra-O-acetyl-β-D-glucopyranosyloxy)-4-{[4-(2-{3-[2-hydroxy-1,1-bis(hydroxymethyl)ethyl]ureido}ethoxy)-2-methylphenyl]methyl}-5-isopropyl-1H-pyrazole (36 mg). This material was dissolved in methanol (2 mL). To the solution was added sodium methoxide (28% methanol solution, 0.018 mL), and the mixture was stirred at room temperature for 1 hour. The reaction mixture was concentrated under reduced pressure, and the residue was purified by solid phase extraction on ODS (washing solvent: distilled water, eluent: methanol) to give the title compound (22 mg).

$^1$H-NMR (CD$_3$OD) δ ppm:
1.05-1.15 (6H, m), 2.29 (3H, s), 2.75-2.85 (1H, m), 3.25-3.4 (4H, m), 3.44 (2H, t, J=5.3 Hz), 3.6-3.75 (9H, m), 3.81 (1H, d, J=11.7 Hz), 3.95 (2H, t, J=5.3 Hz), 5.02 (1H, d, J=6.6 Hz), 6.63 (1H, dd, J=8.5 Hz, 2.4 Hz), 6.73 (1H, d, J=2.4 Hz), 6.86 (1H, d, J=8.5 Hz)

Examples 141-151

The compounds described in Tables 3-4 were prepared in a similar manner to that described in Example 140 using the corresponding starting materials. The synthesis of Example 151 was carried out by catalytic hydrogenation in a similar manner to that described in Example 79 after the completion of the operation of Example 140.

TABLE 3

| Example No. | Structure | $^1$H-NMR (CD$_3$OD) δ ppm: |
|---|---|---|
| Example 141 | 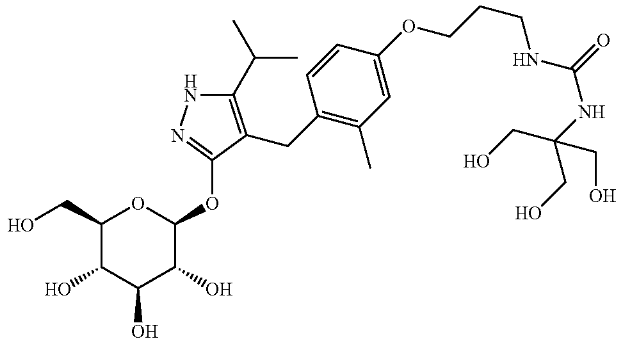 | 1.05-1.15(6H, m), 1.85-1.95(2H, m), 2.29(3H, s), 2.75-2.85(1H, m), 3.2-3.4(6H, m), 3.6-3.75(9H, m), 3.81(1H, d, J = 11.5 Hz), 3.9-4.0(2H, m), 4.95-5.05(1H, m), 6.62(1H, d, J = 8.3 Hz), 6.71(1H, s), 6.85(1H, d, J = 8.3 Hz) |
| Example 142 | 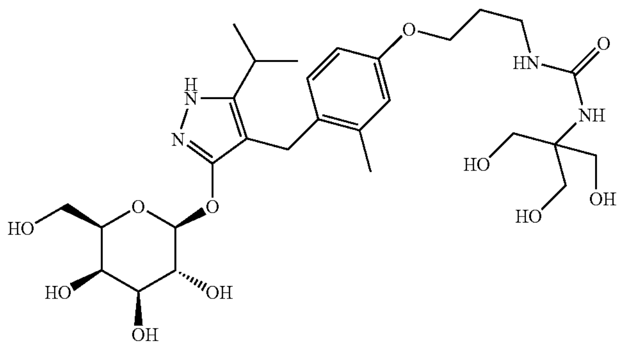 | 1.05-1.15(6H, m), 1.85-1.95(2H, m), 2.28(3H, s), 2.75-2.85(1H, m), 3.25 (2H, t, J = 6.9 Hz), 3.49(1H, dd, J = 9.8 Hz, 3.3 Hz), 3.55-3.8(12H, m), 3.8-3.9(1H, m), 3.96(2H, t, J = 6.1 Hz), 5.03(1H, d, J = 7.8 Hz), 6.61 (1H, dd, J = 8.4 Hz, 2.6 Hz), 6.71(1H, d, J = 2.6 Hz), 6.85(1H, d, J = 8.4 Hz) |
| Example 143 | 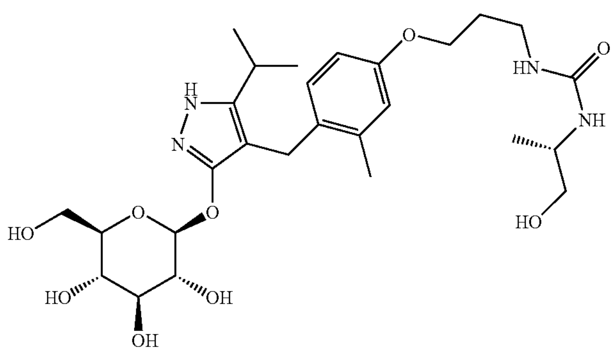 | 1.05-1.15(9H, m), 1.85-1.95(2H, m), 2.28(3H, s), 2.75-2.85(1H, m), 3.2-3.5(8H, m), 3.55-3.85(5H, m), 3.96(2H, t, J = 6.1 Hz), 4.95-5.05(1H, m), 6.62(1H, dd, J = 8.4 Hz, 2.5 Hz), 6.71(1H, d, J = 2.5 Hz), 6.86(1H, d, J = 8.4 Hz) |
| Example 144 | 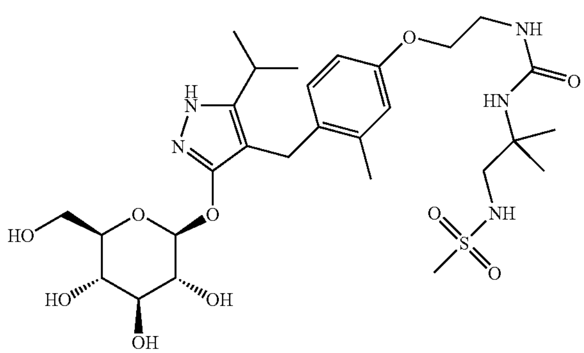 | 1.05-1.15(6H, m), 1.27(6H, s), 2.29 (3H, s), 2.7-2.85(1H, m), 2.89(3H, s), 3.2-3.4(6H, m), 3.42(2H, t, J = 5.3 Hz), 3.55-3.75(3H, m), 3.75-3.85(1H, m), 3.94(2H, t, J = 5.3 Hz), 4.95-5.1(1H, m), 6.63(1H, dd, J = 8.2 Hz, 2.7 Hz), 6.72(1H, d, J = 2.7 Hz), 6.86(1H, d, J = 8.2 Hz) |

TABLE 4

| Example No. | Structure | $^1$H-NMR (CD$_3$OD) δ ppm: |
|---|---|---|
| Example 145 | 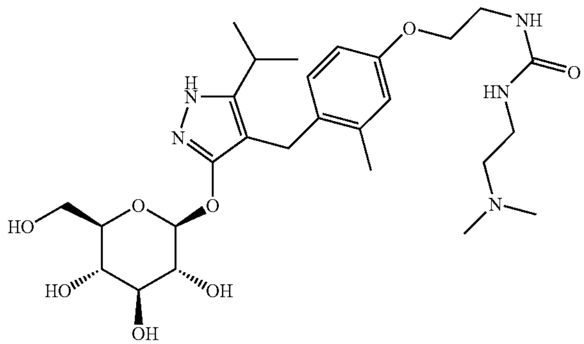 | 1.05-1.15(6H, m), 2.26(6H, s), 2.29(3H, s), 2.43(2H, t, J = 6.8 Hz), 2.75-2.85(1H, m), 3.2-3.4(6H, m), 3.46(2H, t, J = 5.4 Hz), 3.6-3.75 (3H, m), 3.75-3.85(1H, m), 3.95 (2H, t, J = 5.4 Hz), 4.95-5.05(1H, m), 6.62(1H, dd, J = 8.4 Hz, 2.7 Hz), 6.72(1H, d, J = 2.7 Hz), 6.86(1H, d, J = 8.4 Hz) |
| Example 146 | 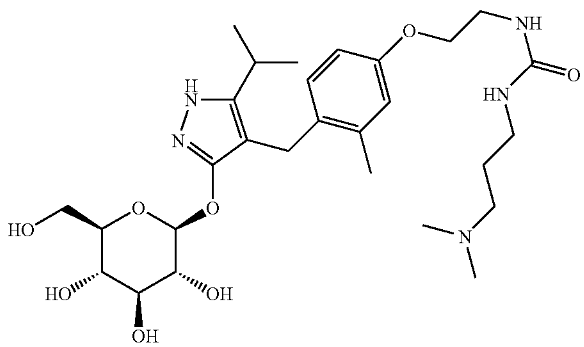 | 1.05-1.15(6H, m), 1.6-1.7(2H, m), 2.23(6H, s), 2.29(3H, s), 2.3-2.4 (2H, m), 2.75-2.85(1H, m), 3.14 (2H, t, J = 7.0 Hz), 3.25-3.4(4H, m), 3.46(2H, t, J = 5.4 Hz), 3.6-3.75 (3H, m), 3.75-3.85(1H, m), 3.95 (2H, t, J = 5.4 Hz), 4.95-5.05(1H, m), 6.63(1H, dd, J = 8.4 Hz, 2.6 Hz), 6.72(1H, d, J = 2.6 Hz), 6.86(1H, d, J = 8.4 Hz) |
| Example 147 | 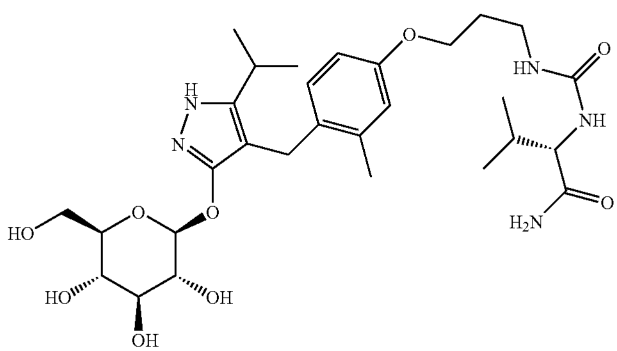 | 0.91(3H, d, J = 6.6 Hz), 0.96(3H, d, J = 6.5 Hz), 1.05-1.15(6H, m), 1.85-1.95(2H, m), 2.0-2.1(1H, m), 2.28(3H, s), 2.75-2.85(1H, m), 3.25-3.4(6H, m), 3.6-3.75(3H, m), 3.81(1H, d, J = 12.4 Hz), 3.97(2H, t, J = 6.2 Hz), 4.06(1H, d, J = 6.1 Hz), 5.02(1H, d, J = 7.0 Hz), 6.62(1H, dd, J = 8.3 Hz, 2.4 Hz), 6.72(1H, d, J = 2.4 Hz), 6.85(1H, d, J = 8.3 Hz) |
| Example 148 | 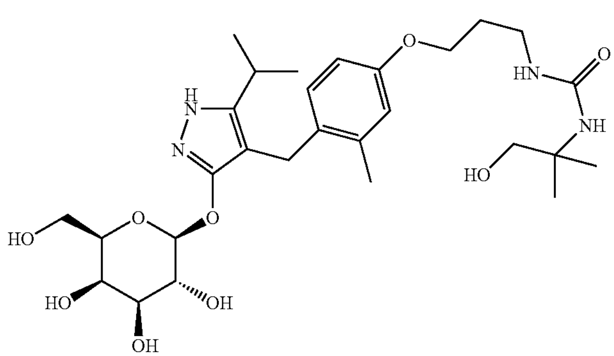 | 1.05-1.15(6H, m), 1.23(6H, s), 1.8-1.95(2H, m), 2.28(3H, s), 2.7-2.85(1H, m), 3.24(2H, t, J = 6.9 Hz), 3.4-3.8(9H, m), 3.84 (1H, d, J = 2.9 Hz), 3.95(2H, t, J = 6.2 Hz), 5.03(1H, d, J = 7.6 Hz), 6.61(1H, dd, J = 8.3 Hz, 2.6 Hz), 6.71 (1H, d, J = 2.6 Hz), 6.85(1H, d, J = 8.3 Hz) |

TABLE 4-continued

| Example No. | Structure | $^1$H-NMR (CD$_3$OD) δ ppm: |
|---|---|---|
| Example 149 | 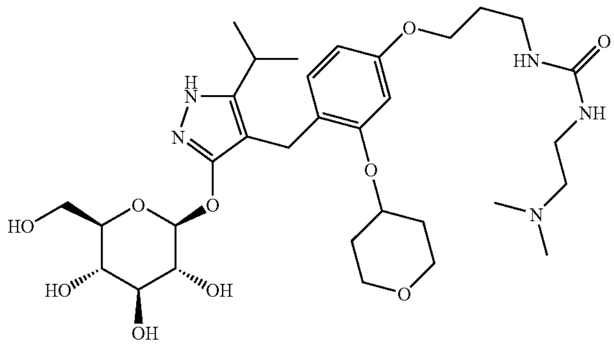 | 1.05-1.2(6H, m), 1.7-1.85(2H, m), 1.85-1.95(2H, m), 1.95-2.1(2H, m), 2.34(6H, s), 2.52(2H, t, J = 6.5 Hz), 2.8-2.95(1H, m), 3.2-3.4(8H, m), 3.55-3.75(5H, m), 3.83(1H, d, J = 12.0 Hz), 3.9-4.0 (4H, m), 4.5-4.65(1H, m), 5.06(1H, d, J = 7.0 Hz), 6.41(1H, dd, J = 8.2 Hz, 2.4 Hz), 6.53(1H, d, J = 2.4 Hz), 6.9 (1H, d, J = 8.2 Hz) |
| Example 150 | 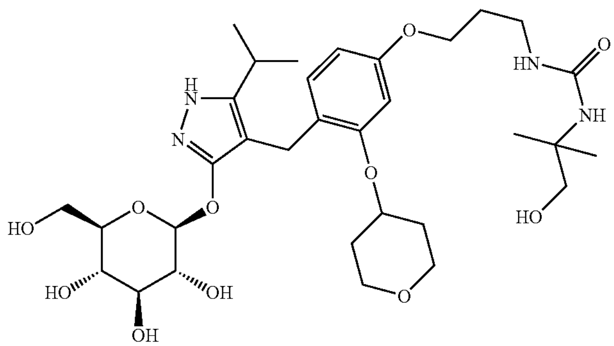 | 1.05-1.2(6H, m), 1.23(6H, s), 1.7-1.95(4H, m), 1.95-2.1(2H, m), 2.8-2.95(1H, m), 3.24(2H, t, J = 6.8 Hz), 3.25-3.4(4H, m), 3.5 (2H, s), 3.55-3.75(5H, m), 3.83 (1H, d, J = 11.1 Hz), 3.9-4.0(4H, m), 4.5-4.65(1H, m), 5.0-5.1(1H, m), 6.41(1H, dd, J = 8.5 Hz, 2.3 Hz), 6.54(1H, d, J = 2.3 Hz), 6.9(1H, d, J = 8.5 Hz) |
| Example 151 | 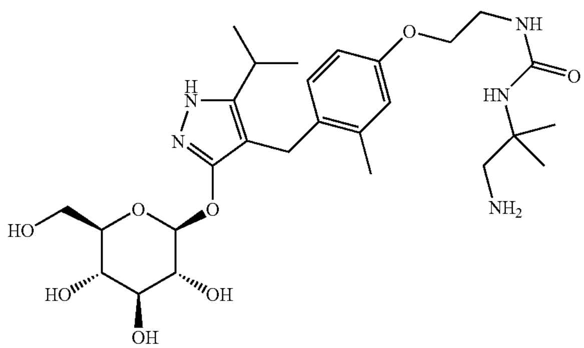 | 1.05-1.15(6H, m), 1.23(6H, s), 2.29(3H, s), 2.75-2.85(3H, m), 3.25-3.4(4H, m), 3.42(2H, t, J = 5.4 Hz), 3.6-3.75(3H, m), 3.75-3.85(1H, m), 3.94(2H, t, J = 5.4 Hz), 5.01(1H, d, J = 7.2 Hz), 6.63(1H, dd, J = 8.3 Hz, 2.7 Hz), 6.72 (1H, d, J = 2.7 Hz), 6.86(1H, d, J = 8.3 Hz) |

Reference Example 75

4-(2-Benzyloxyethyl)-1-bromobenzene

To a suspension of sodium hydride (60%, 1.09 g) in 1,2-dimethoxyethane (25 mL) was added 2-(4-bromophenyl)ethanol (5 g) under ice-cooling, and the mixture was stirred at room temperature for 1.5 hours. To the reaction mixture was added benzyl bromide (3.25 mL), and the mixture was stirred at 80° C. overnight. To the reaction mixture was added a saturated aqueous ammonium chloride solution, and the resulting mixture was extracted with diethyl ether. The extract was washed with water and brine, and dried over anhydrous magnesium sulfate. The solvent was removed under reduced pressure, and the residue was purified by column chromatography on silica gel (eluent: n-hexane-n-hexane/ethyl acetate=50/1-20/1) to give the title compound (6.8 g).

$^1$H-NMR (CDCl$_3$) δ ppm:

2.86 (2H, t, J=6.8 Hz), 3.66 (2H, t, J=6.8 Hz), 4.5 (2H, s), 7.05-7.15 (2H, m), 7.2-7.35 (5H, m), 7.35-7.45 (2H, m)

Reference Example 76

[4-(2-Benzyloxyethyl)phenyl]methanol

To a solution of 4-(2-benzyloxyethyl)-1-bromobenzene (6.8 g) in tetrahydrofuran (80 mL) was added n-butyl lithium (2.6 mol/L n-hexane solution, 8.98 mL) at −78° C. under an argon atmosphere, and the mixture was stirred for 30 minutes. To the reaction mixture was added N,N-dimethylformamide (20 mL), and the mixture was allowed to warm to 0° C. and stirred for 2 hours. The reaction mixture was poured into a saturated aqueous ammonium chloride solution, and the resulting mixture was extracted with ethylacetate. The organic layer was washed with water and brine, and dried over anhydrous magnesium sulfate. The solvent was removed under reduced pressure to give 4-(2-benzyloxyethyl)benzaldehyde (5.6 g). This material was dissolved in methanol (80 mL). To the solution was added sodium borohydride (1.77 g) under ice-cooling, and the mixture was stirred at room temperature overnight. To the reaction mixture was added a saturated aqueous ammonium chloride solution, and the resulting mixture was extracted with diethyl ether. The organic layer was washed with water and brine, and dried over anhydrous magnesium sulfate. The solvent was removed under reduced pressure, and the residue (solid) was treated with n-hexane, collected by filtration and dried under reduced pressure to give the title compound (5.41 g).

$^1$H-NMR (CDCl$_3$) δ ppm:
2.93 (2H, t, J=7.1 Hz), 3.68 (2H, t, J=7.1 Hz), 4.52 (2H, s), 4.65 (2H, s), 7.15-7.4 (9H, m)

Reference Example 77

4-{[4-(2-Benzyloxyethyl)phenyl]methyl}-1,2-dihydro-5-isopropyl-3H-pyrazol-3-one

The title compound was prepared in a similar manner to that described in Reference Example 11 using [4-(2-benzyloxyethyl)phenyl]methanol instead of [4-(3-benzyloxypropoxy)phenyl]methanol.

$^1$H-NMR (DMSO-d$_6$) δ ppm:
1.07 (6H, d, J=7.1 Hz), 2.75-2.9 (3H, m), 3.54 (2H, s), 3.59 (2H, t, J=6.9 Hz), 4.45 (2H, s), 7.0-7.15 (4H, m), 7.2-7.35 (5H, m)

Reference Example 78

3-(2,3,4,6-Tetra-O-acetyl-β-D-glucopyranosyloxy)-4-{[4-(2-benzyloxyethyl)phenyl]methyl}-5-isopropyl-1H-pyrazole The title compound was prepared in a similar manner to that described in Reference Example 17 using 4-{[4-(2-benzyloxyethyl)phenyl]methyl}-1,2-dihydro-5-isopropyl-3H-pyrazol-3-one instead of 4-{[4-(3-benzyloxypropoxy)phenyl]-methyl}-1,2-dihydro-5-isopropyl-3H-pyrazol-3-one.

$^1$H-NMR (CDCl$_3$) δ ppm:
1.1-1.2 (6H, m), 1.83 (3H, s), 2.01 (3H, s), 2.03 (3H, s), 2.05 (3H, s), 2.8-2.95 (3H, m), 3.55-3.7 (4H, m), 3.8-3.9 (1H, m), 4.14 (1H, dd, J=12.5 Hz, 2.4 Hz), 4.31 (1H, dd, J=12.5 Hz, 3.9 Hz), 4.5 (2H, s), 5.15-5.3 (3H, m), 5.5-5.6 (1H, m), 7.0-7.1 (4H, m), 7.2-7.35 (5H, m)

Reference Example 79

3-(2,3,4,6-Tetra-O-acetyl-β-D-galactopyranosyloxy)-4-{[4-(2-benzyloxyethyl)phenyl]methyl}-5-isopropyl-1H-pyrazole The title compound was prepared in a similar manner to that described in Reference Example 17 using 4-{[4-(2-benzyloxyethyl)phenyl]methyl}-1,2-dihydro-5-isopropyl-3H-pyrazol-3-one and acetobromo-α-D-galactose instead of 4-{[4-(3-benzyloxypropoxy)phenyl]methyl}-1,2-dihydro-5-isopropyl-3H-pyrazol-3-one and acetobromo-α-D-glucose, respectively.

$^1$H-NMR (CDCl$_3$) δ ppm:
1.1-1.2 (6H, m), 1.85 (3H, s), 1.99 (3H, s), 2.02 (3H, s), 2.17 (3H, s), 2.85-2.95 (3H, m), 3.61 (1H, d. J=15.9 Hz), 3.65 (2H, t, J=7.2 Hz), 3.69 (1H, d, J=15.9 Hz), 4.0-4.25 (3H, m), 4.51 (2H, s), 5.09 (1H, dd, J=10.6 Hz, 3.3 Hz), 5.4-5.5 (2H, m), 5.55 (1H, d, J=8.2 Hz), 7.0-7.1 (4H, m), 7.2-7.35 (5H, m)

Reference Example 80

3-(2,3,4,6-Tetra-O-acetyl-β-D-glucopyranosyloxy)-4-{[4-(2-hydroxyethyl)phenyl]methyl}-5-isopropyl-1H-pyrazole The title compound was prepared in a similar manner to that described in Reference Example 23 using 3-(2,3,4,6-tetra-O-acetyl-β-D-glucopyranosyloxy)-4-{[4-(2-benzyloxyethyl)phenyl]methyl}-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) δ ppm:
1.18 (6H, d, J=7.2 Hz), 1.87 (3H, s), 2.0 (3H, s), 2.02 (3H, s), 2.05 (3H, s), 2.81 (2H, t, J=6.6 Hz), 2.85-3.0 (1H, m), 3.62 (1H, d, J=16.0 Hz), 3.67 (1H, d, J=16.0 Hz), 3.75-3.9 (3H, m), 4.12 (1H, dd, J=12.4 Hz, 2.4 Hz), 4.29 (1H, dd, J=12.4 Hz, 3.8 Hz), 5.15-5.3 (3H, m), 5.57 (1H, d, J=7.5 Hz), 7.05-7.15 (4H, m)

Reference Example 81

3-(2,3,4,6-Tetra-O-acetyl-β-D-galactopyranosyloxy)-4-{[4-(2-hydroxyethyl)phenyl]methyl}-5-isopropyl-1H-pyrazole The title compound was prepared in a similar manner to that described in Reference Example 23 using 3-(2,3,4,6-tetra-O-acetyl-β-D-galactopyranosyloxy)-4-{[4-(2-benzyloxyethyl)phenyl]methyl}-5-isopropyl-1H-pyrazole instead of 3-(2,3,4,6-tetra-O-acetyl-β-D-glucopyranosyloxy)-4-{[4-(3-benzyloxypropoxy)phenyl]methyl}-5-isopropyl-1H-pyrazole.

$^1$H-NMR (CDCl$_3$) δ ppm:
1.15-1.2 (6H, m), 1.88 (3H, s), 1.98 (3H, s), 2.02 (3H, s), 2.17 (3H, s), 2.81 (2H, t, J=6.4 Hz), 2.85-3.0 (1H, m), 3.63 (1H, d. J=16.1 Hz), 3.7 (1H, d, J=16.1 Hz), 3.8-3.9 (2H, m), 4.0-4.1 (1H, m), 4.1-4.2 (2H, m), 5.08 (1H, dd, J=10.4 Hz, 3.5 Hz), 5.35-5.45 (2H, m), 5.56 (1H, d. J=8.1 Hz), 7.05-7.15 (4H, m)

Example 152

4-{[4-(2-{3-[(S)-1-Carbamoyl-2-(methyl)propyl]ureido}ethyl)phenyl]methyl}-3-(β-D-glucopyranosyloxy)-5-isopropyl-1H-pyrazole To a solution of 3-(2,3,4,6-tetra-O-acetyl-β-D-glucopyranosyloxy)-4-{[4-(2-hydroxyethyl)phenyl]methyl}-5-isopropyl-1H-pyrazole (2.13 g) and triethylamine (0.65 mL) in dichloromethane (20 mL) was added methanesulfonyl chloride (0.36 mL) under ice-cooling, and the mixture was stirred at room temperature for 1 hour. The reaction mixture was poured into water, and the resulting mixture was extracted with ethyl acetate. The extract was washed with water and brine, and dried over anhydrous magnesium sulfate. The solvent was removed under reduced pressure to give 3-(2,3,4,6-tetra-O-acetyl-β-D-glucopyranosyloxy)-5-isopropyl-4-{[4-(2-methanesulfonyloxyethyl)phenyl]methyl}-1H-pyrazole (2.4 g). This material was dissolved in N,N-dimethylformamide (20 mL). To the solution was added sodium azide (0.71 g), and the mixture was stirred at 80° C. for 3 hours. The reaction mixture was poured into water, and the resulting mixture was extracted with ethylacetate. The extract was washed with water and brine, and dried over anhydrous magnesium sulfate. The solvent was removed under reduced pressure, and the residue was purified by column chromatography on silica gel (eluent: n-hexane/ethyl acetate=1/1-1/2) to give 3-(2,3,4,6-tetra-O-acetyl-β-D-glucopyranosyloxy)-4-{[4-(2-azidoethyl)phenyl]methyl}-5-isopropyl-1H-pyrazole (1.55 g). The obtained 3-(2,3,4,6-tetra-O-acetyl-β-D-glucopyranosyloxy)-4-{[4-(2-azidoethyl)phenyl]methyl}-5-isopropyl-1H-pyrazole (1 g) was dissolved in tetrahydrofuran (5 mL). To the solution was added 10% palladium-carbon powder (0.15 g), and the mixture was stirred at room temperature under a hydrogen atmosphere for 6 hours. The insoluble material was removed by filtration, and the filtrate was concentrated under reduced pressure to give 3-(2,3,4,6-tetra-O-acetyl-β-D-glucopyranosyloxy)-4-{[4-(2-aminoethyl)phenyl]methyl}-5-isopropyl-1H-pyrazole (0.96 g). The obtained 3-(2,3,4,6-tetra-O-acetyl-β-D-glucopyranosyloxy)-4-{[4-(2-aminoethyl)phenyl]methyl}-5-isopropyl-1H-pyrazole (0.48 g) was dissolved in dichloromethane (5 mL). To the solution were added triethylamine (0.13 mL) and 4-nitrophenyl chloroformate (0.18 g) under ice-cooling, and the mixture was stirred at room temperature for 2 hours. A 1/6 amount of the reaction mixture was separated. To the part of the reaction mixture were added triethylamine (0.084 mL), L-valine amide hydrochloride (45 mg) and tetrahydrofuran (1 mL), and the mixture was stirred at room temperature for 5 hours. The reaction mixture was purified by column chromatography on silica gel (eluent: ethyl acetate-ethyl acetate/methanol=10/1) to give 3-(2,3,4,6-tetra-O-acetyl-β-D-glucopyranosyloxy)-4-{[4-(2-{3-[(S)-1-carbamoyl-2-(methyl)propyl]ureido}ethyl)phenyl]methyl}-5-isopropyl-1H-pyrazole (48 mg). This material was dissolved in methanol (2 mL). To the solution was added sodium methoxide (28% methanol solution, 0.013 mL), and the mixture was stirred at room temperature for 1 hour. To the reaction mixture was added acetic acid (0.2 mL). The resulting mixture was concentrated under reduced pressure, and the residue was purified by solid phase extraction on ODS (washing solvent: distilled water, eluent: methanol) to give the title compound (29 mg).

$^1$H-NMR (CD$_3$OD) δ ppm:

0.9 (3H, d, J=7.0 Hz), 0.95 (3H, d, J=6.5 Hz), 1.1-1.2 (6H, m), 2.0-2.1 (1H, m), 2.71 (2H, t, J=7.1 Hz), 2.85-3.0 (1H, m), 3.25-3.45 (6H, m), 3.6-3.75 (2H, m), 3.78 (1H, d, J=16.0 Hz), 3.8-3.9 (1H, m), 4.04 (1H, d, J=5.9 Hz), 5.04 (1H, d, J=7.4 Hz), 7.05-7.15 (4H, m)

Examples 153-172

The compounds described in Tables 5-8 were prepared in a similar manner to that described in Example 152 using the corresponding starting materials. The syntheses of Examples 171 and 172 were carried out by catalytic hydrogenation in a similar manner to that described in Example 79 after the completion of the operation of Example 152.

TABLE 5

| Example No. | Structure | $^1$H-NMR (CD$_3$OD) δ ppm: |
|---|---|---|
| Example 153 | 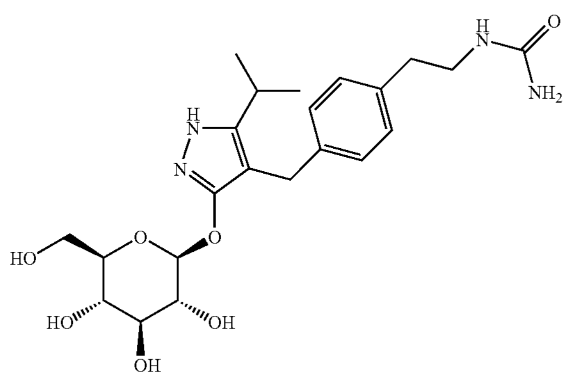 | 1.1-1.2(6H, m), 2.71(2H, t, J = 7.0 Hz), 2.85-3.0(1H, m), 3.2-3.4(6H, m), 3.6-3.9(4H, m), 5.0-5.1(1H, m), 7.05-7.2(4H, m) |
| Example 154 | 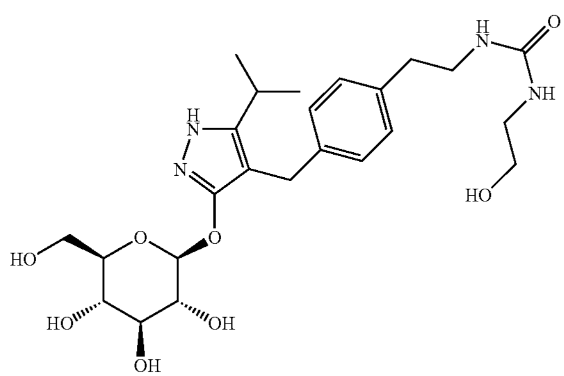 | 1.1-1.2(6H, m), 2.71(2H, t, J = 7.1 Hz), 2.85-3.0(1H, m), 3.2 (2H, t, J = 5.7 Hz), 3.25-3.45(6H, m), 3.5-3.9(6H, m), 5.0-5.1(1H, m), 7.05-7.15(4H, m) |

TABLE 6

| Example No. | Structure | $^1$H-NMR (CD$_3$OD) δ ppm: |
|---|---|---|
| Example 155 | 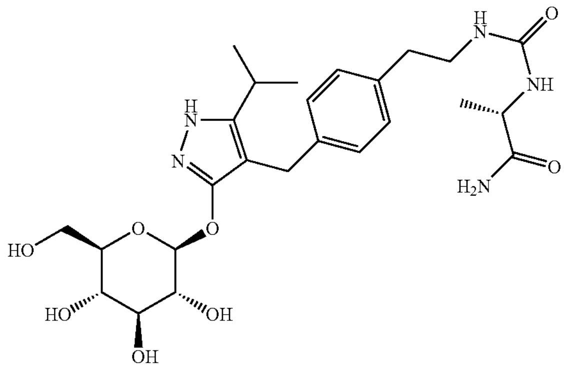 | 1.05-1.2(6H, m), 1.29(3H, d, J = 7.1 Hz), 2.71(2H, t, J = 7.0 Hz), 2.85-3.0(1H, m), 3.25-3.45(6H, m), 3.6-3.9(4H, m), 4.19(1H, q, J = 7.1 Hz), 5.0-5.1(1H, m), 7.05-7.15(4H, m) |
| Example 156 | 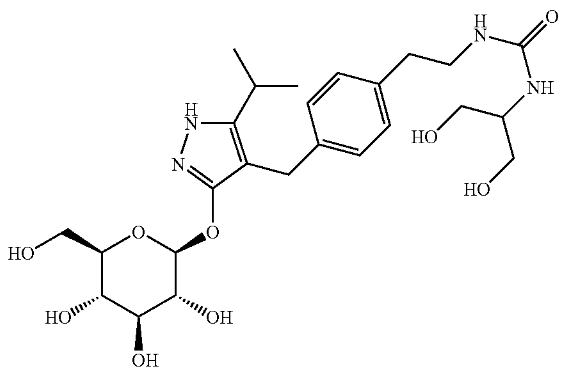 | 1.1-1.2(6H, m), 2.71(2H, t, J = 7.0 Hz), 2.85-3.0(1H, m), 3.25-3.45(6H, m), 3.5-3.9(9H, m), 5.0-5.1(1H, m), 7.05-7.15(4H, m) |
| Example 157 | 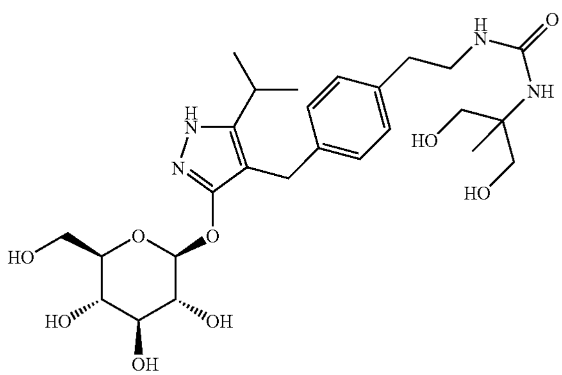 | 1.1-1.2(9H, m), 2.7(2H, t, J = 7.0 Hz), 2.85-3.0(1H, m), 3.2-3.4(6H, m), 3.55(2H, d, J = 11.0 Hz), 3.59(2H, d, J = 11.0 Hz), 3.6-3.9(4H, m), 5.0-5.1(1H, m), 7.05-7.15(4H, m) |
| Example 158 | 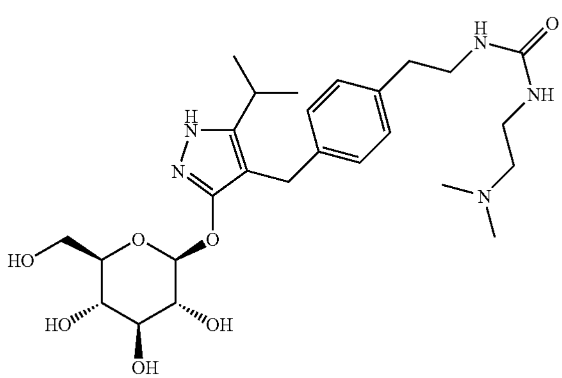 | 1.1-1.2(6H, m), 2.44(6H, s), 2.63 (2H, t, J = 6.3 Hz), 2.71(2H, t, J = 6.8 Hz), 2.9-3.0(1H, m), 3.25-3.4(8H, m), 3.6-3.75(2H, m), 3.75-3.85(2H, m), 5.0-5.05(1H, m), 7.05-7.15(4H, m) |

TABLE 6-continued

| Example No. | Structure | $^1$H-NMR (CD$_3$OD) δ ppm: |
|---|---|---|
| Example 159 | 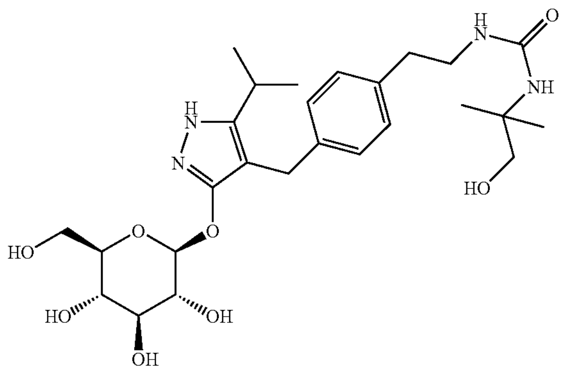 | 1.1-1.2(6H, m), 1.22(6H, s), 2.69 (2H, t, J = 7.1 Hz), 2.85-3.0(1H, m), 3.2-3.4(6H, m), 3.5(2H, s), 3.6-3.75(2H, m), 3.75-3.9(2H, m), 5.0-5.1(1H, m), 7.05-7.15(4H, m) |
| Example 160 | 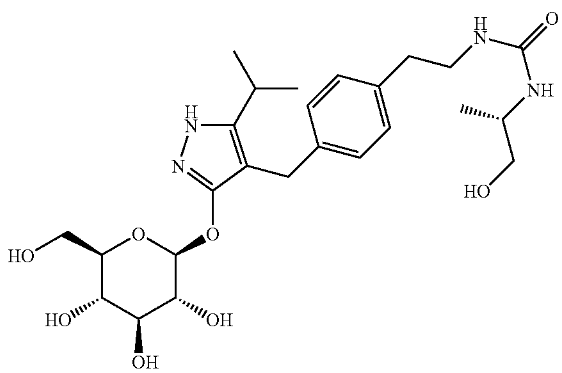 | 1.09(3H, d, J = 6.8 Hz), 1.1-1.2(6H, m), 2.7(2H, t, J = 7.0 Hz), 2.85-3.0 (1H, m), 3.25-3.5(8H, m), 3.6-3.9 (5H, m), 5.0-5.1(1H, m), 7.05-7.15 (4H, m) |

TABLE 7

| Example No. | Structure | $^1$H-NMR (CD$_3$OD) δ ppm: |
|---|---|---|
| Example 161 | 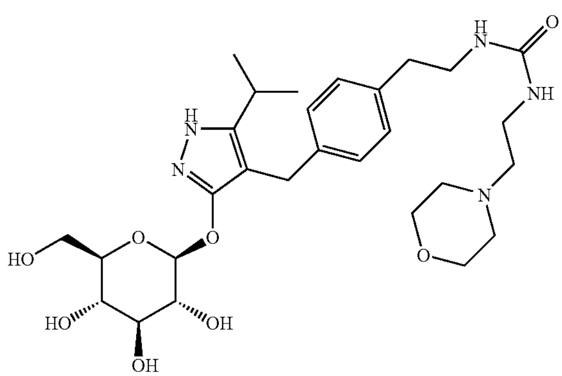 | 1.1-1.2(6H, m), 2.35-2.55(6H, m), 2.71(2H, t, J = 6.9 Hz), 2.85-3.0 (1H, m), 3.23(2H, t, J = 6.2 Hz), 3.25-3.4(6H, m), 3.6-3.9(8H, m), 5.0-5.1(1H, m), 7.05-7.2(4H, m) |

TABLE 7-continued
| Example No. | Structure | ¹H-NMR (CD₃OD) δ ppm: |
|---|---|---|
| Example 162 | 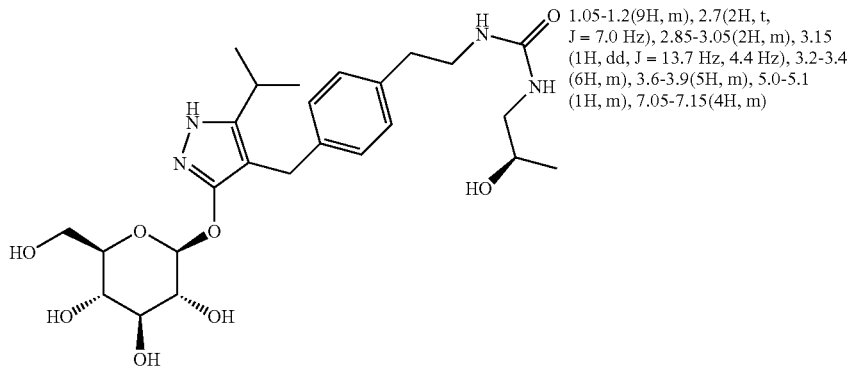 | 1.05-1.2(9H, m), 2.7(2H, t, J = 7.0 Hz), 2.85-3.05(2H, m), 3.15 (1H, dd, J = 13.7 Hz, 4.4 Hz), 3.2-3.4 (6H, m), 3.6-3.9(5H, m), 5.0-5.1 (1H, m), 7.05-7.15(4H, m) |
| Example 163 | 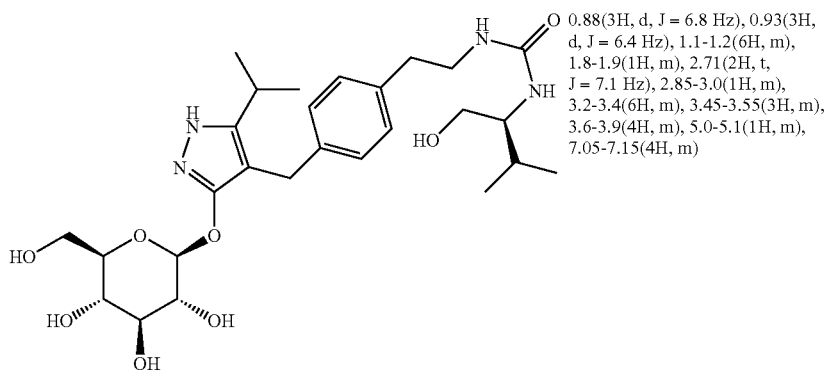 | 0.88(3H, d, J = 6.8 Hz), 0.93(3H, d, J = 6.4 Hz), 1.1-1.2(6H, m), 1.8-1.9(1H, m), 2.71(2H, t, J = 7.1 Hz), 2.85-3.0(1H, m), 3.2-3.4(6H, m), 3.45-3.55(3H, m), 3.6-3.9(4H, m), 5.0-5.1(1H, m), 7.05-7.15(4H, m) |
| Example 164 | 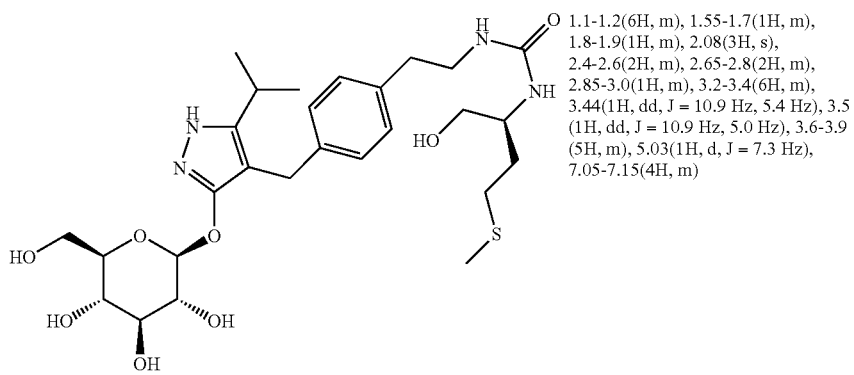 | 1.1-1.2(6H, m), 1.55-1.7(1H, m), 1.8-1.9(1H, m), 2.08(3H, s), 2.4-2.6(2H, m), 2.65-2.8(2H, m), 2.85-3.0(1H, m), 3.2-3.4(6H, m), 3.44(1H, dd, J = 10.9 Hz, 5.4 Hz), 3.5 (1H, dd, J = 10.9 Hz, 5.0 Hz), 3.6-3.9 (5H, m), 5.03(1H, d, J = 7.3 Hz), 7.05-7.15(4H, m) |
| Example 165 | 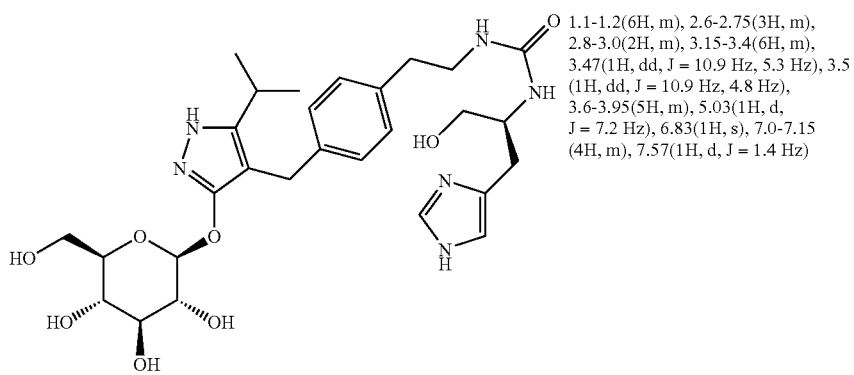 | 1.1-1.2(6H, m), 2.6-2.75(3H, m), 2.8-3.0(2H, m), 3.15-3.4(6H, m), 3.47(1H, dd, J = 10.9 Hz, 5.3 Hz), 3.5 (1H, dd, J = 10.9 Hz, 4.8 Hz), 3.6-3.95(5H, m), 5.03(1H, d, J = 7.2 Hz), 6.83(1H, s), 7.0-7.15 (4H, m), 7.57(1H, d, J = 1.4 Hz) |

TABLE 7-continued

| Example No. | Structure | $^1$H-NMR (CD$_3$OD) δ ppm: |
| --- | --- | --- |
| Example 166 | 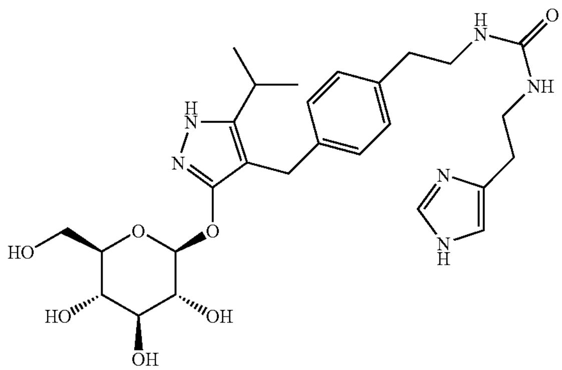 | 1.1-1.2(6H, m), 2.65-2.75(4H, m), 2.85-3.0(1H, m), 3.2-3.4(8H, m), 3.6-3.75(2H, m), 3.77(1H, d, J = 16.1 Hz), 3.83(1H, d, J = 11.8 Hz), 5.04(1H, d, J =32 7.2 Hz), 6.81(1H, s), 7.05-7.15(4H, m), 7.57(1H, d, J = 1.2 Hz) |

TABLE 8

| Example No. | Structure | $^1$H-NMR (CD$_3$OD) δ ppm: |
| --- | --- | --- |
| Example 167 | 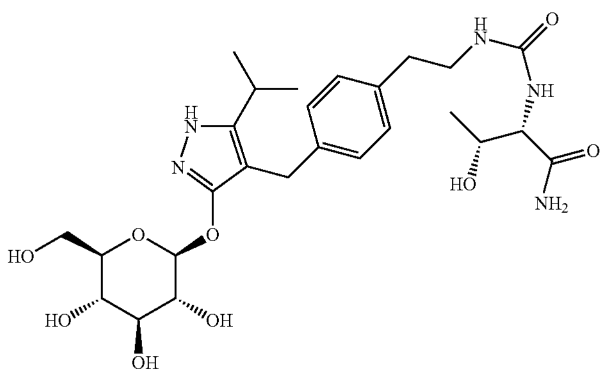 | 1.1-1.2(9H, m), 2.73(2H, t, J = 6.9 Hz), 2.85-3.0(1H, m), 3.25-3.45(6H, m), 3.6-3.75(2H, m), 3.78(1H, d, J = 16.0 Hz), 3.83 (1H, d, J = 12.3 Hz), 4.05-4.15(1H, m), 4.15-4.25(1H, m), 5.04(1H, d, J = 7.0 Hz), 7.05-7.15(4H, m) |
| Example 168 | 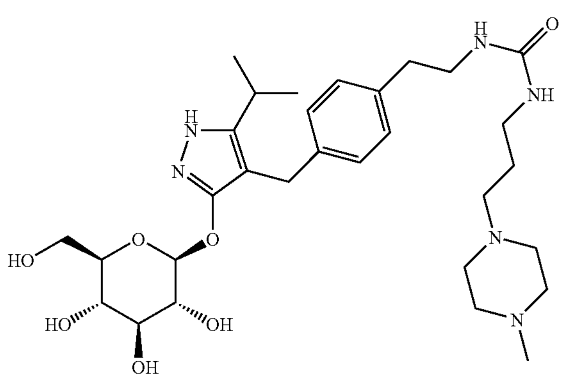 | 1.1-1.2(6H, m), 1.6-1.7(2H, m), 2.15-2.8(15H, m), 2.85-3.0(1H, m), 3.12(2H, t, J = 6.7 Hz), 3.2-3.4 (6H, m), 3.6-3.75(2H, m), 3.78(1H, d, J = 16.0 Hz), 3.83(1H, d, J = 11.9 Hz), 5.0-5.1(1H, m), 7.05-7.15(4H, m) |

TABLE 8-continued
| Example No. | Structure | $^1$H-NMR (CD$_3$OD) δ ppm: |
|---|---|---|
| Example 169 | 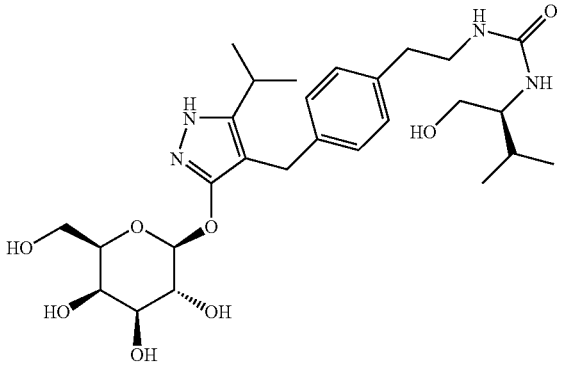 | 0.88(3H, d, J = 6.7 Hz), 0.93(3H, d, J = 6.6 Hz), 1.05-1.2(6H, m), 1.8-1.9(1H, m), 2.71(2H, t, J = 6.9 Hz), 2.85-3.0(1H, m), 3.25-3.4(2H, m), 3.4--3.8(10H, m), 3.8-3.9(1H, m), 5.05(1H, d, J = 7.6 Hz), 7.05-7.15(4H, m) |
| Example 170 | 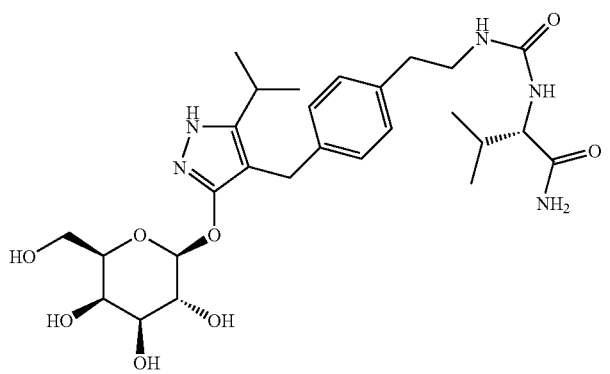 | 0.9(3H, d, J = 7.1 Hz), 0.95(3H, d, J = 6.9 Hz), 1.1-1.2(6H, m), 1.95-2.1(1H, m), 2.71(2H, t, J = 7.2 Hz), 2.85-3.0(1H, m), 3.25-3.4(2H, m), 3.51(1H, dd, J = 9.8 Hz, 3.6 Hz), 3.55-3.65(1H, m), 3.65-3.8(5H, m), 3.8-3.9(1H, m), 4.04(1H, d, J = 6.1 Hz), 5.05(1H, d, J = 7.9 Hz), 7.05-715(4H, m) |
| Example 171 | 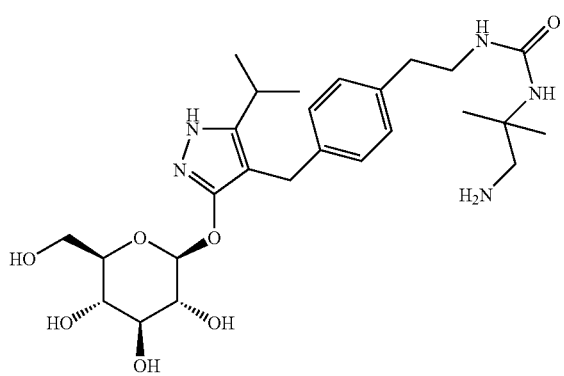 | 1.1-1.2(6H, m), 1.21(6H, s), 2.69 (2H, t, J = 6.9 Hz), 2.78(2H, s), 2.85-3.0(1H, m), 3.2-3.4(6H, m), 3.6-3.9(4H, m), 5.04(1H, d, J = 7.3 Hz), 7.05-7.15(4H, m) |
| Example 172 | 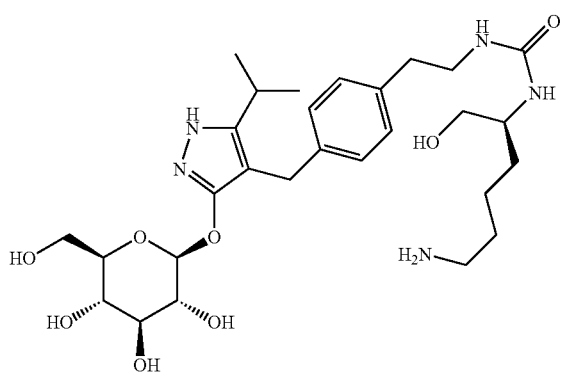 | 1.1-1.2(6H, m), 1.25-1.65(6H, m), 2.6-2.75(4H, m), 2.85-3.0(1H, m), 3.2-3.55(8H, m), 3.6-3.9(5H, m), 5.04(1H, d, J = 7.8 Hz), 7.05-7.15 (4H, m) |

Reference Example 82

4-Bromo-2-methylbenzyl alcohol

To a solution of 4-bromo-2-methylbenzoic acid (10 g) in tetrahydrofuran (60 mL) was added borane-dimethylsulfide complex (7.07 g) under ice-cooling. The reaction mixture was stirred at room temperature for 5 minutes, and stirred at 75° C. for 2 days. The reaction mixture was cooled to room temperature. A saturated aqueous potassium carbonate solution was added to the reaction mixture, and the organic layer was separated. The organic layer was washed with water and brine, and dried over anhydrous magnesium sulfate. The solvent was removed under reduced pressure to give the title compound (9.0 g).

$^1$H-NMR (CDCl$_3$) δ ppm:
1.55-1.65 (1H, m), 2.36 (3H, s), 4.64 (2H, d, J=5.4 Hz), 7.2-7.25 (1H, m), 7.3-7.35 (2H, m)

Reference Example 83

4-{[4-(2-Aminoethyl)-2-methylphenyl]methyl}-1,2-dihydro-5-isopropyl-3H-pyrazol-3-one To a solution of 4-bromo-2-methylbenzyl alcohol (9.0 g) in dichloromethane (50 mL) was added thionyl chloride (3.8 mL) under ice-cooling, and the reaction mixture was stirred at room temperature overnight. The reaction mixture was concentrated under reduced pressure to give 4-bromo-2-methylbenzyl chloride (9.8 g). Sodium hydride (55%, 0.84 g) was suspended in tetrahydrofuran (80 mL). To the suspension was added methyl 4-methyl-3-oxopentanoate (2.94 g) under ice-cooling, and the mixture was stirred at room temperature for 1 hour. To the reaction mixture was added 4-bromo-2-methylbenzyl chloride (4.08 g), and the mixture was stirred at 60° C. for 36 hours. To the reaction mixture was added a saturated aqueous ammonium chloride solution, and the resulting mixture was extracted with diethyl ether. The extract was dried over anhydrous magnesium sulfate, and the solvent was removed under reduced pressure. The residue was dissolved in acetonitrile (24 mL). To the solution were added N-vinylphthalimide (3.29 g), palladium acetate(II) (0.42 g), tris(o-methylphenyl)phosphine (2.27 g) and N,N-diisopropylethylamine (13 mL), and the mixture was stirred at 100° C. for 16 hours. The reaction mixture was concentrated under reduced pressure, and the residue was purified by column chromatography on silica gel (eluent: n-hexane-n-hexane/ethyl acetate=3/1-3/2) to give N-{(E)-2-[4-(2-methoxycarbonyl-4-methyl-3-oxopentyl)-3-methylphenyl]-vinyl}phthalimide (6.45 g). To this material were added methanol (50 mL) and 10% palladium-carbon powder (3 g), and the mixture was stirred at room temperature under a hydrogen atmosphere for 2 hours. The insoluble material was removed by filtration, and the filtrate was concentrated under reduced pressure. A part (1 g) of the residue was dissolved in ethanol (15 mL). To the solution was added hydrazine monohydrate (1.38 mL), and the mixture was stirred at 80° C. for 13 hours. The insoluble material was removed by filtration, and the filtrate was concentrated under reduced pressure. The residue was purified by solid phase extraction on ODS (washing solvent: distilled water, eluent: methanol) and benzenesulfonic acid resin (washing solvent: methanol, eluent: 2 mol/L ammonia-methanol solution) to give the title compound (0.3 g).

$^1$H-NMR (DMSO-d$_6$) δ ppm:
1.04 (6H, d, J=6.7 Hz), 2.25 (3H, s), 2.53 (2H, t, J=7.2 Hz), 2.65-2.8 (3H, m), 3.47 (2H, s), 6.75-6.9 (2H, m), 6.93 (1H, s)

Reference Example 84

4-({4-[2-(Benzyloxycarbonylamino)ethyl]-2-methylphenyl}-methyl)-1,2-dihydro-5-isopropyl-3H-pyrazol-3-one To a solution of 4-{[4-(2-aminoethyl)-2-methylphenyl]methyl}-1,2-dihydro-5-isopropyl-3H-pyrazol-3-one (0.3 g) in tetrahydrofuran (5 mL) was added n-(benzyloxycarbonyloxy)succinimide (0.33 g), and the mixture was stirred at room temperature overnight. The reaction mixture was poured into water, and the resulting mixture was extracted with ethylacetate. The extract was washed with a saturated aqueous sodium hydrogen carbonate solution twice, water and brine, and dried over anhydrous magnesium sulfate. The solvent was removed under reduced pressure to give the title compound (0.34 g).

$^1$H-NMR (CDCl$_3$) δ ppm:
1.11 (6H, d, J=6.7 Hz), 2.31 (3H, s), 2.65-2.95 (3H, m), 3.35-3.5 (2H, m), 3.63 (2H, s), 4.65-4.8 (1H, m), 5.09 (2H, s), 6.85-7.0 (3H, m), 7.25-7.4 (5H, m)

Example 173

3-(2,3,4,6-Tetra-O-acetyl-β-D-glucopyranosyloxy)-4-({4-[2-(benzyloxycarbonylamino)ethyl]-2-methylphenyl}methyl)-5-isopropyl-1H-pyrazole The title compound was prepared in a similar manner to that described in Reference Example 17 using 4-({4-[2-(benzyloxycarbonylamino)ethyl]-2-methylphenyl}methyl)-1,2-dihydro-5-isopropyl-3H-pyrazol-3-one instead of 4-{[4-(3-benzyloxypropoxy)phenyl]methyl}-1,2-dihydro-5-isopropyl-3H-pyrazol-3-one.

$^1$H-NMR (CDCl$_3$) δ ppm:
1.05-1.15 (6H, m), 1.79 (3H, s), 1.98 (3H, s), 2.02 (3H, s), 2.05 (3H, s), 2.26 (3H, s), 2.73 (2H, t, J=6.7 Hz), 2.75-2.9 (1H, m), 3.35-3.45 (2H, m), 3.53 (1H, d, J=16.5 Hz), 3.62 (1H, d, J=16.5 Hz), 3.75-3.85 (1H, m), 4.08 (1H, dd, J=12.5 Hz, 2.7 Hz), 4.27 (1H, dd, J=12.5 Hz, 4.1 Hz), 4.8-4.9 (1H, m), 5.09 (2H, s), 5.1-5.3 (3H, m), 5.55 (1H, d, J=7.7 Hz), 6.8-6.9 (2H, m), 6.93 (1H, s), 7.25-7.4 (5H, m)

Example 174

4-{[4-(2-Aminoethyl)-2-methylphenyl]methyl}-3-(β-D-glucopyranosyloxy)-5-isopropyl-1H-pyrazole 3-(2,3,4,6-Tetra-O-acetyl-β-D-glucopyranosyloxy)-4-({4-[2-(benzyloxycarbonylamino)ethyl]-2-methylphenyl)methyl}-5-isopropyl-1H-pyrazole (20 mg) was dissolved in methanol (1 mL). To the solution was added sodium methoxide (28% methanol solution, 0.005 mL), and the mixture was stirred at room temperature for 2 hours. The reaction mixture was concentrated under reduced pressure, and the residue was purified by solid phase extraction on ODS (washing solvent: distilled water, eluent: methanol) to give 4-({4-[2-(benzyloxycarbonylamino)ethyl]-2-methylphenyl}methyl)-3-(β-D-glucopyranosyloxy)-5-isopropyl-1H-pyrazole. This material was dissolved in methanol (1 mL). To the solution was added 10% palladium-carbon powder (5 mg), and the mixture was stirred at room temperature under a hydrogen atmosphere for 6 hours. The insoluble material was removed by filtration, and the filtrate was concentrated under reduced pressure to give the title compound (11 mg).

¹H-NMR (CD₃OD) δ ppm:
1.05-1.15 (6H, m), 2.31 (3H, s), 2.67 (2H, t, J=7.0 Hz), 2.75-2.9 (3H, m), 3.25-3.4 (4H, m), 3.6-3.85 (4H, m), 4.95-5.05 (1H, m), 6.85-7.0 (3H, m)

Example 175

4-{[4-(2-{3-[(1S,2R)-1-Carbamoyl-2-hydroxypropyl]ureido}ethyl)-2-methylphenyl]methyl}-3-(β-D-glucopyranosyloxy)-5-isopropyl-1H-pyrazole 3-(2,3,4,6-Tetra-O-acetyl-β-D-glucopyranosyloxy)-4-({4-[2-(benzyloxycarbonylamino)ethyl]-2-methylphenyl}methyl)-5-isopropyl-1H-pyrazole (0.3 g) was dissolved in tetrahydrofuran (2 mL). To the solution was added 10% palladium-carbon powder (20 mg), and the mixture was stirred at room temperature under a hydrogen atmosphere for 6 hours. The insoluble material was removed by filtration, and the filtrate was concentrated under reduced pressure to give 3-(2,3,4,6-tetra-O-acetyl-β-D-glucopyranosyloxy)-4-{[4-(2-aminoethyl)-2-methylphenyl]methyl}-5-isopropyl-1H-pyrazole (0.24 g). The obtained 3-(2,3,4,6-tetra-O-acetyl-β-D-glucopyranosyloxy)-4-{[4-(2-aminoethyl)-2-methylphenyl]-methyl}-5-isopropyl-1H-pyrazole (0.13 g) was dissolved in dichloromethane (2.6 mL). To the solution were added triethylamine (0.042 mL) and 4-nitrophenyl chloroformate (52 mg) under ice-cooling, and the mixture was stirred at room temperature for 2 hours. A ¼ amount of the reaction mixture was separated. To the part of the reaction mixture were added triethylamine (0.028 mL) and L-threonine amide hydrochloride (23 mg), and the mixture was stirred at room temperature overnight. The reaction mixture was purified by column chromatography on silica gel (eluent: ethyl acetate-ethyl acetate/methanol=10/1) to give 3-(2,3,4,6-tetra-O-acetyl-β-D-glucopyranosyloxy)-4-{[4-(2-(3-[(1S,2R)-1-carbamoyl-2-hydroxypropyl]-ureido)ethyl)-2-methylphenyl]methyl}-5-isopropyl-1H-pyrazole (30 mg). This material was dissolved in methanol (2 mL). To the solution was added sodium methoxide (28% methanol solution, 0.006 mL), and the mixture was stirred at room temperature for 1 hour. To the reaction mixture was added acetic acid (0.005 mL). The resulting mixture was concentrated under reduced pressure, and the residue was purified by solid phase extraction on ODS (washing solvent: distilled water, eluent: methanol) to give the title compound (21 mg).

¹H-NMR (CD₃OD) δ ppm:
1.1-1.2 (9H, m), 2.31 (3H, s), 2.7 (2H, t, J=7.0 Hz), 2.8-2.9 (1H, m), 3.2-3.45 (6H, m), 3.6-3.75 (3H, m), 3.8 (1H, dd, J=12.1 Hz, 2.1 Hz), 4.05-4.15 (1H, m), 4.15-4.25 (1H, m), 4.97 (1H, d, J=7.0 Hz), 6.85-6.95 (2H, m), 7.0 (1H, s)

Examples 176-181

The compounds described in Tables 9-10 were prepared in a similar manner to that described in Example 175 using the corresponding starting materials. The syntheses of Examples 180 and 181 were carried out by catalytic hydrogenation in a similar manner to that described in Example 79 after the completion of the operation of Example 175.

TABLE 9

| Example No. | Structure | ¹H-NMR (CD₃OD) δ ppm: |
|---|---|---|
| Example 176 | 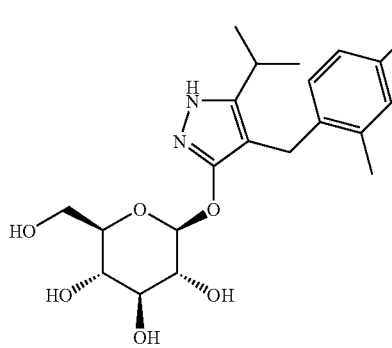 | 1.1-1.2(6H, m), 2.31(3H, s), 2.69 (2H, t, J = 7.0 Hz), 2.75-2.9(1H, m), 3.2-3.4(6H, m), 3.6-3.3.75(3H, m), 3.75-3.85(1H, m), 4.97(1H, d, J = 6.9 Hz), 6.85-6.95(2H, m), 6.99 (1H, s) |
| Example 177 | 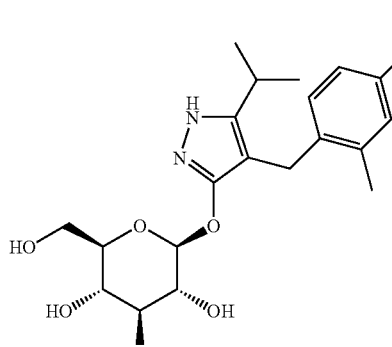 | 1.05-1.2(9H, m), 2.31(3H, s), 2.6-2.75(2H, m), 2.75-2.9(1H, m), 3.2-3.4(6H, m), 3.5-3.75(7H, m), 3.8(1H, d, J = 11.6 Hz), 4.9-5.05 (1H, m), 6.85-6.95(2H, m), 6.99 (1H, s) |

TABLE 10

| Example No. | Structure | $^1$H-NMR (CD$_3$OD) δ ppm: |
|---|---|---|
| Example 178 | 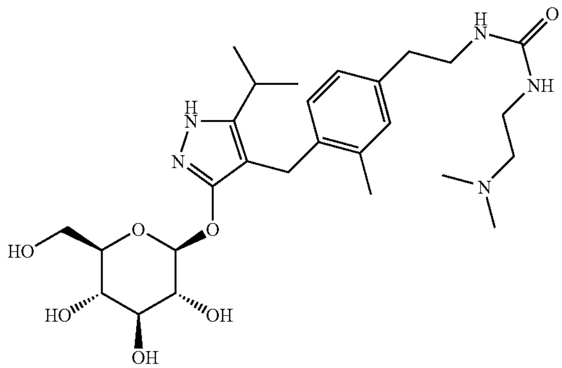 | 1.1-1.2(6H, m), 2.25(6H, s), 2.31 (3H, s), 2.4(2H, t, J = 6.5 Hz), 2.68 (2H, t, J = 6.7 Hz), 2.8-2.9(1H, m), 3.15-3.4(8H, m), 3.6-3.75(3H, m), 3.75-3.85(1H, m), 4.9-5.0(1H, m), 6.85-6.95(2H, m), 6.98(1H, s) |
| Example 179 | 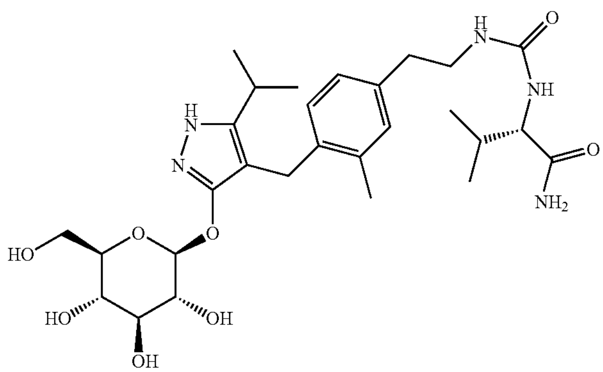 | 0.91(3H, d, J = 6.7 Hz), 0.96(3H, d, J = 6.6 Hz), 1.05-1.2(6H, m), 1.95-2.1(1H, m), 2.3(3H, s), 2.65-2.75(2H, m), 2.8-2.9(1H, m), 3.2-3.45(6H, m), 3.6-3.75(3H, m), 3.75-3.85(1H, m), 4.05(1H, d, J = 6.1 Hz), 4.9-5.05(1H, m), 6.85-6.95(2H, m), 6.99(1H, s) |
| Example 180 | 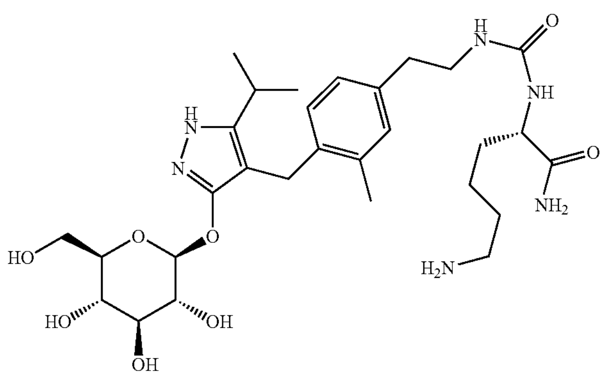 | 1.1-1.2(6H, m), 1.3-1.85(6H, m), 2.31(3H, s), 2.6-2.75(4H, m), 2.8-2.9(1H, m), 3.2-3.45(6H, m), 3.6-3.75(3H, m), 3.75-3.85(1H, m), 4.05-4.2(1H, m), 4.9-5.0(1H, m), 6.85-7.0(3H, m) |
| Example 181 | 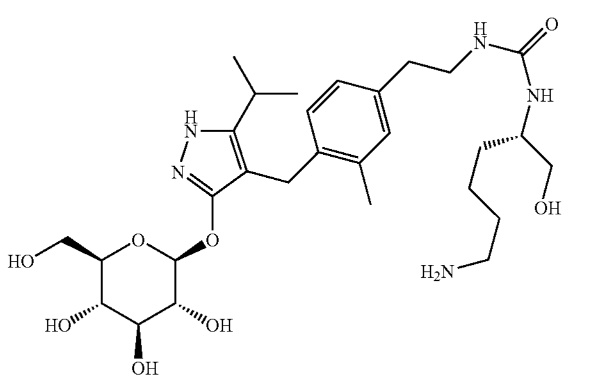 | 1.05-1.2(6H, m), 1.3-1.65(6H, m), 2.31(3H, s), 2.6-2.75(4H, m), 2.8-2.9(1H, m), 3.2-3.55(8H, m), 3.55-3.75(4H, m), 3.75-3.85(1H, m), 4.98(1H, d, J = 7.5 Hz), 6.85-7.0(3H, m) |

Example 182

3-(β-D-Galactopyranosyloxy)-5-isopropyl-4-[(4-{3-[3-(dimethylamino)propylamino]propoxy}-2-methylphenyl)methyl]-1H-pyrazole The title compound was prepared in a similar manner to that described in Example 51 using 3-(2,3,4,6-tetra-O-acetyl-β-D-galactopyranosyloxy)-4-{[4-(3-hydroxypropoxy)-2-methylphenyl]methyl}-5-isopropyl-1H-pyrazole and N,N-dimethyl-N'-(2-nitrobenzenesulfonyl)-1,3-diaminopropane instead of 3-(2,3,4,6-tetra-O-acetyl-β-D-glucopyranosyloxy)-4-{[4-(3-hydroxypropoxy)-2-methylphenyl]methyl}-5-isopropyl-1H-pyrazole and 2-methyl-2-(2-nitrobenzenesulfonylamino)propionamide, respectively.

$^1$H-NMR (CD$_3$OD) δ ppm:
1.05-1.15 (6H, m), 1.65-1.75 (2H, m), 1.9-2.0 (2H, m), 2.23 (6H, s), 2.28 (3H, s), 2.3-2.4 (2H, m), 2.61 (2H, t, J=7.3 Hz), 2.7-2.85 (3H, m), 3.49 (1H, dd, J=9.8 Hz, 3.5 Hz), 3.55-3.8 (6H, m), 3.84 (1H, d, J=3.5 Hz), 3.99 (2H, t, J=6.1 Hz), 5.03 (1H, d, J=7.9 Hz), 6.6 (1H, d, J=8.7 Hz, 2.4 Hz), 6.7 (1H, d, J=2.4 Hz), 6.85 (1H, d, J=8.7 Hz)

Reference Example 85

3-Amino-3-methylbutyramide

To a solution of 3,3-dimethylacrylic acid (5 g) in tetrahydrofuran (15 mL) was added 1,1'-carbonylbis-1H-imidazole (10.5 g), and the mixture was stirred at room temperature for 30 minutes. To the reaction mixture was added 28% aqueous ammonia solution (30 mL), and the mixture was stirred at room temperature for 1 hour. The reaction mixture was concentrated under reduced pressure, and the residue was purified by column chromatography on silica gel (eluent: dichloromethane/methanol=10/1) to give 3,3-dimethylacrylamide (2.05 g). This material was dissolved in 2-propanol (20 mL). An ammonia gas was bubbled into the solution at −15° C. until saturation, and the mixture was stirred at 80° C. for 40 hours. The reaction mixture was concentrated under reduced pressure, and the residue was purified by benzenesulfonic acid resin (washing solvent: methanol, eluent: 2 mol/L ammonia-methanol solution) to give the title compound (0.13 g).

$^1$H-NMR (CD$_3$OD) δ ppm:
1.19 (6H, s), 2.27 (2H, s)

Example 183

4-[(4-{3-[2-Carbamoyl-1,1-di(methyl)ethylamino]propoxy}-2-methylphenyl)methyl]-3-(β-D-galactopyranosyloxy)-5-isopropyl-1H-pyrazole The title compound was prepared in a similar manner to that described in Example 72 using 3-(2,3,4,6-tetra-O-acetyl-β-D-galactopyranosyloxy)-4-{[4-(3-hydroxypropoxy)-2-methylphenyl]methyl}-5-isopropyl-1H-pyrazole and 3-amino-3-methylbutyramide instead of 3-(2,3,4,6-tetra-O-acetyl-β-D-glucopyranosyloxy)-4-{[4-(3-hydroxypropoxy)phenyl]-methyl}-5-isopropyl-1H-pyrazole and 2-[(2-amino-2-(methyl)propionylamino]ethanol, respectively.

MS (ESI, m/z): 565 [M+H]$^+$
$^1$H-NMR (CD$_3$OD) δ ppm:
1.05-1.15 (6H, m), 1.18 (6H, s), 1.85-2.0 (2H, m), 2.28 (3H, s), 2.32 (2H, s), 2.7-2.85 (3H, m), 3.49 (1H, dd, J=9.7 Hz, 3.3 Hz), 3.58 (1H, t, J=5.8 Hz), 3.6-3.8 (5H, m), 3.8-3.9 (1H, m), 4.0 (2H, t, J=5.9 Hz), 5.03 (1H, d, J=7.9 Hz), 6.55-6.65 (1H, m), 6.65-6.75 (1H, m), 6.8-6.9 (1H, m)

Reference Example 86

4-[(4-Benzyloxy-2-methylphenyl)methyl]-5-trifluoromethyl-1,2-dihydro-3H-pyrazol-3-one The title compound was prepared in a similar manner to that described in Reference Example 11 using (4-benzyloxy-2-methylphenyl)methanol and ethyl trifluoroacetoacetate instead of [4-(3-benzyloxypropoxy)phenyl]methanol and ethyl 4-methyl-3-oxopentanoate, respectively.

$^1$H-NMR (DMSO-d$_6$) δ ppm:
2.24 (3H, s), 3.58 (2H, s), 5.02 (2H, s), 6.65 (1H, d, J=8.5 Hz), 6.7 (1H, dd, J=8.5 Hz, 2.7 Hz), 6.81 (1H, d, J=2.7 Hz), 7.25-7.45 (5H, m)

Reference Example 87

3-(2,3,4,6-Tetra-O-acetyl-β-D-galactopyranosyloxy)-4-[(4-benzyloxy-2-methylphenyl)methyl]-5-trifluoromethyl-1H-pyrazole A suspension of 4-[(4-benzyloxy-2-methylphenyl)methyl]-5-trifluoromethyl-1,2-dihydro-3H-pyrazol-3-one (0.5 g), acetobromo-α-D-galactose (0.62 g) and potassium carbonate (0.29 g) in acetonitrile (5 mL) was stirred at room temperature overnight. The reaction mixture was poured into water, and the resulting mixture was extracted with ethyl acetate. The extract was washed with brine, and dried over anhydrous sodium sulfate. The solvent was removed under reduced pressure, and the residue was purified by column chromatography on silica gel (eluent: n-hexane/ethyl acetate=2/1-1/1) to give the title compound (0.66 g).

$^1$H-NMR (CDCl$_3$) δ ppm:
1.78 (3H, s), 1.98 (3H, s), 2.05 (3H, s), 2.17 (3H, s). 2.3 (3H, s), 3.67 (1H, d, J=16.4 Hz), 3.72 (1H, d, J=16.4 Hz), 3.98 (1H, t, J=6.3 Hz), 4.1-4.25 (2H, m), 5.0-5.1 (3H, m), 5.15-5.4 (2H, m), 5.42 (1H, dd, J=3.4 Hz, 1.0 Hz), 6.67 (1H, dd, J=8.5 Hz, 2.6 Hz), 6.75 (1H, d, J=8.5 Hz), 6.8 (1H, d, J=2.6 Hz), 7.25-7.45 (5H, m)

Reference Example 88

3-(2,3,4,6-Tetra-O-acetyl-β-D-galactopyranosyloxy)-5-trifluoromethyl-4-[(4-hydroxy-2-methylphenyl)methyl]-1H-pyrazole The title compound was prepared in a similar manner to that described in Reference Example 58 using 3-(2,3,4,6-tetra-O-acetyl-β-D-galactopyranosyloxy)-4-[(4-benzyloxy-2-methylphenyl)methyl]-5-trifluoromethyl-1H-pyrazole instead of 4-[(4-benzyloxy-2-methylphenyl)methyl]-5-isopropyl-3-(2,3,4,6-tetra-O-pivaloyl-β-D-glucopyranosyloxy)-1H-pyrazole.

$^1$H-NMR (CDCl$_3$) δ ppm:
1.83 (3H, s), 1.98 (3H, s), 2.05 (3H, s), 2.18 (3H, s), 2.27 (3H, s), 3.66 (1H, d, J=16.4 Hz), 3.71 (1H, d, J=16.4 Hz), 3.95-4.0 (1H, m), 4.05-4.2 (2H, m), 4.84 (1H, brs), 5.03 (1H, dd, J=10.3 Hz, 3.4 Hz), 5.2-5.4 (2H, m), 5.41 (1H, dd, J=3.4

Example 184

4-[(4-{3-[2-(Carbamoyl)ethylamino]propoxy}-2-methylphenyl)methyl]-5-trifluoromethyl-3-(β-D-galactopyranosyloxy)-1H-pyrazole 3-(2,3,4,6-Tetra-O-acetyl-β-D-galactopyranosyloxy)-4-[(4-{3-[N-benzyloxycarbonyl-N-(2-carbamoylethyl)amino]-propoxy}-2-methylphenyl)methyl]-5-trifluoromethyl-1H-pyrazole was prepared in a similar manner to that described in Example 96 using 3-(2,3,4,6-tetra-O-acetyl-β-D-galactopyranosyloxy)-5-trifluoromethyl-4-[(4-hydroxy-2-methylphenyl)methyl]-1H-pyrazole instead of 4-[(4-hydroxy-2-methylphenyl)methyl]-5-isopropyl-3-(2,3,4,6-tetra-O-pivaloyl-β-D-glucopyranosyloxy)-1H-pyrazole, and the title compound was prepared in a similar manner to that described in Example 94 using this material instead of 3-(2,3,4,6-tetra-O-acetyl-β-D-galactopyranosyloxy)-4-[(4-{3-[N-benzyl-N-(2-carbamoylethyl)amino]propoxy}-2-methylphenyl)methyl]-5-isopropyl-1H-pyrazole.

MS (ESI, m/z): 563 [M+H]$^+$ $^1$H-NMR (CD$_3$OD) δ ppm:
1.95-2.1 (2H, m), 2.25 (3H, s), 2.41 (2H, t, J=6.9 Hz), 2.63 (2H, t, J=7.1 Hz), 2.83 (2H, t, J=6.9 Hz), 3.53 (1H, dd, J=9.8 Hz, 3.4 Hz), 3.55-3.8 (6H, m), 3.87 (1H, d, J=3.4 Hz), 4.21 (2H, t, J=6.7 Hz), 5.28 (1H, d, J=7.9 Hz), 6.45 (1H, dd, J=8.4 Hz, 2.4 Hz), 6.55-6.65 (2H, m)

Example 185

4-[(4-(2-{[2-{[4-(Benzyloxycarbonyl)piperazin-1-yl]-carbonyl}-2-(methyl)propionylamino]ethoxy}-2-methylphenyl)methyl]-3-(β-D-glucopyranosyloxy)-5-isopropyl-1H-pyrazole To a solution of 3-(2,3,4,6-tetra-O-acetyl-β-D-glucopyranosyloxy)-4-{[4-(2-aminoethoxy)-2-methylphenyl]methyl}-5-isopropyl-1H-pyrazole (0.5 g) in N,N-dimethylformamide (10 mL) were added 1-benzyloxycarbonyl-4-[2-carboxy-2-(methyl)propionyl]piperazine (0.28 g), 1-hydroxybenzotriazole (0.22 g), triethylamine (0.18 mL) and 1-ethyl-3-(3-dimethylaminopropyl)carbodiimide hydrochloride (0.46 g), and the mixture was stirred at room temperature for 2 days. The reaction mixture was poured into water, and the resulting mixture was extracted with diethyl ether. The organic layer was washed with a saturated aqueous sodium hydrogen carbonate solution, water and brine successively, dried over anhydrous magnesium sulfate and concentrated under reduced pressure. The residue was purified by column chromatography on silica gel (eluent: dichloromethane/methanol=30/1) to give 3-(2,3,4,6-tetra-O-acetyl-β-D-glucopyranosyloxy)-4-[(4-{2-[2-{[4-(benzyloxycarbonyl)piperazin-1-yl]-carbonyl}-2-(methyl)propionylamino]ethoxy}-2-methylphenyl)methyl]-5-isopropyl-1H-pyrazole (0.3 g). This material was dissolved in methanol (4 mL). To the solution was added sodium methoxide (28% methanol solution, 0.06 mL), and the mixture was stirred at room temperature for 30 minutes. To the reaction mixture was added acetic acid (0.035 mL), and the resulting mixture was concentrated under reduced pressure. The residue was purified by column chromatography on silica gel (eluent: dichloromethane/methanol=10/1-5/1) to give the title compound (0.23 g).

$^1$H-NMR (CD$_3$OD) δ ppm:
1.05-1.15 (6H, m), 1.37 (6H, s), 2.25 (3H, s), 2.7-2.85 (1H, m), 3.15-3.75 (17H, m), 3.81 (1H, d, J=12.0 Hz), 4.02 (2H, t, J=5.2 Hz), 5.02 (1H, d, J=7.4 Hz), 5.09 (2H, s), 6.55-6.65 (1H, m), 6.69 (1H, d, J=2.2 Hz), 6.84 (1H, d, J=8.7 Hz), 7.25-7.4 (5H, m)

Reference Example 89

4-[(4-{2-[2-{[4-(Benzyloxycarbonyl)piperazin-1-yl]-carbonyl}-2-(methyl)propionylamino]ethoxy}-2-methylphenyl)methyl]-1,2-dihydro-5-isopropyl-3H-pyrazol-3-one A mixture of 4-[(4-{2-[2-{[4-(benzyloxycarbonyl)piperazin-1-yl]carbonyl}-2-(methyl)propionylamino]ethoxy}-2-methylphenyl)methyl]-3-(β-D-glucopyranosyloxy)-5-isopropyl-1H-pyrazole (0.23 g), p-toluenesulfonic acid monohydrate (0.41 g) and 2-propanol (10 mL) was stirred at 50° C. for 2 days. The reaction mixture was poured into a saturated aqueous sodium hydrogen carbonate solution, and the resulting mixture was extracted with ethylacetate. The extract was washed with water and brine, and dried over anhydrous magnesium sulfate. The solvent was removed under reduced pressure, and the residue was purified by column chromatography on silica gel (eluent: dichloromethane/methanol=10/1) to give the title compound (0.18 g).

$^1$H-NMR (CD$_3$OD) δ ppm:
1.06 (6H, d, J=6.7 Hz), 1.37 (6H, s), 2.25 (3H, s) 2.7-2.85 (1H, m), 3.15-3.7 (12H, m), 4.02 (2H, t, J=5.3 Hz), 5.09 (2H, s), 6.6 (1H, dd, J=8.6 Hz, 2.3 Hz), 6.7 (1H, d, J=2.3 Hz), 6.85 (1H, d, J=8.6 Hz), 7.25-7.4 (5H, m)

Example 186

3-(2,3,4,6-Tetra-O-acetyl-β-D-galactopyranosyloxy)-4-[(4-{2-[2-{[4-(benzyloxycarbonyl)piperazin-1-yl]carbonyl}-2-(methyl)propionylamino]ethoxy}-2-methylphenyl)methyl]-5-isopropyl-1H-pyrazole The title compound was prepared in a similar manner to that described in Reference Example 17 using 4-[(4-{2-[2-{[4-(benzyloxycarbonyl)piperazin-1-yl]carbonyl}-2-(methyl)propionylamino]ethoxy}-2-methylphenyl)methyl]-1,2-dihydro-5-isopropyl-3H-pyrazol-3-one and acetobromo-α-D-galactose instead of 4-{[4-(3-benzyloxypropoxy)phenyl]methyl}-1,2-dihydro-5-isopropyl-3H-pyrazol-3-one and acetobromo-α-D-glucose, respectively.

$^1$H-NMR (CDCl$_3$) δ ppm:
1.05-1.15 (6H, m), 1.41 (6H, s), 1.83 (3H, s), 1.98 (3H, s), 2.02 (3H, s), 2.15 (3H, s), 2.25 (3H, s), 2.7-2.85 (1H, m), 3.25-3.7 (12H, m), 3.97 (2H, t, J=4.9 Hz), 4.0-4.1 (1H, m), 4.1-4.2 (2H, m), 5.08 (1H, dd, J=10.4 Hz, 3.5 Hz), 5.12 (2H, s), 5.35-5.45 (2H, m), 5.52 (1H, d, J=8.1 Hz), 5.92 (1H, t, J=5.7 Hz), 6.53 (1H, dd, J=8.4 Hz, 2.6 Hz), 6.63 (1H, d, J=2.6 Hz), 6.81 (1H, d, J=8.4 Hz), 7.25-7.4 (5H, m)

Example 187

3-(β-D-Galactopyranosyloxy)-5-isopropyl-4-{[4-(2-{2-methyl-2-[(piperazin-1-yl)carbonyl]propionylamino}ethoxy)-2-methylphenyl]methyl}-1H-pyrazole To a solution of 3-(2,3,4,6-tetra-O-acetyl-β-D-galactopyranosyloxy)-4-[(4-{2-[2-{[4-(benzyloxycarbonyl)piperazin-1-yl]carbonyl}-2-(methyl)propionylamino]ethoxy}-2-methylphenyl)methyl]-5-isopropyl-1H-pyrazole (0.14 g) in methanol (3 mL) was added sodium methoxide (28% methanol solution, 0.015 mL), and the mixture was stirred at room temperature for 30 minutes. The reaction mixture was purified by column chromatography on silica gel (eluent: dichloromethane/methanol=5/1) to give 4-[(4-{2-[2-{[4-(benzyloxycarbonyl)piperazin-1-yl]-carbonyl}-2-(methyl)propionylamino]ethoxy}-2-methylphenyl)methyl]-3-(β-D-galactopyranosyloxy)-5-isopropyl-1H-pyrazole (70 mg). This material was dissolved in methanol (4 mL). To the solution was added 10% palladium-carbon powder (10 mg), and the mixture was stirred at room temperature under a hydrogen atmosphere for 1 hour. The insoluble material was removed by filtration, and the filtrate was concentrated under reduced pressure to give the title compound (54 mg).

$^1$H-NMR (CD$_3$OD) δ ppm:
1.05-1.2 (6H, m), 1.37 (6H, s), 2.3 (3H, s), 2.35-2.9 (5H, m), 3.1-3.8 (13H, m), 3.85 (1H, d, J=3.3 Hz), 4.02 (2H, t, J=5.5 Hz), 5.04 (1H, d, J=8.0 Hz), 6.62 (1H, dd, J=8.4 Hz, 2.4 Hz), 6.72 (1H, d, J=2.4 Hz), 6.86 (1H, d, J=8.4 Hz)

Test Example 1

Assay for Inhibitory Effects on Human SGLT1 Activity

1) Cloning and Construction of the Vector Expressing Human SGLT1

The cDNA library was prepared for PCR amplification by reverse transcription from total RNA deprived from human small intestine (Ori gene) using oligo-dT as a primer. Using this cDNA library as a template, the DNA fragment coding 1 to 2005 bp of human SGLT1 (ACCESSION: M24847), which was reported by Hediger et al., was amplified by PCR method and inserted into the multi-cloning site of pcDNA3.1(−) (Invitrogen). The DNA sequence inserted was perfectly matched to the previously reported sequence.

2) Establishment of Cell Line Stably Expressing Human SGLT1

The expression vector of human SGLT1 was digested by Sca I into a linear DNA. The linear DNA was transfected into CHO-K1 cells by means of lipofection (Effectene Transfection Reagent: QIAGEN). Neomycin resistant cell lines were selected by culture in the medium containing G418 (1 mg/mL, LIFE TECHNOLOGIES), and then the activity against the uptake of methyl-α-D-glucopyranoside was measured by the method described below. The cell line, which showed the greatest uptake activity, was selected and designated as CS1-5-11D. CS1-5-11D cells were cultured in the presence of G418 at 200 μg/mL.

3) Measurement of the Inhibitory Activity Against the Uptake of Methyl-α-D-glucopyranoside (α-MG)

CS1-5-11D cells were seeded into a 96-well culture plate at a density of 3×10$^4$ cells/well and cultured for 2 days, and were used in the uptake assay. A mixture of non-labeled (Sigma) and $^{14}$C-labeled α-MG (Amersham Pharmcia Biotec) was added to the uptake buffer (pH 7.4: containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid, and 5 mM tris(hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chorine chloride instead of sodium chloride was prepared. After removing the culture medium of CS1-5-11D cells, 180 μL of the pre-treatment buffer (the basal uptake buffer without α-MG) was added to each well and incubated at 37° C. for 10 minutes. After repeating the same treatment, the pre-treatment buffer was removed. To each well was added 75 μL of the measurement buffer or the basal uptake buffer was added and incubated at 37° C. for 1 hour. After removing the measurement buffer, cells were washed twice with 180 μL per well of the washing buffer (the basal uptake buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of micro-scintillation counter TopCount (Packard). One hundred was set to the difference between the uptake in the control group and the basal uptake, and the uptake of methyl α-D-glucopyranoside a teach drug concentration were calculated. The drug concentration, at which 50% uptake of methyl α-D-glucopyranoside was inhibited (IC$_{50}$ value), was calculated using logit plot. The results are shown in Table 11.

TABLE 11

| Test compound | IC$_{50}$ value (nM) |
|---|---|
| Example 6 | 304 |
| Example 9 | 42 |
| Example 10 | 169 |
| Example 13 | 267 |
| Example 21 | 127 |
| Example 22 | 233 |
| Example 24 | 61 |
| Example 28 | 90 |
| Example 29 | 19 |
| Example 30 | 257 |
| Example 31 | 166 |
| Example 32 | 113 |
| Example 33 | 65 |
| Example 35 | 160 |
| Example 36 | 383 |
| Example 37 | 158 |
| Example 38 | 246 |
| Example 45 | 68 |
| Example 48 | 54 |
| Example 49 | 148 |
| Example 50 | 159 |
| Example 51 | 22 |
| Exampel 52 | 131 |
| Example 55 | 98 |
| Example 56 | 38 |
| Example 57 | 43 |
| Example 58 | 100 |
| Example 59 | 71 |
| Example 61 | 199 |
| Example 62 | 138 |
| Example 63 | 322 |
| Example 64 | 178 |

Test Example 2

Assay for Inhibitory Effects on Blood Glucose Level Increase in Rats

1) Preparation of Diabetic Rat Model

Male wistar rats (Japan Charles River), aged 8 weeks old, were injected nicotinamide (230 mg/kg) intraperitoneally. Fifteen minutes after injection, they were injected streptozotocin (85 mg/kg) intravenously from tail vain under anesthesia with ether. After a week, rats were fasted overnight and then glucose tolerance test (2 g/kg) was done. The rats which showed plasma glucose concentration at 1 hour after glucose load was over 300 mg/dL were selected to use liquid meal tolerance test.

2) Liquid Meal Tolerance Test

After overnight fasted, the diabetic rats were orally administered a test compound (1 mg/kg), which was dissolved in distilled water or 0.5% aqueous carboxymethylcellulose solution, in the drug-treating group, or distilled water or 0.5% aqueous carboxymethylcellulose solution alone in a control group. Immediately after the compound administration, 17.25 kcal/kg of liquid meal (No. 038, Control diet, assorted with dextrin and maltose; Oriental Yeast Co., Ltd.) was loaded orally. The blood was collected from tail artery immediately before and after administration with the time course, and treated with heparin immediately. The blood was centrifuged, and the plasma was collected to quantify the plasma glucose concentration by glucose oxidase method. Plasma glucose concentrations at pretreatment (0 h), 0.5 and 1 hour after the drug administration are shown in Table 12. The values in the Table are presented as the mean±S.E.

TABLE 12

| Test compound | Plasma glucose concentration (mg/dL) | | |
|---|---|---|---|
| | 0 h | 0.5 h | 1 h |
| Control | 95 ± 5 | 219 ± 12 | 246 ± 17 |
| Example 6 | 97 ± 10 | 126 ± 12 | 140 ± 13 |
| Control | 122 ± 6 | 258 ± 32 | 260 ± 35 |
| Example 10 | 120 ± 10 | 145 ± 5 | 164 ± 6 |
| Control | 106 ± 4 | 199 ± 8 | 196 ± 15 |
| Example 13 | 108 ± 8 | 127 ± 7 | 135 ± 7 |
| Control | 115 ± 3 | 276 ± 25 | 261 ± 32 |
| Example 21 | 122 ± 11 | 211 ± 22 | 242 ± 35 |
| Example 35 | 113 ± 4 | 188 ± 16 | 229 ± 25 |
| Control | 140 ± 13 | 313 ± 48 | 283 ± 52 |
| Example 24 | 146 ± 7 | 210 ± 33 | 228 ± 50 |
| Control | 131 ± 7 | 330 ± 37 | 306 ± 45 |
| Example 37 | 132 ± 5 | 231 ± 21 | 286 ± 31 |
| Control | 123 ± 10 | 305 ± 18 | 304 ± 23 |
| Example 45 | 129 ± 11 | 169 ± 18 | 182 ± 27 |
| Control | 124 ± 5 | 278 ± 31 | 274 ± 22 |
| Example 52 | 138 ± 4 | 163 ± 5 | 176 ± 10 |
| Control | 123 ± 8 | 292 ± 28 | 294 ± 29 |
| Example 55 | 122 ± 5 | 200 ± 16 | 211 ± 18 |
| Example 59 | 115 ± 7 | 143 ± 4 | 154 ± 13 |
| Control | 121 ± 7 | 313 ± 33 | 303 ± 63 |
| Example 56 | 109 ± 10 | 146 ± 7 | 165 ± 17 |
| Control | 91 ± 12 | 238 ± 4 | 213 ± 22 |
| Example 64 | 116 ± 2 | 141 ± 12 | 148 ± 22 |

Test Example 3

Acute Toxicity Test

Male ICR mice (CLEA Japan, Inc.; 32-37 g, n=5), aged 6 weeks old, were fasted for 4 hours. A test compound, which was dissolved in distilled water, was administered orally at a dose of 1 g/kg, and then mice were observed for 24 hours. The results are shown in the following Table 13.

TABLE 13

| Test compound | Number of death |
|---|---|
| Example 52 | 0/5 |

Industrial Applicability

The pyrazole derivatives represented by the above general formula (I) of the present invention, pharmaceutically acceptable salts thereof and prodrugs thereof exert an inhibitory activity in human SGLT1 and can suppress increase of blood glucose level by inhibiting absorption of carbohydrate such as glucose at the small intestine, and particularly, can suppress remarkably increase of blood glucose level and/or can lower blood galactose level by delaying absorption of glucose and galactose based on the mechanism, and for example, can normalize postprandial hyperglycemia. Therefore, the present invention can provide excellent agents for the prevention or treatment of a disease associated with hyperglycemia such as diabetes, impaired glucose tolerance, impaired fasting glycemia, diabetic complications, obesity or the like, and a disease associated with the increase of blood galactose level such as galactosemia. In addition, since the pyrazole derivatives represented by the above general formula (II) of the present invention and salts thereof are important as intermediates in the production of the pyrazole derivatives represented by the above general formula (I), the compounds represented by the above general formula (I) of the present invention can be readily prepared via such compounds.

The invention claimed is:

1. A pharmaceutical combination which comprises (A) a pyrazole derivative, represented by the general formula:

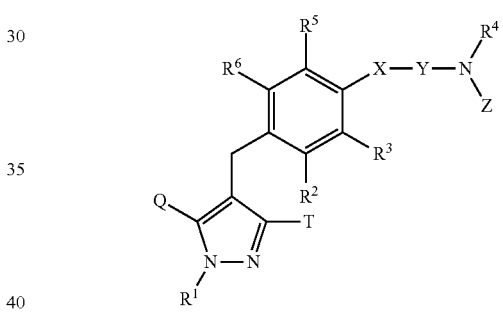

wherein
R$^1$ represents a hydrogen atom, a C$_{1-6}$ alkyl group, a C$_{2-6}$ alkenyl group, a hydroxy(C$_{2-6}$ alkyl) group, a C$_{3-7}$ cycloalkyl group, a C$_{3-7}$ cycloalkyl-substituted (C$_{1-6}$ alkyl) group, an aryl group which may have the same or different 1 to 3 substituents selected from the group consisting of a halogen atom, a hydroxy group, an amino group, a C$_{1-6}$ alkyl group and a C$_{1-6}$ alkoxy group, or an aryl(C$_{1-6}$ alkyl) group which may have the same or different 1 to 3 substituents selected from the group consisting of a halogen atom, a hydroxy group, an amino group, a C$_{1-6}$ alkyl group and a C$_{1-6}$ alkoxy group on the ring;
one of Q and T represents a group represented by the formula:

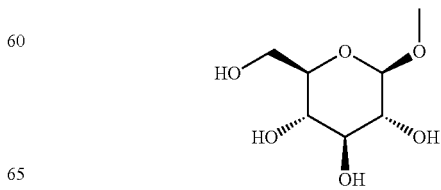

or a group represented by the formula:

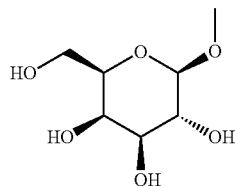

while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;

$R^2$ represents a hydrogen atom, a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or —A—$R^A$ in which A represents a single bond, an oxygen atom, a methylene group, an ethylene group, —OCH$_2$— or —CH$_2$O—; and $R^A$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, or a heteroaryl group which may have a substituent selected from the group consisting of a halogen atom and a $C_{1-6}$ alkyl group;

X represents a single bond, an oxygen atom or a sulfur atom;

Y represents a $C_{1-6}$ alkylene group which may be substituted by a hydroxy group or a $C_{2-6}$ alkenylene group;

Z represents —$R^B$, —COR$^C$, —SO$_2$R$^C$, —CON(R$^D$)R$^E$, —SO$_2$NHR$^F$ or —C(=NR$^G$)N(R$^H$)R$^I$;

$R^C$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i);

$R^4$, $R^B$, $R^D$, $R^E$ and $R^F$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), or both of $R^4$ and $R^B$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, or both of $R^D$ and $R^E$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group;

$R^G$, $R^H$ and $R^I$ are the same or different, and each represents a hydrogen atom, a cyano group, a carbamoyl group, a $C_{2-7}$ acyl group, a $C_{2-7}$ alkoxycarbonyl group, an aryl ($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (i), or both of $R^G$ and $R^H$ bind to form an ethylene group, or both of $R^H$ and $R^I$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl ($C_{1-6}$ alkyl) group, a hydroxy($C_{1-6}$ alkyl) group and a $C_{1-6}$ alkylsulfonylamino-substituted ($C_{1-6}$ alkyl) group;

$R^3$, $R^5$ and $R^6$ are the same or different, and each represents a hydrogen atom, a halogen atom, a $C_{1-6}$ alkyl group or a $C_{1-6}$ alkoxy group; and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON(R$^J$)R$^K$ in which R$^J$ and R$^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of R$^J$ and R$^K$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy ($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent, or a pharmaceutically acceptable salt thereof, and (B) at least one member selected from the group consisting of insulin, glyburide, gliclazide, glimepiride, repaglinide, nateglinide, mitiglinide calcium hydrate, metformin hydrochloride, buformin hydrochloride, rosiglitazone maleate, pioglitazone hydrochloride, acarbose, miglitol, voglibose and exendin-4.

2. A method for the treatment of a disease associated with hyperglycemia or a disease associated with the increase of blood galactose level, which comprises administering an effective amount of (A) a pyrazole derivative represented by the general formula:

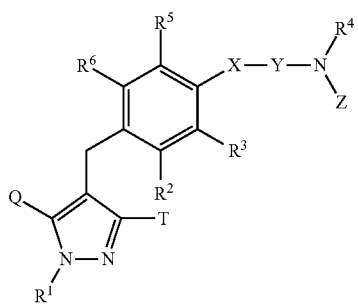

wherein $R^1$ R represents a hydrogen atom, a $C_{1-6}$ alkyl group, a $C_{2-6}$ alkenyl group, a hydroxy($C_{2-6}$ alkyl) group, a $C_{3-7}$ cycloalkyl group, a $C_{3-7}$ cycloalkyl-substituted ($C_{1-6}$ alkyl) group, an aryl group which may have the same or different 1 to 3 substituents selected from the group consisting of a halogen atom, a hydroxy group, an amino group, a $C_{1-6}$ alkyl group and a $C_{1-6}$ alkoxy group, or an aryl($C_{1-6}$ alkyl) group which may have the same or different 1 to 3 substituents selected from the group consisting of a halogen atom, a hydroxy group, an amino group, a $C_{1-6}$ alkyl group and a $C_{1-6}$ alkoxy group on the ring;

one of Q and T represents a group represented by the formula:

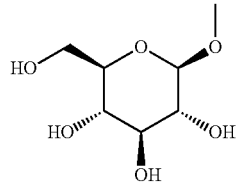

or a group represented by the formula:

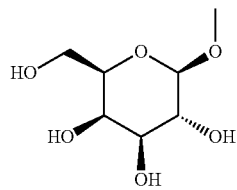

while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;

$R^2$ represents a hydrogen atom, a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or $-A-R^A$ in which A represents a single bond, an oxygen atom, a methylene group, an ethylene group, $-OCH_2-$ or $-CH_2O-$; and $R^A$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, or a heteroaryl group which may have a substituent selected from the group consisting of a halogen atom and a $C_{1-6}$ alkyl group;

X represents a single bond, an oxygen atom or a sulfur atom;

Y represents a $C_{1-6}$ alkylene group which may be substituted by a hydroxy group or a $C_{2-6}$ alkenylene group;

Z represents $-R^B$, $-COR^C$, $-SO_2R^C$, $-CON(R^D)R^E$, $-SO_2NHR^F$ or $-C(=NR^G)N(R^H)R^I$;

$R^C$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i);

$R^4$, $R^B$, $R^D$, $R^E$ and $R^F$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), or both of $R^4$ and $R^B$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy ($C_{1-6}$ alkyl) group and a $C_{1-6}$ alkylsulfonylamino-substituted ($C_{1-6}$ alkyl) group, or both of $R^D$ and $R^E$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group;

$R^G$, $R^H$ and $R^I$ are the same or different, and each represents a hydrogen atom, a cyano group, a carbamoyl group, a $C_{2-7}$ acyl group, a $C_{2-7}$ alkoxycarbonyl group, an aryl ($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (i), or both of $R^G$ and $R^H$ bind to form an ethylene group, or both of $R^H$ and $R^I$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl ($C_{1-6}$ alkyl) group, a hydroxy($C_{1-6}$ alkyl) group and a $C_{1-6}$ alkylsulfonylamino-substituted ($C_{1-6}$ alkyl) group;

$R^3$, $R^5$ and $R^6$ are the same or different, and each represents a hydrogen atom, a halogen atom, a $C_{1-6}$ alkyl group or a $C_{1-6}$ alkoxy group; and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON($R^J$)$R^K$ in which $R^J$ and $R^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of $R^J$ and $R^K$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy ($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent, or a pharmaceutically acceptable salt thereof, and (B) at least one member selected from the group consisting of insulin, glyburide, gliclazide, glimepiride, repaglinide, nateglinide, mitiglinide calcium hydrate, metformin hydrochloride, buformin hydrochloride, rosiglitazone maleate, pioglitazone hydrochloride, acarbose, miglitol, voglibose and exendin-4.

3. A method for the inhibition of advancing impaired glucose tolerance or impaired fasting glycemia into diabetes in a subject, which comprises administering an effective amount of (A) a pyrazole derivative represented by the general formula:

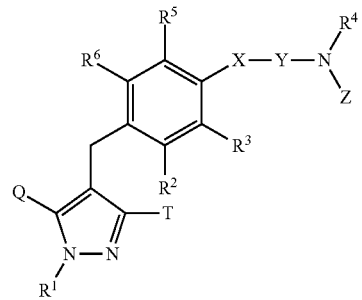

wherein
$R^1$ represents a hydrogen atom, a $C_{1-6}$ alkyl group, a $C_{2-6}$ alkenyl group, a hydroxy($C_{2-6}$ alkyl) group, a $C_{3-7}$ cycloalkyl group, a $C_{3-7}$ cycloalkyl-substituted ($C_{1-6}$ alkyl) group, an aryl group which may have the same or different 1 to 3 substituents selected from the group consisting of a halogen atom, a hydroxy group, an amino group, a $C_{1-6}$ alkyl group and a $C_{1-6}$ alkoxy group, or an aryl($C_{1-6}$ alkyl) group which may have the same or different 1 to 3 substituents selected from the group consisting of a halogen atom, a hydroxy group, an amino group, a $C_{1-6}$ alkyl group and a $C_{1-6}$ alkoxy group on the ring;

one of Q and T represents a group represented by the formula:

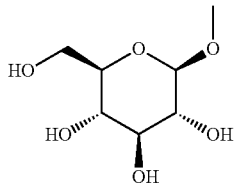

or a group represented by the formula:

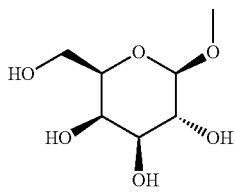

while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;

$R^2$ represents a hydrogen atom, a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or —A—$R^A$ in which A represents a single bond, an oxygen atom, a methylene group, an ethylene group, —OCH$_2$— or —CH$_2$O—; and $R^A$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, or a heteroaryl group which may have a substituent selected from the group consisting of a halogen atom and a $C_{1-6}$ alkyl group;

X represents a single bond, an oxygen atom or a sulfur atom;

Y represents a $C_{1-6}$ alkylene group which may be substituted by a hydroxy group or a $C_{2-6}$ alkenylene group;

Z represents —$R^B$, —$COR^C$, —$SO_2R^C$, —$CON(R^D)R^E$, —$SO_2NHR^F$ or —$C(=NR^C)N(R^H)R^I$;

$R^C$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i);

$R^4$, $R^B$, $R^D$, $R^E$ and $R^F$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), or both of $R^4$ and $R^B$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, or both of $R^D$ and $R^E$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group;

$R^G$, $R^H$ and $R^I$ are the same or different, and each represents a hydrogen atom, a cyano group, a carbamoyl group, a $C_{2-7}$ acyl group, a $C_{2-7}$ alkoxycarbonyl group, an aryl ($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (i), or both of $R^G$ and $R^H$ bind to form an ethylene group, or both of $R^H$ and $R^I$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl ($C_{1-6}$ alkyl) group, a hydroxy($C_{1-6}$ alkyl) group and a $C_{1-6}$ alkylsulfonylamino-substituted ($C_{1-6}$ alkyl) group;

$R^3$, $R^5$ and $R^6$ are the same or different, and each represents a hydrogen atom, a halogen atom, a $C_{1-6}$ alkyl group or a $C_{1-6}$ alkoxy group; and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —$CON(R^J)R^K$ in which $R^J$ and $R^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of $R^J$ and $R^K$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy ($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent, or a pharmaceutically acceptable salt thereof, and (B) at least one member selected from the group consisting of insulin, glyburide, gliclazide, glimepiride, repaglinide, nateglinide, mitiglinide calcium hydrate, metformin hydrochloride, buformin hydrochloride, rosiglitazone maleate, pioglitazone hydrochloride, acarbose, miglitol, voglibose and exendin-4.

* * * * *